US011512090B2

(12) United States Patent
Xiong et al.

(10) Patent No.: US 11,512,090 B2
(45) Date of Patent: Nov. 29, 2022

(54) MUSCARINIC ACETYLCHOLINE $M_1$ RECEPTOR ANTAGONISTS

(71) Applicant: PIPELINE THERAPEUTICS, INC., San Diego, CA (US)

(72) Inventors: Yifeng Xiong, San Diego, CA (US); Thomas Schrader, San Diego, CA (US); Austin Chen, San Diego, CA (US); Jeffrey Roger Roppe, San Diego, CA (US); Jill Melissa Baccei, San Diego, CA (US); Yalda Bravo, San Diego, CA (US)

(73) Assignee: Pipeline Therapeutics, Inc., San Diego, CA (US)

( * ) Notice: Subject to any disclaimer, the term of this patent is extended or adjusted under 35 U.S.C. 154(b) by 0 days.

(21) Appl. No.: 15/734,529

(22) PCT Filed: Jun. 10, 2019

(86) PCT No.: PCT/US2019/036345
§ 371 (c)(1),
(2) Date: Dec. 2, 2020

(87) PCT Pub. No.: WO2019/241131
PCT Pub. Date: Dec. 19, 2019

(65) Prior Publication Data
US 2022/0332721 A1 Oct. 20, 2022

Related U.S. Application Data

(60) Provisional application No. 62/683,538, filed on Jun. 11, 2018.

(51) Int. Cl.
| | | |
|---|---|---|
| *C07D 487/08* | (2006.01) | |
| *C07D 401/12* | (2006.01) | |
| *C07D 417/12* | (2006.01) | |
| *C07D 498/08* | (2006.01) | |
| *C07D 413/12* | (2006.01) | |
| *C07D 519/00* | (2006.01) | |
| *C07D 417/14* | (2006.01) | |

(52) U.S. Cl.
CPC ......... *C07D 487/08* (2013.01); *C07D 401/12* (2013.01); *C07D 413/12* (2013.01); *C07D 417/12* (2013.01); *C07D 417/14* (2013.01); *C07D 498/08* (2013.01); *C07D 519/00* (2013.01)

(58) Field of Classification Search
CPC .................................................. C07D 487/08
USPC .................................................. 514/210.21
See application file for complete search history.

(56) References Cited

U.S. PATENT DOCUMENTS

| | | |
|---|---|---|
| 4,803,203 A | 2/1989 | Caprathe et al. |
| 5,089,497 A | 2/1992 | Jaen et al. |
| 7,071,335 B2 | 7/2006 | Kyle et al. |
| 8,648,074 B2 | 2/2014 | Li et al. |
| 8,999,974 B2 | 4/2015 | Morita et al. |
| 2007/0129378 A1 | 6/2007 | Siddiqui et al. |
| 2013/0178458 A1 | 7/2013 | Lindsley et al. |
| 2021/0155629 A1 | 5/2021 | Schrader et al. |
| 2021/0161889 A1 | 6/2021 | Xiong et al. |

FOREIGN PATENT DOCUMENTS

| | | |
|---|---|---|
| WO | WO-2006/010751 A1 | 2/2006 |
| WO | WO-2018/089433 A1 | 5/2018 |
| WO | WO-2019/158572 A1 | 8/2019 |
| WO | WO-2019/212937 A1 | 11/2019 |
| WO | WO-2019/241131 A1 | 12/2019 |
| WO | WO-2020/051153 A1 | 3/2020 |
| WO | WO-2021/071843 A1 | 4/2021 |

OTHER PUBLICATIONS

Bender, A.M. et al. (Aug. 1, 2017, e-published May 15, 2017). "Discovery and optimization of 3-(4-aryl/heteroarylsulfonyl)piperazin-1-yl)-6-(piperidin-1-yl)pyridazines as novel, CNS penetrant pan-muscarinic antagonists," *Bioorg Med Chem Lett* 27(15):3576-3581.
International Search Report dated Oct. 18, 2019, for PCT Application No. PCT/US2019/036345, filed Jun. 10, 2019, 4 pages.
International Search Report dated Nov. 21, 2019, for PCT Application No. PCT/US2019/049374, filed Sep. 3, 2019, 3 pages.
International Search Report dated Dec. 29, 2020 for PCT Application No. PCT/US2020/054412, filed Oct. 6, 2020, 3 pages.
Melancon, B.J. et al. (Jan. 15, 2012, e-published Dec. 6, 2011). "Development of a more highly selective M1 antagonist from the continued optimization of the MLPCN Probe ML012," *Bioorg Med Chem Lett* 22(2):1044-1048.
Melancon, B.J. et al. (Aug. 1, 2012, e-published Jun. 15, 2012). "Development of novel M1 antagonist scaffolds through the continued optimization of the MLPCN probe ML012," *Bioorg Med Chem Lett* 22(15):5035-5040.
PubChem CID 70746046, (Create Date Mar. 4, 2013), located at <https://pubchem.ncbi.nlm.nih.gov/compound/70746046>, 5 pages.
PubChem CID 101131894, (Create Date Dec. 17, 2015), located at <https://pubchem.ncbi.nlm.nih.gov/compound/101131894>, 7 pages.
PubChem CID 101131895, (Create Date Dec. 17, 2015), located at <https://pubchem.ncbi.nlm.nih.gov/compound/101131895>, 8 pages.
PubChem CID 102350371, (Create Date Dec. 25, 2015), located at <https://pubchem.ncbi.nlm.nih.gov/compound/102350371>, 7 pages.

(Continued)

*Primary Examiner* — Kahsay Habte
(74) *Attorney, Agent, or Firm* — Mintz, Levin, Cohn, Ferris, Glovsky and Popeo, P.C.

(57) ABSTRACT

Provided herein are compounds which are useful as antagonists of the muscarinic acetylcholine receptor $M_1$ (mAChR $M_1$); synthetic methods for making the compounds; pharmaceutical compositions comprising the compounds; and methods of treating neurological and psychiatric disorders associated with muscarinic acetylcholine receptor dysfunction using the compounds and compositions.

19 Claims, No Drawings

(56) References Cited

OTHER PUBLICATIONS

Sheffler, D.J. et al. (Aug. 2009, e-published Apr. 30, 2009). "A novel selective muscarinic acetylcholine receptor subtype 1 antagonist reduces seizures without impairing hippocampus-dependent learning," *Mol Pharmacol* 76(2):356-368.
Written Opinion dated Oct. 18, 2019, for PCT Application No. PCT/US2019/036345, filed Jun. 10, 2019, 6 pages.
Written Opinion dated Nov. 21, 2019, for PCT Application No. PCT/US2019/049374, filed Sep. 3, 2019, 4 pages.
Written Opinion dated Dec. 29, 2020 for PCT Application No. PCT/US2020/054412, filed Oct. 6, 2020, 3 pages.

MUSCARINIC ACETYLCHOLINE M$_1$ RECEPTOR ANTAGONISTS

CROSS-REFERENCE

This application is the national stage filing under 35 U.S.C. § 371 of International Application No. PCT/US2019/036345 filed Jun. 10, 2019, which claims benefit of U.S. Provisional Application No. 62/683,538, filed on Jun. 11, 2018, which are herein incorporated by reference in their entirety.

BACKGROUND

The human muscarinic acetylcholine receptor M$_1$ (mAChR M$_1$) is a protein of 479 amino acids encoded by the CHRM1 gene. The mAChR M$_1$ is one of five members of the family of muscarinic acetylcholine receptors (M$_1$-M$_5$), which are widely expressed throughout the body where they have varying roles in cognitive, sensory, motor, and autonomic functions. The M$_1$ mAChR is found in both the central and peripheral nervous systems, particularly in the cerebral cortex and sympathetic ganglia. Based on the potential role of mAChR M$_1$ in seizure activity and motor control, selective mAChR M$_1$ antagonists have potential utility in the treatment of some epileptic disorders, as well as certain movement disorders, including Parkinson's disease, dystonia, and fragile X syndrome.

BRIEF SUMMARY OF THE INVENTION

This disclosure provides, for example, compounds and compositions which are antagonists of the muscarinic acetylcholine M$_1$ receptor (mAChR M$_1$), and their use as medicinal agents, processes for their preparation, and pharmaceutical compositions that include disclosed compounds as at least one active ingredient. The disclosure also provides for the use of disclosed compounds as medicaments and/or in the manufacture of medicaments for the inhibition of muscarinic acetylcholine M1 receptor activity in patients.

In one aspect is a compound of Formula (I'):

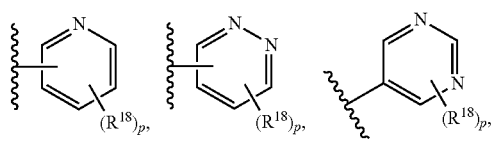

Formula (I')

wherein:

X is —CH$_2$CH$_2$—, —CH$_2$O—, —CH$_2$CH$_2$O—, —O—, —N(R$^{14}$)—, S(O)$_2$, —CH$_2$N(R$^{14}$)—, or —CH$_2$CH$_2$N(R$^{14}$)—;

Y is a bond, —C(R$^{16}$)(R$^{17}$)—, or —N(R$^{15}$)—;

Z is —N— or —C(H)—;

R$^1$ is

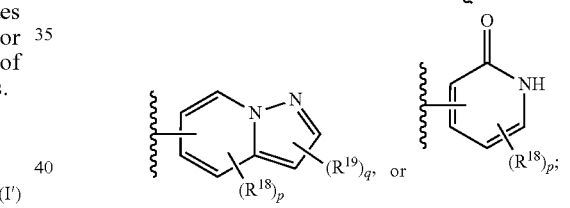

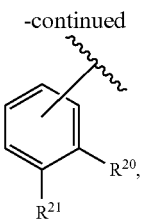

wherein ring A is a heteroaryl ring optionally substituted with halogen, —CN, —N(R$^{22}$)$_2$, C$_{1-6}$ alkyl, C$_{1-6}$alkyl-OH, C$_{1-6}$ alkoxy, C$_{1-6}$haloalkyl, or C$_{1-6}$haloalkoxy, wherein the heteroaryl ring contains 1 or 2 heteroatoms selected from the group consisting of O, N, or S;

each R$^2$ is independently selected from H, halogen, and C$_{1-6}$alkyl;

each R$^3$ is independently selected from H, halogen, and C$_{1-6}$alkyl;

R$^4$, R$^6$, R$^8$, and R$^{10}$ are each independently selected from H and C$_{1-6}$alkyl;

R$^5$, R$^7$, R$^9$, and R$^{11}$ are each independently selected from H and C$_{1-6}$alkyl; or R$^7$ and R$^{11}$ combine to form a ring or R$^5$ and R$^9$ combine to form a ring or R$^7$ and R$^9$ combine to form a ring;

R$^{12}$ is

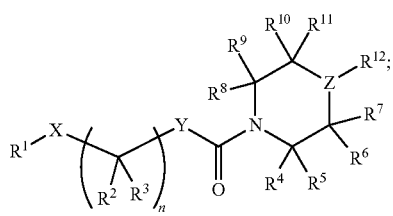

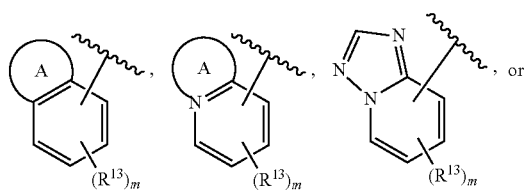

each R$^{13}$ is independently selected from halogen, —CN, C$_{1-6}$alkyl, C$_{1-6}$alkoxy, C$_{1-6}$haloalkyl, and C$_{1-6}$haloalkoxy;

R$^{14}$ is H, C$_{1-6}$alkyl, C$_{3-6}$cycloalkyl, or C$_{2-9}$heterocycloalkyl; or R$^{14}$ and one R$^3$ combine to form a 4-, 5-, or 6-membered heterocycloalkyl ring;

R$^{15}$ is H or C$_{1-6}$alkyl; or R$^{15}$ and one R$^3$ combine to form a 4-, 5-, or 6-membered heterocycloalkyl ring;

R$^{16}$ is H or C$_{1-6}$alkyl;

R$^{17}$ is H or C$_{1-6}$alkyl; or R$^{17}$ and one R$^3$ combine to form a 3-, 4-, 5-, or 6-membered cycloalkyl ring;

each R$^{18}$ and each R$^{19}$ are each independently selected from halogen, —CN, —N(R$^{22}$)$_2$, C$_{1-6}$alkyl, C$_{3-6}$cycloalkyl, hydroxy, C$_{1-6}$alkoxy, C$_{1-6}$haloalkyl, C$_{1-6}$haloalkoxy, and phenyl;

R$^{20}$ and R$^{21}$ combine to form a 5- or 6-membered cycloalkyl ring or a 5-membered heterocycloalkyl ring;

each R$^{22}$ is independently selected from H and C$_{1-6}$alkyl;

m is 0, 1, 2, or 3;

n is 1, 2, 3, 4, or 5;

p is 0, 1, 2, or 3; and q is 0, 1, or 2;

or a pharmaceutically acceptable salt or solvate thereof.

In another aspect is a compound of Formula (I):

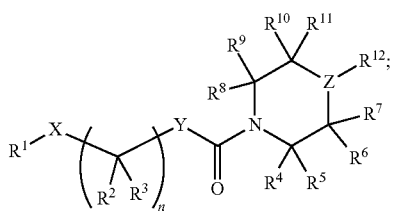

Formula (I)

wherein:
X is —CH$_2$CH$_2$—, —CH$_2$O—, —CH$_2$CH$_2$O—, —O—, —N(R$^{14}$)—, S(O)$_2$, —CH$_2$N(R$^{14}$)—, or —CH$_2$CH$_2$N(R$^{14}$)—;
Y is a bond, —C(R$^{16}$)(R$^{17}$)—, or —N(R$^{15}$)—;
Z is —N— or —C(H)—;
R$^1$ is

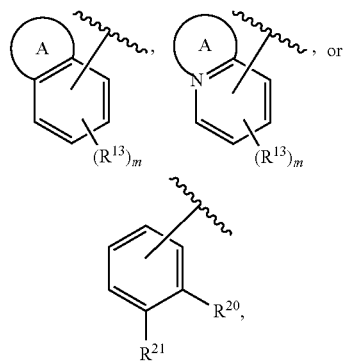

wherein ring A is a heteroaryl ring optionally substituted with halogen, —CN, —N(R$^{22}$)$_2$, C$_{1-6}$ alkyl, C$_{1-6}$ alkyl-OH, C$_{1-6}$ alkoxy, C$_{1-6}$haloalkyl, or C$_{1-6}$haloalkoxy, wherein the heteroaryl ring contains 1 or 2 heteroatoms selected from the group consisting of O, N, or S;
each R$^2$ is independently selected from H and C$_{1-6}$alkyl;
each R$^3$ is independently selected from H and C$_{1-6}$alkyl;
R$^4$, R$^6$, R$^8$, and R$^{10}$ are each independently selected from H and C$_{1-6}$alkyl;
R$^5$, R$^7$, R$^9$, and R$^{11}$ are each independently selected from H and C$_{1-6}$alkyl; or R$^7$ and R$^{11}$ combine to form a ring or R$^5$ and R$^9$ combine to form a ring or R$^7$ and R$^9$ combine to form a ring;
R$^{12}$ is

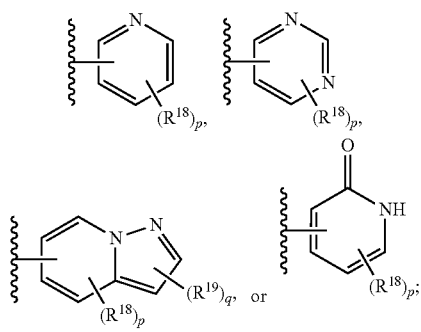

each R$^{13}$ is independently selected from halogen, —CN, C$_{1-6}$alkyl, C$_{1-6}$alkoxy, C$_{1-6}$haloalkyl, and C$_{1-6}$haloalkoxy;
R$^{14}$ is H or C$_{1-6}$alkyl; or R$^{14}$ and one R$^3$ combine to form a 4-, 5-, or 6-membered heterocycloalkyl ring;
R$^{15}$ is H or C$_{1-6}$alkyl; or R$^{15}$ and one R$^3$ combine to form a 4-, 5-, or 6-membered heterocycloalkyl ring;
R$^{16}$ is H or C$_{1-6}$alkyl;
R$^{17}$ is H or C$_{1-6}$alkyl; or R$^{17}$ and one R$^3$ combine to form a 3-, 4-, 5-, or 6-membered cycloalkyl ring;
each R$^{18}$ and each R$^{19}$ are each independently selected from halogen, —CN, C$_{1-6}$alkyl, hydroxy, C$_{1-6}$alkoxy, C$_{1-6}$haloalkyl, and C$_{1-6}$haloalkoxy;
R$^{20}$ and R$^{21}$ combine to form a 5- or 6-membered cycloalkyl ring or a 5-membered heterocycloalkyl ring;
each R$^{22}$ is independently selected from H and C$_{1-6}$alkyl;
m is 0, 1, 2, or 3;
n is 1, 2, 3, 4, or 5;
p is 0, 1, 2, or 3; and
q is 0, 1, or 2;
or a pharmaceutically acceptable salt or solvate thereof.

In some embodiments of a compound of Formula (I) or (I'), or a pharmaceutically acceptable salt or solvate thereof, R$^1$ is

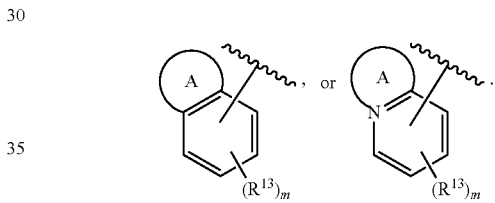

In some embodiments of a compound of Formula (I) or (I'), or a pharmaceutically acceptable salt or solvate thereof, R$^1$ is

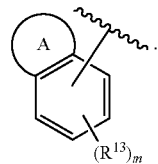

In some embodiments of a compound of Formula (I) or (I'), or a pharmaceutically acceptable salt or solvate thereof, R$^1$ is

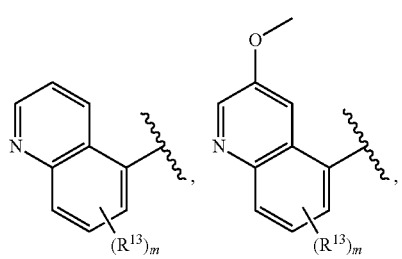

-continued

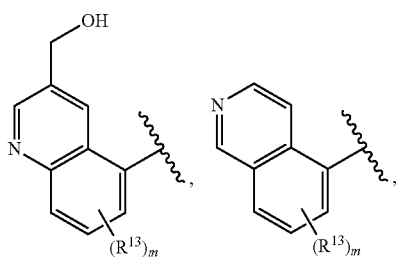

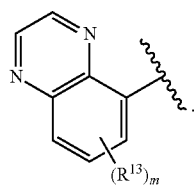

In some embodiments of a compound of Formula (I'), or a pharmaceutically acceptable salt or solvate thereof, $R^1$ is In some embodiments of a compound of Formula (I) or (I'), or a pharmaceutically acceptable salt or solvate thereof, $R^1$ is

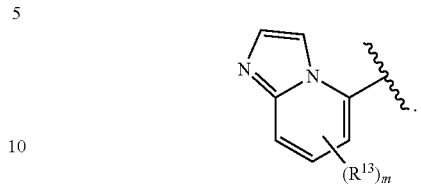

In some embodiments of a compound of Formula (I'), or a pharmaceutically acceptable salt or solvate thereof, $R^1$ is

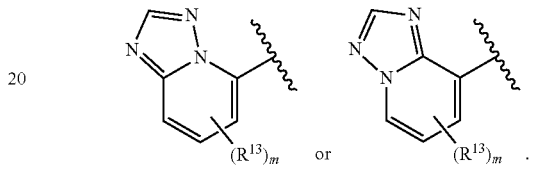

In some embodiments of a compound of Formula (I) or (I'), or a pharmaceutically acceptable salt or solvate thereof, m is 0. In some embodiments of a compound of Formula (I) or (I'), or a pharmaceutically acceptable salt or solvate thereof, Z is —N—. In some embodiments of a compound of Formula (I) or (I'), or a pharmaceutically acceptable salt or solvate thereof, Z is —C(H)—.

In some embodiments is a compound of Formula (I), or a pharmaceutically acceptable salt or solvate thereof, having the structure of Formula (Ia), or a pharmaceutically acceptable salt or solvate thereof:

Formula (Ia)

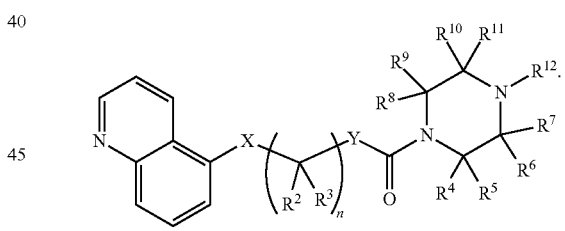

In some embodiments is a compound of Formula (I), or a pharmaceutically acceptable salt or solvate thereof, having the structure of Formula (Ib), or a pharmaceutically acceptable salt or solvate thereof:

Formula (Ib)

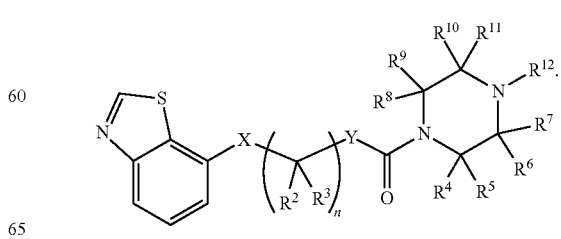

In some embodiments of a compound of Formula (I) or (I'), or a pharmaceutically acceptable salt or solvate thereof, $R^1$ is

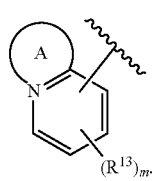

In some embodiments of a compound of Formula (I), Formula (I'), Formula (Ia), or Formula (Ib), or a pharmaceutically acceptable salt or solvate thereof, R$^{12}$ is

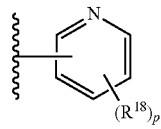

In some embodiments of a compound of Formula (I), Formula (I'), Formula (Ia), or Formula (Ib), or a pharmaceutically acceptable salt or solvate thereof, R$^{12}$ is

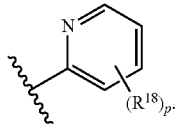

In some embodiments of a compound of Formula (I), Formula (I'), Formula (Ia), or Formula (Ib), or a pharmaceutically acceptable salt or solvate thereof, R$^{12}$ is

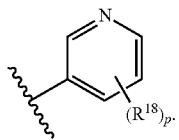

In some embodiments of a compound of Formula (I), Formula (I'), Formula (Ia), or Formula (Ib), or a pharmaceutically acceptable salt or solvate thereof, R$^{12}$ is

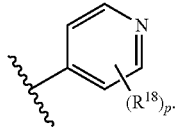

In some embodiments of a compound of Formula (I), Formula (I'), Formula (Ia), or Formula (Ib), or a pharmaceutically acceptable salt or solvate thereof, R$^{12}$ is

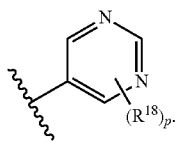

In some embodiments of a compound of Formula (I), Formula (I'), Formula (Ia), or Formula (Ib), or a pharmaceutically acceptable salt or solvate thereof, R$^{12}$ is

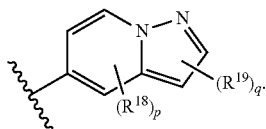

In some embodiments of a compound of Formula (I), Formula (I'), Formula (Ia), or Formula (Ib), or a pharmaceutically acceptable salt or solvate thereof, q is 1. In some embodiments of a compound of Formula (I), Formula (I'), Formula (Ia), or Formula (Ib), or a pharmaceutically acceptable salt or solvate thereof, q is 0.

In another aspect is a compound of Formula (II):

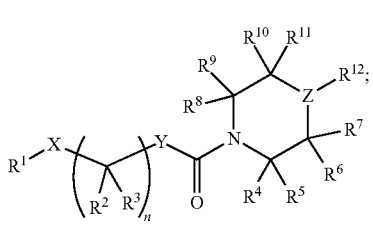

Formula (II)

wherein:

X is —CH$_2$CH$_2$—, —CH$_2$O—, —CH$_2$CH$_2$O—, —O—, —N(R$^{14}$)—, S(O)$_2$, —CH$_2$N(R$^{14}$)—, or —CH$_2$CH$_2$N(R$^{14}$)—;

Y is a bond, —C(R$^{16}$)(R$^{17}$)—, or —N(R$^{15}$)—;

Z is —N— or —C(H)—;

R$^1$ is

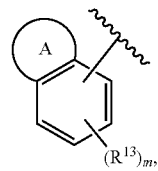

wherein ring A is a heteroaryl ring optionally substituted with halogen, —CN, —N(R$^{22}$)$_2$, C$_{1-6}$alkyl, C$_{1-6}$alkyl-OH, C$_{1-6}$alkoxy, C$_{1-6}$haloalkyl, or C$_{1-6}$haloalkoxy, wherein the heteroaryl ring contains 1 nitrogen atom and 0 or 1 oxygen or sulfur atoms;

each R$^2$ is independently selected from H and C$_{1-6}$alkyl;

each R$^3$ is independently selected from H and C$_{1-6}$alkyl;

R$^4$, R$^6$, R$^8$, and R$^{10}$ are each independently selected from H and C$_{1-6}$alkyl;

R$^5$, R$^7$, R$^9$, and R$^{11}$ are each independently selected from H and C$_{1-6}$alkyl; or R$^7$ and R$^{11}$ combine to form a ring or R$^5$ and R$^9$ combine to form a ring or R$^7$ and R$^9$ combine to form a ring;

R$^{12}$ is

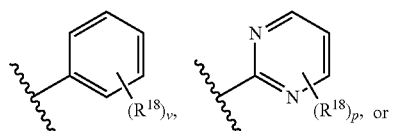

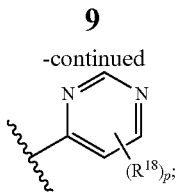

each $R^{13}$ is independently selected from halogen, —CN, $C_{1-6}$alkyl, $C_{1-6}$alkoxy, $C_{1-6}$haloalkyl, and $C_{1-6}$haloalkoxy;

$R^{14}$ is H or $C_{1-6}$alkyl; or $R^{14}$ and one $R^3$ combine to form a 4-, 5-, or 6-membered heterocycloalkyl ring;

$R^{15}$ is H or $C_{1-6}$alkyl; or $R^{15}$ and one $R^3$ combine to form a 4-, 5-, or 6-membered heterocycloalkyl ring;

$R^{16}$ is H or $C_{1-6}$alkyl;

$R^{17}$ is H or $C_{1-6}$alkyl; or $R^{17}$ and one $R^3$ combine to form a 3-, 4-, 5-, or 6-membered cycloalkyl ring;

each $R^{18}$ is independently selected from halogen, —CN, $C_{1-6}$alkyl, $C_{1-6}$alkoxy, $C_{1-6}$haloalkyl, and $C_{1-6}$haloalkoxy;

each $R^{22}$ is independently selected from H and $C_{1-6}$alkyl;

m is 0, 1, 2, or 3;
n is 1, 2, 3, 4, or 5;
p is 0, 1, 2, or 3; and
v is 0, 1, 2, 3, 4, or 5;

or a pharmaceutically acceptable salt or solvate thereof.

In some embodiments of a compound of Formula (II), or a pharmaceutically acceptable salt or solvate thereof, $R^1$ is

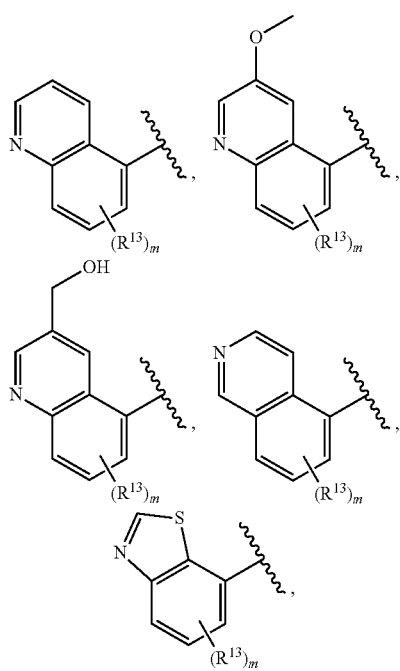

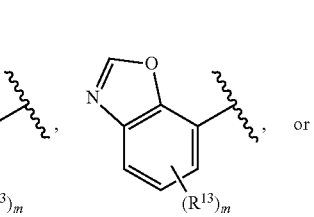

or

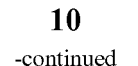

In some embodiments of a compound of Formula (II), or a pharmaceutically acceptable salt or solvate thereof, m is 0. In some embodiments of a compound of Formula (II), or a pharmaceutically acceptable salt or solvate thereof, Z is —N—. In some embodiments of a compound of Formula (II), or a pharmaceutically acceptable salt or solvate thereof, Z is —C(H)—.

In some embodiments is a compound of Formula (II), or a pharmaceutically acceptable salt or solvate thereof, having the structure of Formula (IIa), or a pharmaceutically acceptable salt or solvate thereof:

Formula (IIa)

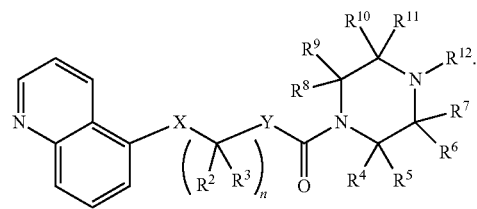

In some embodiments is a compound of Formula (II), or a pharmaceutically acceptable salt or solvate thereof, having the structure of Formula (IIb), or a pharmaceutically acceptable salt or solvate thereof:

Formula (IIb)

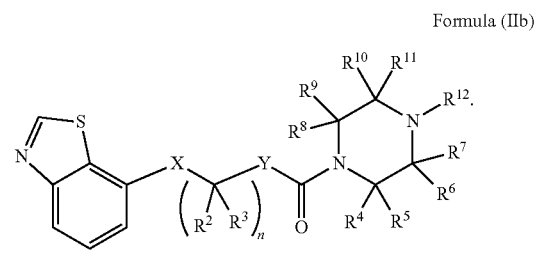

In some embodiments of a compound of Formula (II), Formula (IIa), or Formula (IIb), or a pharmaceutically acceptable salt or solvate thereof, $R^{12}$ is

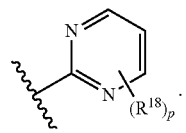

In some embodiments of a compound of Formula (II), Formula (IIa), or Formula (IIb), or a pharmaceutically acceptable salt or solvate thereof, $R^{12}$ is

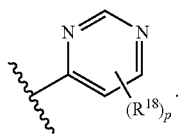

In some embodiments of a compound of Formula (II), Formula (IIa), or Formula (IIb), or a pharmaceutically acceptable salt or solvate thereof, p is 1 or 2. In some embodiments of a compound of Formula (II), Formula (IIa), or Formula (IIb), or a pharmaceutically acceptable salt or solvate thereof, p is 2. In some embodiments of a compound of Formula (II), Formula (IIa), or Formula (IIb), or a pharmaceutically acceptable salt or solvate thereof, p is 1. In some embodiments of a compound of Formula (II), Formula (IIa), or Formula (IIb), or a pharmaceutically acceptable salt or solvate thereof, p is 0.

In some embodiments of a compound of Formula (II), Formula (IIa), or Formula (IIb), or a pharmaceutically acceptable salt or solvate thereof, $R^{12}$ is

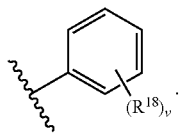

In some embodiments of a compound of Formula (II), Formula (IIa), or Formula (IIb), or a pharmaceutically acceptable salt or solvate thereof, v is 1, 2, or 3. In some embodiments of a compound of Formula (II), Formula (IIa), or Formula (IIb), or a pharmaceutically acceptable salt or solvate thereof, v is 1. In some embodiments of a compound of Formula (II), Formula (IIa), or Formula (IIb), or a pharmaceutically acceptable salt or solvate thereof, v is 2. In some embodiments of a compound of Formula (II), Formula (IIa), or Formula (IIb), or a pharmaceutically acceptable salt or solvate thereof, v is 3. In some embodiments of a compound of Formula (II), Formula (IIa), or Formula (IIb), or a pharmaceutically acceptable salt or solvate thereof, v is 0.

In some embodiments of a compound of Formula (I), Formula (I'), Formula (Ia), Formula (Ib), Formula (II), Formula (IIa), or Formula (IIb), or a pharmaceutically acceptable salt or solvate thereof, X is —CH$_2$CH$_2$— and Y is a bond. In some embodiments of a compound of Formula (I), Formula (I'), Formula (Ia), Formula (Ib), Formula (II), Formula (IIa), or Formula (IIb), or a pharmaceutically acceptable salt or solvate thereof, X is —CH$_2$O— and Y is a bond. In some embodiments of a compound of Formula (I), Formula (I'), Formula (Ia), Formula (Ib), Formula (II), Formula (IIa), or Formula (IIb), or a pharmaceutically acceptable salt or solvate thereof, X is —CH$_2$N(H)— and Y is a bond. In some embodiments of a compound of Formula (I), Formula (I'), Formula (Ia), Formula (Ib), Formula (II), Formula (IIa), or Formula (IIb), or a pharmaceutically acceptable salt or solvate thereof, X is S(O)$_2$ and Y is a bond. In some embodiments of a compound of Formula (I), Formula (I'), Formula (Ia), Formula (Ib), Formula (II), Formula (IIa), or Formula (IIb), or a pharmaceutically acceptable salt or solvate thereof, each $R^2$ and each $R^3$ are H. In some embodiments of a compound of Formula (I), Formula (I'), Formula (Ia), Formula (Ib), Formula (II), Formula (IIa), or Formula (IIb), or a pharmaceutically acceptable salt or solvate thereof, X is —O—, Y is —C($R^{16}$)($R^{17}$)—, and $R^{17}$ and one $R^3$ combine to form a 3- or 4-membered cycloalkyl ring. In some embodiments of a compound of Formula (I), Formula (I'), Formula (Ia), Formula (Ib), Formula (II), Formula (IIa), or Formula (IIb), or a pharmaceutically acceptable salt or solvate thereof, X is —N($R^{14}$)—; Y is bond; and $R^{14}$ and one $R^3$ combine to form a 4-, 5-, or 6-membered heterocycloalkyl ring. In some embodiments of a compound of Formula (I), Formula (I'), Formula (Ia), Formula (Ib), Formula (II), Formula (IIa), or Formula (IIb), or a pharmaceutically acceptable salt or solvate thereof, X is —O—; Y is —N($R^{15}$)—; and $R^{15}$ and one $R^3$ combine to form a 4-, 5-, or 6-membered heterocycloalkyl ring. In some embodiments of a compound of Formula (I), Formula (I'), Formula (Ia), Formula (Ib), Formula (II), Formula (IIa), or Formula (IIb), or a pharmaceutically acceptable salt or solvate thereof, each $R^{18}$ is independently selected from halogen, —CN, $C_{1-6}$alkoxy, and $C_{1-6}$haloalkyl. In some embodiments of a compound of Formula (I), Formula (I'), Formula (Ia), Formula (Ib), Formula (II), Formula (IIa), or Formula (IIb), or a pharmaceutically acceptable salt or solvate thereof, each $R^{18}$ is independently selected from halogen, —CN, $C_{1-6}$alkyl, and $C_{1-6}$haloalkyl. In some embodiments of a compound of Formula (I), Formula (I'), Formula (Ia), Formula (Ib), Formula (II), Formula (IIa), or Formula (IIb), or a pharmaceutically acceptable salt or solvate thereof, n is 1, 2, or 3. In some embodiments of a compound of Formula (I), Formula (I'), Formula (Ia), Formula (Ib), Formula (II), Formula (IIa), or Formula (IIb), or a pharmaceutically acceptable salt or solvate thereof, n is 3. In some embodiments of a compound of Formula (I), Formula (I'), Formula (Ia), Formula (Ib), Formula (II), Formula (IIa), or Formula (IIb), or a pharmaceutically acceptable salt or solvate thereof, n is 2. In some embodiments of a compound of Formula (I), Formula (I'), Formula (Ia), Formula (Ib), Formula (II), Formula (IIa), or Formula (IIb), or a pharmaceutically acceptable salt or solvate thereof, n is 1.

In some embodiments of a compound of Formula (I), Formula (I'), Formula (Ia), Formula (Ib), Formula (II), Formula (IIa), or Formula (IIb), or a pharmaceutically acceptable salt or solvate thereof, $R^4$, $R^6$, $R^8$, and $R^{10}$ are H. In some embodiments of a compound of Formula (I), Formula (I'), Formula (Ia), Formula (Ib), Formula (II), Formula (IIa), or Formula (IIb), or a pharmaceutically acceptable salt or solvate thereof, $R^5$, $R^7$, $R^9$, and $R^{11}$ are H. In some embodiments of a compound of Formula (I), Formula (I'), Formula (Ia), Formula (Ib), Formula (II), Formula (IIa), or Formula (IIb), or a pharmaceutically acceptable salt or solvate thereof, $R^5$ is $C_{1-6}$alkyl, and $R^7$, $R^9$, and $R^{11}$ are H. In some embodiments of a compound of Formula (I), Formula (I'), Formula (Ia), Formula (Ib), Formula (II), Formula (IIa), or Formula (IIb), or a pharmaceutically acceptable salt or solvate thereof, $R^7$ is $C_{1-6}$alkyl, and $R^5$, $R^9$, and $R^{11}$ are H. In some embodiments of a compound of Formula (I), Formula (I'), Formula (Ia), Formula (Ib), Formula (II), Formula (IIa), or Formula (IIb), or a pharmaceutically acceptable salt or solvate thereof, $R^5$ and $R^9$ are H, and $R^7$ and $R^{11}$ combine to form a ring. In some embodiments of a compound of Formula (I), Formula (I'), Formula (Ia), Formula (Ib), Formula (II), Formula (IIa), or Formula (IIb), or a pharmaceutically acceptable salt or solvate thereof, $R^5$ and $R^{11}$ are H, and $R^7$ and $R^9$ combine to form a ring. In some embodiments of a compound of Formula (I), Formula (I'), Formula (Ia), Formula (Ib), Formula (II), Formula (IIa), or Formula (IIb), or a pharmaceutically acceptable salt or solvate thereof, $R^7$ and $R^{11}$ are H, and $R^5$ and $R^9$ combine to form a ring.

Any combination of the groups described above or below for the various variables is contemplated herein. Throughout the specification, groups and substituents thereof are chosen by one skilled in the field to provide stable moieties and compounds.

In another aspect is a pharmaceutical composition comprising a compound of Formula (I), Formula (I'), Formula (Ia), Formula (Ib), Formula (II), Formula (IIa), or Formula (IIb), or a pharmaceutically acceptable salt or solvate thereof, and at least one pharmaceutically acceptable excipient.

In another aspect is a method of treating a neurodegenerative disorder in a subject in need thereof, comprising administering to subject a therapeutically effective amount of a compound of Formula (I), Formula (I'), Formula (Ia), Formula (Ib), Formula (II), Formula (IIa), or Formula (IIb), or a pharmaceutically acceptable salt or solvate thereof.

In another aspect is a method of treating a demyelinating disease in a subject in need thereof, comprising administering to the subject a therapeutically effective amount of a compound of Formula (I), Formula (I'), Formula (Ia), Formula (Ib), Formula (II), Formula (IIa), or Formula (IIb), or a pharmaceutically acceptable salt or solvate thereof. In some embodiments is a method of treating a demyelinating disease in a subject in need thereof, comprising administering to the subject a therapeutically effective amount of a compound of Formula (I), Formula (I'), Formula (Ia), Formula (Ib), Formula (II), Formula (IIa), or Formula (IIb), or a pharmaceutically acceptable salt or solvate thereof, wherein the demyelinating disease is a demyelinating disease of the central nervous system. In some embodiments is a method of treating a demyelinating disease in a subject in need thereof, comprising administering to the subject a therapeutically effective amount of a compound of Formula (I), Formula (I'), Formula (Ia), Formula (Ib), Formula (II), Formula (IIa), or Formula (IIb), or a pharmaceutically acceptable salt or solvate thereof, wherein the demyelinating disease is multiple sclerosis. In some embodiments is a method of treating a demyelinating disease in a subject in need thereof, comprising administering to the subject a therapeutically effective amount of a compound of Formula (I), Formula (I'), Formula (Ia), Formula (Ib), Formula (II), Formula (IIa), or Formula (IIb), or a pharmaceutically acceptable salt or solvate thereof, wherein the demyelinating disease is a demyelinating disease of the peripheral nervous system.

In some embodiments of the methods described herein, the method further comprises the administration of one or more immunomodulatory agents. In some embodiments, the one or more immunomodulatory agents are selected from: an IFN-β 1 molecule; a corticosteroid; a polymer of glutamic acid, lysine, alanine and tyrosine or glatiramer; an antibody or fragment thereof against alpha-4 integrin or natalizumab; an anthracenedione molecule or mitoxantrone; a fingolimod or FTY720 or other SIP1 functional modulator; a dimethyl fumarate; an antibody to the alpha subunit of the IL-2 receptor of T cells (CD25) or daclizumab; an antibody against CD52 or alemtuzumab; an antibody against CD20; and an inhibitor of a dihydroorotate dehydrogenase or teriflunomide.

In another aspect is a method of modulating muscarinic acetylcholine receptor $M_1$ activity in a subject comprising administering to the subject a compound of Formula (I), Formula (I'), Formula (Ia), Formula (Ib), Formula (II), Formula (IIa), or Formula (IIb), or a pharmaceutically acceptable salt or solvate thereof.

DETAILED DESCRIPTION OF THE INVENTION

This disclosure is directed, at least in part, to compounds capable of inhibiting the muscarinic acetylcholine M1 receptor.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range varies between 1% and 15% of the stated number or numerical range. The term "comprising" (and related terms such as "comprise" or "comprises" or "having" or "including") is not intended to exclude that which in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

As used herein, $C_1$-$C_x$ includes $C_1$-$C_2$, $C_1$-$C_3$ ... $C_1$-$C_x$. $C_1$-$C_x$ refers to the number of carbon atoms that make up the moiety to which it designates (excluding optional substituents).

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Alkyl" or "alkylene" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to six carbon atoms (e.g., $C_1$-$C_6$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), and 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —$OC(O)R^a$, —$N(R^a)_2$, —$C(O)R^a$, —$C(O)OR^a$, —$C(O)N(R^a)_2$, —$N(R^a)C(O)OR^f$, —$OC(O)$—$NR^aR^f$, —$N(R^a)S(O)_tR^f$ (where t is 1 or 2), —$S(O)_tOR^a$ (where t is 1 or 2), —$S(O)_tR^f$ (where t is 1 or 2) and —$S(O)_tN(R^a)_2$ (where t is 1 or 2) where each $R^a$ is independently hydrogen, alkyl, fluoroalkyl, cycloalkyl, aryl, aralkyl, heterocycloalkyl, heteroaryl or heteroarylalkyl, and each $R^f$ is independently alkyl, fluoroalkyl, cycloalkyl, aryl, aralkyl, heterocycloalkyl, heteroaryl or heteroarylalkyl.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —$OC(O)$—$R^f$, —$N(R^a)_2$, —$C(O)R^a$, —$C(O)OR^a$, —$C(O)N(R^a)_2$, —$N(R^a)C(O)OR^f$, —$OC(O)$—$NR^aR^f$, —$N(R^a)C(O)R^f$, —$N(R^a)S(O)_tR^f$ (where t is 1 or 2), —$S(O)OR^a$ (where t is 1 or 2), —$S(O)_tR^f$ (where t is 1 or 2) and —$S(O)_tN(R^a)_2$ (where t is 1 or 2) where each $R^a$ is independently hydrogen, alkyl, fluoroalkyl, cycloalkyl, aryl, aralkyl, heterocycloalkyl, heteroaryl or heteroarylalkyl, and each $R^f$ is independently alkyl, fluoroalkyl, cycloalkyl, aryl, aralkyl, heterocycloalkyl, heteroaryl or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —$OR^a$, —$SR^a$, —$OC(O)R^a$, —$N(R^a)_2$, —$C(O)R^a$, —$C(O)OR^a$, —$C(O)N(R^a)_2$, —$N(R^a)C(O)OR^f$, —$OC(O)$—$NR^aR^f$, —$N(R^a)C(O)R^f$, —$N(R^a)S(O)_tR^f$ (where t is 1 or 2), —$S(O)_tOR^a$ (where t is 1 or 2), —$S(O)_tR^f$ (where t is 1 or 2) and —$S(O)_tN(R^a)_2$ (where t is 1 or 2) where each $R^a$ is independently hydrogen, alkyl, fluoroalkyl, cycloalkyl, aryl, aralkyl, heterocycloalkyl, heteroaryl or heteroarylalkyl, and each $R^f$ is independently alkyl, fluoroalkyl, cycloalkyl, aryl, aralkyl, heterocycloalkyl, heteroaryl or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, aryl, aralkyl, aralkenyl, aralkynyl, cycloalkyl, heterocycloalkyl, heteroaryl, heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)$ $R^a$, —$R^b$—$N(R^a)S(O)_tR^a$ (where t is 1 or 2), —$R^b$—$S(O)_tOR^a$ (where t is 1 or 2), —$R^b$—$S(O)_tR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl (optionally substituted with one or more halo groups), aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

"Aryloxy" refers to a radical bonded through an oxygen atom of the formula —O-aryl, where aryl is as defined above.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkyloxy" refers to a radical bonded through an oxygen atom of the formula —O— aralkyl, where aralkyl is as defined above.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Cycloalkyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a cycloalkyl comprises three to ten carbon atoms. In other embodiments, a cycloalkyl comprises five to seven carbon atoms. The cycloalkyl is attached to the rest of the molecule by a single bond. Cycloalkyls are saturated, (i.e., containing single C—C bonds only) or partially unsaturated (i.e., containing one or more double bonds or triple bonds.) Examples of monocyclic cycloalkyls include, e.g., cyclopropyl, cyclobutyl, cyclopentyl, cyclohexyl, cycloheptyl, and cyclooctyl. In certain embodiments, a cycloalkyl comprises three to eight carbon atoms (e.g., $C_3$-$C_8$ cycloalkyl). In other embodiments, a cycloalkyl comprises three to seven carbon atoms (e.g., $C_3$-$C_7$ cycloalkyl). In other embodiments, a cycloalkyl comprises three to six carbon atoms (e.g., $C_3$-$C_6$ cycloalkyl). In other embodiments, a cycloalkyl comprises three to five carbon atoms (e.g., $C_3$-$C_5$ cycloalkyl). In other embodiments, a cycloalkyl comprises three to four carbon atoms (e.g., $C_3$-$C_4$ cycloalkyl). A partially unsaturated cycloalkyl is also referred to as "cycloalkenyl." Examples of monocyclic cycloalkenyls include, e.g., cyclopentenyl, cyclohexenyl, cycloheptenyl, and cyclooctenyl. Polycyclic cycloalkyl radicals include, for example, adamantyl, norbornyl (i.e., bicyclo[2.2.1]heptanyl), norbornenyl, decalinyl, 7,7-dimethyl-bicyclo[2.2.1] heptanyl, and the like. Unless otherwise stated specifically in the specification, the term "cycloalkyl" is meant to include cycloalkyl radicals optionally substituted by one or more substituents independently selected from alkyl, alkenyl, alkynyl, halo, fluoroalkyl, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$OR^a$ (where t is 1 or 2), —$R^b$—S(O)$_t$$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl (optionally substituted with one or more halo groups), aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

"Halo" or "halogen" refers to bromo, chloro, fluoro or iodo substituents.

"Haloalkyl" refers to an alkyl radical, as defined above, that is substituted by one or more halo radicals, as defined above.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical are optionally substituted as defined above for an alkyl group.

"Haloalkoxy" refers to an alkoxy radical, as defined above, that is substituted by one or more halo radicals, as defined above.

"Heterocycloalkyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocycloalkyl radical is a monocyclic, bicyclic, tricyclic or tetracyclic ring system, which include fused, spiro, or bridged ring systems. The heteroatoms in the heterocycloalkyl radical are optionally oxidized. One or more nitrogen atoms, if present, are optionally quaternized. The heterocycloalkyl radical is partially or fully saturated. In some embodiments, the heterocycloalkyl is attached to the rest of the molecule through any atom of the ring(s). Examples of such heterocycloalkyl radicals include, but are not limited to, dioxolanyl, thienyl[1,3] dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocycloalkyl" is meant to include heterocycloalkyl radicals as defined above that are optionally substituted by one or more substituents selected from alkyl, alkenyl, alkynyl, halo, fluoroalkyl, oxo, thioxo, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N (R^a)$_2$, —$R^b$—C(O)$R^a$, —$R^b$—C(O)$OR^a$, —$R^b$—C(O)N (R^a)$_2$, —$R^b$—O—$R^c$—C(O)N($R^a$)$_2$, —$R^b$—N($R^a$)C(O) $OR^a$, —$R^b$—N($R^a$)C(O) $R^a$, —$R^b$—N($R^a$)S(O)$_t$$R^a$ (where t is 1 or 2), —$R^b$—S(O)$_t$$OR^a$ (where t is 1 or 2), —$R^b$—S (O)$_t$$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

"Heteroaryl" refers to a radical derived from a 5- to 18-membered aromatic ring radical that comprises one to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Unless stated otherwise specifically in the specification, the term "heteroaryl" is meant to include heteroaryl radicals as defined above that are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC (O)—$OR^a$, —$R^b$—OC(O)—N($R^a$)$_2$—$R^b$—N($R^a$)$_2$—$R^b$—C (O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C (O)$R^a$, —$R^b$—N($R^a$)S(O)$_t$$R^a$ (where t is 1 or 2), —$R^b$—S (O)$_t$$OR^a$ (where t is 1 or 2), —$R^b$—S(O)$_t$$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroaryloxy" refers to radical bonded through an oxygen atom of the formula —O— heteroaryl, where heteroaryl is as defined above.

"Heteroarylalkyl" refers to a radical of the formula —R$^c$-heteroaryl, where R$^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—R$^c$-heteroaryl, where R$^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

"Optional" or "optionally" means that a subsequently described event or circumstance may or may not occur and that the description includes instances when the event or circumstance occurs and instances in which it does not. For example, "optionally substituted aryl" means that the aryl radical are or are not substituted and that the description includes both substituted aryl radicals and aryl radicals having no substitution.

A "tautomer" refers to a molecule wherein a proton shift from one atom of a molecule to another atom of the same molecule is possible. In certain embodiments, the compounds presented herein exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

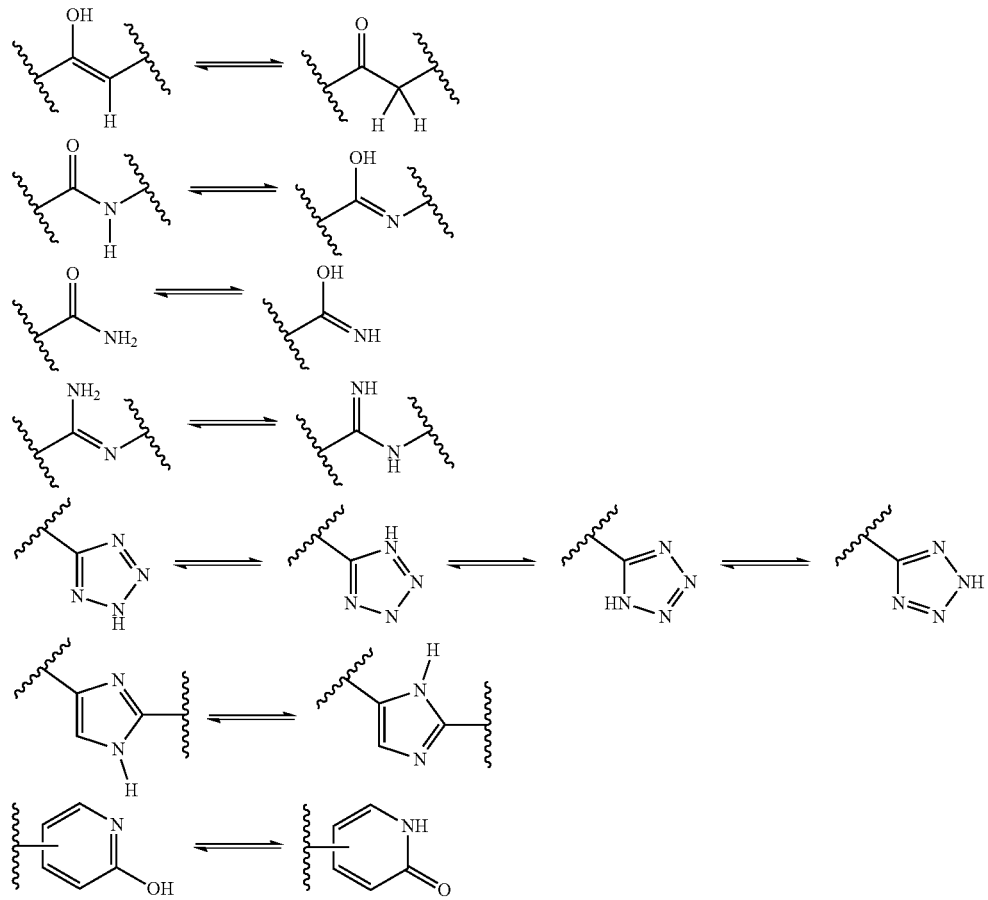

"Pharmaceutically acceptable salt" includes both acid and base addition salts. A pharmaceutically acceptable salt of any one of the pyrazole compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Prodrug" is meant to indicate a compound that is, in some embodiments, converted under physiological conditions or by solvolysis to a biologically active compound described herein. Thus, the term "prodrug" refers to a precursor of a biologically active compound that is pharmaceutically acceptable. A prodrug is typically inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987.

The term "prodrug" is also meant to include any covalently bonded carriers, which release the active compound in vivo when such prodrug is administered to a mammalian subject. Prodrugs of an active compound, as described herein, are prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

"Pharmaceutically acceptable solvate" refers to a composition of matter that is the solvent addition form. In some embodiments, solvates contain either stoichiometric or non-stoichiometric amounts of a solvent, and are formed during the process of making with pharmaceutically acceptable solvents such as water, ethanol, and the like. "Hydrates" are formed when the solvent is water, or alcoholates are formed when the solvent is alcohol. Solvates of compounds described herein are conveniently prepared or formed during the processes described herein. The compounds provided herein optionally exist in either unsolvated as well as solvated forms.

The terms "allosteric site" and "allosteric binding site" refer to a ligand binding site that is topographically distinct from the orthosteric binding site.

The term "ligand" refers to a natural or synthetic molecule that is capable of binding to or associating with a receptor to form a complex and mediate, prevent, or modify a biological effect. The term "ligand" is meant to encompass allosteric modulators, inhibitors, activators, agonists, antagonists, natural substrates, and analogs of natural substrates.

The terms "natural ligand" and "endogenous ligand" refer to a naturally occurring ligand which binds to a receptor.

The terms "orthosteric site" and "orthosteric binding site" refer to the primary binding site on a receptor that is recognized by an endogenous ligand or agonist for the receptor. For example, the orthosteric site on the muscarinic acetylcholine M1 receptor is the is the site that acetylcholine binds.

The term "mAChR $M_1$ receptor antagonist" refers to any exogenously administered compound or agent that is capable of partially or completely inhibiting, or reversing, the effect of an agonist (e.g. acetylcholine) on the mAChR $M_1$ receptor. The term is inclusive of compounds or agents characterized or described as antagonists, partial antagonists, and negative allosteric modulators. For example, mAChR $M_1$ receptor antagonists can mediate their effects by binding to the orthosteric site or to allosteric sites, or they may interact at unique binding sites not normally involved in the biological regulation of the receptor's activity. Thus, a mAChR $M_1$ receptor antagonist directly or indirectly inhibits the activity of the mAChR $M_1$ receptor in the presence or in the absence of acetylcholine, or another agonist, in an animal, in particular a mammal, for example a human. In various aspects, a mAChR $M_1$ receptor antagonist decreases the activity of the mAChR $M_1$ receptor in a cell in the presence of extracellular acetylcholine. In some embodiments, a compound that is a "mAChR $M_1$ receptor antagonist" includes a compound that is a "mAChR $M_1$ receptor competitive antagonist," a "mAChR $M_1$ receptor noncompetitive antagonist," a "mAChR M1 receptor partial antagonist," and a "mAChR $M_1$ receptor negative allosteric modulator."

The term "mAChR $M_1$ receptor competitive antagonist" refers to any exogenously administered compound or agent that is capable of binding to the orthosteric site of mAChR $M_1$ receptors without activating the receptor. Thus, a competitive antagonist can interact with a mAChR $M_1$ receptor and compete with the endogenous ligand, acetylcholine, for binding to the receptor and decrease the ability of the receptor to transduce an intracellular signal in response to endogenous ligand binding.

The term "mAChR $M_1$ receptor noncompetitive antagonist" refers to any exogenously administered compound or agent that binds to site that is not the orthosteric binding site of mAChR $M_1$ receptors, and is capable of partially or completely inhibiting, or reversing, the effect of an agonist (e.g. acetylcholine) on the mAChR $M_1$ receptor. Thus, a non-competitive antagonist can interact with a mAChR $M_1$ receptor and decrease the binding of the endogenous ligand, acetylcholine, to the receptor and/or decrease the ability of the receptor to transduce an intracellular signal in response to endogenous ligand binding.

The term "mAChR $M_1$ partial antagonist" refers to any exogenously administered compound or agent that can bind to an orthosteric or an allosteric site, but the effect of binding is to only partially block effect of mAChR $M_1$ receptor response to an agonist, e.g. acetylcholine. Thus, a non-competitive antagonist can interact with a mAChR $M_1$ receptor and but is not capable of fully inhibiting the response of the mAChR M1 receptor to an agonist, e.g. acetylcholine.

The term "mAChR $M_1$ negative allosteric modulator" refers to any exogenously administered compound or agent that binds an allosteric site that directly or indirectly inhibits the activity of the mAChR $M_1$ receptor in the presence of acetylcholine, or another agonist, in an animal, in particular a mammal, for example a human. For example, while not intended to be limiting towards the present invention, a selective muscarinic $M_1$ negative allosteric modulator can preferentially bind to the muscarinic $M_1$ receptor and decrease muscarinic $M_1$ signaling by acting as a non-competitive antagonist. In one aspect, a mAChR $M_1$ receptor negative allosteric modulator decreases the activity of the mAChR M1 receptor in a cell in the presence of extracellular acetylcholine.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the subject is a human.

As used herein, "treatment" or "treating" or "palliating" or "ameliorating" are used interchangeably herein. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are administered to a patient at risk of developing a particular disease, or to a patient reporting one or more of the physiological symptoms of a disease, even though a diagnosis of this disease has not been made.

As used herein, "$EC_{50}$" is intended to refer to the concentration of a substance (e.g., a compound or a drug) that is required for 50% activation or enhancement of a biological process, or component of a process, including a protein, subunit, organelle, ribonucleoprotein, etc. For example, $EC_{50}$ can refer to the concentration of agonist that provokes a response halfway between the baseline and maximum response in an in vitro assay. In some embodiments, in vitro assay systems utilize a cell line that either expresses endogenously a target of interest, or has been transfected with a suitable expression vector that directs expression of a recombinant form of the target.

As used herein, "$IC_{50}$" is intended to refer to the concentration of a substance (e.g., a compound or a drug) that is required for 50% inhibition of a biological process, or component of a process, including a protein, subunit, organelle, ribonucleoprotein, etc. For example, $IC_{50}$ refers to the half maximal (50%) inhibitory concentration (IC) of a substance as determined in a suitable assay. For example, an $IC_{50}$ for mAChR $M_1$ receptor can be determined in an in vitro assay system.

Compounds

This disclosure provides, compounds which are antagonists of the muscarinic acetylcholine $M_1$ receptor (mAChR $M_1$). These compounds, and compositions comprising these compounds, are useful for the treatment or prevention of neurological disorders. In some embodiments, the compounds described herein are useful for treating Parkinson's disease.

In some embodiments provided herein is a compound having the structure of Formula (I'):

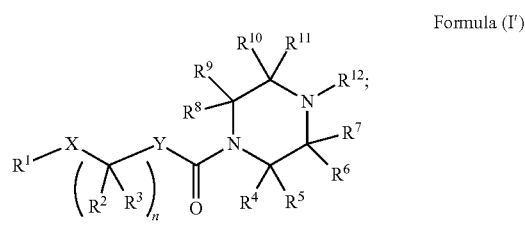

Formula (I')

wherein:

X is —$CH_2CH_2$—, —$CH_2O$—, —$CH_2CH_2O$—, —O—, —N($R^{14}$)—, $S(O)_2$, —$CH_2N(R^{14})$—, or —$CH_2CH_2N(R^{14})$—;

Y is a bond, —$C(R^{16})(R^{17})$—, or —$N(R^{15})$—;

Z is —N— or —C(H)—;

$R^1$ is

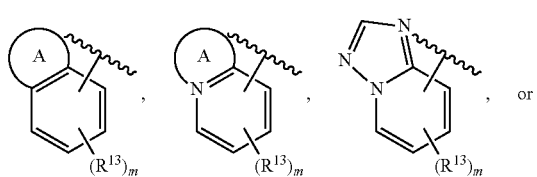

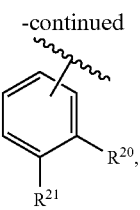

wherein ring A is a heteroaryl ring optionally substituted with halogen, —CN, —N($R^{22}$)$_2$, $C_{1-6}$ alkyl, $C_{1-6}$ alkyl-OH, $C_{1-6}$ alkoxy, $C_{1-6}$haloalkyl, or $C_{1-6}$haloalkoxy, wherein the heteroaryl ring contains 1 or 2 heteroatoms selected from the group consisting of O, N, or S;

each $R^2$ is independently selected from H, halogen, and $C_{1-6}$alkyl;

each $R^3$ is independently selected from H, halogen, and $C_{1-6}$alkyl;

$R^4$, $R^6$, $R^8$, and $R^{10}$ are each independently selected from H and $C_{1-6}$alkyl;

$R^5$, $R^7$, $R^9$, and $R^{11}$ are each independently selected from H and $C_{1-6}$alkyl; or $R^7$ and $R^{11}$ combine to form a ring or $R^5$ and $R^9$ combine to form a ring or $R^7$ and $R^9$ combine to form a ring;

$R^{12}$ is

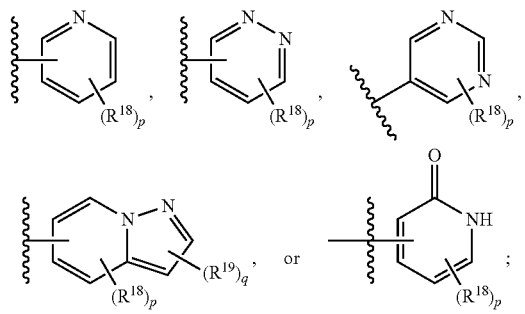

each $R^{13}$ is independently selected from halogen, —CN, $C_{1-6}$alkoxy, $C_{1-6}$haloalkyl, and $C_{1-6}$haloalkoxy;

$R^{14}$ is H, $C_{1-6}$alkyl, $C_{3-6}$cycloalkyl, or $C_{2-9}$heterocycloalkyl; or $R^{14}$ and one $R^3$ combine to form a 4-, 5-, or 6-membered heterocycloalkyl ring;

$R^{15}$ is H or $C_{1-6}$alkyl; or $R^{15}$ and one $R^3$ combine to form a 4-, 5-, or 6-membered heterocycloalkyl ring;

$R^{16}$ is H or $C_{1-6}$alkyl;

$R^{17}$ is H or $C_{1-6}$alkyl; or $R^{17}$ and one $R^3$ combine to form a 3-, 4-, 5-, or 6-membered cycloalkyl ring;

each $R^{18}$ and each $R^{19}$ are each independently selected from halogen, —CN, —N($R^{22}$)$_2$, $C_{1-6}$alkyl, $C_{3-6}$cycloalkyl, hydroxy, $C_{1-6}$alkoxy, $C_{1-6}$haloalkyl, $C_{1-6}$haloalkoxy, and phenyl;

$R^{20}$ and $R^{21}$ combine to form a 5- or 6-membered cycloalkyl ring or a 5-membered heterocycloalkyl ring;

each $R^{22}$ is independently selected from H and $C_{1-6}$alkyl;

m is 0, 1, 2, or 3;

n is 1, 2, 3, 4, or 5;

p is 0, 1, 2, or 3; and q is 0, 1, or 2;

or a pharmaceutically acceptable salt or solvate thereof.

In some embodiments of a compound of Formula (I'), or a pharmaceutically acceptable salt or solvate thereof, $R^1$ is

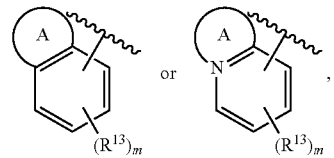

wherein ring A is a heteroaryl ring optionally substituted with halogen, —CN, —N($R^{22}$)$_2$, $C_{1-6}$alkyl, $C_{1-6}$alkyl-OH, $C_{1-6}$alkoxy, $C_{1-6}$haloalkyl, or $C_{1-6}$haloalkoxy, wherein the heteroaryl ring contains 1 or 2 heteroatoms selected from the group consisting of O, N, or S. In some embodiments, $R^1$ is

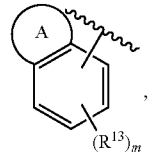

wherein ring A is a heteroaryl ring optionally substituted with halogen, —CN, —N($R^{22}$)$_2$, $C_{1-6}$alkyl, $C_{1-6}$alkyl-OH, $C_{1-6}$alkoxy, $C_{1-6}$haloalkyl, or $C_{1-6}$haloalkoxy, wherein the heteroaryl ring contains 1 or 2 heteroatoms selected from the group consisting of O, N, or S. In some embodiments, $R^1$ is

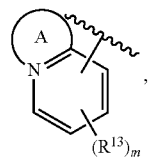

wherein ring A is a heteroaryl ring optionally substituted with halogen, —CN, —N($R^{22}$)$_2$, $C_{1-6}$alkyl, $C_{1-6}$alkyl-OH, $C_{1-6}$alkoxy, $C_{1-6}$haloalkyl, or $C_{1-6}$haloalkoxy, wherein the heteroaryl ring contains 1 or 2 heteroatoms selected from the group consisting of O, N, or S.

In some embodiments of a compound of Formula (I'), or a pharmaceutically acceptable salt or solvate thereof, ring A is a 5- or 6-membered heteroaryl ring optionally substituted with halogen, —CN, —N($R^{22}$)$_2$, $C_{1-6}$alkyl, $C_{1-6}$alkyl-OH, $C_{1-6}$alkoxy, $C_{1-6}$haloalkyl, or $C_{1-6}$haloalkoxy, wherein the heteroaryl ring contains 1 or 2 heteroatoms selected from the group consisting of O, N, or S. In some embodiments, ring A is a 5-membered heteroaryl ring optionally substituted with halogen, —CN, —N($R^{22}$)$_2$, $C_{1-6}$ alkyl, $C_{1-6}$ alkyl-OH, $C_{1-6}$ alkoxy, $C_{1-6}$haloalkyl, or $C_{1-6}$haloalkoxy, wherein the heteroaryl ring contains 1 or 2 heteroatoms selected from the group consisting of O, N, or S. In some embodiments, ring A is a 6-membered heteroaryl ring optionally substituted with halogen, —CN, —N($R^{22}$)$_2$, $C_{1-6}$ alkyl, $C_{1-6}$ alkyl-OH, $C_{1-6}$ alkoxy, $C_{1-6}$haloalkyl, or $C_{1-6}$haloalkoxy, wherein the heteroaryl ring contains 1 or 2 heteroatoms selected from the group consisting of O, N, or S. In some embodiments, ring A is a heteroaryl ring optionally substituted with halogen, —CN, —N($R^{22}$)$_2$, $C_{1-6}$ alkyl, $C_{1-6}$ alkyl-OH, $C_{1-6}$ alkoxy, $C_{1-6}$haloalkyl, or $C_{1-6}$haloalkoxy, wherein the heteroaryl ring is selected from the group consisting of pyrrolyl, pyrazolyl, imidazolyl, furanyl, thiophenyl, oxazolyl, isoxazolyl, thiazolyl, isothiazolyl, oxadiazolyl, thiadiazolyl, triazolyl, pyridinyl, pyridazinyl, pyrimidinyl, and pyrazinyl. In some embodiments, ring A is a heteroaryl ring optionally substituted with halogen, —CN, —N(R$^{22}$)$_2$, C$_{1-6}$ alkyl, C$_{1-6}$ alkyl-OH, C$_{1-6}$alkoxy, C$_{1-6}$haloalkyl, or C$_{1-6}$haloalkoxy, wherein the heteroaryl ring is selected from the group consisting of pyrrolyl, pyrazolyl, imidazolyl, furanyl, thiophenyl, oxazolyl, isoxazolyl, thiazolyl, and isothiazolyl. In some embodiments, ring A is a heteroaryl ring optionally substituted with halogen, —CN, —N(R$^{22}$)$_2$, C$_{1-6}$ alkyl, C$_{1-6}$ alkyl-OH, C$_{1-6}$ alkoxy, C$_{1-6}$haloalkyl, or C$_{1-6}$haloalkoxy, wherein the heteroaryl ring is selected from the group consisting of imidazolyl, oxazolyl, and thiazolyl. In some embodiments, ring A is an imidazolyl ring optionally substituted with halogen, —CN, —N(R$^{22}$)$_2$, C$_{1-6}$ alkyl, C$_{1-6}$ alkyl-OH, C$_{1-6}$ alkoxy, C$_{1-6}$haloalkyl, or C$_{1-6}$haloalkoxy. In some embodiments, ring A is a oxazolyl ring optionally substituted with halogen, —CN, —N(R$^{22}$)$_2$, C$_{1-6}$ alkyl, C$_{1-6}$ alkyl-OH, C$_{1-6}$ alkoxy, C$_{1-6}$haloalkyl, or C$_{1-6}$haloalkoxy. In some embodiments, ring A is a thiazolyl ring optionally substituted with halogen, —CN, —N(R$^{22}$)$_2$, C$_{1-6}$alkyl, C$_{1-6}$alkyl-OH, C$_{1-6}$alkoxy, C$_{1-6}$haloalkyl, or C$_{1-6}$haloalkoxy. In some embodiments, ring A is a heteroaryl ring optionally substituted with halogen, —CN, —N(R$^{22}$)$_2$, C$_{1-6}$alkyl, C$_{1-6}$alkyl-OH, C$_{1-6}$alkoxy, C$_{1-6}$haloalkyl, or C$_{1-6}$haloalkoxy, wherein the heteroaryl ring is selected from the group consisting of pyridinyl, pyridazinyl, pyrimidinyl, and pyrazinyl. In some embodiments, ring A is a heteroaryl ring optionally substituted with halogen, —CN, —N(R$^{22}$)$_2$, C$_{1-6}$alkyl, C$_{1-6}$alkyl-OH, C$_{1-6}$alkoxy, C$_{1-6}$haloalkyl, or C$_{1-6}$haloalkoxy, wherein the heteroaryl ring is selected from the group consisting of pyridinyl and pyrimidinyl. In some embodiments, ring A is a pyridyl ring optionally substituted with halogen, —CN, —N(R$^{22}$)$_2$, C$_{1-6}$ alkyl, C$_{1-6}$ alkyl-OH, C$_{1-6}$ alkoxy, C$_{1-6}$haloalkyl, or C$_{1-6}$haloalkoxy. In some embodiments, ring A is a pyrimidinyl ring optionally substituted with halogen, —CN, —N(R$^{22}$)$_2$, C$_{1-6}$ alkyl, C$_{1-6}$ alkyl-OH, C$_{1-6}$ alkoxy, C$_{1-6}$haloalkyl, or C$_{1-6}$haloalkoxy. In some embodiments, ring A is optionally substituted with —N(R$^{22}$)$_2$, C$_{1-6}$alkyl, C$_{1-6}$ alkyl-OH, or C$_{1-6}$alkoxy. In some embodiments, ring A is optionally substituted with —NH$_2$, methyl, —CH$_2$OH, or methoxy. In some embodiments, ring A is unsubstituted.

In some embodiments of a compound of Formula (I'), or a pharmaceutically acceptable salt or solvate thereof, R$^1$ is

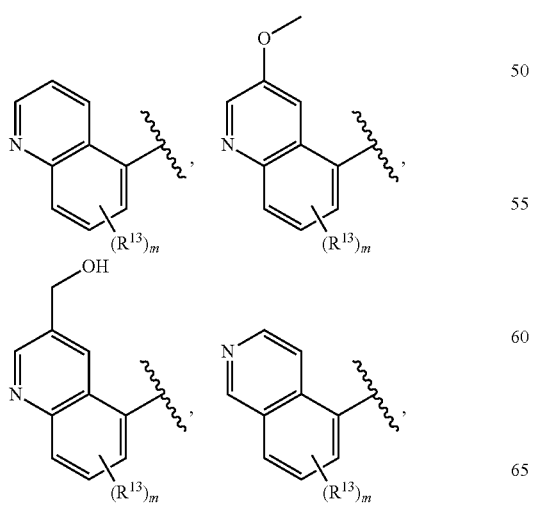

-continued

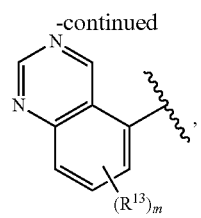

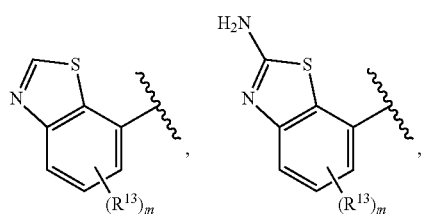

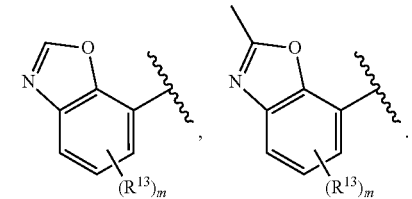

In some embodiments, R$^1$ is

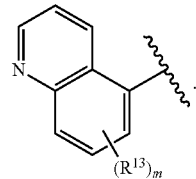

In some embodiments, R$^1$ is

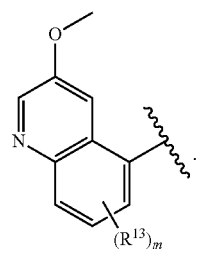

In some embodiments, R¹ is
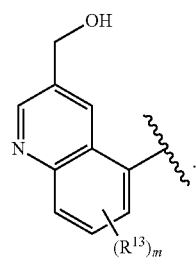
In some embodiments, R¹ is
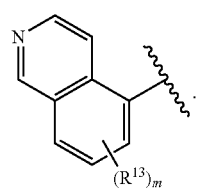
In some embodiments, R¹ is
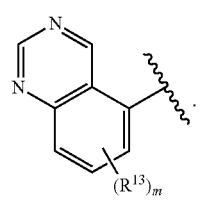
In some embodiments, R¹ is
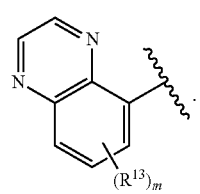
In some embodiments, R¹ is
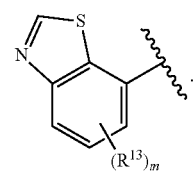
In some embodiments, R¹ is
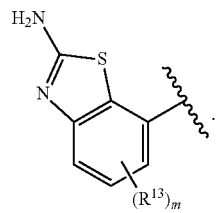
In some embodiments, R¹ is
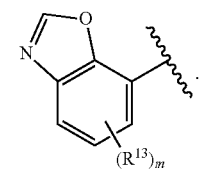
In some embodiments, R¹ is
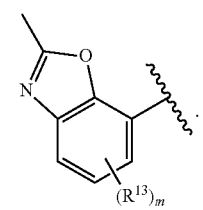
In some embodiments, R¹ is
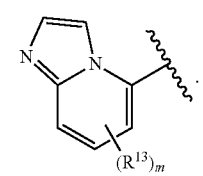
In some embodiments, R¹ is
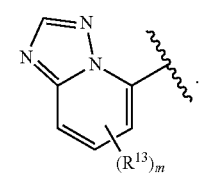
In some embodiments, R¹ is
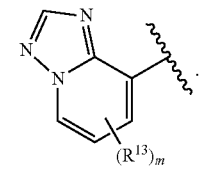

In some embodiments of a compound of Formula (I'), or a pharmaceutically acceptable salt or solvate thereof, each $R^{13}$ is independently selected from halogen, —CN, $C_{1-6}$alkoxy, $C_{1-6}$haloalkyl, and $C_{1-6}$haloalkoxy. In some embodiments, each $R^{13}$ is independently selected from halogen, —CN, $C_{1-6}$ alkyl, and $C_{1-6}$ alkoxy.

In some embodiments of a compound of Formula (I'), or a pharmaceutically acceptable salt or solvate thereof, m is 0, 1 or 2. In some embodiments, m is 0 to 1, 0 to 2, 0 to 3, 1 to 2, 1 to 3, or 2 to 3. In some embodiments, m is 0. In some embodiments, m is 1. In some embodiments, m is 2. In some embodiments, m is 3.

In some embodiments of a compound of Formula (I'), or a pharmaceutically acceptable salt or solvate thereof, $R^1$ is

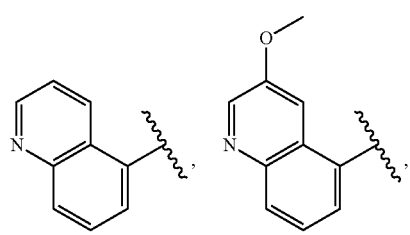

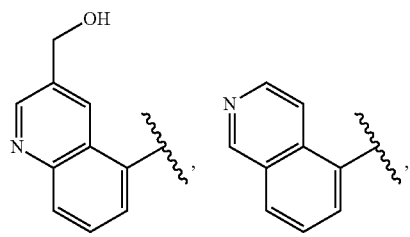

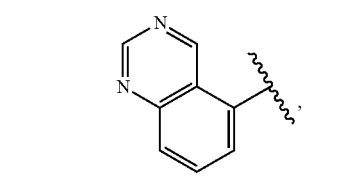

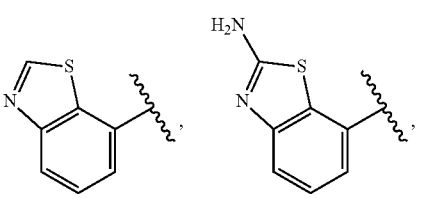

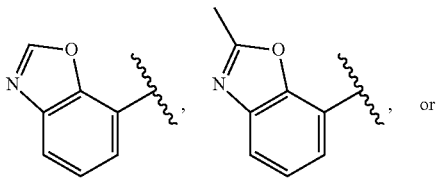, or

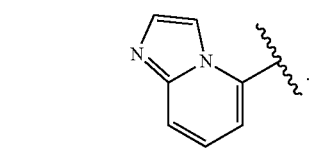

In some embodiments, $R^1$ is

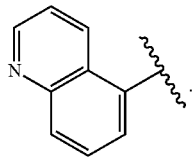 [SMILES: *c1cccc2ncccc12]

In some embodiments, $R^1$ is

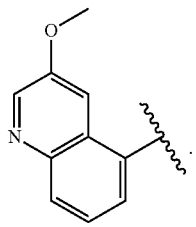 [SMILES: *c1cccc2ncc(OC)cc12]

In some embodiments, $R^1$ is

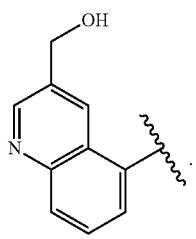 [SMILES: *c1cccc2ncc(CO)cc12]

In some embodiments, $R^1$ is

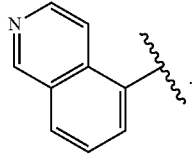

In some embodiments, $R^1$ is

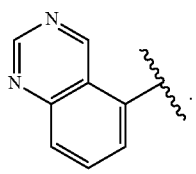 [SMILES: *c1cccc2ncncc12]

In some embodiments, $R^1$ is

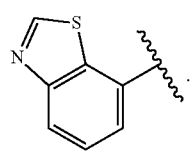

In some embodiments, $R^1$ is

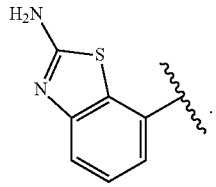 [SMILES: *c1cccc2nc(N)sc12]

In some embodiments, $R^1$ is

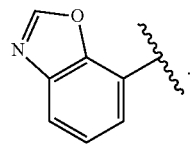 [SMILES: *c1cccc2ncoc12]

In some embodiments, $R^1$ is

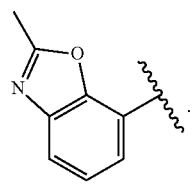 [SMILES: *c1cccc2nc(C)oc12]

In some embodiments, $R^1$ is

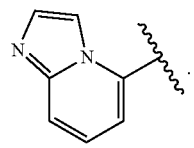

In some embodiments of a compound of Formula (I'), or a pharmaceutically acceptable salt or solvate thereof, $R^1$ is

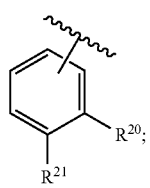

and $R^{20}$ and $R^{21}$ combine to form a 5- or 6-membered cycloalkyl ring or a 5-membered heterocycloalkyl ring. In some embodiments of a compound of Formula (I'), or a pharmaceutically acceptable salt or solvate thereof, $R^1$ is

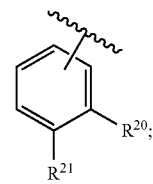

and $R^{20}$ and $R^{21}$ combine to form a 5-membered cycloalkyl ring. In some embodiments, $R^1$ is

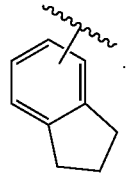

In some embodiments of a compound of Formula (I'), or a pharmaceutically acceptable salt or solvate thereof, $R^1$ is

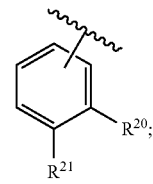

and $R^{20}$ and $R^{21}$ combine to form a 6-membered cycloalkyl ring. In some embodiments, $R^1$ is

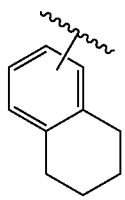

In some embodiments of a compound of Formula (I'), or a pharmaceutically acceptable salt or solvate thereof, $R^1$ is

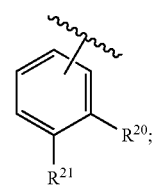

and $R^{20}$ and $R^{21}$ combine to form a 5-membered heterocycloalkyl ring. In some embodiments, $R^1$ is

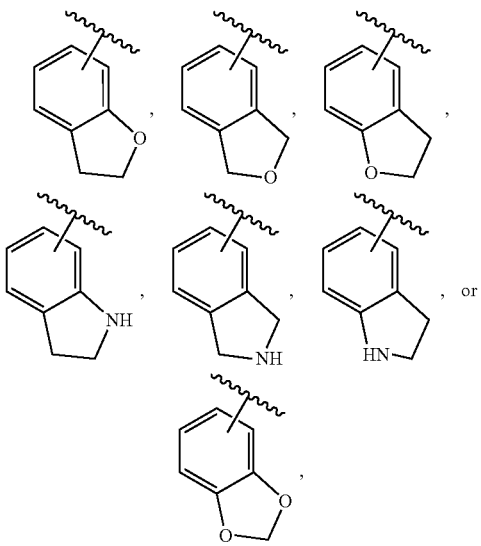

In some embodiments of a compound of Formula (I'), or a pharmaceutically acceptable salt or solvate thereof, Z is —N—. In some embodiments of a compound of Formula (I'), or a pharmaceutically acceptable salt or solvate thereof, Z is —C(H)—.

In some embodiments provided herein is a compound having the structure of Formula (I):

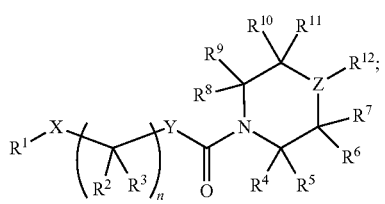

Formula (I)

wherein:
X is —CH$_2$CH$_2$—, —CH$_2$O—, —CH$_2$CH$_2$O—, —O—, —N(R$^{14}$)—, S(O)$_2$, —CH$_2$N(R$^{14}$)—, or —CH$_2$CH$_2$N(R$^{14}$)—;
Y is a bond, —C(R$^{16}$)(R$^{17}$)—, or —N(R$^{15}$)—;
Z is —N— or —C(H)—;
R$^1$ is

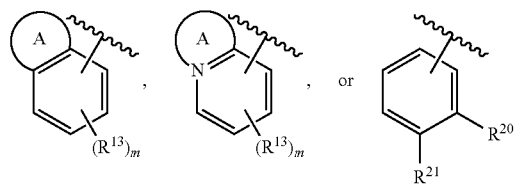

wherein ring A is a heteroaryl ring optionally substituted with halogen, —CN, —N(R$^{22}$)$_2$, C$_{1-6}$ alkyl, C$_{1-6}$ alkyl-OH, C$_{1-6}$ alkoxy, C$_{1-6}$haloalkyl, or C$_{1-6}$haloalkoxy, wherein the heteroaryl ring contains 1 or 2 heteroatoms selected from the group consisting of O, N, or S;
each R$^2$ is independently selected from H and C$_{1-6}$alkyl;
each R$^3$ is independently selected from H and C$_{1-6}$alkyl;
R$^4$, R$^6$, R$^8$, and R$^{10}$ are each independently selected from H and C$_{1-6}$alkyl;

R$^5$, R$^7$, R$^9$, and R$^{11}$ are each independently selected from H and C$_{1-6}$alkyl; or R$^7$ and R$^{11}$ combine to form a ring or R$^5$ and R$^9$ combine to form a ring or R$^7$ and R$^9$ combine to form a ring;
R$^{12}$ is

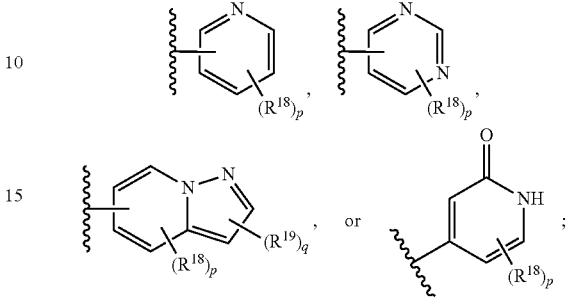

each R$^{13}$ is independently selected from halogen, —CN, C$_{1-6}$alkyl, C$_{1-6}$alkoxy, C$_{1-6}$haloalkyl, and C$_{1-6}$haloalkoxy;
R$^{14}$ is H or C$_{1-6}$alkyl; or R$^{14}$ and one R$^3$ combine to form a 4-, 5-, or 6-membered heterocycloalkyl ring;
R$^{15}$ is H or C$_{1-6}$alkyl; or R$^{15}$ and one R$^3$ combine to form a 4-, 5-, or 6-membered heterocycloalkyl ring;
R$^{16}$ is H or C$_{1-6}$alkyl;
R$^{17}$ is H or C$_{1-6}$alkyl; or R$^{17}$ and one R$^3$ combine to form a 3-, 4-, 5-, or 6-membered cycloalkyl ring;
each R$^{18}$ and each R$^{19}$ are each independently selected from halogen, —CN, C$_{1-6}$alkyl, hydroxy, C$_{1-6}$alkoxy, C$_{1-6}$haloalkyl, and C$_{1-6}$haloalkoxy;
R$^{20}$ and R$^{21}$ combine to form a 5- or 6-membered cycloalkyl ring or a 5-membered heterocycloalkyl ring;
each R$^{22}$ is independently selected from H and C$_{1-6}$alkyl;
m is 0, 1, 2, or 3;
n is 1, 2, 3, 4, or 5;
p is 0, 1, 2, or 3; and
q is 0, 1, or 2;
or a pharmaceutically acceptable salt or solvate thereof.

In some embodiments of a compound of Formula (I), or a pharmaceutically acceptable salt or solvate thereof, R$^1$ is

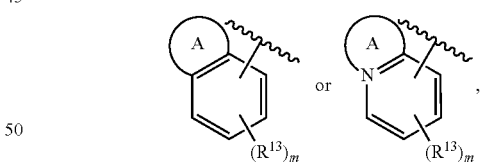

wherein ring A is a heteroaryl ring optionally substituted with halogen, —CN, —N(R$^{22}$)$_2$, C$_{1-6}$ alkyl, C$_{1-6}$ alkyl-OH, C$_{1-6}$ alkoxy, C$_{1-6}$haloalkyl, or C$_{1-6}$haloalkoxy, wherein the heteroaryl ring contains 1 or 2 heteroatoms selected from the group consisting of O, N, or S. In some embodiments, R$^1$ is

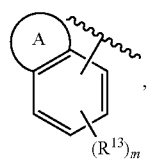

wherein ring A is a heteroaryl ring optionally substituted with halogen, —CN, —N(R$^{22}$)$_2$, C$_{1-6}$alkyl, C$_{1-6}$alkyl-OH, C$_{1-6}$alkoxy, C$_{1-6}$haloalkyl, or C$_{1-6}$haloalkoxy, wherein the heteroaryl ring contains 1 or 2 heteroatoms selected from the group consisting of O, N, or S. In some embodiments, R$^1$ is

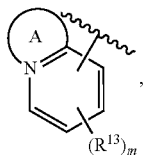

wherein ring A is a heteroaryl ring optionally substituted with halogen, —CN, —N(R$^{22}$)$_2$, C$_{1-6}$alkyl, C$_{1-6}$alkyl-OH, C$_{1-6}$alkoxy, C$_{1-6}$haloalkyl, or C$_{1-6}$haloalkoxy, wherein the heteroaryl ring contains 1 or 2 heteroatoms selected from the group consisting of O, N, or S.

In some embodiments of a compound of Formula (I), or a pharmaceutically acceptable salt or solvate thereof, ring A is a 5- or 6-membered heteroaryl ring optionally substituted with halogen, —CN, —N(R$^{22}$)$_2$, C$_{1-6}$alkyl, C$_{1-6}$alkyl-OH, C$_{1-6}$alkoxy, C$_{1-6}$haloalkyl, or C$_{1-6}$haloalkoxy, wherein the heteroaryl ring contains 1 or 2 heteroatoms selected from the group consisting of O, N, or S. In some embodiments, ring A is a 5-membered heteroaryl ring optionally substituted with halogen, —CN, —N(R$^{22}$)$_2$, C$_{1-6}$alkyl, C$_{1-6}$alkyl-OH, C$_{1-6}$alkoxy, C$_{1-6}$haloalkyl, or C$_{1-6}$ haloalkoxy, wherein the heteroaryl ring contains 1 or 2 heteroatoms selected from the group consisting of O, N, or S. In some embodiments, ring A is a 6-membered heteroaryl ring optionally substituted with halogen, —CN, —N(R$^{22}$)$_2$, C$_{1-6}$alkyl, C$_{1-6}$alkyl-OH, C$_{1-6}$alkoxy, C$_{1-6}$ haloalkyl, or C$_{1-6}$haloalkoxy, wherein the heteroaryl ring contains 1 or 2 heteroatoms selected from the group consisting of O, N, or S. In some embodiments, ring A is a heteroaryl ring optionally substituted with halogen, —CN, —N(R$^{22}$)$_2$, C$_{1-6}$alkyl, C$_{1-6}$alkyl-OH, C$_{1-6}$alkoxy, C$_{1-6}$ haloalkyl, or C$_{1-6}$haloalkoxy, wherein the heteroaryl ring is selected from the group consisting of pyrrolyl, pyrazolyl, imidazolyl, furanyl, thiophenyl, oxazolyl, isoxazolyl, thiazolyl, isothiazolyl, pyridinyl, pyridazinyl, pyrimidinyl, and pyrazinyl. In some embodiments, ring A is a heteroaryl ring optionally substituted with halogen, —CN, —N(R$^{22}$)$_2$, C$_{1-6}$alkyl, C$_{1-6}$alkyl-OH, C$_{1-6}$alkoxy, C$_{1-6}$ haloalkyl, or C$_{1-6}$haloalkoxy, wherein the heteroaryl ring is selected from the group consisting of pyrrolyl, pyrazolyl, imidazolyl, furanyl, thiophenyl, oxazolyl, isoxazolyl, thiazolyl, and isothiazolyl. In some embodiments, ring A is a heteroaryl ring optionally substituted with halogen, —CN, —N(R$^{22}$)$_2$, C$_{1-6}$alkyl, C$_{1-6}$alkyl-OH, C$_{1-6}$alkoxy, C$_{1-6}$haloalkyl, or C$_{1-6}$haloalkoxy, wherein the heteroaryl ring is selected from the group consisting of imidazolyl, oxazolyl, and thiazolyl. In some embodiments, ring A is an imidazolyl ring optionally substituted with halogen, —CN, —N(R$^{22}$)$_2$, C$_{1-6}$alkyl, C$_{1-6}$alkyl-OH, C$_{1-6}$alkoxy, C$_{1-6}$haloalkyl, or C$_{1-6}$haloalkoxy. In some embodiments, ring A is a oxazolyl ring optionally substituted with halogen, —CN, —N(R$^{22}$)$_2$, C$_{1-6}$ alkyl, C$_{1-6}$alkyl-OH, C$_{1-6}$alkoxy, C$_{1-6}$haloalkyl, or C$_{1-6}$haloalkoxy. In some embodiments, ring A is a thiazolyl ring optionally substituted with halogen, —CN, —N(R$^{22}$)$_2$, C$_{1-6}$alkyl, C$_{1-6}$alkyl-OH, C$_{1-6}$alkoxy, C$_{1-6}$haloalkyl, or C$_{1-6}$haloalkoxy. In some embodiments, ring A is a heteroaryl ring optionally substituted with halogen, —CN, —N(R$^{22}$)$_2$, C$_{1-6}$ alkyl, C$_{1-6}$ alkyl-OH, C$_{1-6}$ alkoxy, C$_{1-6}$haloalkyl, or C$_{1-6}$haloalkoxy, wherein the heteroaryl ring is selected from the group consisting of pyridinyl, pyridazinyl, pyrimidinyl, and pyrazinyl. In some embodiments, ring A is a heteroaryl ring optionally substituted with halogen, —CN, —N(R$^{22}$)$_2$, C$_{1-6}$ alkyl, C$_{1-6}$ alkyl-OH, C$_{1-6}$ alkoxy, C$_{1-6}$haloalkyl, or C$_{1-6}$haloalkoxy, wherein the heteroaryl ring is selected from the group consisting of pyridinyl and pyrimidinyl. In some embodiments, ring A is a pyridyl ring optionally substituted with halogen, —CN, —N(R$^{22}$)$_2$, C$_{1-6}$ alkyl, C$_{1-6}$ alkyl-OH, C$_{1-6}$ alkoxy, C$_{1-6}$haloalkyl, or C$_{1-6}$haloalkoxy. In some embodiments, ring A is a pyrimidinyl ring optionally substituted with halogen, —CN, —N(R$^{22}$)$_2$, C$_{1-6}$ alkyl, C$_{1-6}$ alkyl-OH, C$_{1-6}$ alkoxy, C$_{1-6}$haloalkyl, or C$_{1-6}$haloalkoxy. In some embodiments, ring A is optionally substituted with —N(R$^{22}$)$_2$, C$_{1-6}$alkyl, C$_{1-6}$alkyl-OH, or C$_{1-6}$alkoxy. In some embodiments, ring A is optionally substituted with —NH$_2$, methyl, —CH$_2$OH, or methoxy. In some embodiments, ring A is unsubstituted.

In some embodiments of a compound of Formula (I), or a pharmaceutically acceptable salt or solvate thereof, R$^1$ is

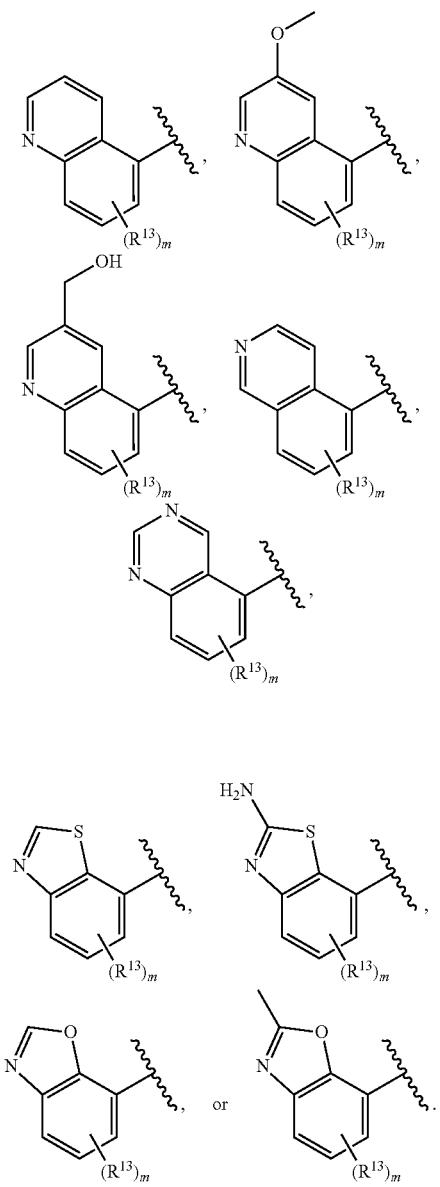

In some embodiments, R¹ is

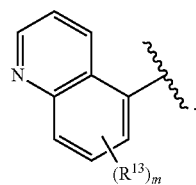

In some embodiments, R¹ is

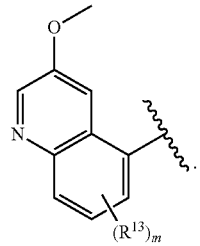

In some embodiments, R¹ is

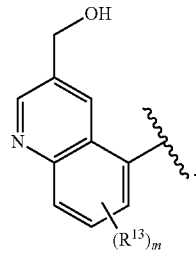

In some embodiments, R¹ is

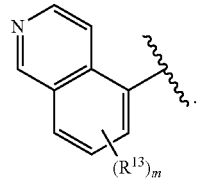

In some embodiments, R¹ is

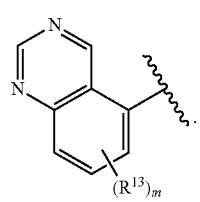

In some embodiments, R¹ is

In some embodiments, R¹ is

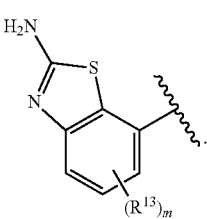

In some embodiments, R¹ is

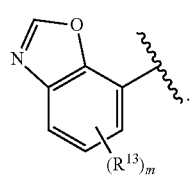

In some embodiments, R¹ is

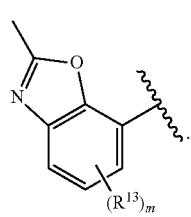

In some embodiments, R¹ is

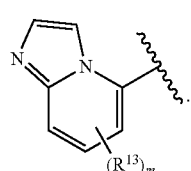
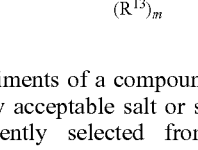

In some embodiments of a compound of Formula (I), or a pharmaceutically acceptable salt or solvate thereof, each $R^{13}$ is independently selected from halogen, —CN, $C_{1-6}$alkoxy, $C_{1-6}$haloalkyl, and $C_{1-6}$haloalkoxy. In some embodiments, each $R^{13}$ is independently selected from halogen, —CN, $C_{1-6}$ alkyl, and $C_{1-6}$ alkoxy.

In some embodiments of a compound of Formula (I), or a pharmaceutically acceptable salt or solvate thereof, m is 0, 1, 2, or 3. In some embodiments, m is 0 to 1, 0 to 2, 0 to 3, 1 to 2, 1 to 3, or 2 to 3. In some embodiments, m is 0. In some embodiments, m is 1. In some embodiments, m is 2. In some embodiments, m is 3.
In some embodiments of a compound of Formula (I), or a pharmaceutically acceptable salt or solvate thereof, $R^1$ is
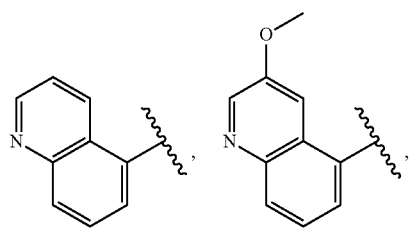
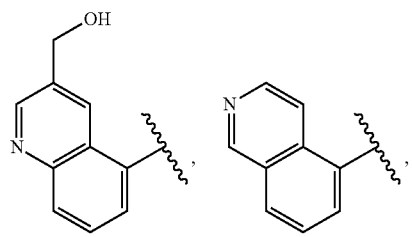
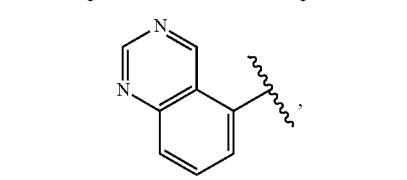
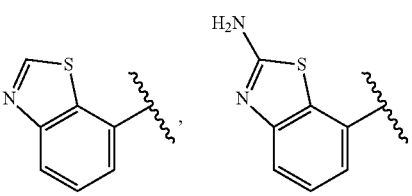
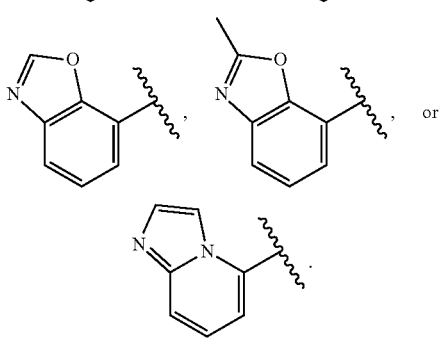
In some embodiments, $R^1$ is
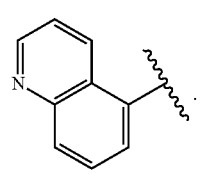
In some embodiments, $R^1$ is
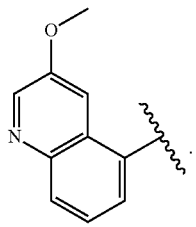 [SMILES: *c1cccc2ncc(OC)cc12]
In some embodiments, $R^1$ is
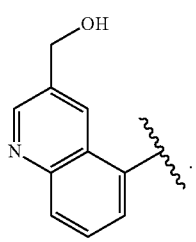 [SMILES: *c1cccc2ncc(CO)cc12]
In some embodiments, $R^1$ is
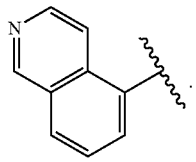
In some embodiments, $R^1$ is
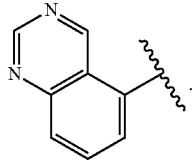
In some embodiments, $R^1$ is
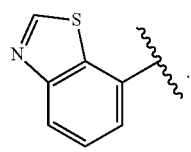

In some embodiments, $R^1$ is

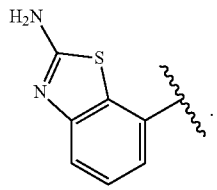

In some embodiments, $R^1$ is

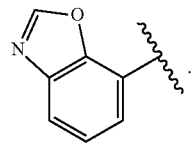

In some embodiments, $R^1$ is

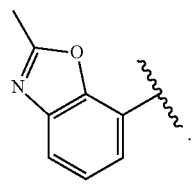

In some embodiments, $R^1$ is

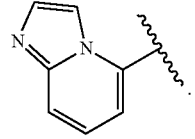

In some embodiments of a compound of Formula (I), or a pharmaceutically acceptable salt or solvate thereof, $R^1$ is

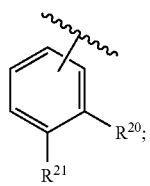

and $R^{20}$ and $R^{21}$ combine to form a 5- or 6-membered cycloalkyl ring or a 5-membered heterocycloalkyl ring. In some embodiments of a compound of Formula (I), or a pharmaceutically acceptable salt or solvate thereof, $R^1$ is

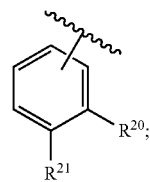

and $R^{20}$ and $R^{21}$ combine to form a 5-membered cycloalkyl ring. In some embodiments, $R^1$ is

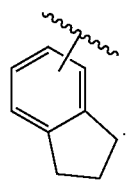

In some embodiments of a compound of Formula (I), or a pharmaceutically acceptable salt or solvate thereof, $R^1$ is

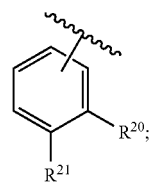

and $R^{20}$ and $R^{21}$ combine to form a 6-membered cycloalkyl ring. In some embodiments, $R^1$ is

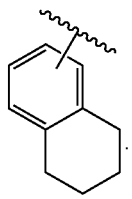

In some embodiments of a compound of Formula (I), or a pharmaceutically acceptable salt or solvate thereof, $R^1$ is

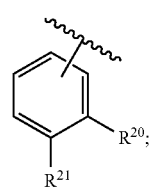

and $R^{20}$ and $R^{21}$ combine to form a 5-membered heterocycloalkyl ring. In some embodiments, $R^1$ is

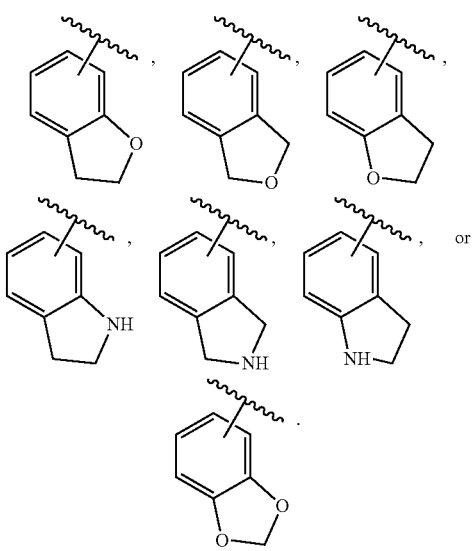

In some embodiments of a compound of Formula (I), or a pharmaceutically acceptable salt or solvate thereof, Z is —N—. In some embodiments of a compound of Formula (I), or a pharmaceutically acceptable salt or solvate thereof, Z is —C(H)—.

In some embodiments is a compound of Formula (I), or a pharmaceutically acceptable salt or solvate thereof, having the structure of Formula (Ia), or a pharmaceutically acceptable salt or solvate thereof:

Formula (Ia)

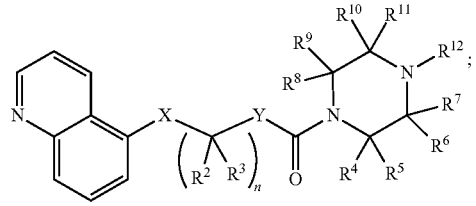

X is —CH$_2$CH$_2$—, —CH$_2$O—, —CH$_2$CH$_2$O—, —O—, —N(R$^{14}$)—, S(O)$_2$, —CH$_2$N(R$^{14}$)—, or —CH$_2$CH$_2$N(R$^{14}$)—;

Y is a bond, —C(R$^{16}$)(R$^{17}$)—, or —N(R$^{15}$)—;

each R$^2$ is independently selected from H and C$_{1-6}$alkyl;

each R$^3$ is independently selected from H and C$_{1-6}$alkyl;

R$^4$, R$^6$, R$^8$, and R$^{10}$ are each independently selected from H and C$_{1-6}$alkyl;

R$^5$, R$^7$, R$^9$, and R$^{11}$ are each independently selected from H and C$_{1-6}$alkyl; or R$^7$ and R$^{11}$ combine to form a ring or R$^5$ and R$^9$ combine to form a ring or R$^7$ and R$^9$ combine to form a ring;

R$^{12}$ is

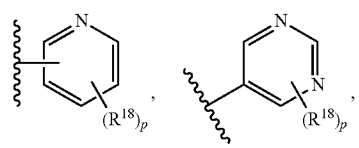

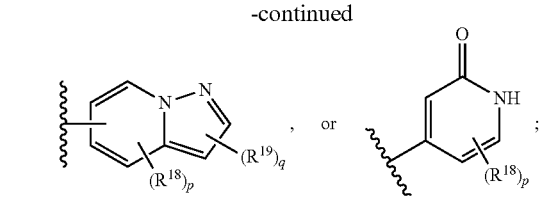

R$^{14}$ is H or C$_{1-6}$alkyl; or R$^{14}$ and one R$^3$ combine to form a 4-, 5-, or 6-membered heterocycloalkyl ring;

R$^{15}$ is H or C$_{1-6}$alkyl; or R$^{15}$ and one R$^3$ combine to form a 4-, 5-, or 6-membered heterocycloalkyl ring;

R$^{16}$ is H or C$_{1-6}$alkyl;

R$^{17}$ is H or C$_{1-6}$alkyl; or R$^{17}$ and one R$^3$ combine to form a 3-, 4-, 5-, or 6-membered cycloalkyl ring;

each R$^{18}$ and each R$^{19}$ are each independently selected from halogen, —CN, C$_{1-6}$alkyl, hydroxy, C$_{1-6}$alkoxy, C$_{1-6}$haloalkyl, and C$_{1-6}$haloalkoxy;

n is 1, 2, 3, 4, or 5;

p is 0, 1, 2, or 3; and q is 0, 1, or 2.

In some embodiments is a compound of Formula (I), or a pharmaceutically acceptable salt or solvate thereof, having the structure of Formula (Ib), or a pharmaceutically acceptable salt or solvate thereof:

Formula (Ib)

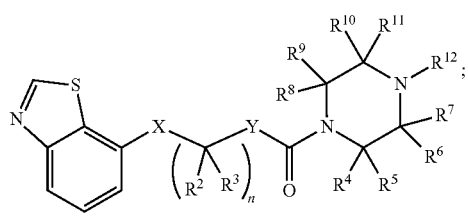

X is —CH$_2$CH$_2$—, —CH$_2$O—, —CH$_2$CH$_2$O—, —O—, —N(R$^{14}$)—, S(O)$_2$, —CH$_2$N(R$^{14}$)—, or —CH$_2$CH$_2$N(R$^{14}$)—;

Y is a bond, —C(R$^{16}$)(R$^{17}$)—, or —N(R$^{15}$)—;

each R$^2$ is independently selected from H and C$_{1-6}$alkyl;

each R$^3$ is independently selected from H and C$_{1-6}$alkyl;

R$^4$, R$^6$, R$^8$, and R$^{10}$ are each independently selected from H and C$_{1-6}$alkyl;

R$^5$, R$^7$, R$^9$, and R$^{11}$ are each independently selected from H and C$_{1-6}$alkyl; or R$^7$ and R$^{11}$ combine to form a ring or R$^5$ and R$^9$ combine to form a ring or R$^7$ and R$^9$ combine to form a ring;

R$^{12}$ is

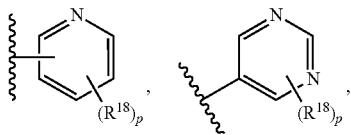

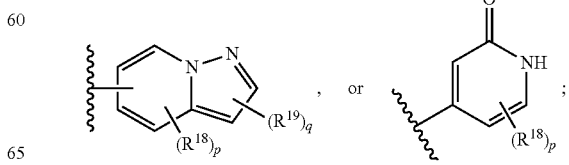

$R^{14}$ is H or $C_{1-6}$alkyl; or $R^{14}$ and one $R^3$ combine to form a 4-, 5-, or 6-membered heterocycloalkyl ring;

$R^{15}$ is H or $C_{1-6}$alkyl; or $R^{15}$ and one $R^3$ combine to form a 4-, 5-, or 6-membered heterocycloalkyl ring;

$R^{16}$ is H or $C_{1-6}$alkyl;

$R^{17}$ is H or $C_{1-6}$alkyl; or $R^{17}$ and one $R^3$ combine to form a 3-, 4-, 5-, or 6-membered cycloalkyl ring;

each $R^{18}$ and each $R^{19}$ are each independently selected from halogen, —CN, $C_{1-6}$alkyl, hydroxy, $C_{1-6}$alkoxy, $C_{1-6}$haloalkyl, and $C_{1-6}$haloalkoxy;

n is 1, 2, 3, 4, or 5;

p is 0, 1, 2, or 3; and q is 0, 1, or 2.

In some embodiments of a compound of Formula (I), Formula (I'), Formula (Ia), or Formula (Ib), or a pharmaceutically acceptable salt or solvate thereof, $R^{12}$ is

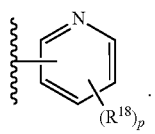

In some embodiments, $R^{12}$ is

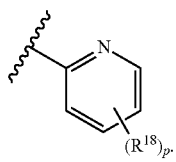

In some embodiments, $R^{12}$ is

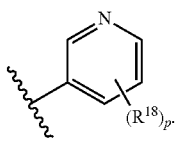

In some embodiments, $R^{12}$ is

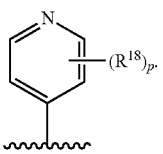

In some embodiments, $R^{12}$ is

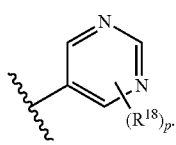

In some embodiments, $R^{12}$ is

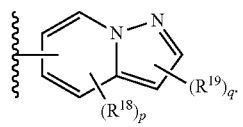

In some embodiments, $R^{12}$ is

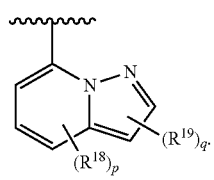

In some embodiments, $R^{12}$ is

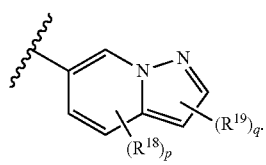

In some embodiments, $R^{12}$ is

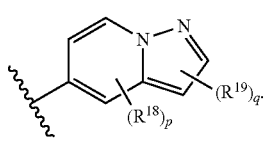

In some embodiments, $R^{12}$ is

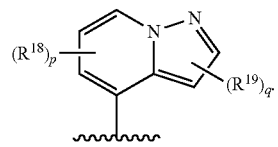

In some embodiments, $R^{12}$ is

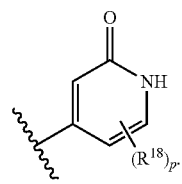

In some embodiments of a compound of Formula (I'), or a pharmaceutically acceptable salt or solvate thereof, $R^{12}$ is

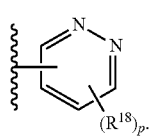

In some embodiments of a compound of Formula (I), Formula (I'), Formula (Ia), or Formula (Ib), or a pharmaceutically acceptable salt or solvate thereof, $R^{18}$ is selected from halogen, —CN, $C_{1-6}$alkyl, $C_{1-6}$alkoxy, and $C_{1-6}$haloalkyl. In some embodiments of a compound of Formula (I), Formula (I'), Formula (Ia), or Formula (Ib), or a pharmaceutically acceptable salt or solvate thereof, $R^{18}$ is selected from halogen, —CN, $C_{1-6}$alkyl, and $C_{1-6}$haloalkyl. In some embodiments, $R^{18}$ is selected from —F, —Cl, —Br, —CN, $C_{1-4}$alkyl, $C_{1-4}$alkoxy, and $C_{1-4}$haloalkyl. In some embodiments, $R^{18}$ is selected from —F, —Cl, —CN, methyl, methoxy, and trifluoromethyl.

In some embodiments of a compound of Formula (I), Formula (I'), Formula (Ia), or Formula (Ib), or a pharmaceutically acceptable salt or solvate thereof, p is 0, 1, 2, or 3. In some embodiments, p is 0 to 1, 0 to 2, 0 to 3, 1 to 2, 1 to 3, or 2 to 3. In some embodiments, p is 0. In some embodiments, p is 1. In some embodiments, p is 2. In some embodiments, p is 3.

In some embodiments of a compound of Formula (I), Formula (I'), Formula (Ia), or Formula (Ib), or a pharmaceutically acceptable salt or solvate thereof, $R^{19}$ is selected from halogen, —CN, $C_{1-6}$alkyl, $C_{1-6}$alkoxy, and $C_{1-6}$haloalkyl. In some embodiments, $R^{19}$ is selected from —F, —Cl, —Br, —CN, $C_{1-4}$alkyl, $C_{1-4}$alkoxy, and $C_{1-4}$haloalkyl. In some embodiments, $R^{19}$ is selected from —F, —CN, methyl, methoxy, and trifluoromethyl.

In some embodiments of a compound of Formula (I), Formula (I'), Formula (Ia), or Formula (Ib), or a pharmaceutically acceptable salt or solvate thereof, q is 0, 1, or 2. In some embodiments, q is 0 to 1, 0 to 2, or 1 to 2. In some embodiments, q is 0. In some embodiments, q is 1. In some embodiments, q is 2.

In some embodiments of a compound of Formula (I), Formula (I'), Formula (Ia), or Formula (Ib), or a pharmaceutically acceptable salt or solvate thereof, $R^{12}$ is

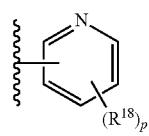

and p is 0. In some embodiments, $R^{12}$ is

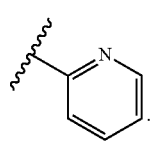

In some embodiments, $R^{12}$ is

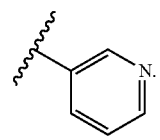 [SMILES: *c1cccnc1]

In some embodiments, $R^{12}$ is

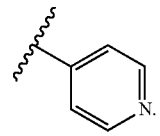 [SMILES: *c1ccncc1]

In some embodiments, $R^{12}$ is

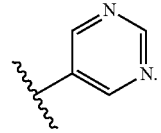

In some embodiments, $R^{12}$ is

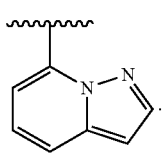 [SMILES: *c1cccc2ccnn12]

In some embodiments, $R^{12}$ is

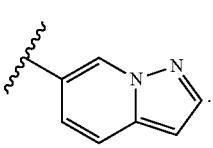 [SMILES: *c1ccc2ccnn2c1]

In some embodiments, $R^{12}$ is

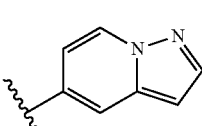

In some embodiments, $R^{12}$ is

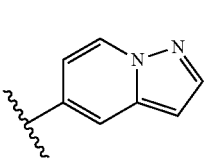

In some embodiments, $R^{12}$ is

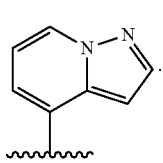

In some embodiments, $R^{12}$ is

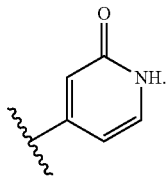 [SMILES: *c1cc[nH]c(=O)c1]

In some embodiments of a compound of Formula (I), Formula (I'), Formula (Ia), or Formula (Ib), or a pharmaceutically acceptable salt or solvate thereof, $R^{12}$ is

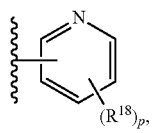

p is 1, and $R^{18}$ is selected from halogen, —CN, $C_{1-6}$alkyl, $C_{1-6}$alkoxy, and $C_{1-6}$haloalkyl. In some embodiments, $R^{12}$ is

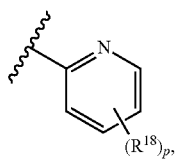

p is 1, and $R^{18}$ is selected from halogen, —CN, $C_{1-6}$alkyl, $C_{1-6}$alkoxy, and $C_{1-6}$haloalkyl. In some embodiments, $R^{12}$ is

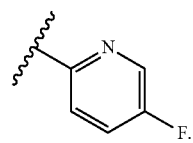 [SMILES: *c1ccc(F)cn1]

In some embodiments, $R^{12}$ is

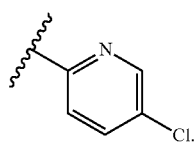 [SMILES: *c1ccc(Cl)cn1]

In some embodiments, $R^{12}$ is

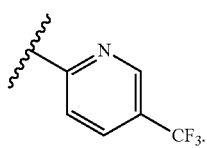 [SMILES: *c1ccc(C(F)(F)F)cn1]

In some embodiments, $R^{12}$ is

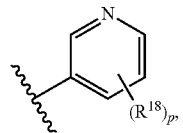

p is 1, and $R^{18}$ is selected from halogen, —CN, $C_{1-6}$alkyl, $C_{1-6}$alkoxy, and $C_{1-6}$haloalkyl. In some embodiments, $R^{12}$ is

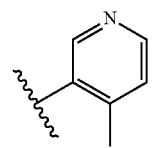

In some embodiments, $R^{12}$ is

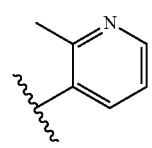

In some embodiments, $R^{12}$ is

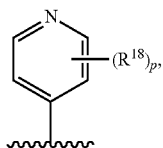

and $R^{18}$ is selected from halogen, —CN, $C_{1-6}$alkyl, $C_{1-6}$alkoxy, and $C_{1-6}$haloalkyl. In some embodiments, $R^{12}$ is

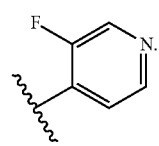 [SMILES: *c1ccncc1F]

In some embodiments, $R^{12}$ is

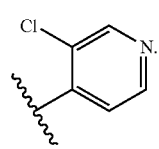

In some embodiments, $R^{12}$ is

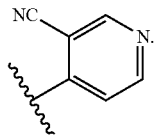 [SMILES: *c1ccncc1C#N]

In some embodiments, $R^{12}$ is

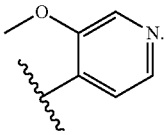 [SMILES: *c1ccncc1OC]

In some embodiments, $R^{12}$ is

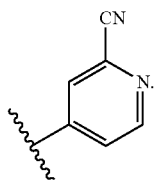 [SMILES: *c1ccnc(C#N)c1]

In some embodiments, $R^{12}$ is

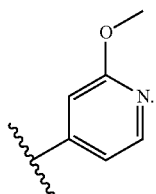 [SMILES: *c1ccnc(OC)c1]

In some embodiments, $R^{12}$ is

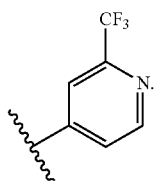 [SMILES: *c1ccnc(C(F)(F)F)c1]

In some embodiments, $R^{12}$ is

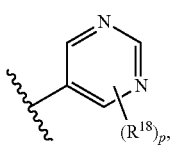

p is 1, and $R^{18}$ is selected from halogen, —CN, $C_{1-6}$alkyl, $C_{1-6}$alkoxy, and $C_{1-6}$haloalkyl. In some embodiments, $R^{12}$ is

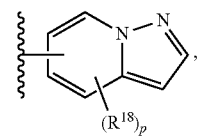

p is 1, and $R^{18}$ is selected from halogen, —CN, $C_{1-6}$alkyl, $C_{1-6}$alkoxy, and $C_{1-6}$haloalkyl. In some embodiments, $R^{12}$ is

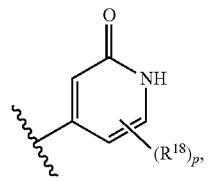

p is 1, and $R^{18}$ is selected from halogen, —CN, $C_{1-6}$alkyl, $C_{1-6}$alkoxy, and $C_{1-6}$haloalkyl.

In some embodiments of a compound of Formula (I), Formula (I'), Formula (Ia), or Formula (Ib), or a pharmaceutically acceptable salt or solvate thereof, $R^{12}$ is

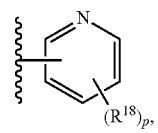

p is 2, and $R^{18}$ is selected from halogen, —CN, $C_{1-6}$alkyl, $C_{1-6}$alkoxy, and $C_{1-6}$haloalkyl. In some embodiments of a compound of Formula (I), Formula (I'), Formula (Ia), or Formula (Ib), or a pharmaceutically acceptable salt or solvate thereof, $R^{12}$ is

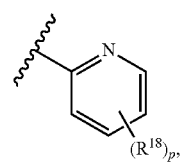

p is 2, and $R^{18}$ is selected from halogen, —CN, $C_{1-6}$alkyl, $C_{1-6}$alkoxy, and $C_{1-6}$haloalkyl. In some embodiments, $R^{12}$ is

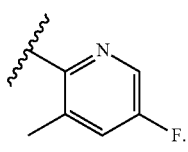

In some embodiments, $R^{12}$ is

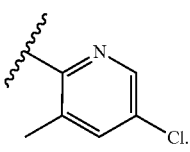 [SMILES: *c1ncc(Cl)cc1C]

In some embodiments, $R^{12}$ is

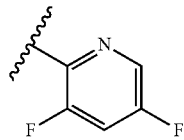 [SMILES: *c1ncc(F)cc1F]

In some embodiments, $R^{12}$ is

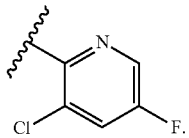 [SMILES: *c1ncc(F)cc1Cl]

In some embodiments, $R^{12}$ is

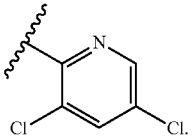 [SMILES: *c1ncc(Cl)cc1Cl]

In some embodiments, $R^{12}$ is

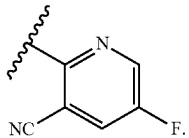 [SMILES: *c1ncc(F)cc1C#N]

In some embodiments, $R^{12}$ is

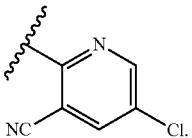 [SMILES: *c1ncc(Cl)cc1C#N]

In some embodiments of a compound of Formula (I), Formula (I'), Formula (Ia), or Formula (Ib), or a pharmaceutically acceptable salt or solvate thereof, $R^{12}$ is

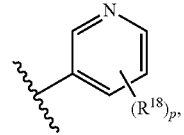

p is 2, and $R^{18}$ is selected from halogen, —CN, $C_{1-6}$alkyl, $C_{1-6}$alkoxy, and $C_{1-6}$haloalkyl. In some embodiments of a compound of Formula (I), Formula (I'), Formula (Ia), or Formula (Ib), or a pharmaceutically acceptable salt or solvate thereof, $R^{12}$ is

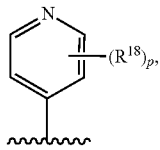

p is 2, and $R^{18}$ is selected from halogen, —CN, $C_{1-6}$alkyl, $C_{1-6}$alkoxy, and $C_{1-6}$haloalkyl.

In some embodiments of a compound of Formula (I'), or a pharmaceutically acceptable salt or solvate thereof, $R^{12}$ is

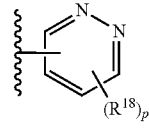

and p is 0. In some embodiments of a compound of Formula (I'), or a pharmaceutically acceptable salt or solvate thereof, $R^{12}$ is

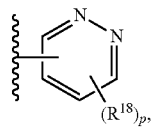

p is 1, and $R^{18}$ is selected from halogen, —CN, $C_{1-6}$alkyl, $C_{1-6}$alkoxy, and $C_{1-6}$haloalkyl. In some embodiments of a compound of Formula (I'), or a pharmaceutically acceptable salt or solvate thereof, $R^{12}$ is

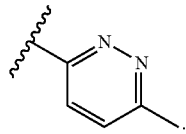 [SMILES: *c1ccc(C)nn1]

In some embodiments of a compound of Formula (I), Formula (I'), Formula (Ia), or Formula (Ib), or a pharmaceutically acceptable salt or solvate thereof, each $R^2$ is independently selected from H and $C_{1-4}$alkyl. In some embodiments, each $R^2$ is independently selected from H and methyl. In some embodiments, each $R^2$ is H. In some embodiments, each $R^2$ is $C_{1-4}$alkyl. In some embodiments, each $R^2$ is methyl.

In some embodiments of a compound of Formula (I), Formula (I'), Formula (Ia), or Formula (Ib), or a pharmaceutically acceptable salt or solvate thereof, each $R^3$ is independently selected from H and $C_{1-4}$alkyl. In some embodiments, each $R^3$ is independently selected from H and methyl. In some embodiments, each $R^3$ is H. In some embodiments, each $R^3$ is $C_{1-4}$alkyl. In some embodiments, each $R^3$ is methyl.

In some embodiments of a compound of Formula (I), Formula (I'), Formula (Ia), or Formula (Ib), or a pharmaceutically acceptable salt or solvate thereof, each $R^2$ and $R^3$ is H.

In some embodiments of a compound of Formula (I), Formula (I'), Formula (Ia), or Formula (Ib), or a pharmaceutically acceptable salt or solvate thereof, X is —CH$_2$CH$_2$—. In some embodiments, X is —CH$_2$O—. In some embodiments, X is —CH$_2$CH$_2$O—. In some embodiments, X is —O—. In some embodiments, X is —N(R$^{14}$)—. In some embodiments, X is S(O)$_2$. In some embodiments, X is —CH$_2$N(R$^{14}$)—. In some embodiments, X is —CH$_2$CH$_2$N(R$^{14}$)—. In some embodiments, X is —NH—. In some embodiments, X is —CH$_2$NH—. In some embodiments, X is —CH$_2$CH$_2$NH—. In some embodiments, X is —N(CH$_3$)—. In some embodiments, X is —CH$_2$N(CH$_3$)—. In some embodiments, X is —CH$_2$CH$_2$N(CH$_3$)—.

In some embodiments of a compound of Formula (I), Formula (I'), Formula (Ia), or Formula (Ib), or a pharmaceutically acceptable salt or solvate thereof, Y is a bond. In some embodiments, Y is —C(R$^{16}$)R(R$^{17}$)—. In some embodiments, Y is —CH(R$^{17}$)—. In some embodiments, Y is —CH$_2$—. In some embodiments, Y is or —N(R$^{15}$)—. In some embodiments, Y is or —NH—. In some embodiments, Y is or —N(CH$_3$)—.

In some embodiments of a compound of Formula (I), Formula (I'), Formula (Ia), or Formula (Ib), or a pharmaceutically acceptable salt or solvate thereof, R$^{14}$ is H or C$_{1-4}$alkyl. In some embodiments, R$^{14}$ is H or methyl. In some embodiments, R$^{14}$ is H. In some embodiments, R$^{14}$ is methyl.

In some embodiments of a compound of Formula (I), Formula (I'), Formula (Ia), or Formula (Ib), or a pharmaceutically acceptable salt or solvate thereof, R$^{14}$ and one R$^3$ combine to form a 4-, 5-, or 6-membered heterocycloalkyl ring. In some embodiments, R$^{14}$ and one R$^3$ combine to form an azetidinyl ring, pyrrolidinyl, or piperidinyl. In some embodiments, R$^{14}$ and one R$^3$ combine to form an azetidinyl ring.

In some embodiments of a compound of Formula (I), Formula (I'), Formula (Ia), or Formula (Ib), or a pharmaceutically acceptable salt or solvate thereof, R$^{15}$ is H or C$_{1-4}$alkyl. In some embodiments, R$^{15}$ is H or methyl. In some embodiments, R$^{15}$ is H. In some embodiments, R$^{15}$ is methyl.

In some embodiments of a compound of Formula (I), Formula (I'), Formula (Ia), or Formula (Ib), or a pharmaceutically acceptable salt or solvate thereof, R$^{15}$ and one R$^3$ combine to form a 4-, 5-, or 6-membered heterocycloalkyl ring. In some embodiments, R$^{15}$ and one R$^3$ combine to form an azetidinyl, pyrrolidinyl, or piperidinyl ring. In some embodiments, R$^{15}$ and one R$^3$ combine to form an azetidinyl ring.

In some embodiments of a compound of Formula (I), Formula (I'), Formula (Ia), or Formula (Ib), or a pharmaceutically acceptable salt or solvate thereof, R$^{16}$ is H or C$_{1-4}$alkyl. In some embodiments, R$^{16}$ is H or methyl. In some embodiments, R$^{16}$ is H.

In some embodiments of a compound of Formula (I), Formula (I'), Formula (Ia), or Formula (Ib), or a pharmaceutically acceptable salt or solvate thereof, R$^{17}$ is H or C$_{1-4}$alkyl. In some embodiments, R$^{17}$ is H or methyl. In some embodiments, R$^{17}$ is H.

In some embodiments of a compound of Formula (I), Formula (I'), Formula (Ia), or Formula (Ib), or a pharmaceutically acceptable salt or solvate thereof, R$^{17}$ and one R$^3$ combine to form a 4-, 5-, or 6-membered cycloalkyl ring. In some embodiments, R$^{17}$ and one R$^3$ combine to form a cyclobutyl, cyclopentyl, or cyclohexyl ring. In some embodiments, R$^{14}$ and one R$^3$ combine to form a cyclobutyl ring.

In some embodiments of a compound of Formula (I), Formula (I'), Formula (Ia), or Formula (Ib), or a pharmaceutically acceptable salt or solvate thereof, n is 1, 2, 3, 4, or 5. In some embodiments, n is 1 to 2, 1 to 3, 1 to 4, 1 to 5, 2 to 3, 2 to 4, 2 to 5, 3 to 4, 3 to 5, or 4 to 5. In some embodiments, n is 1. In some embodiments, n is 2. In some embodiments, n is 3. In some embodiments, n is 4 In some embodiments, n is 5.

In some embodiments of a compound of Formula (I), Formula (I'), Formula (Ia), or Formula (Ib), or a pharmaceutically acceptable salt or solvate thereof, X is —CH$_2$CH$_2$— and Y is a bond.

In some embodiments of a compound of Formula (I), Formula (I'), Formula (Ia), or Formula (Ib), or a pharmaceutically acceptable salt or solvate thereof, X is —CH$_2$O— and Y is a bond.

In some embodiments of a compound of Formula (I), Formula (I'), Formula (Ia), or Formula (Ib), or a pharmaceutically acceptable salt or solvate thereof, X is —CH$_2$N(H)— and Y is a bond.

In some embodiments of a compound of Formula (I), Formula (I'), Formula (Ia), or Formula (Ib), or a pharmaceutically acceptable salt or solvate thereof, X is S(O)$_2$ and Y is a bond.

In some embodiments of a compound of Formula (I), Formula (I'), Formula (Ia), or Formula (Ib), or a pharmaceutically acceptable salt or solvate thereof, X is —O—, Y is —C(R$^{16}$)(R$^{17}$)—, and R$^{17}$ and one R$^3$ combine to form a 3- or 4-membered cycloalkyl ring.

In some embodiments of a compound of Formula (I), Formula (I'), Formula (Ia), or Formula (Ib), or a pharmaceutically acceptable salt or solvate thereof, X is —N(R$^{14}$)—; Y is bond; and R$^{14}$ and one R$^3$ combine to form a 4-, 5-, or 6-membered heterocycloalkyl ring.

In some embodiments of a compound of Formula (I), Formula (I'), Formula (Ia), or Formula (Ib), or a pharmaceutically acceptable salt or solvate thereof, X is —O—; Y is —N(R$^{15}$)—; and R$^{15}$ and one R$^3$ combine to form a 4-, 5-, or 6-membered heterocycloalkyl ring.

In some embodiments of a compound of Formula (I), Formula (I'), Formula (Ia), or Formula (Ib), or a pharmaceutically acceptable salt or solvate thereof, wherein

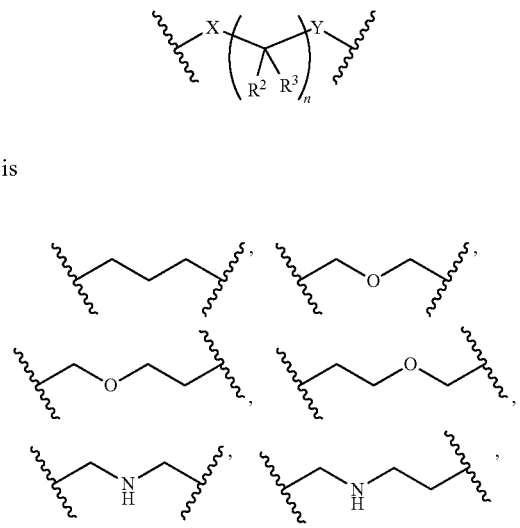

is

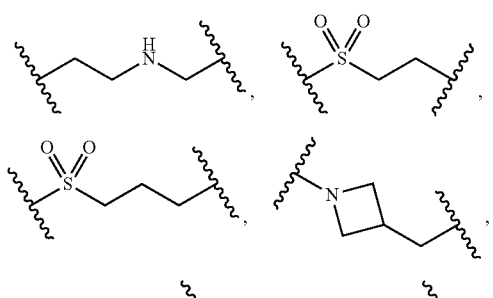
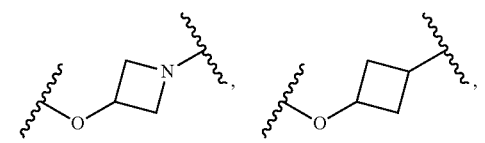
In some embodiments,
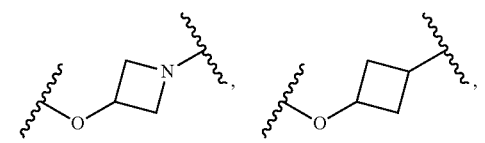
is
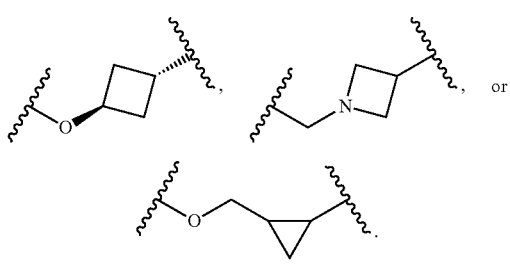
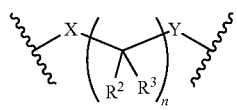
In some embodiments,
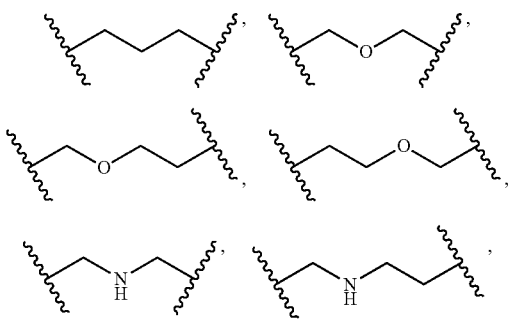

In some embodiments,
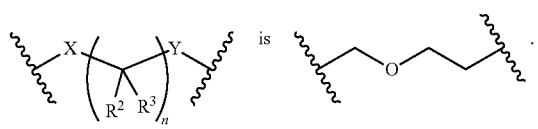 is 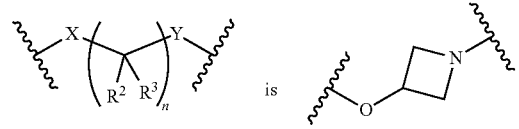
In some embodiments,
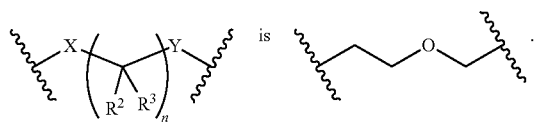 is 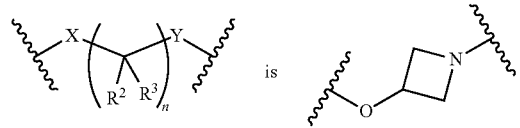
In some embodiments,
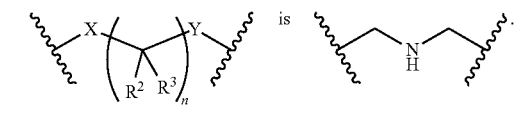 is 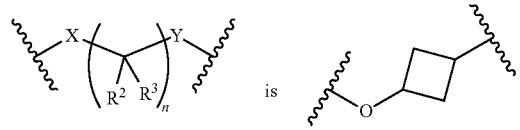
In some embodiments,
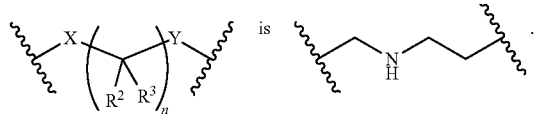 is 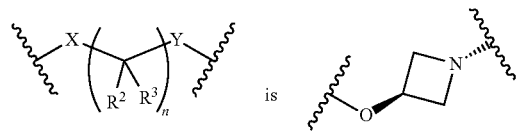
In some embodiments,
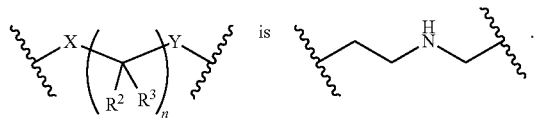 is 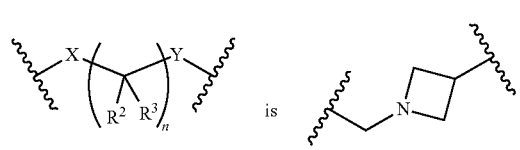
In some embodiments,
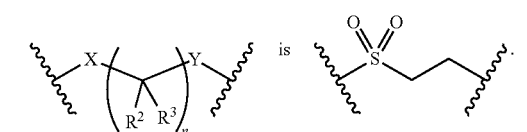 is 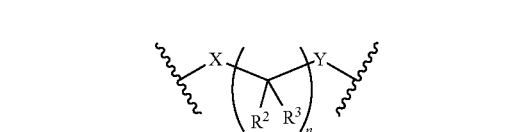
In some embodiments,
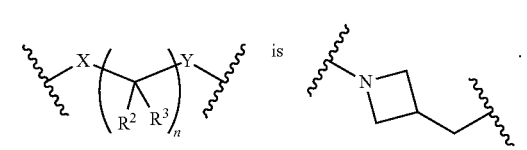
In some embodiments is a compound of Formula (I), or a pharmaceutically acceptable salt or solvate thereof, having the structure of Formula (I-1), Formula (I-2), or a pharmaceutically acceptable salt or solvate thereof:

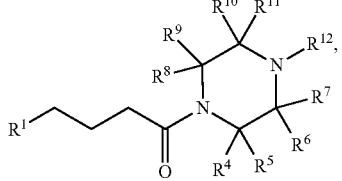

Formula (I-1)

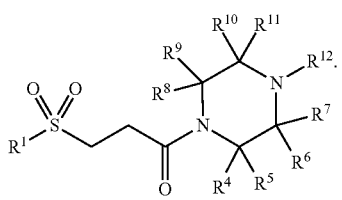

Formula (I-2)

In some embodiments is a compound of Formula (Ia), or a pharmaceutically acceptable salt or solvate thereof, having the structure of Formula (Ia-1), Formula (Ia-2), or a pharmaceutically acceptable salt or solvate thereof:

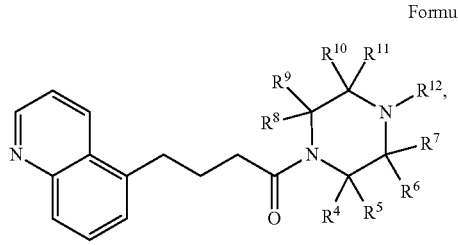

Formula (Ia-1)

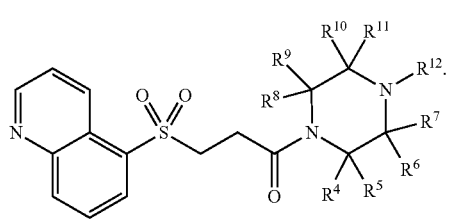

Formula (Ia-2)

In some embodiments is a compound of Formula (Ib), or a pharmaceutically acceptable salt or solvate thereof, having the structure of Formula (Ib-1), Formula (Ib-2), or a pharmaceutically acceptable salt or solvate thereof:

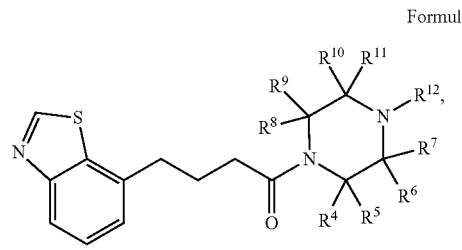

Formula (Ib-1)

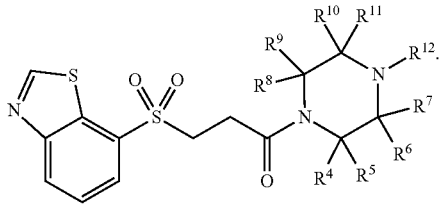

Formula (Ib-2)

In some embodiments of a compound of Formula (I), Formula (I-1), Formula (I-2), Formula (Ia), Formula (Ia-1), Formula (Ia-2), Formula (Ib), Formula (Ib-1), or Formula (Ib-2), or a pharmaceutically acceptable salt or solvate thereof, $R^4$, $R^6$, $R^8$, and $R^{10}$ are each independently selected from H and $C_{1-4}$alkyl. In some embodiments, $R^4$, $R^6$, $R^8$, and $R^{10}$ are each independently selected from H, methyl, ethyl, n-propyl, i-propyl, n-butyl, i-butyl, s-butyl, and t-butyl. In some embodiments, $R^4$, $R^6$, $R^8$, and $R^{10}$ are each independently selected from H, methyl, ethyl, n-propyl, i-propyl, and i-butyl. In some embodiments, $R^4$, $R^6$, $R^8$, and $R^{10}$ are each independently selected from H and methyl. In some embodiments, $R^4$, $R^6$, $R^8$, and $R^{10}$ are each H.

In some embodiments of a compound of Formula (I), Formula (I-1), Formula (I-2), Formula (Ia), Formula (Ia-1), Formula (Ia-2), Formula (Ib), Formula (Ib-1), or Formula (Ib-2), or a pharmaceutically acceptable salt or solvate thereof, $R^5$, $R^7$, $R^9$, and $R^{11}$ are each independently selected from H and $C_{1-4}$alkyl. In some embodiments, $R^5$, $R^7$, $R^9$, and $R^{11}$ are each independently selected from H, methyl, ethyl, n-propyl, i-propyl, n-butyl, i-butyl, s-butyl, and t-butyl. In some embodiments, $R^5$, $R^7$, $R^9$, and $R^{11}$ are each independently selected from H, methyl, ethyl, n-propyl, i-propyl, and i-butyl. In some embodiments, $R^5$, $R^7$, $R^9$, and $R^{11}$ are each independently selected from H and methyl. In some embodiments, $R^5$, $R^7$, $R^9$, and $R^{11}$ are each H.

In some embodiments of a compound of Formula (I), Formula (I-1), Formula (I-2), Formula (Ia), Formula (Ia-1), Formula (Ia-2), Formula (Ib), Formula (Ib-1), or Formula (Ib-2), or a pharmaceutically acceptable salt or solvate thereof, $R^5$ is selected from H and $C_{1-6}$alkyl. In some embodiments, $R^5$ is selected from H and $C_{1-4}$alkyl. In some embodiments, $R^5$ is selected from H, methyl, ethyl, n-propyl, i-propyl, n-butyl, i-butyl, s-butyl, and t-butyl. In some embodiments, $R^5$ is selected from H, methyl, ethyl, n-propyl, i-propyl, and i-butyl. In some embodiments, $R^5$ is selected from H and methyl. In some embodiments, $R^5$ is H. In some embodiments, $R^5$ is methyl. In some embodiments, $R^5$ is $C_{1-6}$alkyl. In some embodiments, $R^5$ is $C_{1-6}$alkyl; and $R^7$, $R^9$, and $R^{11}$ are H.

In some embodiments of a compound of Formula (I), Formula (I-1), Formula (I-2), Formula (Ia), Formula (Ia-1), Formula (Ia-2), Formula (Ib), Formula (Ib-1), or Formula (Ib-2), or a pharmaceutically acceptable salt or solvate thereof, $R^7$ is selected from H and $C_{1-6}$alkyl. In some embodiments, $R^7$ is selected from H and $C_{1-4}$alkyl. In some embodiments, $R^7$ is selected from H, methyl, ethyl, n-propyl, i-propyl, n-butyl, i-butyl, s-butyl, and t-butyl. In some embodiments, $R^7$ is selected from H, methyl, ethyl, n-propyl, i-propyl, and i-butyl. In some embodiments, $R^7$ is selected from H and methyl. In some embodiments, $R^7$ is H. In some embodiments, $R^7$ is methyl. In some embodiments, $R^7$ is $C_{1-6}$alkyl. In some embodiments, $R^7$ is $C_{1-6}$alkyl; and $R^5$, $R^9$, and $R^{11}$ are H.

In some embodiments of a compound of Formula (I), Formula (I-1), Formula (I-2), Formula (Ia), Formula (Ia-1), Formula (Ia-2), Formula (Ib), Formula (Ib-1), or Formula (Ib-2), or a pharmaceutically acceptable salt or solvate thereof, $R^9$ is selected from H and $C_{1-6}$alkyl. In some embodiments, $R^9$ is selected from H and $C_{1-4}$alkyl. In some embodiments, $R^9$ is selected from H, methyl, ethyl, n-propyl, i-propyl, n-butyl, i-butyl, s-butyl, and t-butyl. In some embodiments, $R^9$ is selected from H, methyl, ethyl, n-propyl, i-propyl, and i-butyl. In some embodiments, $R^9$ is selected from H and methyl. In some embodiments, $R^9$ is H. In some embodiments, $R^9$ is methyl. In some embodiments, $R^9$ is $C_{1-6}$alkyl. In some embodiments, $R^9$ is $C_{1-6}$alkyl; and $R^5$, $R^7$, and $R^{11}$ are H.

In some embodiments of a compound of Formula (I), Formula (I-1), Formula (I-2), Formula (Ia), Formula (Ia-1), Formula (Ia-2), Formula (Ib), Formula (Ib-1), or Formula (Ib-2), or a pharmaceutically acceptable salt or solvate thereof, $R^{11}$ is selected from H and $C_{1-6}$alkyl. In some embodiments, $R^{11}$ is selected from H and $C_{1-4}$alkyl. In some embodiments, $R^{11}$ is selected from H, methyl, ethyl, n-propyl, i-propyl, n-butyl, i-butyl, s-butyl, and t-butyl. In some embodiments, $R^{11}$ is selected from H, methyl, ethyl, n-propyl, i-propyl, and i-butyl. In some embodiments, $R^{11}$ is selected from H and methyl. In some embodiments, $R^{11}$ is H. In some embodiments, $R^{11}$ is methyl. In some embodiments, $R^{11}$ is $C_{1-6}$alkyl. In some embodiments, is $C_{1-6}$alkyl; and $R^5$, $R^7$, and $R^9$ are H.

In some embodiments of a compound of Formula (I), Formula (I-1), Formula (I-2), Formula (Ia), Formula (Ia-1), Formula (Ia-2), Formula (Ib), Formula (Ib-1), or Formula (Ib-2), or a pharmaceutically acceptable salt or solvate thereof, $R^7$ and $R^{11}$ combine to form a ring. In some embodiments, $R^7$ and $R^{11}$ combine to form a ring; and $R^5$ and $R^9$ are H.

In some embodiments of a compound of Formula (I), Formula (I-1), Formula (I-2), Formula (Ia), Formula (Ia-1), Formula (Ia-2), Formula (Ib), Formula (Ib-1), or Formula (Ib-2), or a pharmaceutically acceptable salt or solvate thereof, $R^7$ and $R^9$ combine to form a ring. In some embodiments, $R^7$ and $R^9$ combine to form a ring; and $R^5$ and $R^{11}$ are H.

In some embodiments of a compound of Formula (I), Formula (I-1), Formula (I-2), Formula (Ia), Formula (Ia-1), Formula (Ia-2), Formula (Ib), Formula (Ib-1), or Formula (Ib-2), or a pharmaceutically acceptable salt or solvate thereof, $R^5$ and $R^9$ combine to form a ring. In some embodiments, $R^5$ and $R^9$ combine to form a ring; and $R^7$ and $R^{11}$ are H.

In some embodiments of a compound of Formula (I), Formula (I-1), Formula (I-2), Formula (Ia), Formula (Ia-1), Formula (Ia-2), Formula (Ib), Formula (Ib-1), or Formula (Ib-2), or a pharmaceutically acceptable salt or solvate thereof,

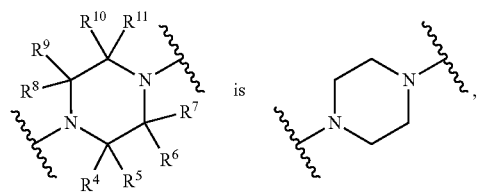 is 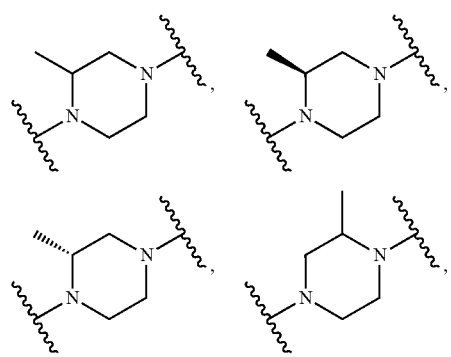

In some embodiments,

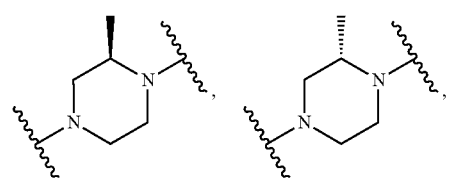 is 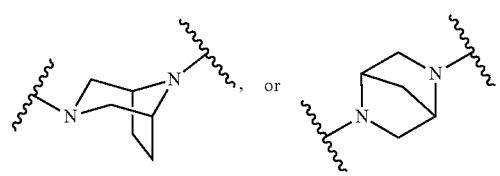

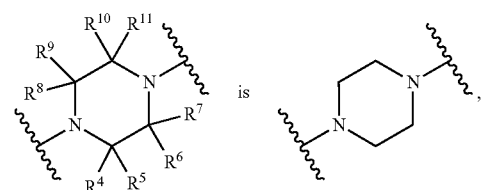, or 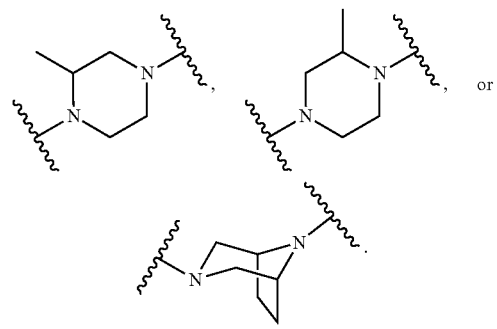.

In some embodiments,

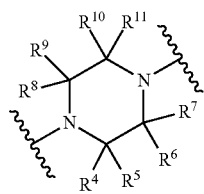

is

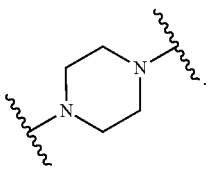 [SMILES: *N1CCN(*)CC1]

In some embodiments,

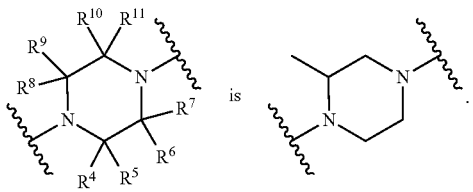

In some embodiments,

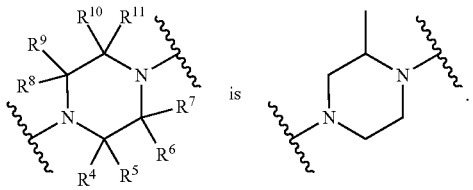

In some embodiments,

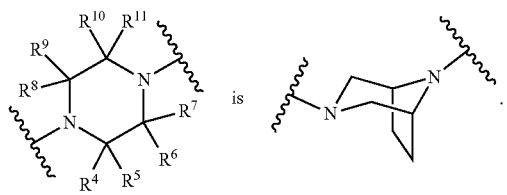

In another aspect, provided herein is a compound having the structure of Formula (II):

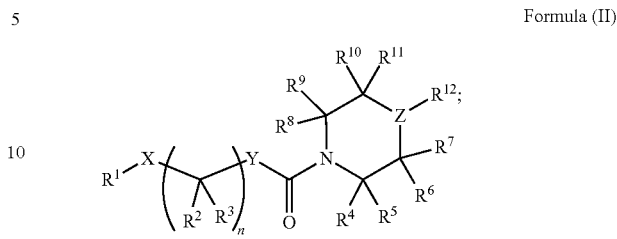

Formula (II)

wherein:

X is —CH$_2$CH$_2$—, —CH$_2$O—, —CH$_2$CH$_2$O—, —O—, —N(R$^{14}$)—, S(O)$_2$, —CH$_2$N(R$^{14}$)—, or —CH$_2$CH$_2$N(R$^{14}$)—;

Y is a bond, —C(R$^{16}$)(R$^{17}$)—, or —N(R$^{15}$)—;

Z is —N— or —C(H)—;

R$^1$ is

![structure](A with (R$^{13}$)$_m$)

wherein ring A is a heteroaryl ring optionally substituted with halogen, —CN, —N(R$^{22}$)$_2$, C$_{1-6}$alkyl, C$_{1-6}$alkoxy, C$_{1-6}$haloalkyl, or C$_{1-6}$haloalkoxy, wherein the heteroaryl ring contains 1 nitrogen atom and 0 or 1 oxygen or sulfur atoms;

each R$^2$ is independently selected from H and C$_{1-6}$alkyl;

each R$^3$ is independently selected from H and C$_{1-6}$alkyl;

R$^4$, R$^6$, R$^8$, and R$^{10}$ are each independently selected from H and C$_{1-6}$alkyl;

R$^5$, R$^7$, R$^9$, and R$^{11}$ are each independently selected from H and C$_{1-6}$alkyl; or R$^7$ and R$^{11}$ combine to form a ring or R$^5$ and R$^9$ combine to form a ring or R$^7$ and R$^9$ combine to form a ring;

R$^{12}$ is

![phenyl with (R$^{18}$)$_v$], ![pyrimidinyl with (R$^{18}$)$_p$], or

![pyrimidinyl with (R$^{18}$)$_p$];

each R$^{13}$ is independently selected from halogen, —CN, C$_{1-6}$alkyl, C$_{1-6}$alkoxy, C$_{1-6}$haloalkyl, and C$_{1-6}$haloalkoxy;

R$^{14}$ is H or C$_{1-6}$alkyl; or R$^{14}$ and one R$^3$ combine to form a 4-, 5-, or 6-membered heterocycloalkyl ring;

R$^{15}$ is H or C$_{1-6}$alkyl; or R$^{15}$ and one R$^3$ combine to form a 4-, 5-, or 6-membered heterocycloalkyl ring;

R$^{16}$ is H or C$_{1-6}$alkyl;

R$^{17}$ is H or C$_{1-6}$alkyl; or R$^{17}$ and one R$^3$ combine to form a 3-, 4-, 5-, or 6-membered cycloalkyl ring;

each $R^{18}$ is independently selected from halogen, —CN, $C_{1-6}$alkyl, $C_{1-6}$alkoxy, $C_{1-6}$haloalkyl, and $C_{1-6}$haloalkoxy;

each $R^{22}$ is independently selected from H and $C_{1-6}$alkyl;

m is 0, 1, 2, or 3;

n is 1, 2, 3, 4, or 5;

p is 0, 1, 2, or 3; and v is 0, 1, 2, 3, 4, or 5;

or a pharmaceutically acceptable salt or solvate thereof.

In some embodiments of a compound of Formula (II), or a pharmaceutically acceptable salt or solvate thereof, ring A is a 5- or 6-membered heteroaryl ring optionally substituted with halogen, —CN, —N($R^{22}$)$_2$, $C_{1-6}$alkyl, $C_{1-6}$alkoxy, $C_{1-6}$haloalkyl, or $C_{1-6}$haloalkoxy, wherein the heteroaryl ring contains 1 nitrogen atom and 0 or 1 oxygen or sulfur atoms. In some embodiments, ring A is a 5-membered heteroaryl ring optionally substituted with halogen, —CN, —N($R^{22}$)$_2$, $C_{1-6}$alkyl, $C_{1-6}$alkoxy, $C_{1-6}$haloalkyl, or $C_{1-6}$haloalkoxy, wherein the heteroaryl ring contains 1 nitrogen atom and 0 or 1 oxygen or sulfur atoms. In some embodiments, ring A is a 6-membered heteroaryl ring optionally substituted with halogen, —CN, —N($R^{22}$)$_2$, $C_{1-6}$alkyl, $C_{1-6}$alkoxy, $C_{1-6}$haloalkyl, or $C_{1-6}$haloalkoxy, wherein the heteroaryl ring contains 1 nitrogen atom and 0 or 1 oxygen or sulfur atoms. In some embodiments, ring A is a heteroaryl ring optionally substituted with halogen, —CN, —N($R^{22}$)$_2$, $C_{1-6}$ alkyl, $C_{1-6}$ alkyl-OH, $C_{1-6}$alkoxy, $C_{1-6}$haloalkyl, or $C_{1-6}$haloalkoxy, wherein the heteroaryl ring is selected from the group consisting of pyrrolyl, oxazolyl, isoxazolyl, thiazolyl, isothiazolyl, and pyridinyl. In some embodiments, ring A is a heteroaryl ring optionally substituted with halogen, —CN, —N($R^{22}$)$_2$, $C_{1-6}$alkyl, $C_{1-6}$alkoxy, $C_{1-6}$haloalkyl, or $C_{1-6}$haloalkoxy, wherein the heteroaryl ring is selected from the group consisting of pyrrolyl, oxazolyl, isoxazolyl, thiazolyl, and isothiazolyl. In some embodiments, ring A is a pyridinyl ring optionally substituted with halogen, —CN, —N($R^{22}$)$_2$, $C_{1-6}$ alkyl, $C_{1-6}$ alkyl-OH, $C_{1-6}$ alkoxy, $C_{1-6}$haloalkyl, or $C_{1-6}$haloalkoxy. In some embodiments, ring A is optionally substituted with —N($R^{22}$)$_2$, $C_{1-6}$alkyl, or $C_{1-6}$alkoxy. In some embodiments, ring A is optionally substituted with —NH$_2$, methyl, —CH$_2$OH, or methoxy. In some embodiments, ring A is unsubstituted.

In some embodiments of a compound of Formula (II), or a pharmaceutically acceptable salt or solvate thereof, $R^1$ is

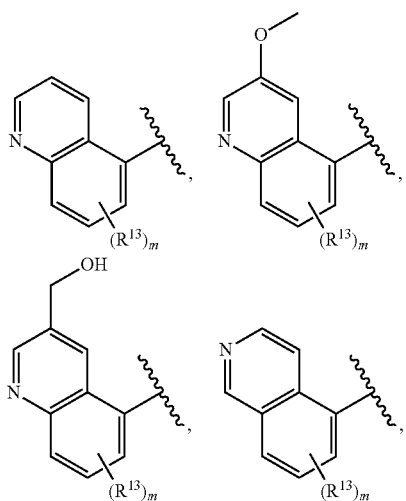

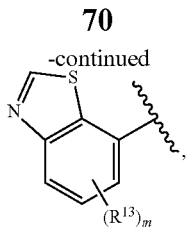

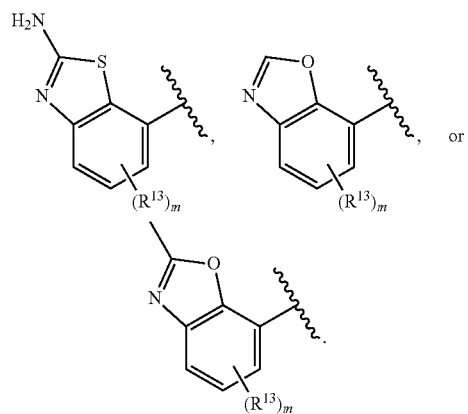

In some embodiments, $R^1$ is

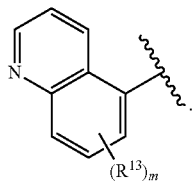

In some embodiments, $R^1$ is

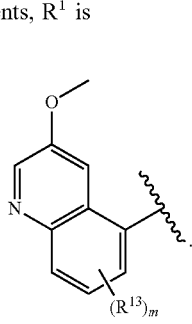

In some embodiments, $R^1$ is

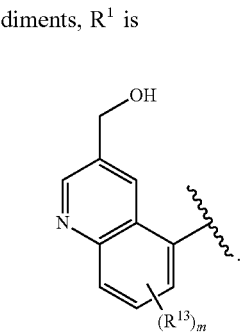

In some embodiments, $R^1$ is

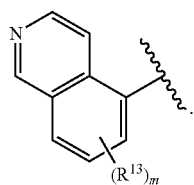

In some embodiments, $R^1$ is

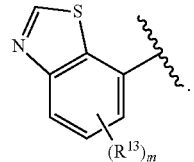

In some embodiments, $R^1$ is

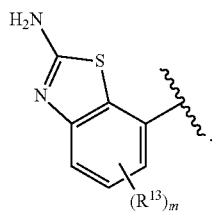

In some embodiments, $R^1$ is

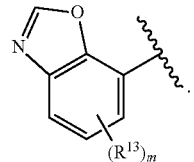

In some embodiments, $R^1$ is

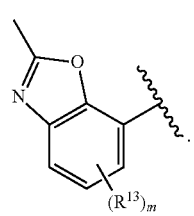

In some embodiments of a compound of Formula (II), or a pharmaceutically acceptable salt or solvate thereof, each $R^{13}$ is independently selected from halogen, —CN, $C_{1-6}$alkoxy, $C_{1-6}$haloalkyl, and $C_{1-6}$haloalkoxy. In some embodiments, each $R^{13}$ is independently selected from halogen, —CN, $C_{1-6}$alkyl, and $C_{1-6}$alkoxy.

In some embodiments of a compound of Formula (II), or a pharmaceutically acceptable salt or solvate thereof, m is 0, 1, 2, or 3. In some embodiments, m is 0 to 1, 0 to 2, 0 to 3, 1 to 2, 1 to 3, or 2 to 3. In some embodiments, m is 0. In some embodiments, m is 1. In some embodiments, m is 2. In some embodiments, m is 3.

In some embodiments of a compound of Formula (II), or a pharmaceutically acceptable salt or solvate thereof, $R^1$ is

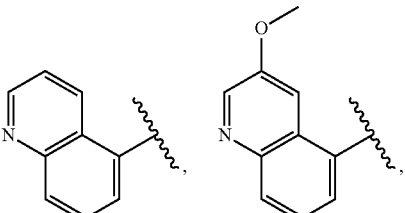

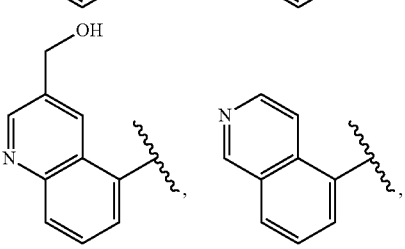

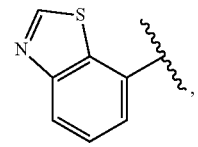

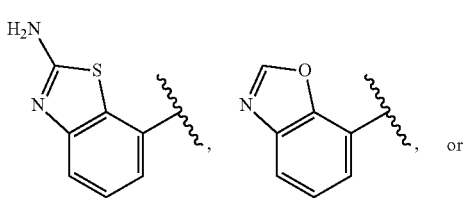

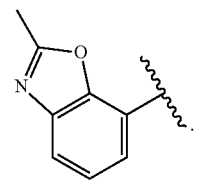

In some embodiments, $R^1$ is

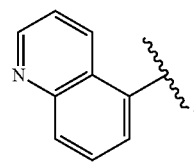

In some embodiments, R¹ is

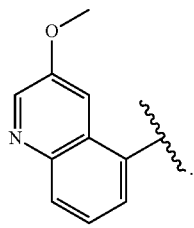 [SMILES: *c1cccc2ncc(OC)cc12]

In some embodiments, R¹ is

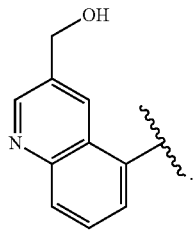 [SMILES: *c1cccc2ncc(CO)cc12]

In some embodiments, R¹ is

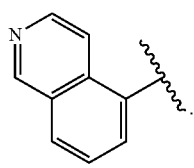

In some embodiments, R¹ is

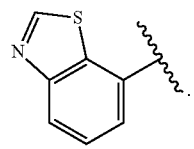

In some embodiments, R¹ is

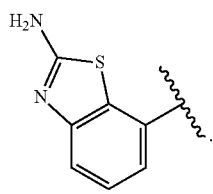 [SMILES: *c1cccc2nc(N)sc12]

In some embodiments, R¹ is

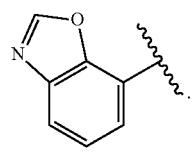

In some embodiments, R¹ is

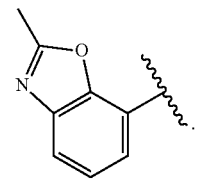 [SMILES: *c1cccc2nc(C)oc12]

In some embodiments of a compound of Formula (II), or a pharmaceutically acceptable salt or solvate thereof, Z is —N—. In some embodiments of a compound of Formula (II), or a pharmaceutically acceptable salt or solvate thereof, Z is —C(H)—.

In some embodiments is a compound of Formula (II), or a pharmaceutically acceptable salt or solvate thereof, having the structure of Formula (IIa), or a pharmaceutically acceptable salt or solvate thereof:

Formula (IIa)

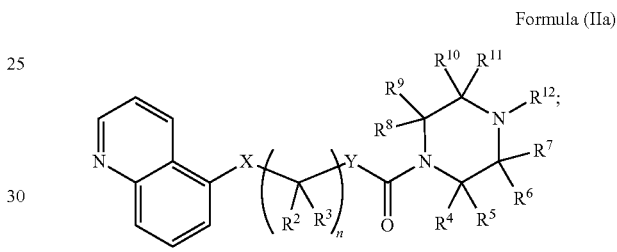

X is —CH₂CH₂—, —CH₂O—, —CH₂CH₂O—, —O—, —N(R¹⁴)—, S(O)₂, —CH₂N(R¹⁴)—, or —CH₂CH₂N(R¹⁴)—;
Y is a bond, —C(R¹⁶)(R¹⁷)—, or —N(R¹⁵)—;
each R² is independently selected from H and $C_{1-6}$alkyl;
each R³ is independently selected from H and $C_{1-6}$alkyl;
R⁴, R⁶, R⁸, and R¹⁰ are each independently selected from H and $C_{1-6}$alkyl;
R⁵, R⁷, R⁹, and R¹¹ are each independently selected from H and $C_{1-6}$alkyl; or R⁷ and R¹¹ combine to form a ring or R⁵ and R⁹ combine to form a ring or R⁷ and R⁹ combine to form a ring;
R¹² is

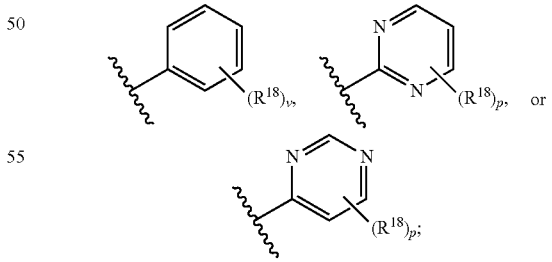

R¹⁴ is H or $C_{1-6}$alkyl; or R¹⁴ and one R³ combine to form a 4-, 5-, or 6-membered heterocycloalkyl ring;
R¹⁵ is H or $C_{1-6}$alkyl; or R¹⁵ and one R³ combine to form a 4-, 5-, or 6-membered heterocycloalkyl ring;
R¹⁶ is H or $C_{1-6}$alkyl;
R¹⁷ is H or $C_{1-6}$alkyl; or R¹⁷ and one R³ combine to form a 3-, 4-, 5-, or 6-membered cycloalkyl ring;

each R[18] is independently selected from halogen, —CN, $C_{1-6}$alkyl, $C_{1-6}$alkoxy, $C_{1-6}$haloalkyl, and $C_{1-6}$haloalkoxy;

n is 1, 2, 3, 4, or 5;

p is 0, 1, 2, or 3; and v is 0, 1, 2, 3, 4, or 5.

In some embodiments is a compound of Formula (II), or a pharmaceutically acceptable salt or solvate thereof, having the structure of Formula (IIb), or a pharmaceutically acceptable salt or solvate thereof:

Formula (IIb)

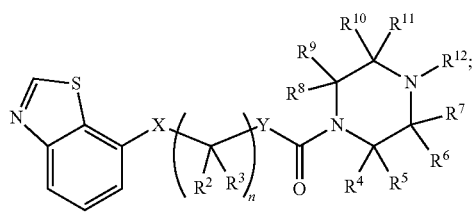

X is —$CH_2CH_2$—, —$CH_2O$—, —$CH_2CH_2O$—, —O—, —N(R[14])—, $S(O)_2$, —$CH_2N(R^{14})$—, or —$CH_2CH_2N(R^{14})$—;

Y is a bond, —C(R[16])(R[17])—, or —N(R[15])—;

each R[2] is independently selected from H and $C_{1-6}$alkyl;

each R[3] is independently selected from H and $C_{1-6}$alkyl;

R[4], R[6], R[8], and R[10] are each independently selected from H and $C_{1-6}$alkyl;

R[5], R[7], R[9], and R[11] are each independently selected from H and $C_{1-6}$alkyl; or R[7] and R[11] combine to form a ring or R[5] and R[9] combine to form a ring or R[7] and R[9] combine to form a ring;

R[12] is

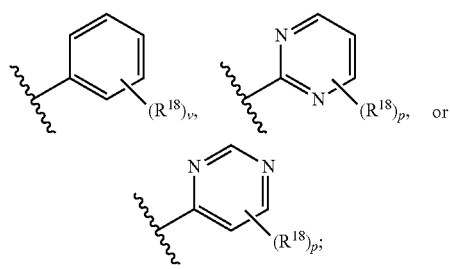

R[14] is H or $C_{1-6}$alkyl; or R[14] and one R[3] combine to form a 4-, 5-, or 6-membered heterocycloalkyl ring;

R[15] is H or $C_{1-6}$alkyl; or R[15] and one R[3] combine to form a 4-, 5-, or 6-membered heterocycloalkyl ring;

R[16] is H or $C_{1-6}$alkyl;

R[17] is H or $C_{1-6}$alkyl; or R[17] and one R[3] combine to form a 3-, 4-, 5-, or 6-membered cycloalkyl ring;

each R[18] is independently selected from halogen, —CN, $C_{1-6}$alkoxy, $C_{1-6}$haloalkyl, and $C_{1-6}$haloalkoxy;

n is 1, 2, 3, 4, or 5;

p is 0, 1, 2, or 3; and v is 0, 1, 2, 3, 4, or 5.

In some embodiments of a compound of Formula (II), Formula (IIa), or Formula (IIb), or a pharmaceutically acceptable salt or solvate thereof, R[12] is

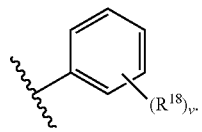

In some embodiments, R[12] is

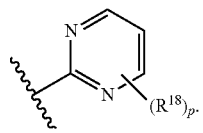

In some embodiments, R[12] is

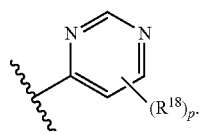

In some embodiments of a compound of Formula (II), Formula (IIa), or Formula (IIb), or a pharmaceutically acceptable salt or solvate thereof, R[18] is selected from halogen, —CN, $C_{1-6}$alkyl, $C_{1-6}$alkoxy, and $C_{1-6}$haloalkyl. In some embodiments of a compound of Formula (II), Formula (IIa), or Formula (IIb), or a pharmaceutically acceptable salt or solvate thereof, R[18] is selected from halogen, —CN, $C_{1-6}$alkyl, and $C_{1-6}$haloalkyl. In some embodiments, R[18] is selected from —F, —Cl, —Br, —CN, $C_{1-4}$alkoxy, and $C_{1-4}$haloalkyl. In some embodiments, R[18] is selected from —F, —Cl, —CN, methyl, methoxy, and trifluoromethyl.

In some embodiments of a compound of Formula (II), Formula (IIa), or Formula (IIb), or a pharmaceutically acceptable salt or solvate thereof, p is 0, 1, 2, or 3. In some embodiments, p is 0 to 1, 0 to 2, 0 to 3, 1 to 2, 1 to 3, or 2 to 3. In some embodiments, p is 0. In some embodiments, p is 1. In some embodiments, p is 2. In some embodiments, p is 3.

In some embodiments of a compound of Formula (II), Formula (IIa), or Formula (IIb), or a pharmaceutically acceptable salt or solvate thereof, v is 0, 1, 2, 3, 4, or 5. In some embodiments, v is 0 to 1, 0 to 2, 0 to 3, 0 to 4, 0 to 5, 1 to 2, 1 to 3, 1 to 4, 1 to 5, 2 to 3, 3 to 4, 3 to 5, or 4 to 5. In some embodiments, v is 0. In some embodiments, v is 1. In some embodiments, v is 2. In some embodiments, v is 3. In some embodiments, v is 4. In some embodiments, v is 5. 1, 2, 3, 4, or 5.

In some embodiments of a compound of Formula (II), Formula (IIa), or Formula (IIb), or a pharmaceutically acceptable salt or solvate thereof, R[12] is

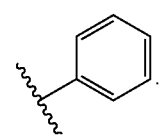 [SMILES: *c1ccccc1]

In some embodiments of a compound of Formula (II), Formula (IIa), or Formula (IIb), or a pharmaceutically acceptable salt or solvate thereof, R$^{12}$ is

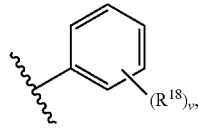

v is 1, and R$^{18}$ is selected from halogen, —CN, C$_{1-6}$alkyl, C$_{1-6}$alkoxy, and C$_{1-6}$haloalkyl. In some embodiments, R$^{12}$ is

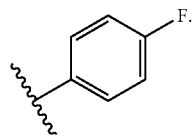 [SMILES: *c1ccc(F)cc1]

In some embodiments, R$^{12}$ is

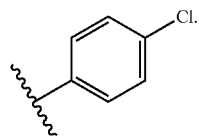 [SMILES: *c1ccc(Cl)cc1]

In some embodiments, R$^{12}$ is

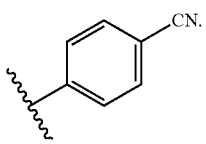 [SMILES: *c1ccc(C#N)cc1]

In some embodiments, R$^{12}$ is

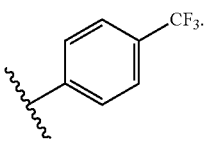 [SMILES: *c1ccc(C(F)(F)F)cc1]

In some embodiments of a compound of Formula (II), Formula (IIa), or Formula (IIb), or a pharmaceutically acceptable salt or solvate thereof, R$^{12}$ is

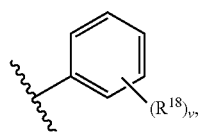

v is 2, and R$^{18}$ is selected from halogen, —CN, C$_{1-6}$alkyl, C$_{1-6}$alkoxy, and C$_{1-6}$haloalkyl. In some embodiments, R$^{12}$ is

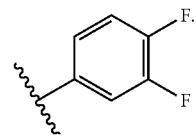 [SMILES: *c1ccc(F)c(F)c1]

In some embodiments, R$^{12}$ is

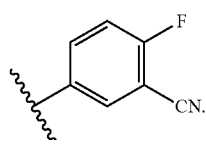 [SMILES: *c1ccc(F)c(C#N)c1]

In some embodiments of a compound of Formula (II), Formula (IIa), or Formula (IIb), or a pharmaceutically acceptable salt or solvate thereof, R$^{12}$ is

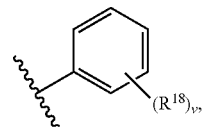

v is 3, and R$^{18}$ is selected from halogen, —CN, C$_{1-6}$alkyl, C$_{1-6}$alkoxy, and C$_{1-6}$haloalkyl. In some embodiments, R$^{12}$ is

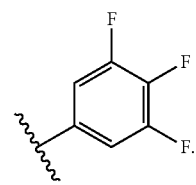 [SMILES: *c1cc(F)c(F)c(F)c1]

In some embodiments of a compound of Formula (II), Formula (IIa), or Formula (IIb), or a pharmaceutically acceptable salt or solvate thereof, R$^{12}$ is

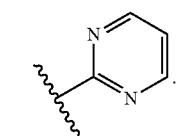 [SMILES: *c1ncccn1]

In some embodiments of a compound of Formula (II), Formula (IIa), or Formula (IIb), or a pharmaceutically acceptable salt or solvate thereof, R$^{12}$ is

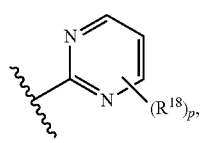

p is 1, and R$^{18}$ is selected from halogen, —CN, C$_{1-6}$alkyl, C$_{1-6}$alkoxy, and C$_{1-6}$haloalkyl. In some embodiments, R$^{12}$ is In some embodiments, $R^{12}$ is

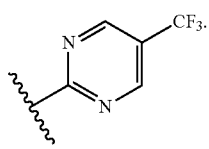 [SMILES: *c1ncc(C(F)(F)F)cn1]

In some embodiments, $R^{12}$ is

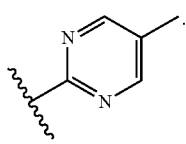 [SMILES: *c1ncc(C)cn1]

In some embodiments, $R^{12}$ is

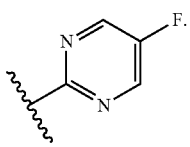 [SMILES: *c1ncc(F)cn1]

In some embodiments of a compound of Formula (II), Formula (IIa), or Formula (IIb), or a pharmaceutically acceptable salt or solvate thereof, $R^{12}$ is

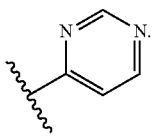 [SMILES: *c1ccncn1]

In some embodiments of a compound of Formula (II), Formula (IIa), or Formula (IIb), or a pharmaceutically acceptable salt or solvate thereof, $R^{12}$ is

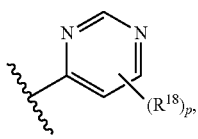

p is 1, and $R^{18}$ is selected from halogen, —CN, $C_{1-6}$alkyl, $C_{1-6}$alkoxy, and $C_{1-6}$haloalkyl.

In some embodiments of a compound of Formula (II), Formula (IIa), or Formula (IIb), or a pharmaceutically acceptable salt or solvate thereof, each $R^2$ is independently selected from H and $C_{1-4}$alkyl. In some embodiments, each $R^2$ is independently selected from H and methyl. In some embodiments, each $R^2$ is H.

In some embodiments of a compound of Formula (II), Formula (IIa), or Formula (IIb), or a pharmaceutically acceptable salt or solvate thereof, each $R^3$ is independently selected from H and $C_{1-4}$alkyl. In some embodiments, each $R^3$ is independently selected from H and methyl. In some embodiments, each $R^3$ is H.

In some embodiments of a compound of Formula (II), Formula (IIa), or Formula (IIb), or a pharmaceutically acceptable salt or solvate thereof, each $R^2$ and $R^3$ is H.

In some embodiments of a compound of Formula (II), Formula (IIa), or Formula (IIb), or a pharmaceutically acceptable salt or solvate thereof, X is —CH$_2$CH$_2$—. In some embodiments, X is —CH$_2$O—. In some embodiments, X is —CH$_2$CH$_2$O—. In some embodiments, X is —O—. In some embodiments, X is —N(R$^{14}$)—. In some embodiments, X is S(O)$_2$. In some embodiments, X is —CH$_2$N(R$^{14}$)—. In some embodiments, X is —CH$_2$CH$_2$N(R$^{14}$)—. In some embodiments, X is —NH—. In some embodiments, X is —CH$_2$NH—. In some embodiments, X is —CH$_2$CH$_2$NH—. In some embodiments, X is —N(CH$_3$)—. In some embodiments, X is —CH$_2$N(CH$_3$)—. In some embodiments, X is —CH$_2$CH$_2$N(CH$_3$)—.

In some embodiments of a compound of Formula (II), Formula (IIa), or Formula (IIb), or a pharmaceutically acceptable salt or solvate thereof, Y is a bond. In some embodiments, Y is —C(R$^{16}$)(R$^{17}$)—. In some embodiments, Y is —CH(R$^{17}$)—. In some embodiments, Y is —CH$_2$—. In some embodiments, Y is or —N(R$^{15}$)—. In some embodiments, Y is or —NH—. In some embodiments, Y is or —N(CH$_3$)—.

In some embodiments of a compound of Formula (II), Formula (IIa), or Formula (IIb), or a pharmaceutically acceptable salt or solvate thereof, $R^{14}$ is H or $C_{1-4}$alkyl. In some embodiments, $R^{14}$ is H or methyl. In some embodiments, $R^{14}$ is H. In some embodiments, $R^{14}$ is methyl.

In some embodiments of a compound of Formula (II), Formula (IIa), or Formula (IIb), or a pharmaceutically acceptable salt or solvate thereof, $R^{14}$ and one $R^3$ combine to form a 4-, 5-, or 6-membered heterocycloalkyl ring. In some embodiments, $R^{14}$ and one $R^3$ combine to form an azetidinyl ring, pyrrolidinyl, or piperidinyl. In some embodiments, $R^{14}$ and one $R^3$ combine to form an azetidinyl ring.

In some embodiments of a compound of Formula (II), Formula (IIa), or Formula (IIb), or a pharmaceutically acceptable salt or solvate thereof, $R^{15}$ is H or $C_{1-4}$alkyl. In some embodiments, $R^{15}$ is H or methyl. In some embodiments, $R^{15}$ is H. In some embodiments, $R^{15}$ is methyl.

In some embodiments of a compound of Formula (II), Formula (IIa), or Formula (IIb), or a pharmaceutically acceptable salt or solvate thereof, $R^{15}$ and one $R^3$ combine to form a 4-, 5-, or 6-membered heterocycloalkyl ring. In some embodiments, $R^{15}$ and one $R^3$ combine to form an azetidinyl, pyrrolidinyl, or piperidinyl ring. In some embodiments, $R^{15}$ and one $R^3$ combine to form an azetidinyl ring.

In some embodiments of a compound of Formula (II), Formula (IIa), or Formula (IIb), or a pharmaceutically acceptable salt or solvate thereof, $R^{16}$ is H or $C_{1-4}$alkyl. In some embodiments, $R^{16}$ is H or methyl. In some embodiments, $R^{16}$ is H.

In some embodiments of a compound of Formula (II), Formula (IIa), or Formula (IIb), or a pharmaceutically acceptable salt or solvate thereof, $R^{17}$ is H or $C_{1-4}$alkyl. In some embodiments, $R^{17}$ is H or methyl. In some embodiments, $R^{17}$ is H.

In some embodiments of a compound of Formula (II), Formula (IIa), or Formula (IIb), or a pharmaceutically acceptable salt or solvate thereof, $R^{17}$ and one $R^3$ combine to form a 4-, 5-, or 6-membered cycloalkyl ring. In some embodiments, $R^{17}$ and one $R^3$ combine to form a cyclobutyl, cyclopentyl, or cyclohexyl ring. In some embodiments, $R^{14}$ and one $R^3$ combine to form a cyclobutyl ring.

In some embodiments of a compound of Formula (II), Formula (IIa), or Formula (IIb), or a pharmaceutically acceptable salt or solvate thereof, n is 1, 2, 3, 4, or 5. In some embodiments, n is 1 to 2, 1 to 3, 1 to 4, 1 to 5, 2 to 3, 2 to 4, 2 to 5, 3 to 4, 3 to 5, or 4 to 5. In some embodiments, n is 1. In some embodiments, n is 2. In some embodiments, n is 3. In some embodiments, n is 4 In some embodiments, n is 5.

In some embodiments of a compound of Formula (II), Formula (IIa), or Formula (IIb), or a pharmaceutically acceptable salt or solvate thereof, X is —CH$_2$CH$_2$— and Y is a bond.

In some embodiments of a compound of Formula (II), Formula (IIa), or Formula (IIb), or a pharmaceutically acceptable salt or solvate thereof, X is —CH$_2$O— and Y is a bond.

In some embodiments of a compound of Formula (II), Formula (IIa), or Formula (IIb), or a pharmaceutically acceptable salt or solvate thereof, X is —CH$_2$N(H)— and Y is a bond.

In some embodiments of a compound of Formula (II), Formula (IIa), or Formula (IIb), or a pharmaceutically acceptable salt or solvate thereof, X is S(O)$_2$ and Y is a bond.

In some embodiments of a compound of Formula (II), Formula (IIa), or Formula (IIb), or a pharmaceutically acceptable salt or solvate thereof, X is —O—, Y is —C(R$^{16}$)(R$^{17}$)—, and R$^{17}$ and one R$^3$ combine to form a 3- or 4-membered cycloalkyl ring.

In some embodiments of a compound of Formula (II), Formula (IIa), or Formula (IIb), or a pharmaceutically acceptable salt or solvate thereof, X is —N(R$^{14}$)—; Y is bond; and R$^{14}$ and one R$^3$ combine to form a 4-, 5-, or 6-membered heterocycloalkyl ring.

In some embodiments of a compound of Formula (II), Formula (IIa), or Formula (IIb), or a pharmaceutically acceptable salt or solvate thereof, X is —O—; Y is —N(R$^{15}$)—; and R$^{15}$ and one R$^3$ combine to form a 4-, 5-, or 6-membered heterocycloalkyl ring.

In some embodiments of a compound of Formula (II), Formula (IIa), or Formula (IIb), or a pharmaceutically acceptable salt or solvate thereof, wherein

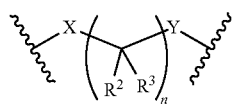

is

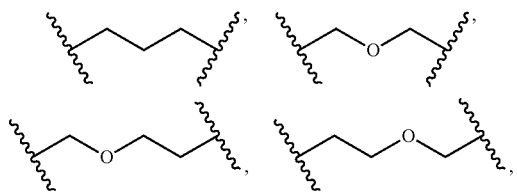

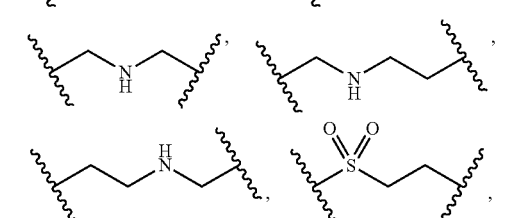

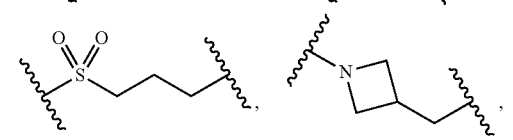

-continued

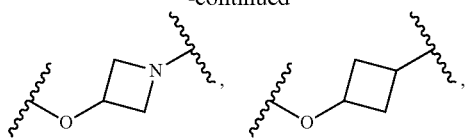

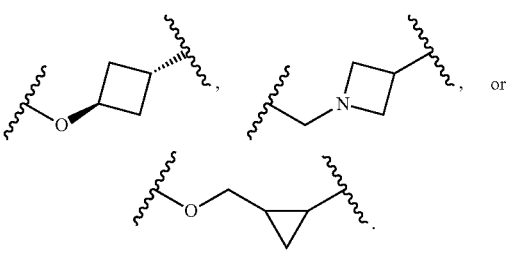

In some embodiments,

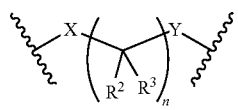

is

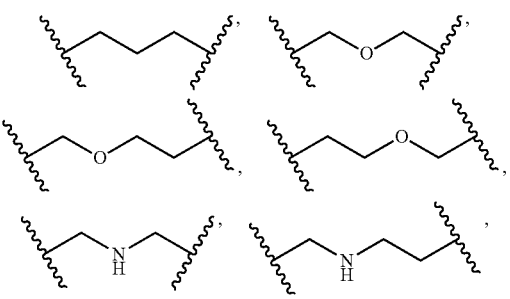

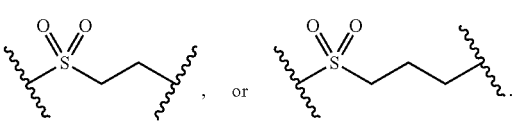 [SMILES: *CCS(*)(=O)=O ; *CCCS(*)(=O)=O]

In some embodiments,

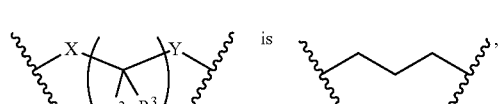

is

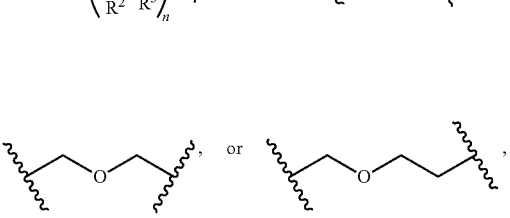

-continued
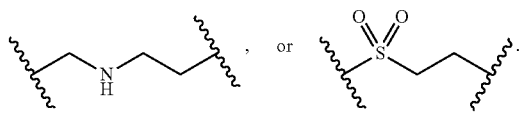
In some embodiments,
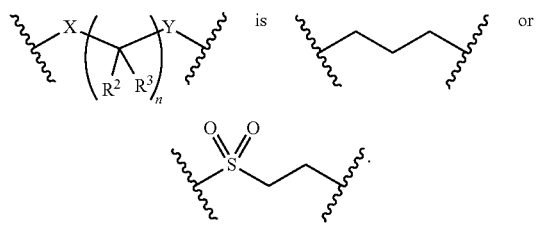
In some embodiments,
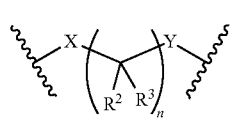
is
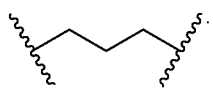 [SMILES: *CCC*]
In some embodiments,
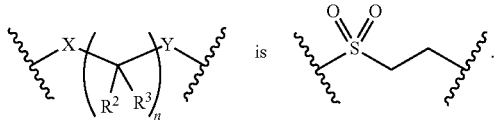
In some embodiments,
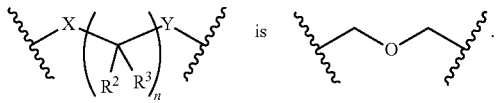
In some embodiments,
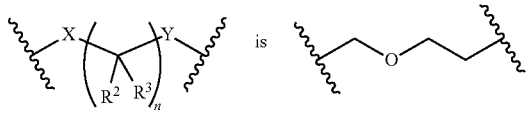
In some embodiments,
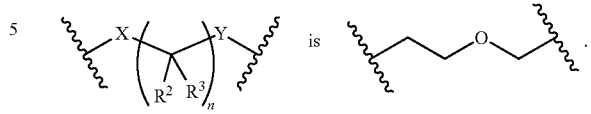
In some embodiments,
In some embodiments,
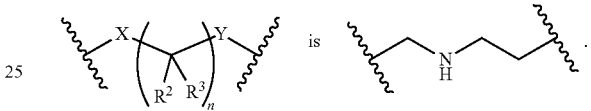
In some embodiments,
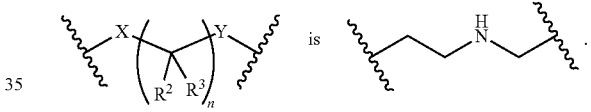
In some embodiments,
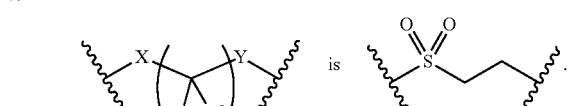
In some embodiments,
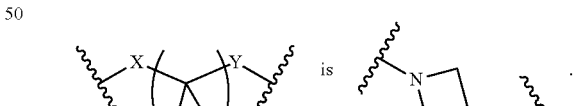
In some embodiments,
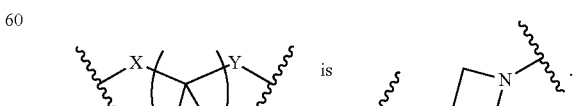

In some embodiments,

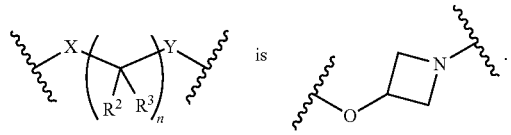 is 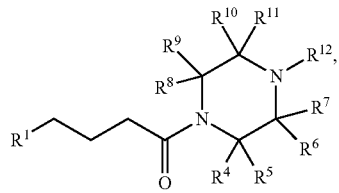.

In some embodiments,

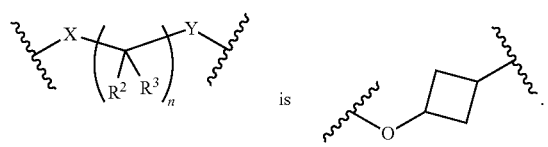 is 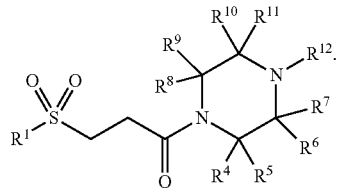.

In some embodiments,

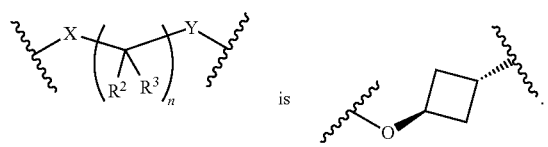 is

In some embodiments,

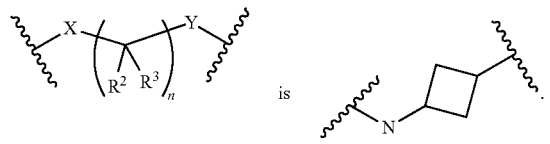 is

In some embodiments,

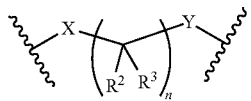

is

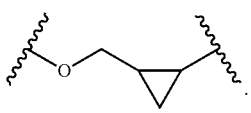 [SMILES: *OCC1CC1*].

In some embodiments is a compound of Formula (II), or a pharmaceutically acceptable salt or solvate thereof, having the structure of Formula (II-1), Formula (II-2), or a pharmaceutically acceptable salt or solvate thereof:

Formula (II-1)

Formula (II-2)

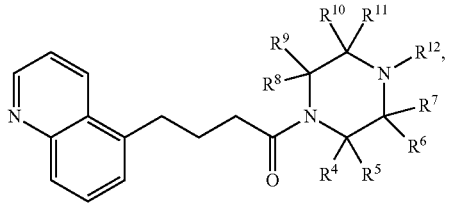

In some embodiments is a compound of Formula (IIa), or a pharmaceutically acceptable salt or solvate thereof, having the structure of Formula (IIa-1), Formula (IIa-2), or a pharmaceutically acceptable salt or solvate thereof:

Formula (IIa-1)

Formula (IIa-2)

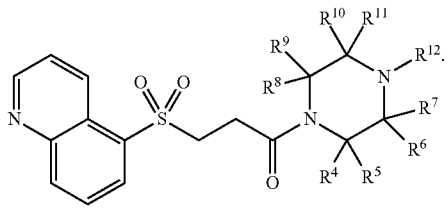

In some embodiments is a compound of Formula (IIb), or a pharmaceutically acceptable salt or solvate thereof, having the structure of Formula (IIb-1), Formula (IIb-2), or a pharmaceutically acceptable salt or solvate thereof:

Formula (IIb-1)

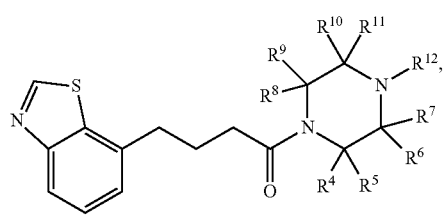

Formula (IIb-2)

[Structure: benzothiazole-SO2-CH2CH2-C(=O)-N(piperazine with R4-R12 substituents)]

In some embodiments of a compound of Formula (II), Formula (II-1), Formula (II-2), Formula (IIa), Formula (IIa-1), Formula (IIa-2), Formula (IIb), Formula (IIb-1), or Formula (IIb-2), or a pharmaceutically acceptable salt or solvate thereof, $R^4$, $R^6$, $R^8$, and $R^{10}$ are each independently selected from H and $C_{1-4}$alkyl. In some embodiments, $R^4$, $R^6$, $R^8$, and $R^{10}$ are each independently selected from H, methyl, ethyl, n-propyl, i-propyl, n-butyl, i-butyl, s-butyl, and t-butyl. In some embodiments, $R^4$, $R^6$, $R^8$, and $R^{10}$ are each independently selected from H, methyl, ethyl, n-propyl, i-propyl, and i-butyl. In some embodiments, $R^4$, $R^6$, $R^8$, and $R^{10}$ are each independently selected from H and methyl. In some embodiments, $R^4$, $R^6$, $R^8$, and $R^{10}$ are each H.

In some embodiments of a compound of Formula (II), Formula (II-1), Formula (II-2), Formula (IIa), Formula (IIa-1), Formula (IIa-2), Formula (IIb), Formula (IIb-1), or Formula (IIb-2), or a pharmaceutically acceptable salt or solvate thereof, $R^5$, $R^7$, $R^9$, and $R^{11}$ are each independently selected from H and $C_{1-4}$alkyl. In some embodiments, $R^5$, $R^7$, $R^9$, and $R^{11}$ are each independently selected from H, methyl, ethyl, n-propyl, i-propyl, n-butyl, i-butyl, s-butyl, and t-butyl. In some embodiments, $R^5$, $R^7$, $R^9$, and $R^{11}$ are each independently selected from H, methyl, ethyl, n-propyl, i-propyl, and i-butyl. In some embodiments, $R^5$, $R^7$, $R^9$, and $R^{11}$ are each independently selected from H and methyl. In some embodiments, $R^5$, $R^7$, $R^9$, and $R^{11}$ are each H.

In some embodiments of a compound of Formula (II), Formula (II-1), Formula (II-2), Formula (IIa), Formula (IIa-1), Formula (IIa-2), Formula (IIb), Formula (IIb-1), or Formula (IIb-2), or a pharmaceutically acceptable salt or solvate thereof, $R^5$ is selected from H and $C_{1-6}$alkyl. In some embodiments, $R^5$ is selected from H and $C_{1-4}$alkyl. In some embodiments, $R^5$ is selected from H, methyl, ethyl, n-propyl, i-propyl, n-butyl, i-butyl, s-butyl, and t-butyl. In some embodiments, $R^5$ is selected from H, methyl, ethyl, n-propyl, i-propyl, and i-butyl. In some embodiments, $R^5$ is selected from H and methyl. In some embodiments, $R^5$ is H. In some embodiments, $R^5$ is methyl. In some embodiments, $R^5$ is $C_{1-6}$alkyl. In some embodiments, $R^5$ is $C_{1-6}$alkyl; and $R^7$, $R^9$, and $R^{11}$ are H.

In some embodiments of a compound of Formula (II), Formula (II-1), Formula (II-2), Formula (IIa), Formula (IIa-1), Formula (IIa-2), Formula (IIb), Formula (IIb-1), or Formula (IIb-2), or a pharmaceutically acceptable salt or solvate thereof, $R^7$ is selected from H and $C_{1-6}$alkyl. In some embodiments, $R^7$ is selected from H and $C_{1-4}$alkyl. In some embodiments, $R^7$ is selected from H, methyl, ethyl, n-propyl, i-propyl, n-butyl, i-butyl, s-butyl, and t-butyl. In some embodiments, $R^7$ is selected from H, methyl, ethyl, n-propyl, i-propyl, and i-butyl. In some embodiments, $R^7$ is selected from H and methyl. In some embodiments, $R^7$ is H. In some embodiments, $R^7$ is methyl. In some embodiments, $R^7$ is $C_{1-6}$alkyl. In some embodiments, $R^7$ is $C_{1-6}$alkyl; and $R^5$, $R^9$, and $R^{11}$ are H.

In some embodiments of a compound of Formula (II), Formula (II-1), Formula (II-2), Formula (IIa), Formula (IIa-1), Formula (IIa-2), Formula (IIb), Formula (IIb-1), or Formula (IIb-2), or a pharmaceutically acceptable salt or solvate thereof, $R^9$ is selected from H and $C_{1-6}$alkyl. In some embodiments, $R^9$ is selected from H and $C_{1-4}$alkyl. In some embodiments, $R^9$ is selected from H, methyl, ethyl, n-propyl, i-propyl, n-butyl, i-butyl, s-butyl, and t-butyl. In some embodiments, $R^9$ is selected from H, methyl, ethyl, n-propyl, i-propyl, and i-butyl. In some embodiments, $R^9$ is selected from H and methyl. In some embodiments, $R^9$ is H. In some embodiments, $R^9$ is methyl. In some embodiments, $R^9$ is $C_{1-6}$alkyl. In some embodiments, $R^9$ is $C_{1-6}$alkyl; and $R^5$, $R^7$, and $R^{11}$ are H.

In some embodiments of a compound of Formula (II), Formula (II-1), Formula (II-2), Formula (IIa), Formula (IIa-1), Formula (IIa-2), Formula (IIb), Formula (IIb-1), or Formula (IIb-2), or a pharmaceutically acceptable salt or solvate thereof, $R^{11}$ is selected from H and $C_{1-6}$alkyl. In some embodiments, $R^{11}$ is selected from H and $C_{1-4}$alkyl. In some embodiments, $R^{11}$ is selected from H, methyl, ethyl, n-propyl, i-propyl, n-butyl, i-butyl, s-butyl, and t-butyl. In some embodiments, $R^{11}$ is selected from H, methyl, ethyl, n-propyl, i-propyl, and i-butyl. In some embodiments, $R^{11}$ is selected from H and methyl. In some embodiments, $R^{11}$ is H. In some embodiments, $R^{11}$ is methyl. In some embodiments, $R^{11}$ is $C_{1-6}$alkyl. In some embodiments, is $C_{1-6}$alkyl; and $R^5$, $R^7$, and $R^9$ are H.

In some embodiments of a compound of Formula (II), Formula (II-1), Formula (II-2), Formula (IIa), Formula (IIa-1), Formula (IIa-2), Formula (IIb), Formula (IIb-1), or Formula (IIb-2), or a pharmaceutically acceptable salt or solvate thereof, $R^7$ and $R^{11}$ combine to form a ring. In some embodiments, $R^7$ and $R^{11}$ combine to form a ring; and $R^5$ and $R^9$ are H.

In some embodiments of a compound of Formula (II), Formula (II-1), Formula (II-2), Formula (IIa), Formula (IIa-1), Formula (IIa-2), Formula (IIb), Formula (IIb-1), or Formula (IIb-2), or a pharmaceutically acceptable salt or solvate thereof, $R^7$ and $R^9$ combine to form a ring. In some embodiments, $R^7$ and $R^9$ combine to form a ring; and $R^5$ and $R^{11}$ are H.

In some embodiments of a compound of (II), Formula (II-1), Formula (II-2), Formula (IIa), Formula (IIa-1), Formula (IIa-2), Formula (IIb), Formula (IIb-1), or Formula (IIb-2), or a pharmaceutically acceptable salt or solvate thereof, $R^5$ and $R^9$ combine to form a ring. In some embodiments, $R^5$ and $R^9$ combine to form a ring; and $R^7$ and $R^{11}$ are H.

In some embodiments of a compound of Formula (II), Formula (II-1), Formula (II-2), Formula (IIa), Formula (IIa-1), Formula (IIa-2), Formula (IIb), Formula (IIb-1), or Formula (IIb-2), or a pharmaceutically acceptable salt or solvate thereof,

[Structure: piperazine ring with R4-R11 substituents is piperazine]

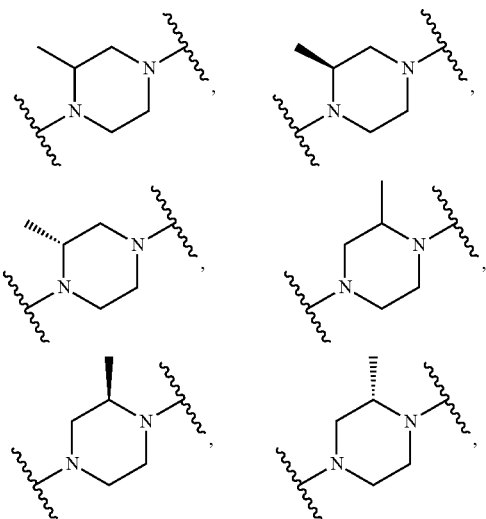
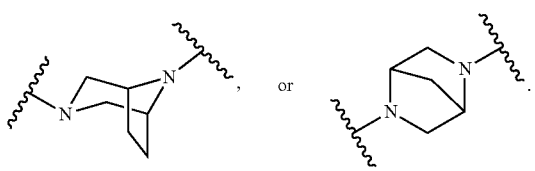 [SMILES: *N1CC2CCC(C1)N2* ; *N1CC2CC1CN2*]
or
In some embodiments,
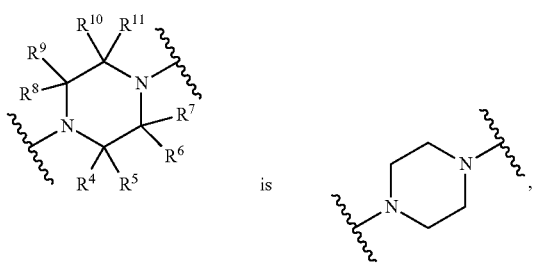
In some embodiments,
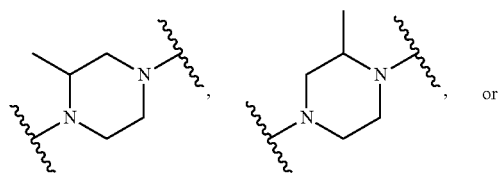
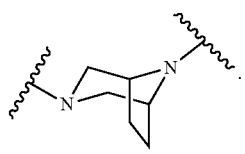.
In some embodiments,
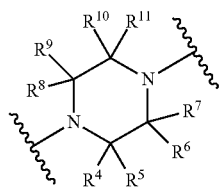 is 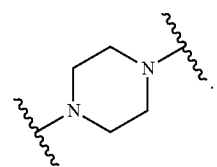 [SMILES: *N1CCN(*)CC1].
In some embodiments,
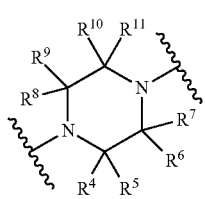 is 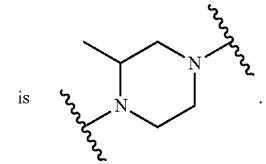.
In some embodiments,
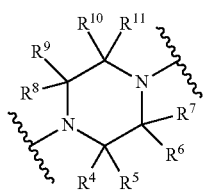 is 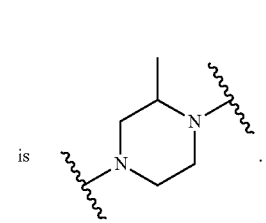.
In some embodiments,
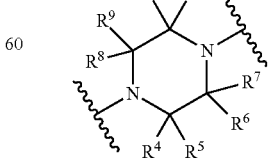 is 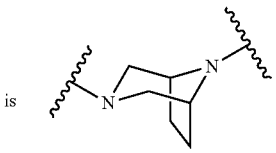.

In some embodiments provided herein is a compound having the structure of Formula (III):

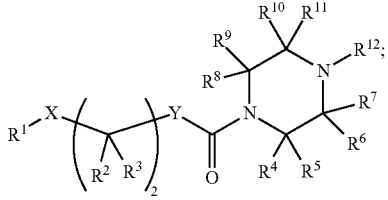

Formula (III)

wherein:
X is —CH₂CH₂—, —CH₂O—, —CH₂CH₂O—, —O—, —N(R¹⁴)—, S(O)₂, —S(O)₂N(R¹⁶)—, —CH₂N(R¹⁴)—, or —CH₂CH₂N(R¹⁴)—;
Y is a bond, —C(R¹⁶)(R¹⁷)—, or —N(R¹⁵)—;
R¹ is

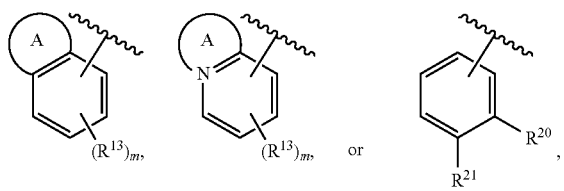

wherein ring A is a heteroaryl ring optionally substituted with halogen, —CN, —N(R²²)₂, $C_{1-6}$ alkyl, $C_{1-6}$ alkyl-OH, $C_{1-6}$ alkoxy, $C_{1-6}$haloalkyl, or $C_{1-6}$haloalkoxy;
each R² is independently selected from H and $C_{1-6}$alkyl;
each R³ is independently selected from H and $C_{1-6}$alkyl;
R⁴, R⁶, R⁸, and R¹⁰ are each independently selected from H and $C_{1-6}$alkyl;
R⁵, R⁷, R⁹, and R¹¹ are each independently selected from H and $C_{1-6}$alkyl; wherein one of R⁷ and R¹¹, R⁵ and R⁹, or R⁷ and R⁹ combine to form a ring;
R¹² is

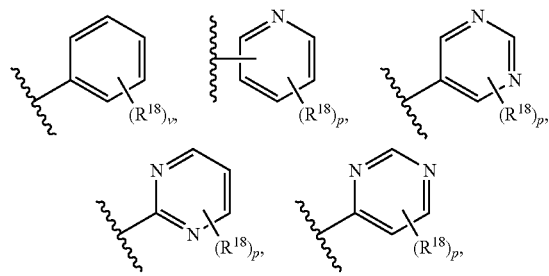

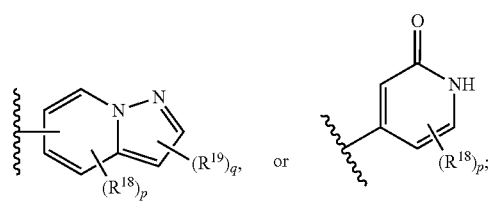

each R¹³ is independently selected from halogen, —CN, $C_{1-6}$alkyl, $C_{1-6}$alkoxy, $C_{1-6}$haloalkyl, and $C_{1-6}$haloalkoxy;

R¹⁴ is H or $C_{1-6}$alkyl; or R¹⁴ and one R³ combine to form a 4-, 5-, or 6-membered heterocycloalkyl ring;
R¹⁵ is H or $C_{1-6}$alkyl; or R¹⁵ and one R³ combine to form a 4-, 5-, or 6-membered heterocycloalkyl ring;
each R¹⁶ is independently H or $C_{1-6}$alkyl;
R¹⁷ is H or $C_{1-6}$alkyl; or R¹⁷ and one R³ combine to form a 3-, 4-, 5-, or 6-membered cycloalkyl ring;
each R¹⁸ and each R¹⁹ are each independently selected from halogen, —CN, $C_{1-6}$alkyl, hydroxy, $C_{1-6}$alkoxy, $C_{1-6}$haloalkyl, and $C_{1-6}$haloalkoxy;
R²⁰ and R²¹ combine to form a 5- or 6-membered cycloalkyl ring or a 5-membered heterocycloalkyl ring;
each R²² is independently selected from H and $C_{1-6}$alkyl;
m is 0, 1, 2, or 3;
n is 1, 2, 3, 4, or 5;
p is 0, 1, 2, or 3;
q is 0, 1, or 2; and
v is 0, 1, 2, 3, 4, or 5
or a pharmaceutically acceptable salt or solvate thereof.

In some embodiments of a compound of Formula (III), or a pharmaceutically acceptable salt or solvate thereof, R¹ is

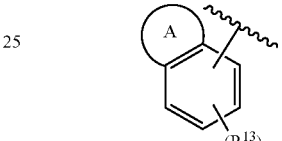

wherein ring A is a heteroaryl ring optionally substituted with halogen, —CN, —N(R²²)₂, $C_{1-6}$ alkyl, $C_{1-6}$ alkyl-OH, $C_{1-6}$ alkoxy, $C_{1-6}$haloalkyl, or $C_{1-6}$haloalkoxy. In some embodiments, R¹ is

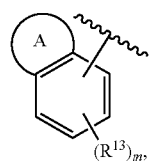

wherein ring A is a heteroaryl ring optionally substituted with halogen, —CN, —N(R²²)₂, $C_{1-6}$alkyl, $C_{1-6}$alkyl-OH, $C_{1-6}$alkoxy, $C_{1-6}$haloalkyl, or $C_{1-6}$haloalkoxy. In some embodiments, R¹ is

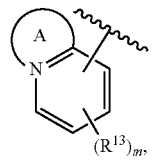

wherein ring A is a heteroaryl ring optionally substituted with halogen, —CN, —N(R²²)₂, $C_{1-6}$alkyl, $C_{1-6}$alkyl-OH, $C_{1-6}$alkoxy, $C_{1-6}$haloalkyl, or $C_{1-6}$haloalkoxy.

In some embodiments of a compound of Formula (III), or a pharmaceutically acceptable salt or solvate thereof, ring A is a 5- or 6-membered heteroaryl ring optionally substituted with halogen, —CN, —N(R²²)₂, $C_{1-6}$ alkyl, $C_{1-6}$ alkyl-OH, $C_{1-6}$ alkoxy, $C_{1-6}$haloalkyl, or $C_{1-6}$haloalkoxy. In some embodiments, ring A is a 5-membered heteroaryl ring optionally substituted with halogen, —CN, —N(R²²)₂, C$_{1-6}$alkyl, C$_{1-6}$alkyl-OH, C$_{1-6}$alkoxy, C$_{1-6}$haloalkyl, or C$_{1-6}$haloalkoxy. In some embodiments, ring A is a 6-membered heteroaryl ring optionally substituted with halogen, —CN, —N(R$^{22}$)$_2$, C$_{1-6}$alkyl, C$_{1-6}$alkyl-OH, C$_{1-6}$alkoxy, C$_{1-6}$haloalkyl, or C$_{1-6}$haloalkoxy. In some embodiments, ring A is a heteroaryl ring optionally substituted with halogen, —CN, —N(R$^{22}$)$_2$, C$_{1-6}$ alkyl, C$_{1-6}$ alkyl-OH, C$_{1-6}$alkoxy, C$_{1-6}$haloalkyl, or C$_{1-6}$haloalkoxy, wherein the heteroaryl ring is selected from the group consisting of pyrrolyl, pyrazolyl, imidazolyl, furanyl, thiophenyl, oxazolyl, isoxazolyl, thiazolyl, isothiazolyl, pyridinyl, pyridazinyl, pyrimidinyl, and pyrazinyl. In some embodiments, ring A is a heteroaryl ring optionally substituted with halogen, —CN, —N(R$^{22}$)$_2$, C$_{1-6}$ alkyl, C$_{1-6}$ alkyl-OH, C$_{1-6}$ alkoxy, C$_{1-6}$haloalkyl, or C$_{1-6}$haloalkoxy, wherein the heteroaryl ring is selected from the group consisting of pyrrolyl, pyrazolyl, imidazolyl, furanyl, thiophenyl, oxazolyl, isoxazolyl, thiazolyl, and isothiazolyl. In some embodiments, ring A is a heteroaryl ring optionally substituted with halogen, —CN, —N(R$^{22}$)$_2$, C$_{1-6}$ alkyl, C$_{1-6}$ alkyl-OH, C$_{1-6}$ alkoxy, C$_{1-6}$haloalkyl, or C$_{1-6}$haloalkoxy, wherein the heteroaryl ring is selected from the group consisting of imidazolyl, oxazolyl, and thiazolyl. In some embodiments, ring A is an imidazolyl ring optionally substituted with halogen, —CN, —N(R$^{22}$)$_2$, C$_{1-6}$ alkyl, C$_{1-6}$ alkyl-OH, C$_{1-6}$ alkoxy, C$_{1-6}$haloalkyl, or C$_{1-6}$haloalkoxy. In some embodiments, ring A is a oxazolyl ring optionally substituted with halogen, —CN, —N(R$^{22}$)$_2$, C$_{1-6}$ alkyl, C$_{1-6}$ alkyl-OH, C$_{1-6}$ alkoxy, C$_{1-6}$haloalkyl, or C$_{1-6}$haloalkoxy. In some embodiments, ring A is a thiazolyl ring optionally substituted with halogen, —CN, —N(R$^{22}$)$_2$, C$_{1-6}$alkyl, C$_{1-6}$alkyl-OH, C$_{1-6}$alkoxy, C$_{1-6}$haloalkyl, or C$_{1-6}$haloalkoxy. In some embodiments, ring A is a heteroaryl ring optionally substituted with halogen, —CN, —N(R$^{22}$)$_2$, C$_{1-6}$alkyl, C$_{1-6}$alkyl-OH, C$_{1-6}$alkoxy, C$_{1-6}$haloalkyl, or C$_{1-6}$haloalkoxy, wherein the heteroaryl ring is selected from the group consisting of pyridinyl, pyridazinyl, pyrimidinyl, and pyrazinyl. In some embodiments, ring A is a heteroaryl ring optionally substituted with halogen, —CN, —N(R$^{22}$)$_2$, C$_{1-6}$alkyl, C$_{1-6}$alkyl-OH, C$_{1-6}$alkoxy, C$_{1-6}$haloalkyl, or C$_{1-6}$haloalkoxy, wherein the heteroaryl ring is selected from the group consisting of pyridinyl and pyrimidinyl. In some embodiments, ring A is a pyridyl ring optionally substituted with halogen, —CN, —N(R$^{22}$)$_2$, C$_{1-6}$ alkyl, C$_{1-6}$ alkyl-OH, C$_{1-6}$ alkoxy, C$_{1-6}$haloalkyl, or C$_{1-6}$haloalkoxy. In some embodiments, ring A is a pyrimidinyl ring optionally substituted with halogen, —CN, —N(R$^{22}$)$_2$, C$_{1-6}$ alkyl, C$_{1-6}$ alkyl-OH, C$_{1-6}$ alkoxy, C$_{1-6}$haloalkyl, or C$_{1-6}$haloalkoxy. In some embodiments, ring A is optionally substituted with —N(R$^{22}$)$_2$, C$_{1-6}$alkyl, C$_{1-6}$alkyl-OH, or C$_{1-6}$alkoxy. In some embodiments, ring A is optionally substituted with —NH$_2$, methyl, —CH$_2$OH, or methoxy. In some embodiments, ring A is unsubstituted.

In some embodiments of a compound of Formula (III), or a pharmaceutically acceptable salt or solvate thereof, R$^1$ is

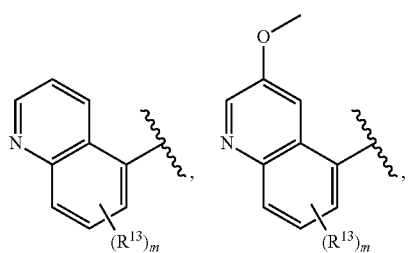

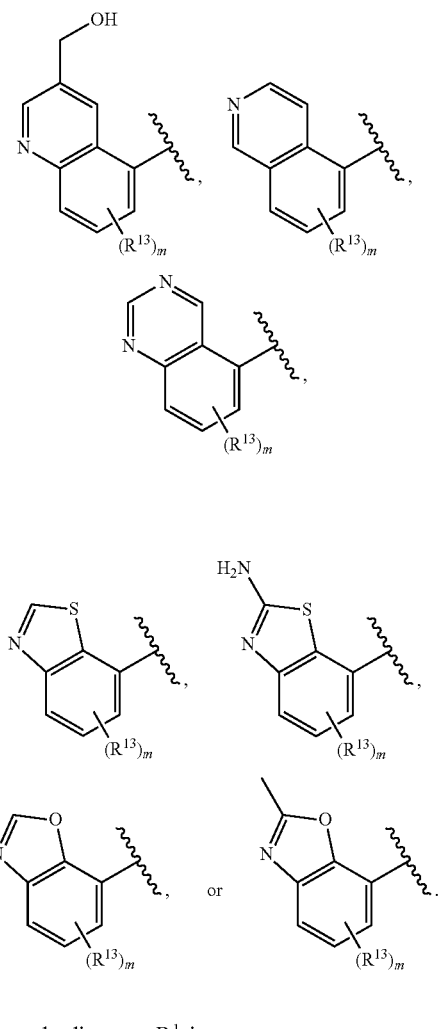

In some embodiments, R$^1$ is

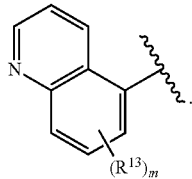

In some embodiments, R$^1$ is

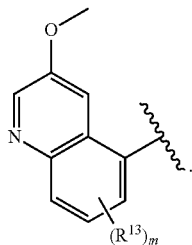

In some embodiments, R¹ is

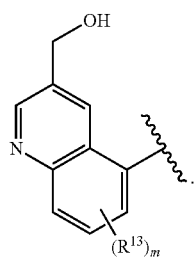

In some embodiments, R¹ is

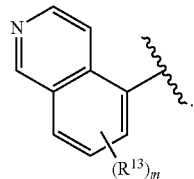

In some embodiments, R¹ is

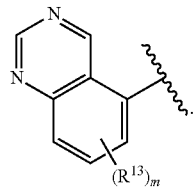

In some embodiments, R¹ is

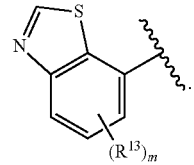

In some embodiments, R¹ is

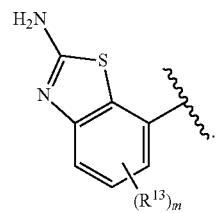

In some embodiments, R¹ is

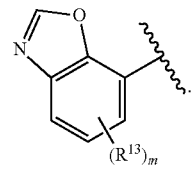

In some embodiments, R¹ is

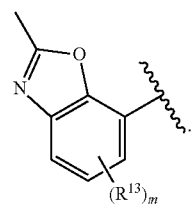

In some embodiments, R¹ is

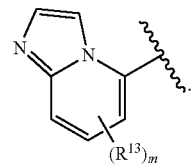

In some embodiments of a compound of Formula (III), or a pharmaceutically acceptable salt or solvate thereof, each $R^{13}$ is independently selected from halogen, —CN, $C_{1-6}$alkyl, $C_{1-6}$alkoxy, $C_{1-6}$haloalkyl, and $C_{1-6}$haloalkoxy. In some embodiments, each $R^{13}$ is independently selected from halogen, —CN, $C_{1-6}$ alkyl, and $C_{1-6}$ alkoxy.

In some embodiments of a compound of Formula (III), or a pharmaceutically acceptable salt or solvate thereof, m is 0, 1, 2, or 3. In some embodiments, m is 0 to 1, 0 to 2, 0 to 3, 1 to 2, 1 to 3, or 2 to 3. In some embodiments, m is 0. In some embodiments, m is 1. In some embodiments, m is 2. In some embodiments, m is 3.

In some embodiments of a compound of Formula (III), or a pharmaceutically acceptable salt or solvate thereof, R¹ is

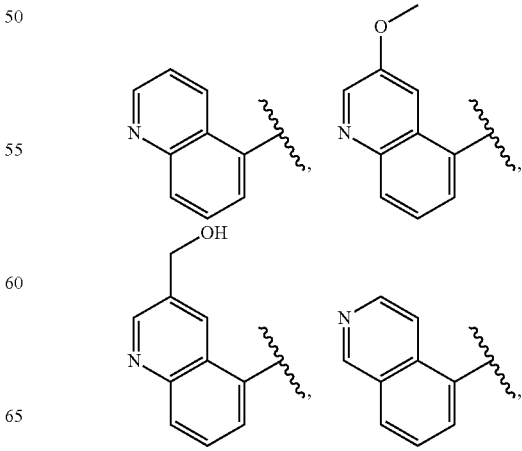

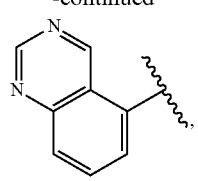,
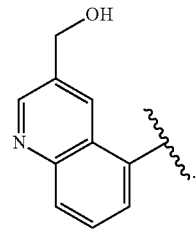
In some embodiments, R¹ is
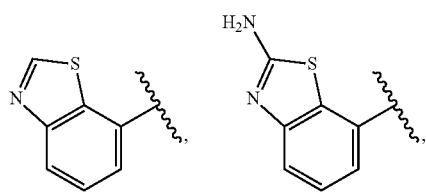 or
In some embodiments, R¹ is
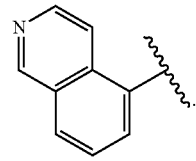
In some embodiments, R¹ is
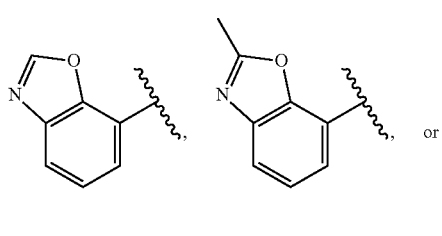
In some embodiments, R¹ is
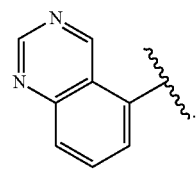
In some embodiments, R¹ is
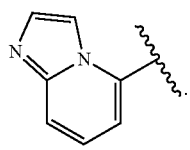.
In some embodiments, R¹ is
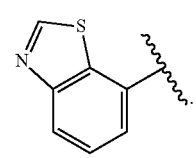
In some embodiments, R¹ is
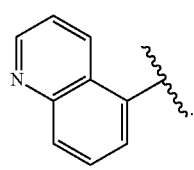.
In some embodiments, R¹ is
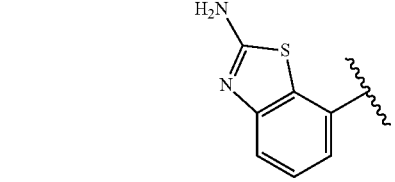
In some embodiments, R¹ is
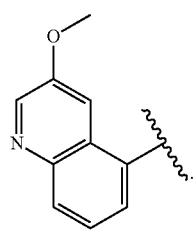
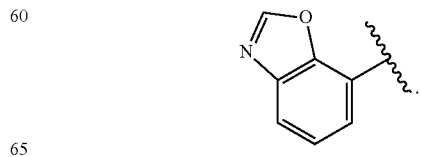

In some embodiments, $R^1$ is

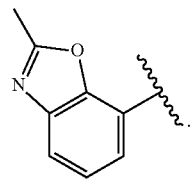

In some embodiments, $R^1$ is

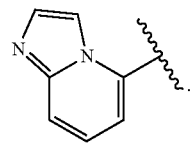

In some embodiments of a compound of Formula (III), or a pharmaceutically acceptable salt or solvate thereof, $R^1$ is

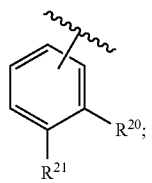

and $R^{20}$ and $R^{21}$ combine to form a 5- or 6-membered cycloalkyl ring or a 5-membered heterocycloalkyl ring. In some embodiments of a compound of Formula (III), or a pharmaceutically acceptable salt or solvate thereof, $R^1$ is

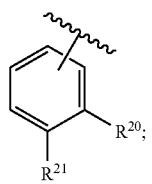

and $R^{20}$ and $R^{21}$ combine to form a 5-membered cycloalkyl ring. In some embodiments, $R^1$ is

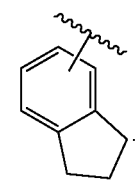

In some embodiments of a compound of Formula (III), or a pharmaceutically acceptable salt or solvate thereof, $R^1$ is

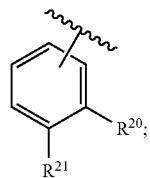

and $R^{20}$ and $R^{21}$ combine to form a 6-membered cycloalkyl ring. In some embodiments, $R^1$ is

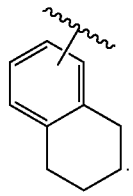

In some embodiments of a compound of Formula (III), or a pharmaceutically acceptable salt or solvate thereof, $R^1$ is

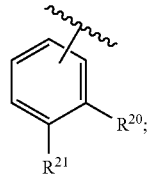

and $R^{20}$ and $R^{21}$ combine to form a 5-membered heterocycloalkyl ring. In some embodiments, $R^1$ is

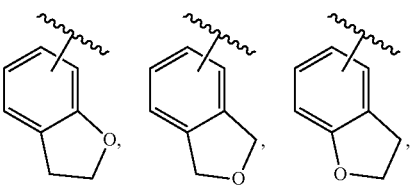

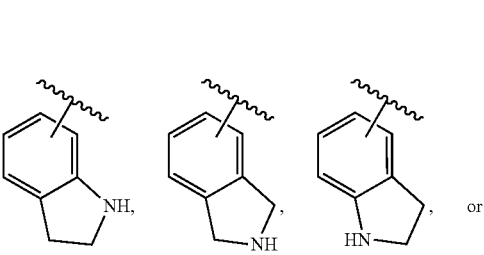

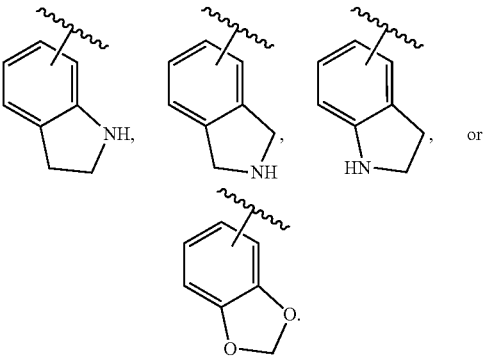

In some embodiments of a compound of Formula (III), or a pharmaceutically acceptable salt or solvate thereof, $R^4$, $R^5$, $R^6$, $R^8$, $R^9$, and $R^{10}$ are each independently selected from H and $C_{1-6}$alkyl; and $R^7$ and $R^{11}$ combine to form a ring. In some embodiments of a compound of Formula (III), or a pharmaceutically acceptable salt or solvate thereof, $R^4$, $R^5$, $R^6$, $R^8$, $R^9$, and $R^{10}$ are each H; and $R^7$ and $R^{11}$ combine to form a ring. In some embodiments of a compound of Formula (III), or a pharmaceutically acceptable salt or solvate thereof,

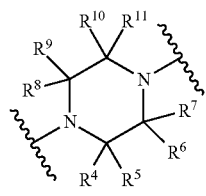 is 

In some embodiments of a compound of Formula (III), or a pharmaceutically acceptable salt or solvate thereof, $R^4$, $R^6$, $R^7$, $R^8$, $R^{10}$, and $R^{11}$ are each independently selected from H and $C_{1-6}$alkyl; and $R^5$ and $R^9$ combine to form a ring. In some embodiments of a compound of Formula (III), or a pharmaceutically acceptable salt or solvate thereof, $R^4$, $R^6$, $R^7$, $R^8$, $R^{10}$ and $R^{11}$ are each H; and $R^5$ and $R^9$ combine to form a ring. In some embodiments of a compound of Formula (III), or a pharmaceutically acceptable salt or solvate thereof,

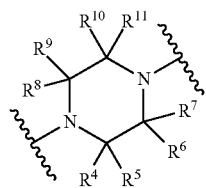 is 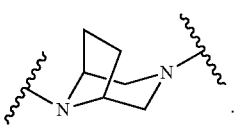

In some embodiments of a compound of Formula (III), or a pharmaceutically acceptable salt or solvate thereof, $R^4$, $R^5$, $R^6$, $R^8$, $R^{10}$, and $R^{11}$ are each independently selected from H and $C_{1-6}$alkyl; and $R^7$ and $R^9$ combine to form a ring. In some embodiments of a compound of Formula (III), or a pharmaceutically acceptable salt or solvate thereof, $R^4$, $R^5$, $R^6$, $R^8$, $R^{10}$ and $R^{11}$ are each H; and $R^7$ and $R^9$ combine to form a ring. In some embodiments of a compound of Formula (III), or a pharmaceutically acceptable salt or solvate thereof,

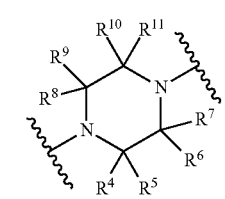 is 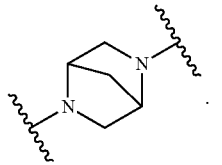

In some embodiments of a compound of Formula (III), or a pharmaceutically acceptable salt or solvate thereof, $R^{12}$ is

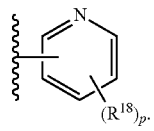

In some embodiments, $R^{12}$ is

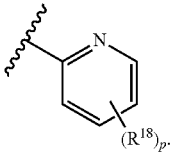

In some embodiments, $R^{12}$ is

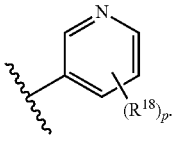

In some embodiments, $R^{12}$ is

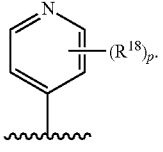

In some embodiments, $R^{12}$ is

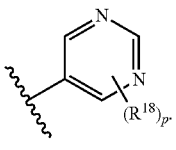

In some embodiments, $R^{12}$ is

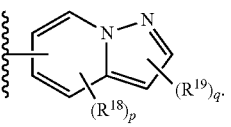

In some embodiments, $R^{12}$ is

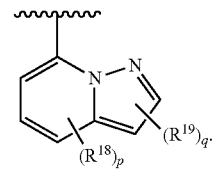

In some embodiments, R$^{12}$ is

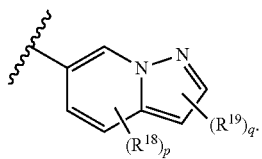

In some embodiments, R$^{12}$ is

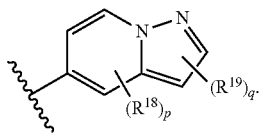

In some embodiments, R$^{12}$ is

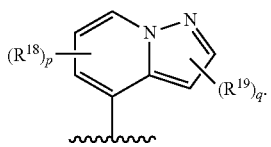

In some embodiments, R$^{12}$ is

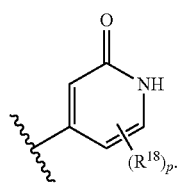

In some embodiments of a compound of Formula (III), or a pharmaceutically acceptable salt or solvate thereof, R$^{18}$ is selected from halogen, —CN, C$_{1-6}$alkoxy, and C$_{1-6}$haloalkyl. In some embodiments, R$^{18}$ is selected from —F, —Cl, —Br, —CN, C$_{1-4}$alkoxy, and C$_{1-4}$haloalkyl. In some embodiments, R$^{18}$ is selected from —F, —Cl, —CN, methyl, methoxy, and trifluoromethyl.

In some embodiments of a compound of Formula (III), or a pharmaceutically acceptable salt or solvate thereof, p is 0, 1, 2, or 3. In some embodiments, p is 0 to 1, 0 to 2, 0 to 3, 1 to 2, 1 to 3, or 2 to 3. In some embodiments, p is 0. In some embodiments, p is 1. In some embodiments, p is 2. In some embodiments, p is 3.

In some embodiments of a compound of Formula (III), or a pharmaceutically acceptable salt or solvate thereof, R$^{19}$ is selected from halogen, —CN, C$_{1-6}$alkoxy, and C$_{1-6}$haloalkyl. In some embodiments, R$^{19}$ is selected from —F, —Cl, —Br, —CN, C$_{1-4}$alkoxy, and C$_{1-4}$haloalkyl. In some embodiments, R$^{19}$ is selected from —F, —Cl, —CN, methyl, methoxy, and trifluoromethyl.

In some embodiments of a compound of Formula (III), or a pharmaceutically acceptable salt or solvate thereof, q is 0, 1, or 2. In some embodiments, q is 0 to 1, 0 to 2, or 1 to 2. In some embodiments, q is 0. In some embodiments, q is 1. In some embodiments, q is 2.

In some embodiments of a compound of Formula (III), or a pharmaceutically acceptable salt or solvate thereof, R$^{12}$ is

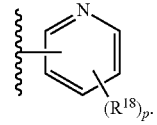

and p is 0. In some embodiments, R$^{12}$ is

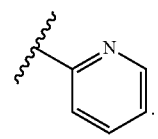

In some embodiments, R$^{12}$ is

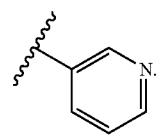 [SMILES: *c1cccnc1]

In some embodiments, R$^{12}$ is

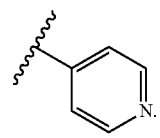 [SMILES: *c1ccncc1]

In some embodiments, R$^{12}$ is

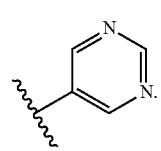

In some embodiments, R$^{12}$ is

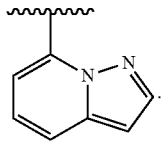 [SMILES: *c1cccc2ccnn12]

In some embodiments, $R^{12}$ is

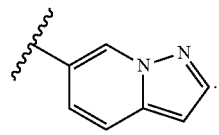 [SMILES: *c1ccc2ccnn2c1]

In some embodiments, $R^{12}$ is

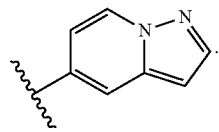 [SMILES: *c1ccn2nccc2c1]

In some embodiments, $R^{12}$ is

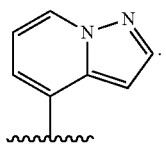 [SMILES: *c1cccn2nccc12]

In some embodiments, $R^{12}$ is

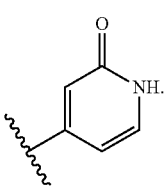 [SMILES: *c1cc[nH]c(=O)c1]

In some embodiments of a compound of Formula (III), or a pharmaceutically acceptable salt or solvate thereof, $R^{12}$ is

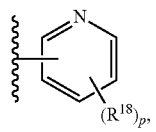

p is 1, and $R^{18}$ is selected from halogen, —CN, $C_{1-6}$alkyl, $C_{1-6}$alkoxy, and $C_{1-6}$haloalkyl. In some embodiments, $R^{12}$ is

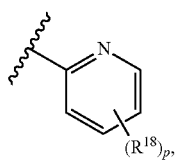

p is 1, and $R^{18}$ is selected from halogen, —CN, $C_{1-6}$ alkyl, $C_{1-6}$alkoxy, and $C_{1-6}$haloalkyl. In some embodiments, $R^{12}$ is

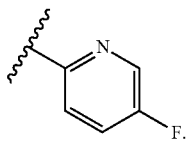 [SMILES: *c1ccc(F)cn1]

In some embodiments, $R^{12}$ is

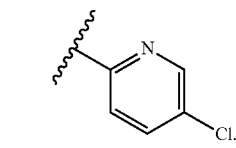 [SMILES: *c1ccc(Cl)cn1]

In some embodiments, $R^{12}$ is

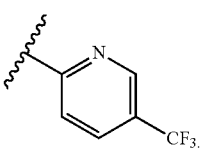

In some embodiments, $R^{12}$ is

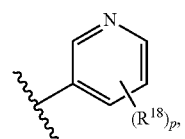

p is 1, and $R^{18}$ is selected from halogen, —CN, $C_{1-6}$alkoxy, and $C_{1-6}$haloalkyl. In some embodiments, $R^{12}$ is

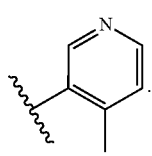

In some embodiments, $R^{12}$ is

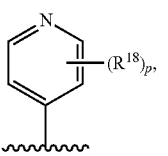

In some embodiments, $R^{12}$ is and R[18] is selected from halogen, —CN, C$_{1-6}$alkyl, C$_{1-6}$alkoxy, and C$_{1-6}$haloalkyl. In some embodiments, R[12] is

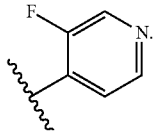 [SMILES: *c1ccncc1F]

In some embodiments, R[12] is

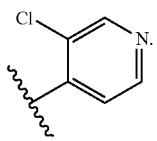

In some embodiments, R[12] is

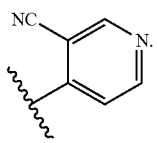 [SMILES: *c1ccncc1C#N]

In some embodiments, R[12] is

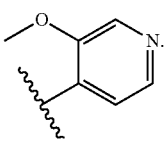 [SMILES: *c1ccncc1OC]

In some embodiments, R[12] is

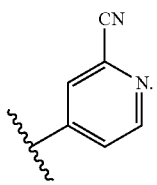

In some embodiments, R[12] is

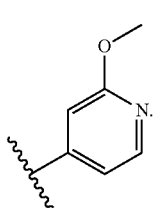 [SMILES: *c1ccnc(OC)c1]

In some embodiments, R[12] is

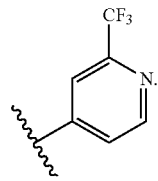

In some embodiments, R[12] is

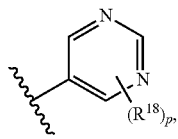

p is 1, and R[18] is selected from halogen, —CN, C$_{1-6}$alkyl, C$_{1-6}$alkoxy, and C$_{1-6}$haloalkyl. In some embodiments, R[12] is

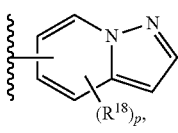

p is 1, and R[18] is selected from halogen, —CN, C$_{1-6}$alkyl, C$_{1-6}$alkoxy, and C$_{1-6}$haloalkyl. In some embodiments, R[12] is

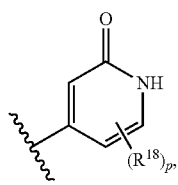

p is 1, and R[18] is selected from halogen, —CN, C$_{1-6}$alkyl, C$_{1-6}$alkoxy, and C$_{1-6}$haloalkyl. In some embodiments of a compound of Formula (III), or a pharmaceutically acceptable salt or solvate thereof, R[12] is

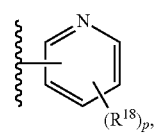

p is 2, and R[18] is selected from halogen, —CN, C$_{1-6}$alkyl, C$_{1-6}$alkoxy, and C$_{1-6}$haloalkyl. In some embodiments of a compound of Formula (III), or a pharmaceutically acceptable salt or solvate thereof, R[12] is

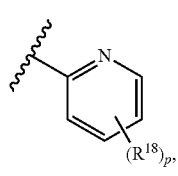

p is 2, and $R^{18}$ is selected from halogen, —CN, $C_{1-6}$alkyl, $C_{1-6}$alkoxy, and $C_{1-6}$haloalkyl. In some embodiments, $R^{12}$ is

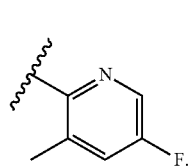 [SMILES: *c1ncc(F)cc1C]

In some embodiments, $R^{12}$ is

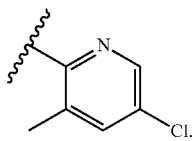 [SMILES: *c1ncc(Cl)cc1C]

In some embodiments, $R^{12}$ is

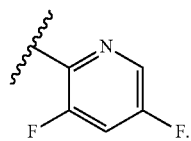

In some embodiments, $R^{12}$ is

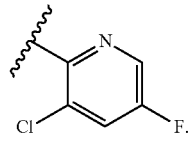 [SMILES: *c1ncc(F)cc1Cl]

In some embodiments, $R^{12}$ is

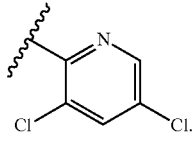 [SMILES: *c1ncc(Cl)cc1Cl]

In some embodiments, $R^{12}$ is

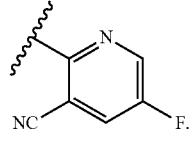 [SMILES: *c1ncc(F)cc1C#N]

In some embodiments, $R^{12}$ is

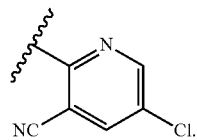 [SMILES: *c1ncc(Cl)cc1C#N]

In some embodiments of a compound of Formula (III), or a pharmaceutically acceptable salt or solvate thereof, $R^{12}$ is

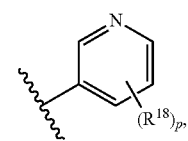

p is 2, and $R^{18}$ is selected from halogen, —CN, $C_{1-6}$alkyl, $C_{1-6}$alkoxy, and $C_{1-6}$haloalkyl. In some embodiments of a compound of Formula (III), or a pharmaceutically acceptable salt or solvate thereof, $R^{12}$ is

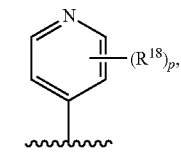

p is 2, and $R^{18}$ is selected from halogen, —CN, $C_{1-6}$alkyl, $C_{1-6}$alkoxy, and $C_{1-6}$haloalkyl.

In some embodiments of a compound of Formula (III), or a pharmaceutically acceptable salt or solvate thereof, $R^{12}$ is

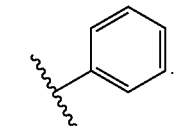

In some embodiments of a compound of Formula (III), or a pharmaceutically acceptable salt or solvate thereof, $R^{12}$ is

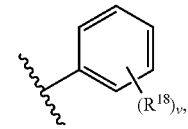

v is 1, and $R^{18}$ is selected from halogen, —CN, $C_{1-6}$alkyl, $C_{1-6}$alkoxy, and $C_{1-6}$haloalkyl. In some embodiments, $R^{12}$ is

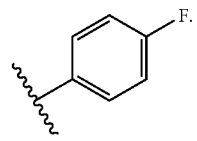

In some embodiments, $R^{12}$ is

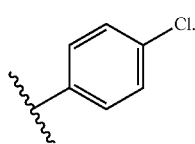 [SMILES: *c1ccc(Cl)cc1]

In some embodiments, $R^{12}$ is

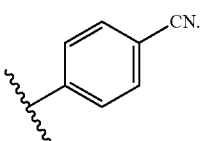 [SMILES: *c1ccc(C#N)cc1]

In some embodiments, $R^{12}$ is

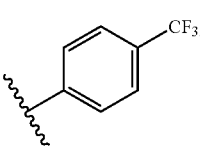

In some embodiments of a compound of Formula (III), or a pharmaceutically acceptable salt or solvate thereof, $R^{12}$ is

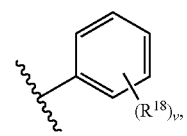

v is 2, and $R^{18}$ is selected from halogen, —CN, $C_{1-6}$alkyl, $C_{1-6}$alkoxy, and $C_{1-6}$haloalkyl. In some embodiments, $R^{12}$ is

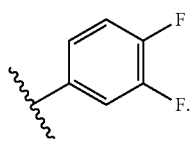

In some embodiments, $R^{12}$ is

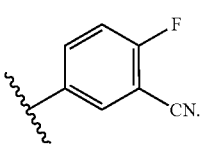 [SMILES: *c1ccc(F)c(C#N)c1]

In some embodiments of a compound of Formula (III), or a pharmaceutically acceptable salt or solvate thereof, $R^{12}$ is

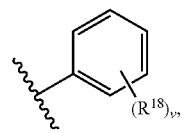

v is 3, and $R^{18}$ is selected from halogen, —CN, $C_{1-6}$alkyl, $C_{1-6}$alkoxy, and $C_{1-6}$haloalkyl. In some embodiments, $R^{12}$ is

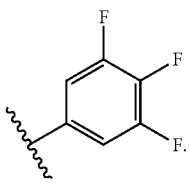 [SMILES: *c1cc(F)c(F)c(F)c1]

In some embodiments of a compound of Formula (III), or a pharmaceutically acceptable salt or solvate thereof, $R^{12}$ is

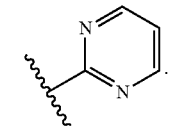

In some embodiments of a compound of Formula (III), or a pharmaceutically acceptable salt or solvate thereof, $R^{12}$ is

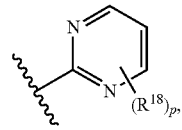

p is 1, and $R^{18}$ is selected from halogen, —CN, $C_{1-6}$alkyl, $C_{1-6}$alkoxy, and $C_{1-6}$haloalkyl. In some embodiments, $R^{12}$ is

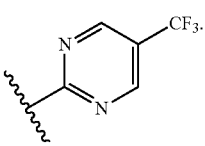

In some embodiments, $R^{12}$ is

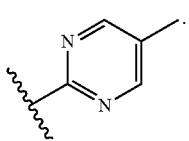

In some embodiments, $R^{12}$ is

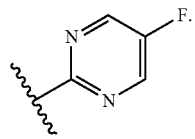

In some embodiments of a compound of Formula (III), or a pharmaceutically acceptable salt or solvate thereof, $R^{12}$ is

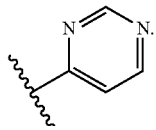 [SMILES: *c1ccncn1]

In some embodiments of a compound of Formula (III), or a pharmaceutically acceptable salt or solvate thereof, $R^{12}$ is

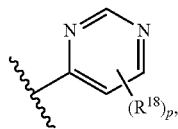

p is 1, and $R^{18}$ is selected from halogen, —CN, $C_{1-6}$alkyl, $C_{1-6}$alkoxy, and $C_{1-6}$haloalkyl.

In some embodiments of a compound of Formula (III), or a pharmaceutically acceptable salt or solvate thereof, each $R^2$ is independently selected from H and $C_{1-4}$alkyl. In some embodiments, each $R^2$ is independently selected from H and methyl. In some embodiments, each $R^2$ is H. In some embodiments, each $R^2$ is $C_{1-4}$alkyl. In some embodiments, each $R^2$ is methyl.

In some embodiments of a compound of Formula (III), or a pharmaceutically acceptable salt or solvate thereof, each $R^3$ is independently selected from H and $C_{1-4}$alkyl. In some embodiments, each $R^3$ is independently selected from H and methyl. In some embodiments, each $R^3$ is H. In some embodiments, each $R^3$ is $C_{1-4}$alkyl. In some embodiments, each $R^3$ is methyl.

In some embodiments of a compound of Formula (III), or a pharmaceutically acceptable salt or solvate thereof, each $R^2$ and $R^3$ is H.

In some embodiments of a compound of Formula (III), or a pharmaceutically acceptable salt or solvate thereof, X is —$CH_2CH_2$—. In some embodiments, X is —$CH_2O$—. In some embodiments, X is —$CH_2CH_2O$—. In some embodiments, X is —O—. In some embodiments, X is —$N(R^{14})$—. In some embodiments, X is $S(O)_2$. In some embodiments, X is —$S(O)_2N(R^{16})$—. In some embodiments, X is —$CH_2N(R^{14})$—. In some embodiments, X is —$CH_2CH_2N(R^{14})$—. In some embodiments, X is —NH—. In some embodiments, X is —$CH_2NH$—. In some embodiments, X is —$CH_2CH_2NH$—. In some embodiments, X is —$N(CH_3)$—. In some embodiments, X is —$CH_2N(CH_3)$—. In some embodiments, X is —$CH_2CH_2N(CH_3)$—.

In some embodiments of a compound of Formula (III), or a pharmaceutically acceptable salt or solvate thereof, Y is a bond. In some embodiments, Y is —$C(R^{16})(R^{17})$—. In some embodiments, Y is —$CH(R^{17})$—. In some embodiments, Y is —$CH_2$—. In some embodiments, Y is or —$N(R^{15})$—. In some embodiments, Y is or —NH—. In some embodiments, Y is or —$N(CH_3)$—.

In some embodiments of a compound of Formula (III), or a pharmaceutically acceptable salt or solvate thereof, $R^{14}$ is H or $C_{1-4}$alkyl. In some embodiments, $R^{14}$ is H or methyl. In some embodiments, $R^{14}$ is H. In some embodiments, $R^{14}$ is methyl.

In some embodiments of a compound of Formula (III), or a pharmaceutically acceptable salt or solvate thereof, $R^{14}$ and one $R^3$ combine to form a 4-, 5-, or 6-membered heterocycloalkyl ring. In some embodiments, $R^{14}$ and one $R^3$ combine to form an azetidinyl ring, pyrrolidinyl, or piperidinyl. In some embodiments, $R^{14}$ and one $R^3$ combine to form an azetidinyl ring.

In some embodiments of a compound of Formula (III), or a pharmaceutically acceptable salt or solvate thereof, $R^{15}$ is H or $C_{1-4}$alkyl. In some embodiments, $R^{15}$ is H or methyl. In some embodiments, $R^{15}$ is H. In some embodiments, $R^{15}$ is methyl.

In some embodiments of a compound of Formula (III), or a pharmaceutically acceptable salt or solvate thereof, $R^{15}$ and one $R^3$ combine to form a 4-, 5-, or 6-membered heterocycloalkyl ring. In some embodiments, $R^{15}$ and one $R^3$ combine to form an azetidinyl, pyrrolidinyl, or piperidinyl ring. In some embodiments, $R^{15}$ and one $R^3$ combine to form an azetidinyl ring.

In some embodiments of a compound of Formula (III), or a pharmaceutically acceptable salt or solvate thereof, $R^{16}$ is H or $C_{1-4}$alkyl. In some embodiments, $R^{16}$ is H or methyl. In some embodiments, $R^{16}$ is H.

In some embodiments of a compound of Formula (III), or a pharmaceutically acceptable salt or solvate thereof, $R^{17}$ is H or $C_{1-4}$alkyl. In some embodiments, $R^{17}$ is H or methyl. In some embodiments, $R^{17}$ is H.

In some embodiments of a compound of Formula (III), or a pharmaceutically acceptable salt or solvate thereof, $R^{17}$ and one $R^3$ combine to form a 4-, 5-, or 6-membered cycloalkyl ring. In some embodiments, $R^{17}$ and one $R^3$ combine to form a cyclobutyl, cyclopentyl, or cyclohexyl ring. In some embodiments, $R^{14}$ and one $R^3$ combine to form a cyclobutyl ring.

In some embodiments of a compound of Formula (III), or a pharmaceutically acceptable salt or solvate thereof, n is 1, 2, 3, 4, or 5. In some embodiments, n is 1 to 2, 1 to 3, 1 to 4, 1 to 5, 2 to 3, 2 to 4, 2 to 5, 3 to 4, 3 to 5, or 4 to 5. In some embodiments, n is 1. In some embodiments, n is 2. In some embodiments, n is 3. In some embodiments, n is 4 In some embodiments, n is 5.

In some embodiments of a compound of Formula (III), or a pharmaceutically acceptable salt or solvate thereof, X is —$CH_2CH_2$— and Y is a bond.

In some embodiments of a compound of Formula (III), or a pharmaceutically acceptable salt or solvate thereof, X is —$CH_2O$— and Y is a bond.

In some embodiments of a compound of Formula (III), or a pharmaceutically acceptable salt or solvate thereof, X is —$CH_2N(H)$— and Y is a bond.

In some embodiments of a compound of Formula (III), or a pharmaceutically acceptable salt or solvate thereof, X is $S(O)_2$ and Y is a bond.

In some embodiments of a compound of Formula (III), or a pharmaceutically acceptable salt or solvate thereof, X is —$S(O)_2N(H)$— and Y is a bond.

In some embodiments of a compound of Formula (III), or a pharmaceutically acceptable salt or solvate thereof, X is —O—, Y is —C(R$^{16}$)(R$^{17}$)—, and R$^{17}$ and one R$^3$ combine to form a 3- or 4-membered cycloalkyl ring.

In some embodiments of a compound of Formula (III), or a pharmaceutically acceptable salt or solvate thereof, X is —N(R$^{14}$)—; Y is bond; and R$^{14}$ and one R$^3$ combine to form a 4-, 5-, or 6-membered heterocycloalkyl ring.

In some embodiments of a compound of Formula (III), or a pharmaceutically acceptable salt or solvate thereof, X is —O—; Y is —N(R$^{15}$)—; and R$^{15}$ and one R$^3$ combine to form a 4-, 5-, or 6-membered heterocycloalkyl ring. In some embodiments of a compound of Formula (III), or a pharmaceutically acceptable salt or solvate thereof, wherein

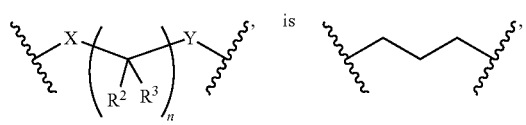

is

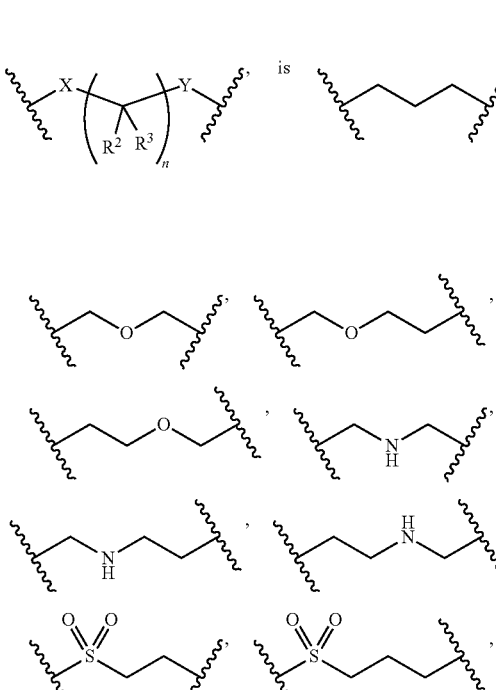

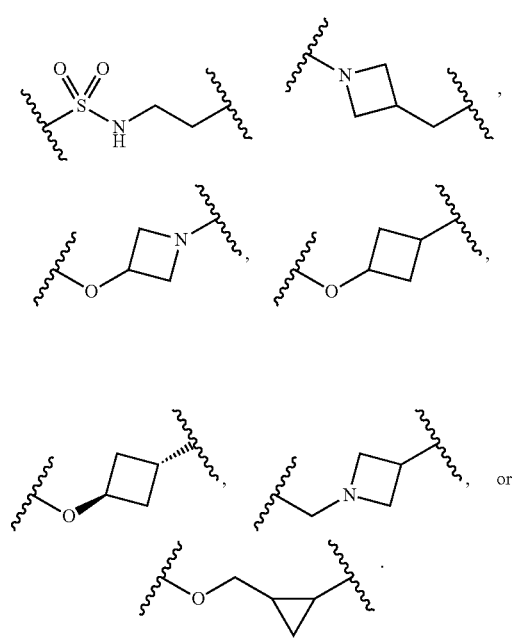

In some embodiments,

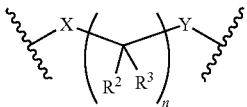

is

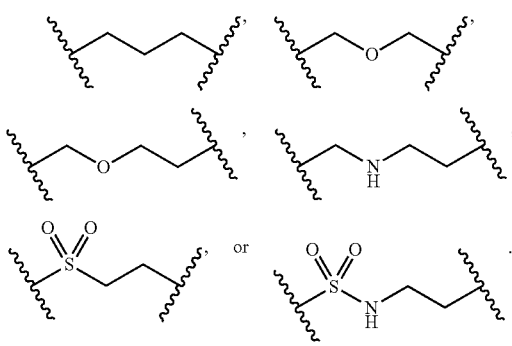

In some embodiments,

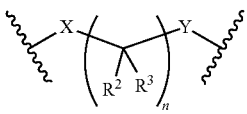

is

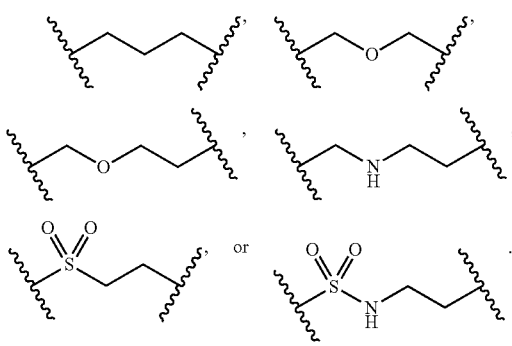

In some embodiments,
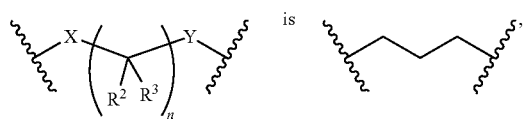 is 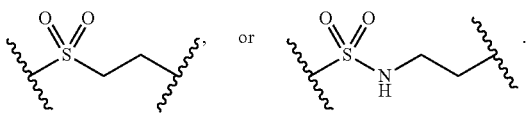,
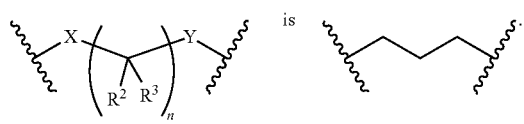 or 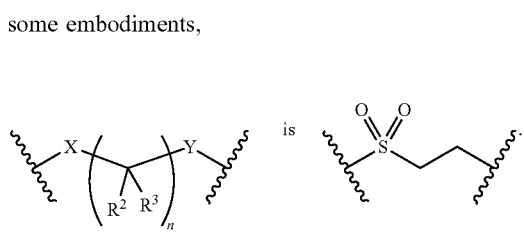.
In some embodiments,
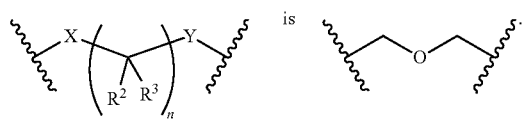 is 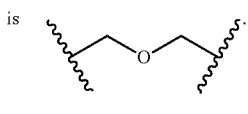.
In some embodiments,
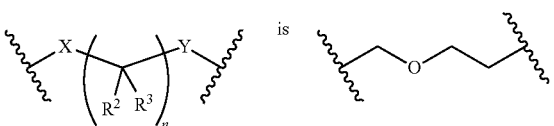 is 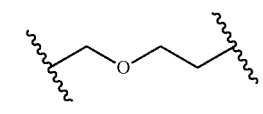.
In some embodiments,
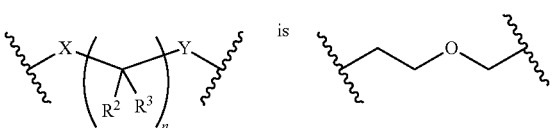 is 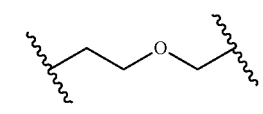.
In some embodiments,
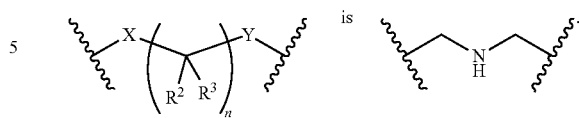 is 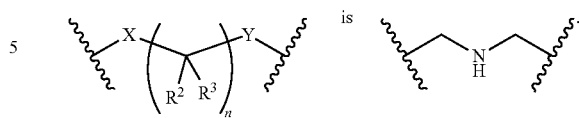.
In some embodiments,
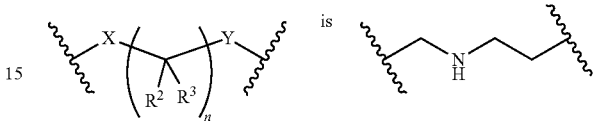 is 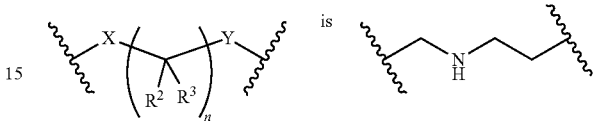.
In some embodiments,
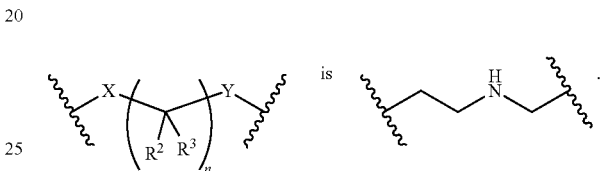 is 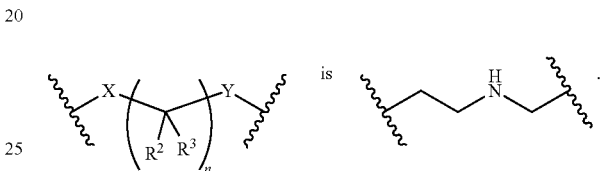.
In some embodiments,
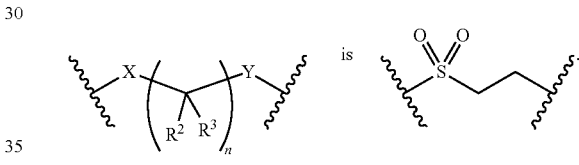 is 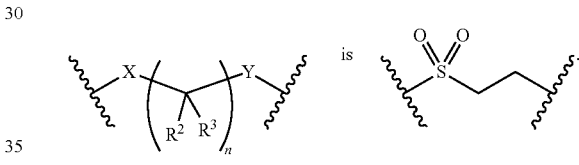.
In some embodiments,
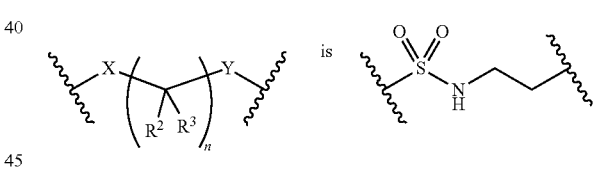 is 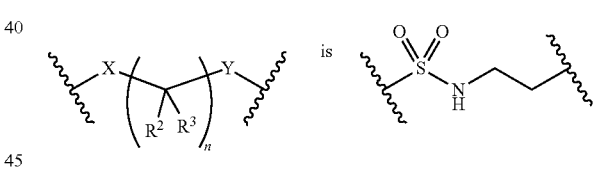.
In some embodiments,
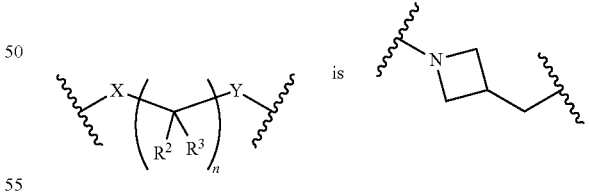 is 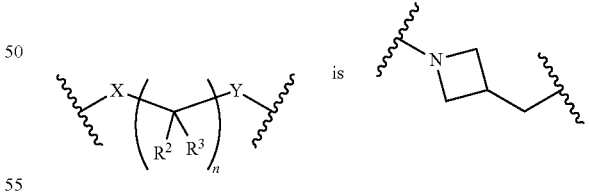.
In some embodiments,
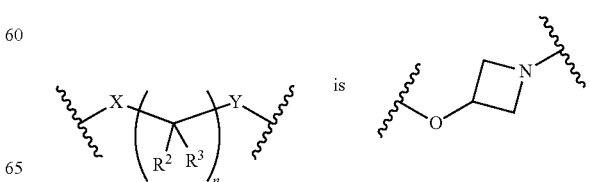 is 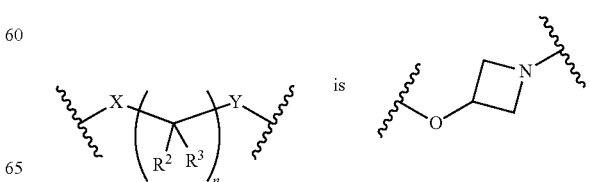.

In some embodiments,

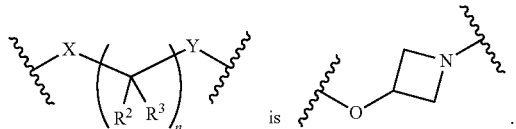 is 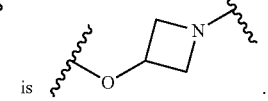.

In some embodiments,

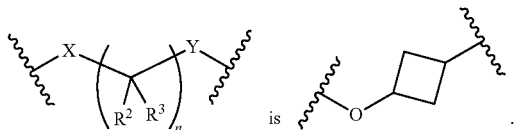 is 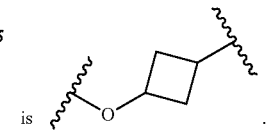.

In some embodiments,

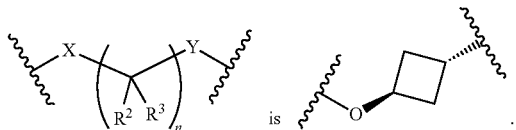 is 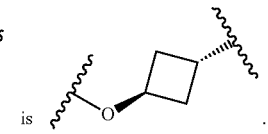.

In some embodiments,

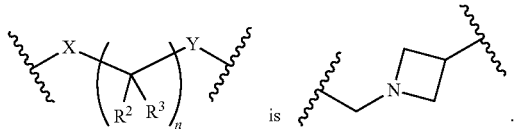 is 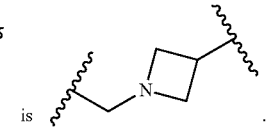.

In some embodiments,

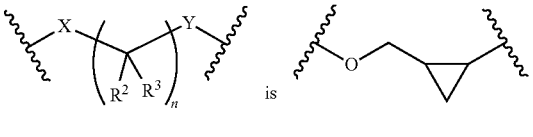 is 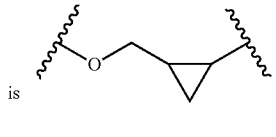.

Any combination of the groups described above for the various variables is contemplated herein. Throughout the specification, groups and substituents thereof can be chosen to provide stable moieties and compounds.

In some embodiments is a compound selected from:

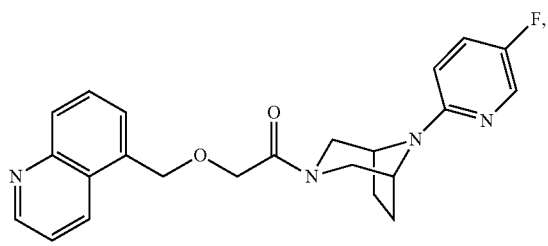

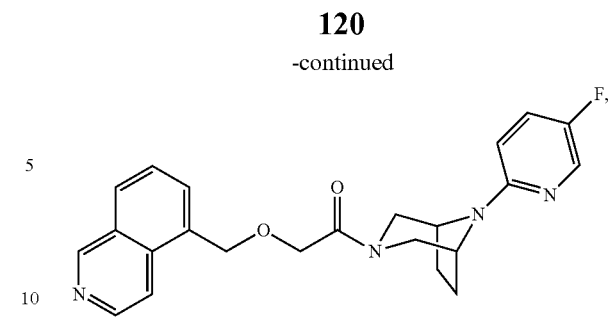

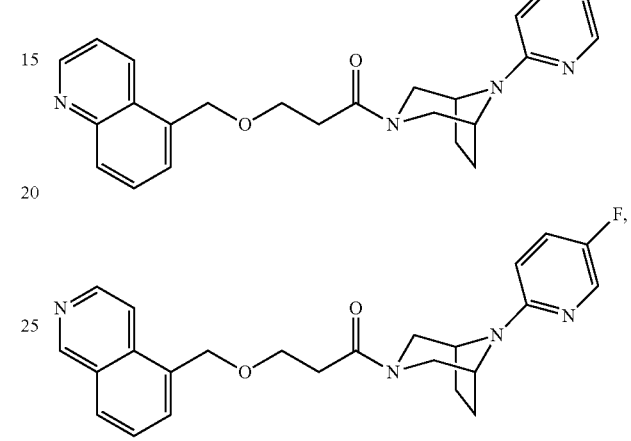

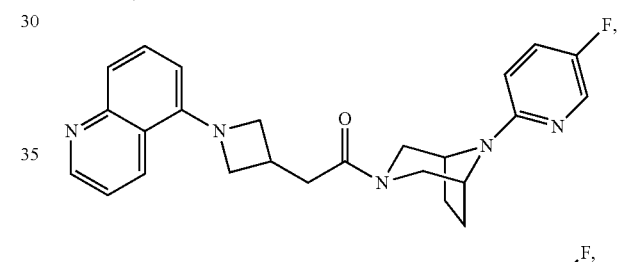

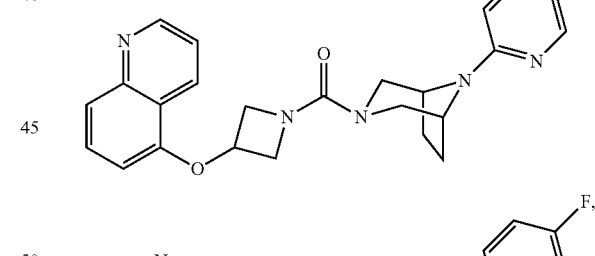

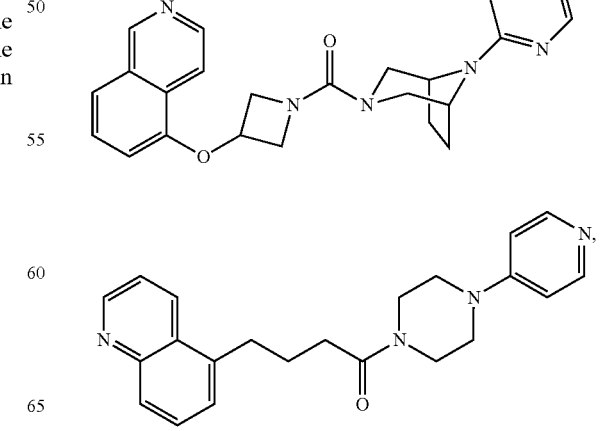

121
-continued
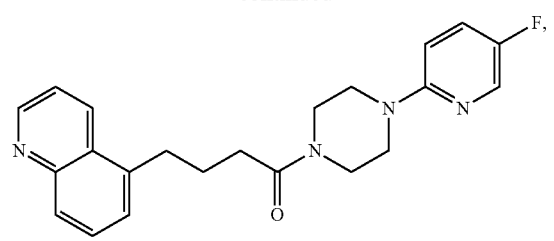
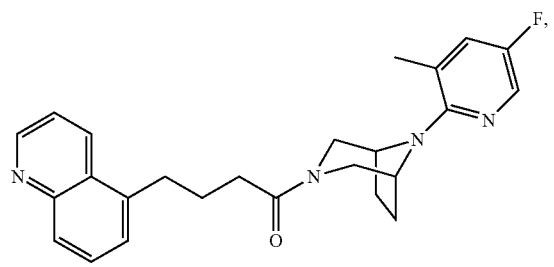
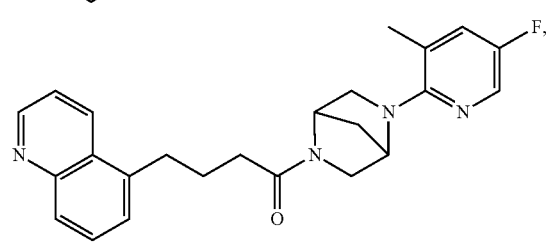
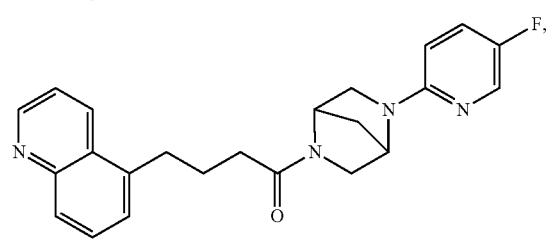
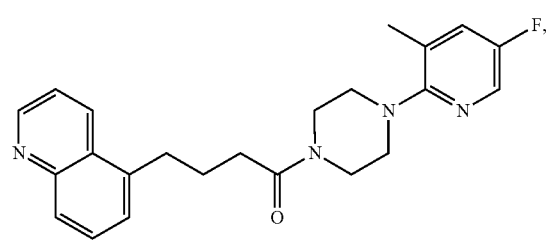
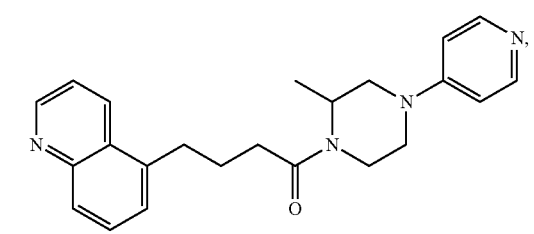
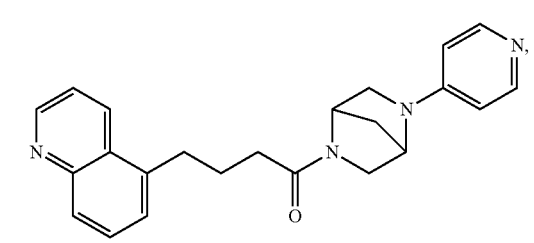
122
-continued
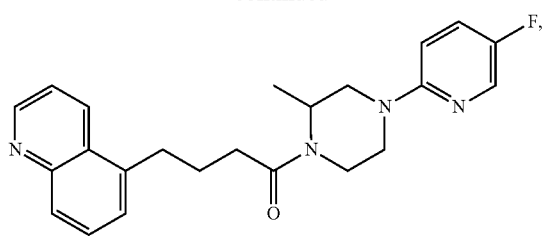
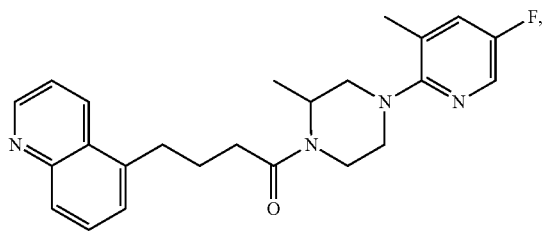
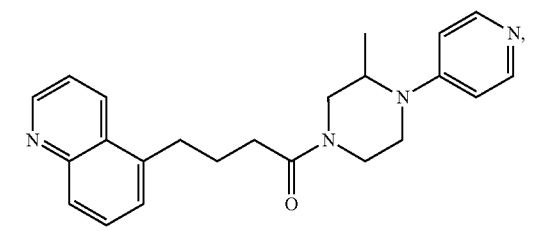
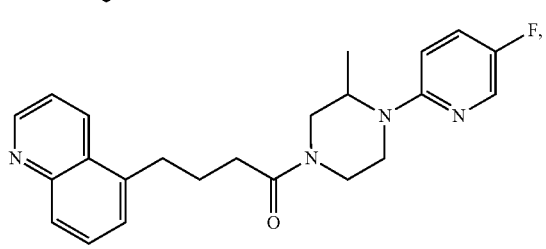
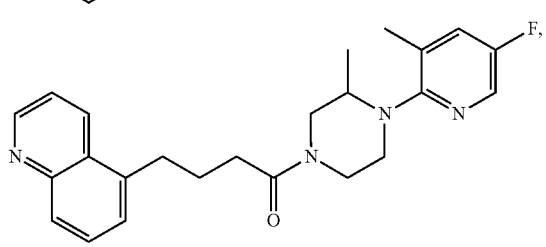
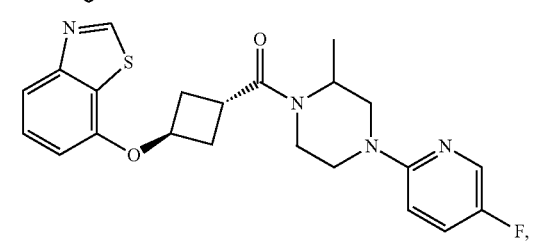
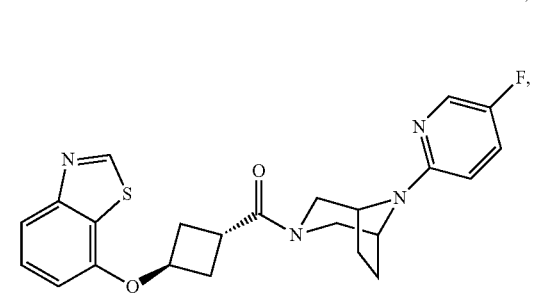

123
-continued
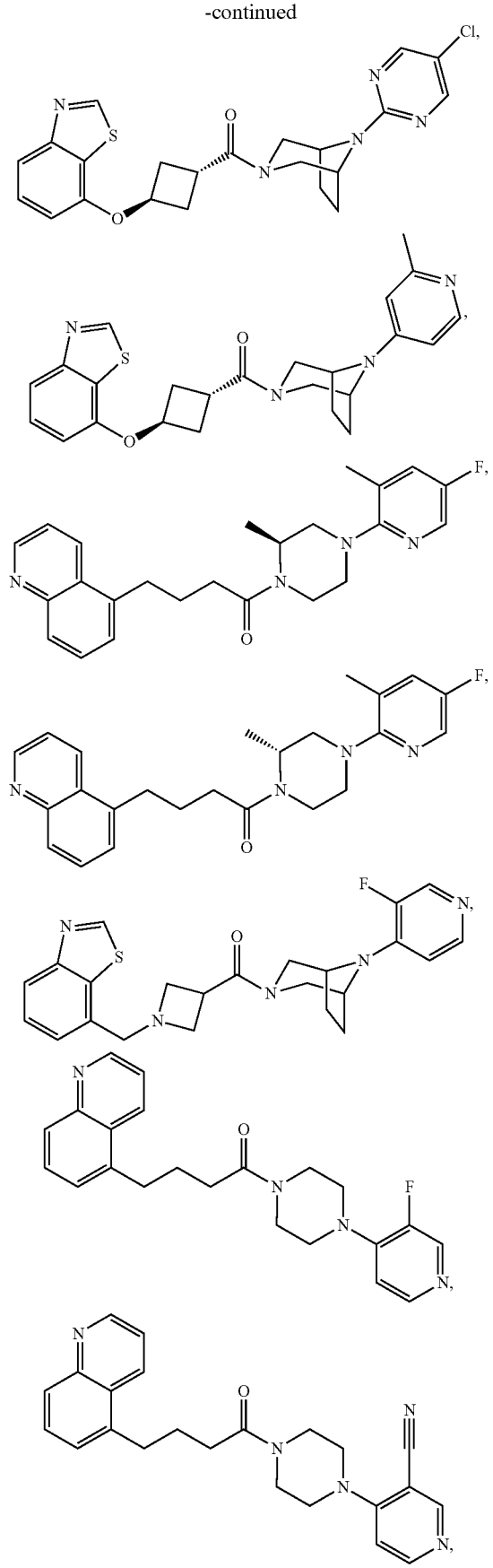
124
-continued
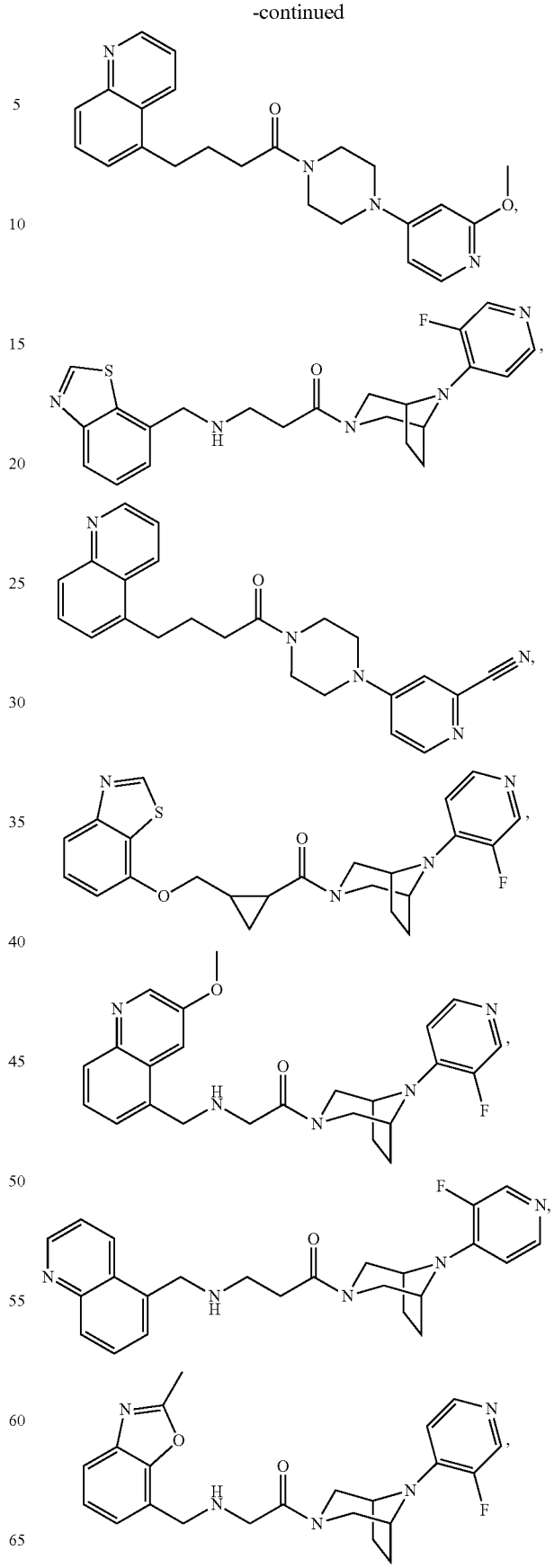

125
-continued
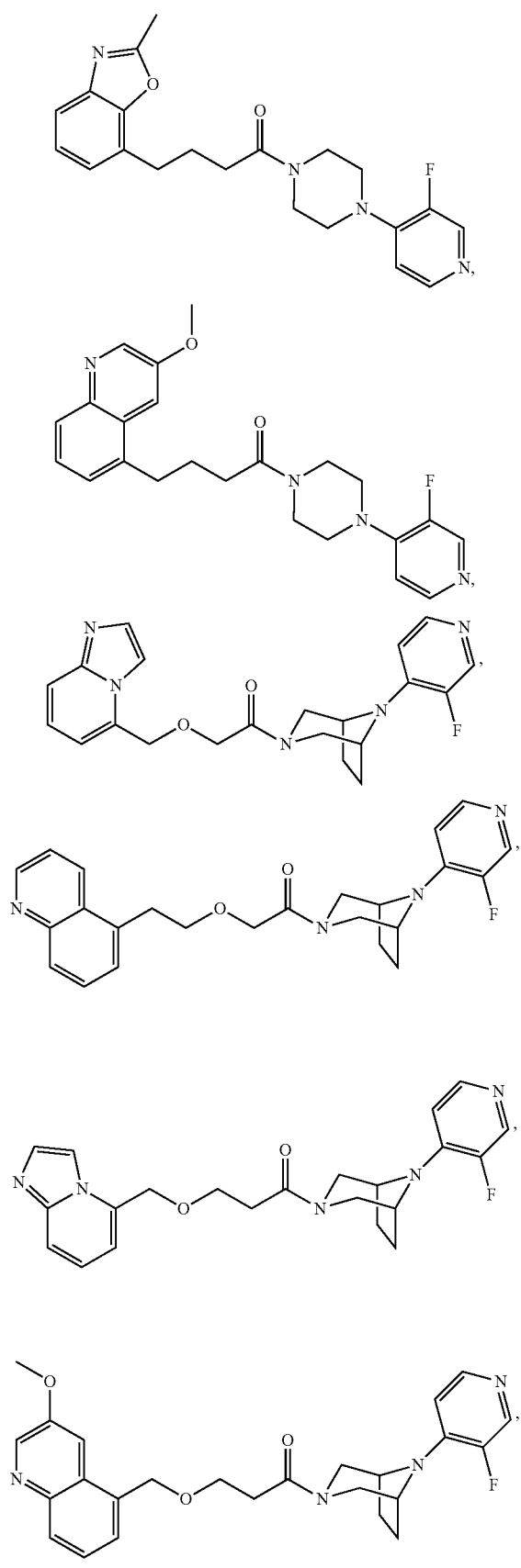
126
-continued
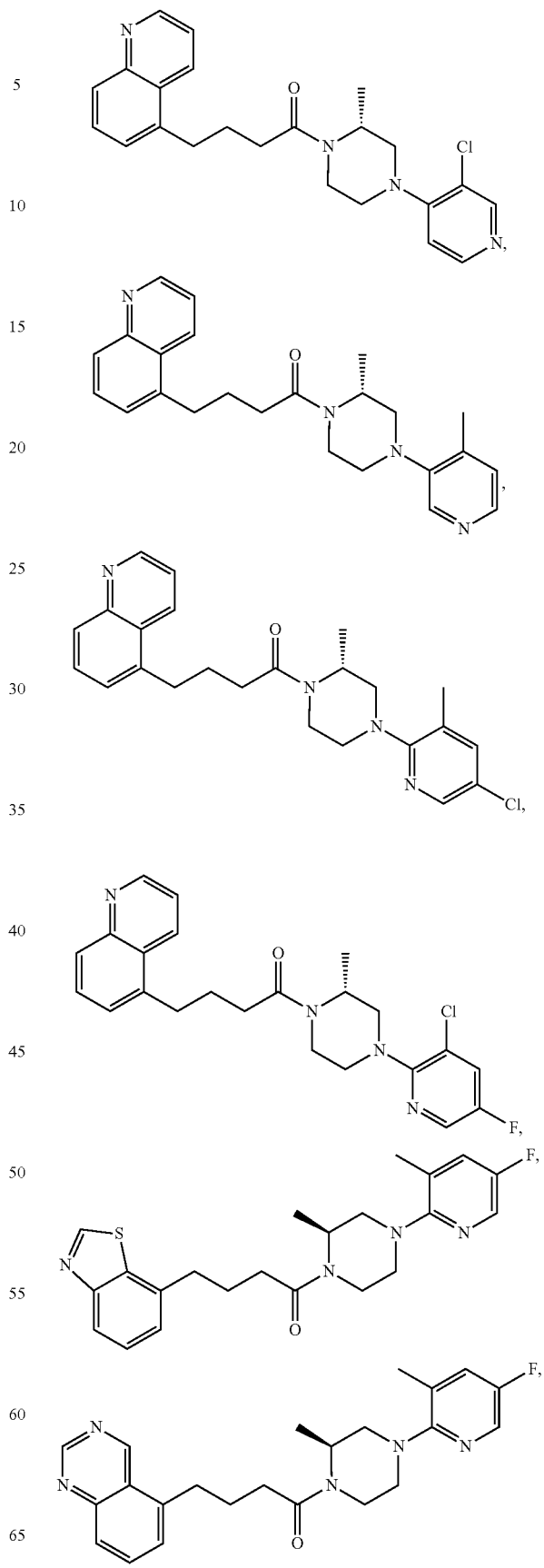

127
-continued
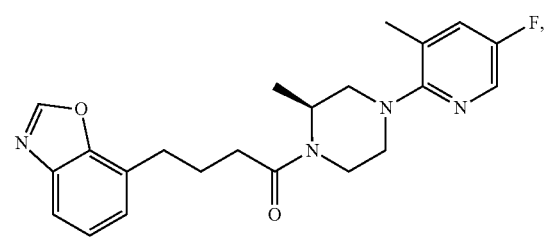
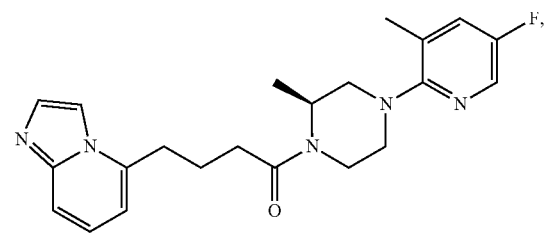
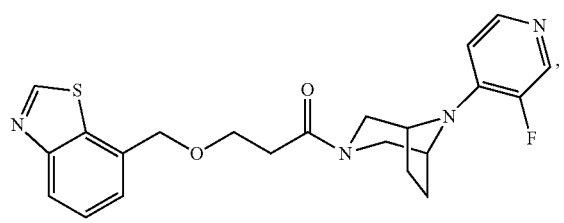
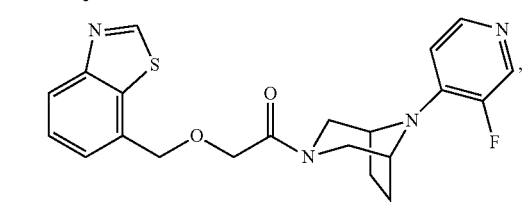
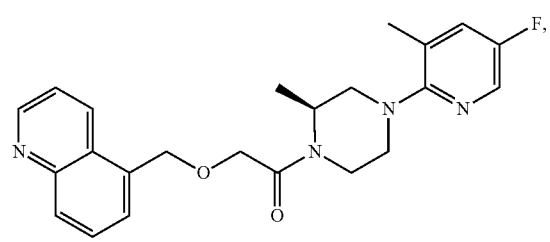
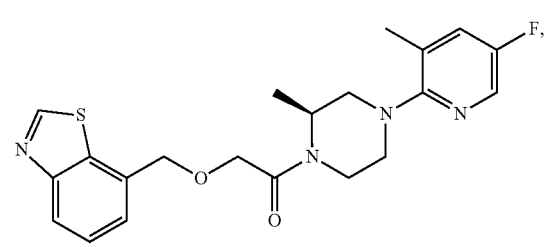
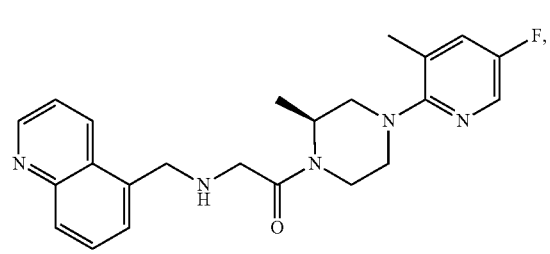
128
-continued
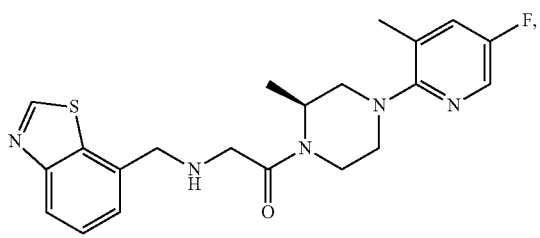
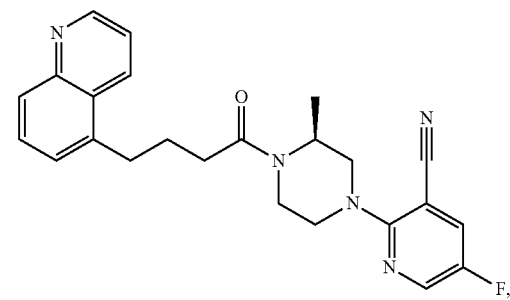
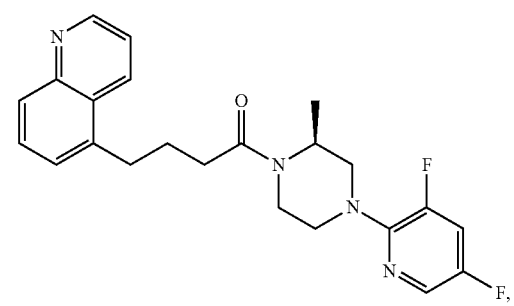
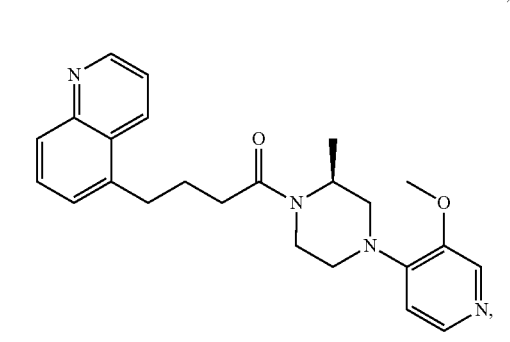
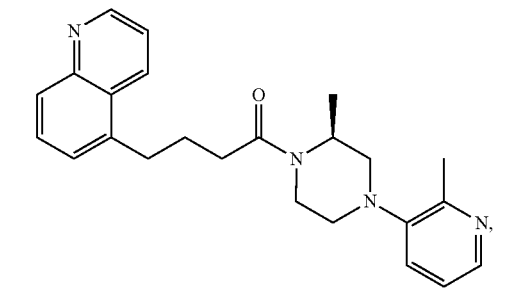
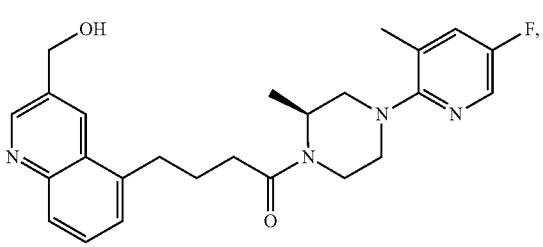

-continued
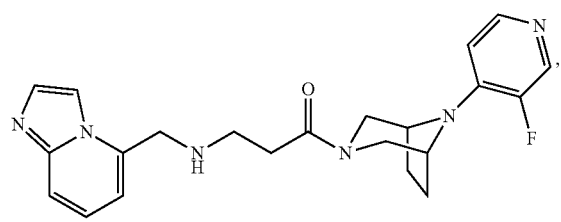
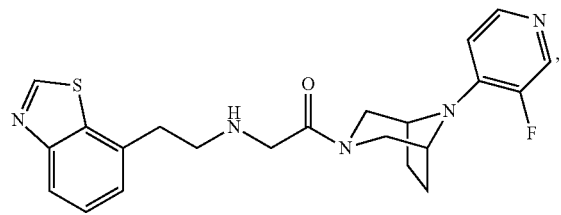
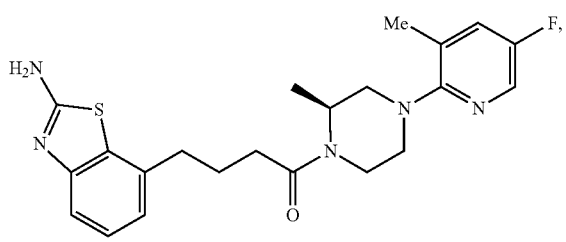
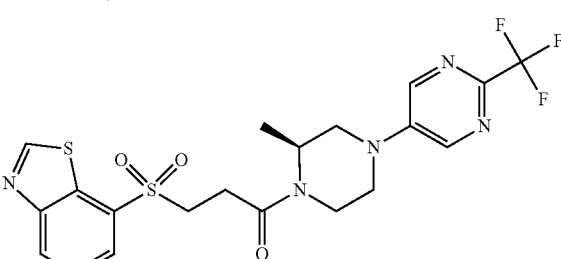
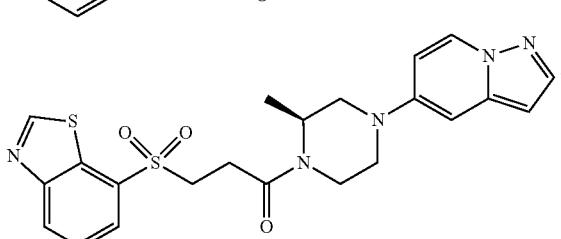
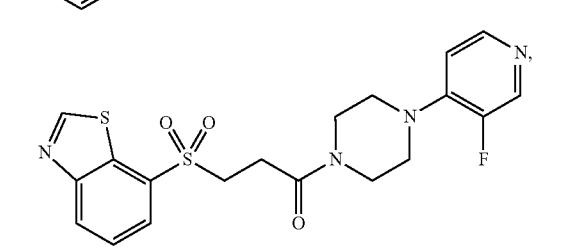
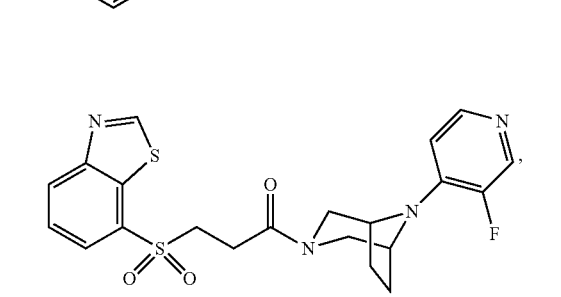
-continued
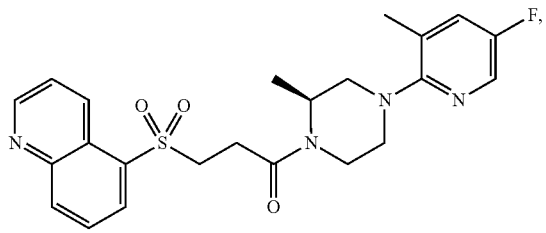
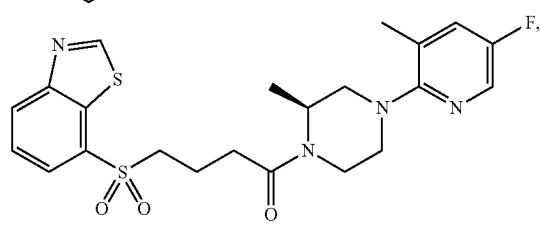
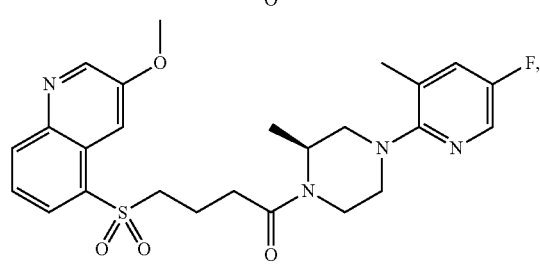
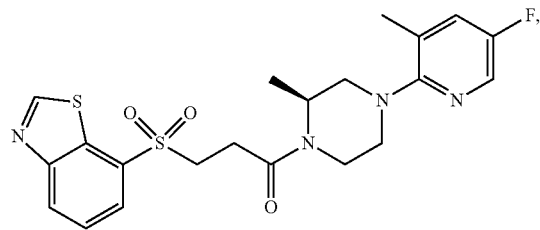
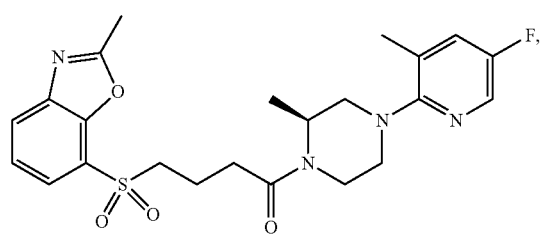
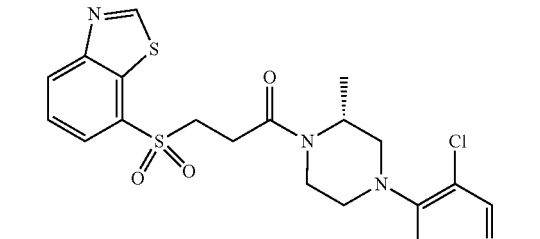
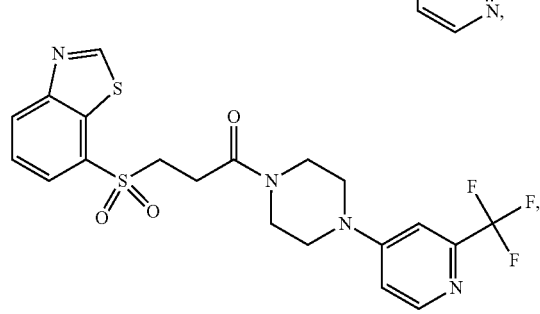

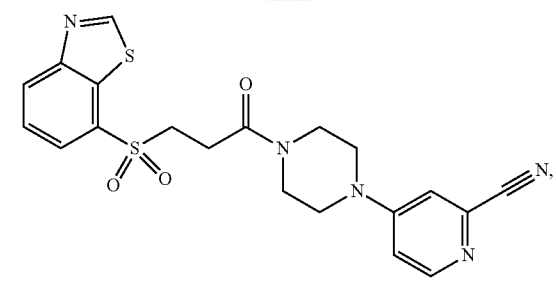
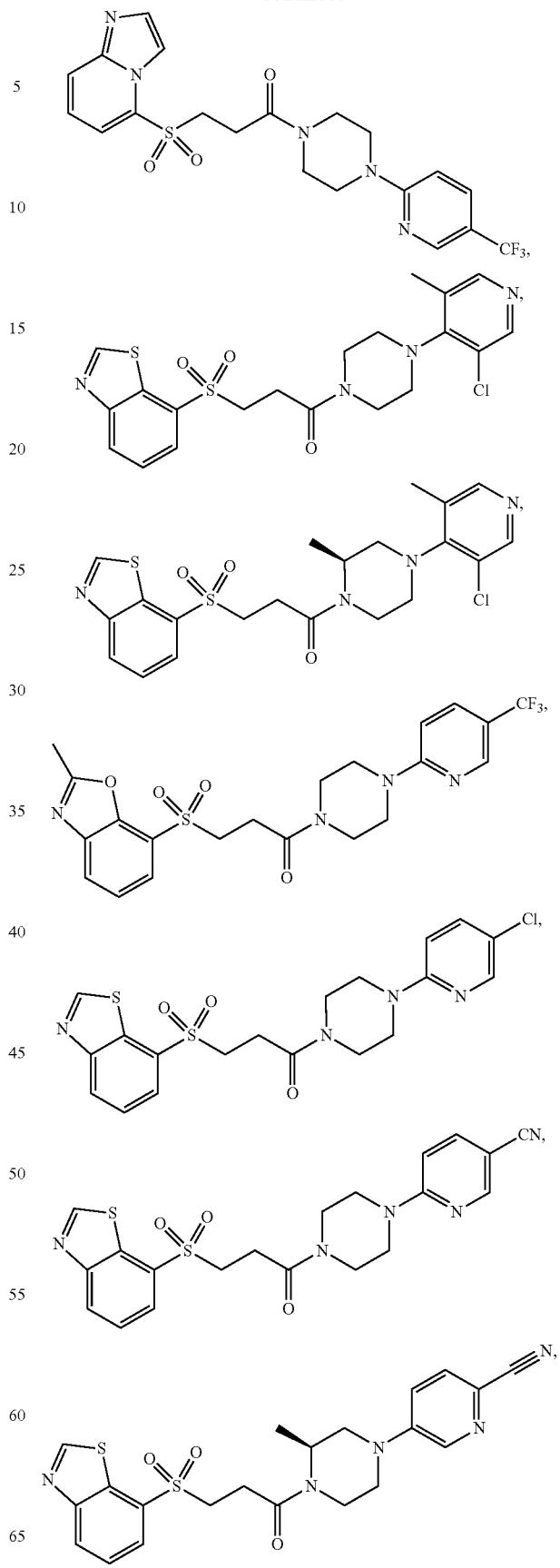

133
-continued
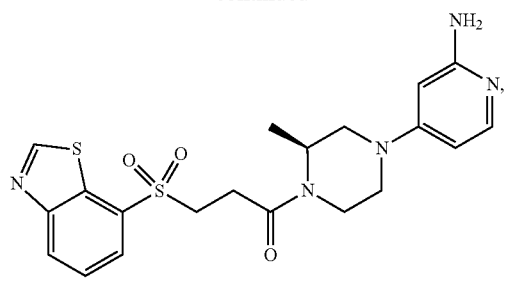
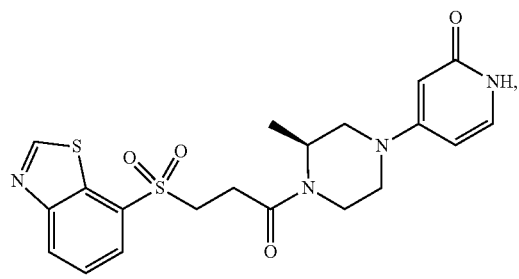
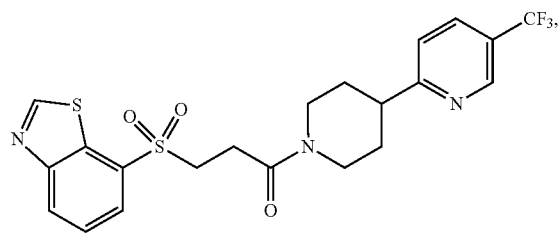
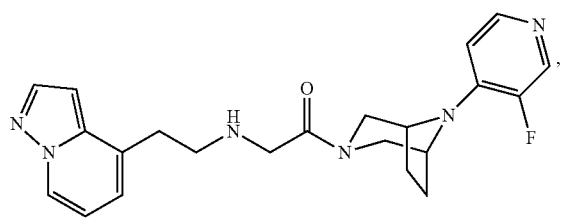
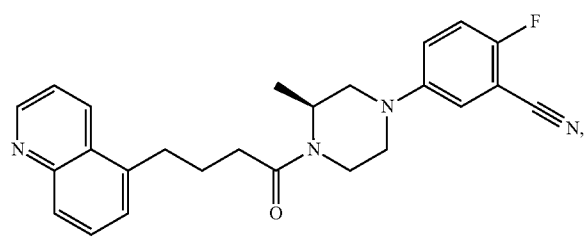
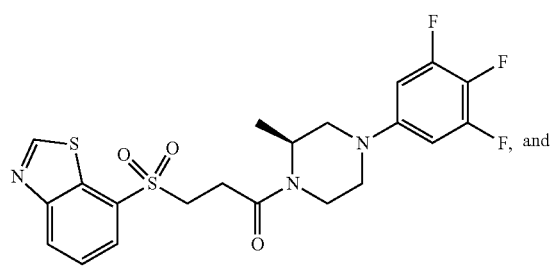
134
-continued
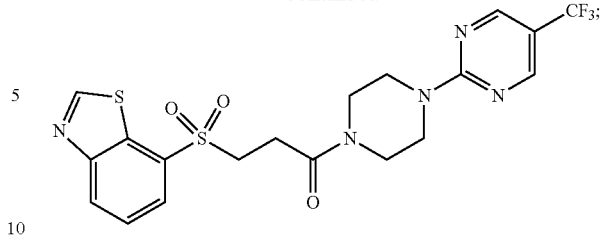
or a pharmaceutically acceptable salt or solvate thereof.
In some embodiments is a compound selected from:
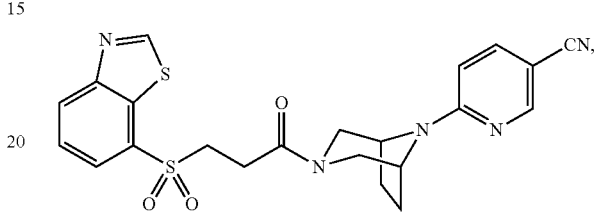
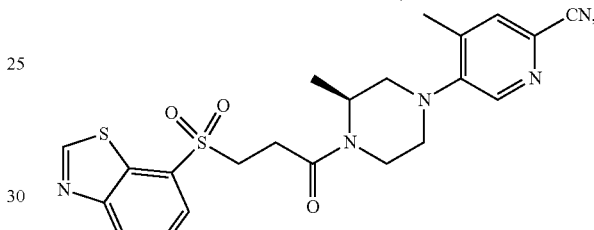
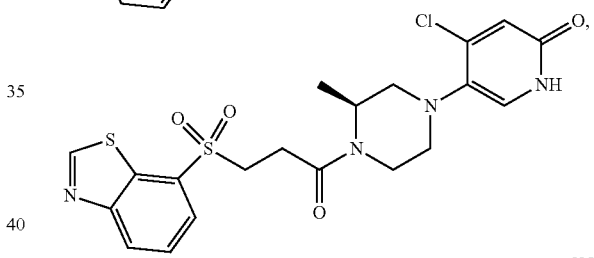
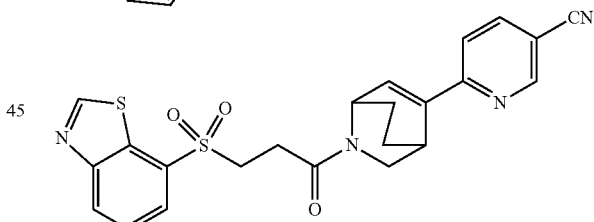
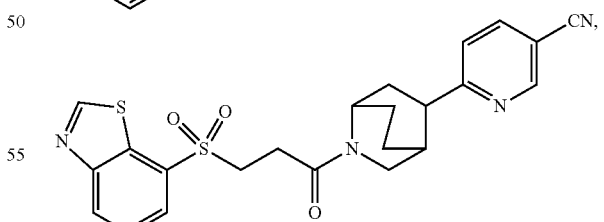
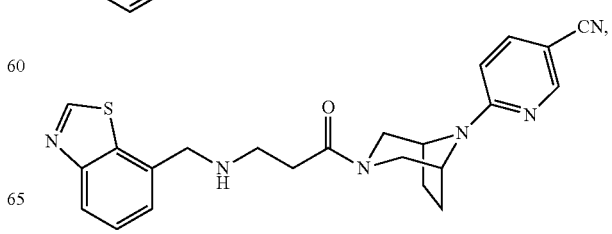

135
-continued
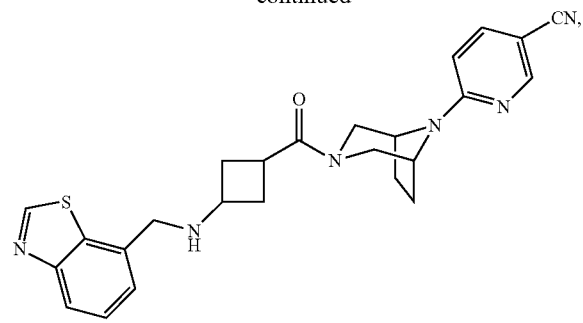
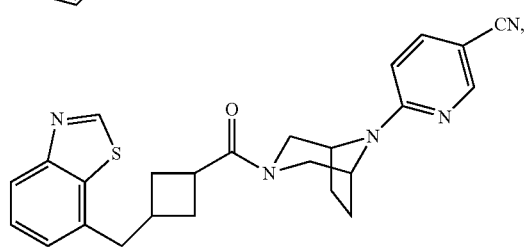
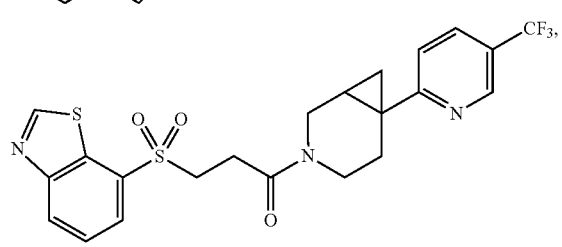
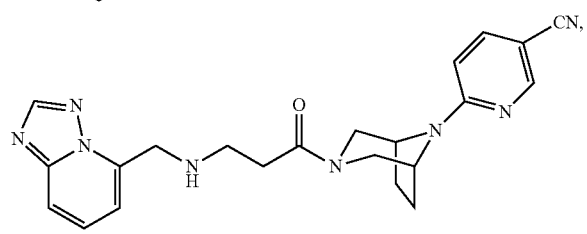
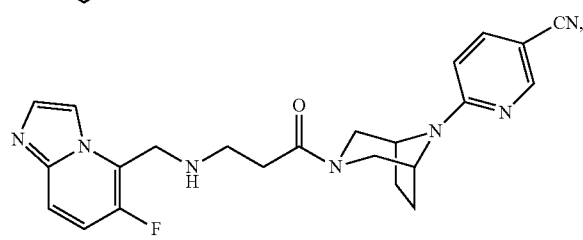
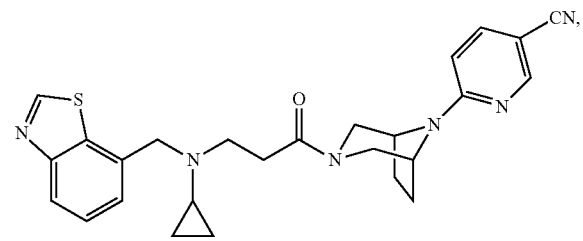
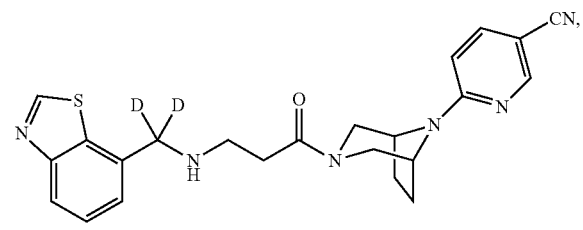
136
-continued
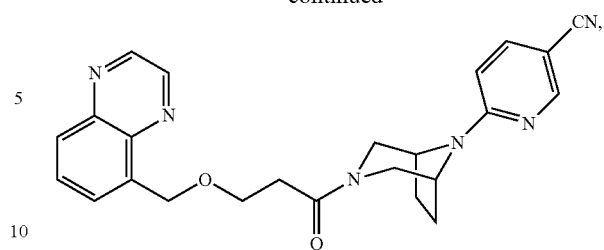
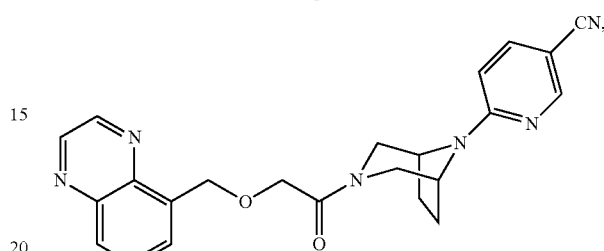
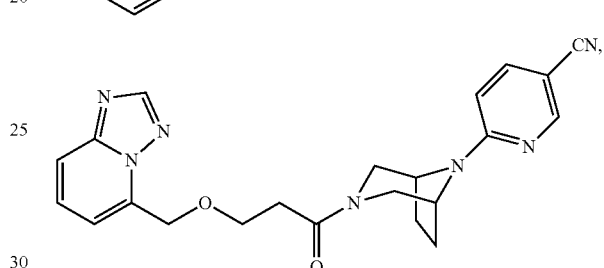
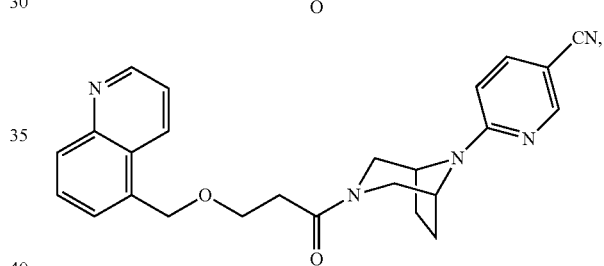
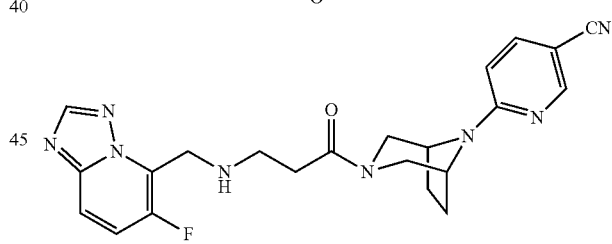
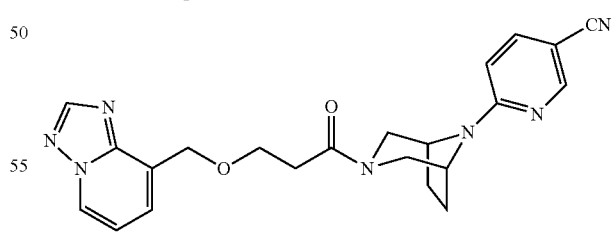
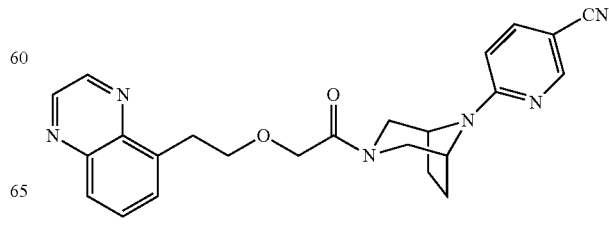

137
-continued
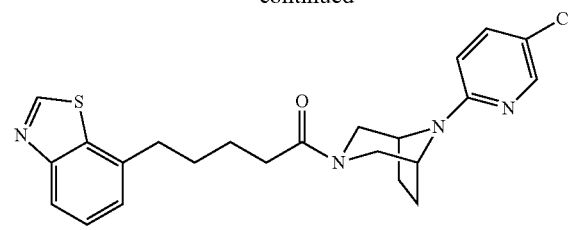
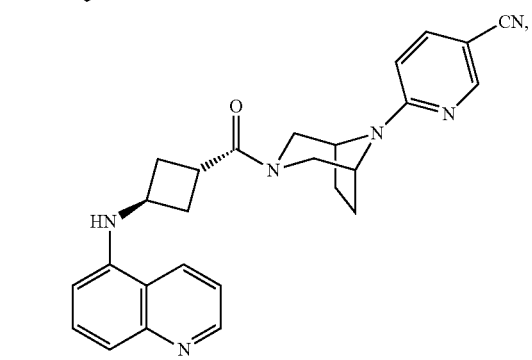
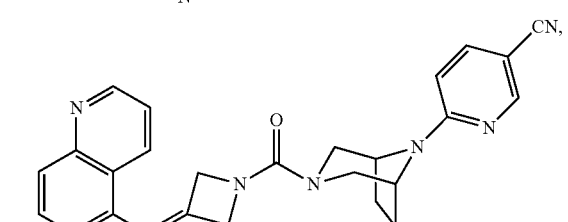
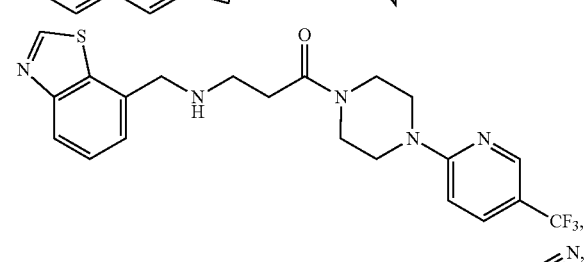
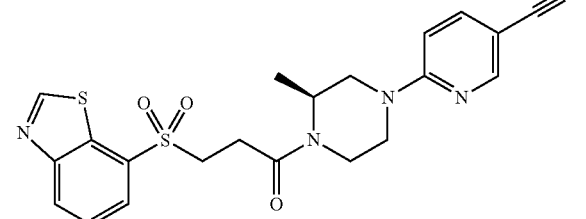
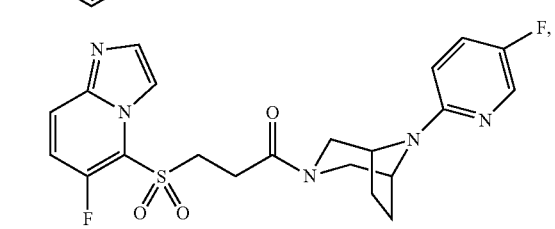
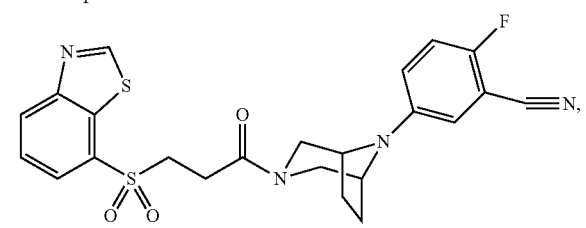
138
-continued
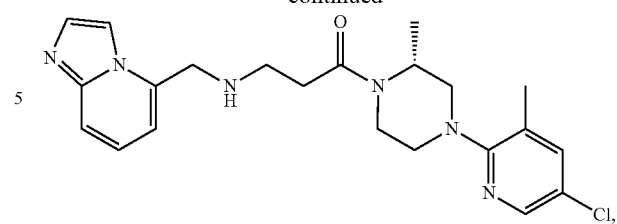
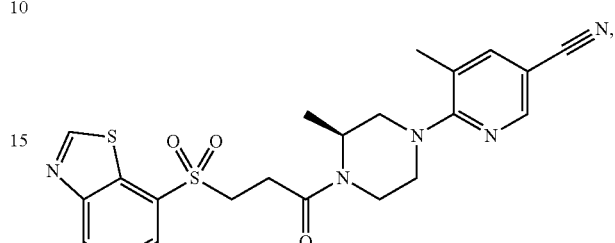
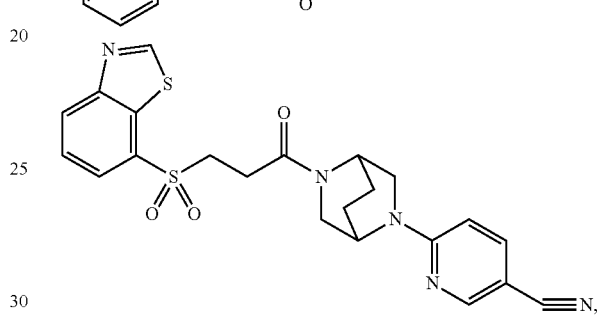
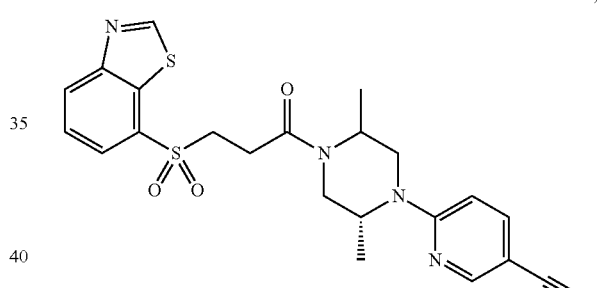
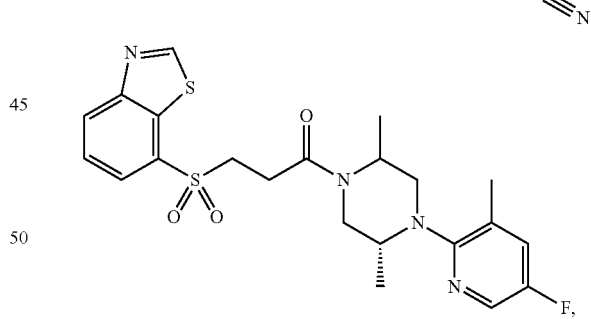
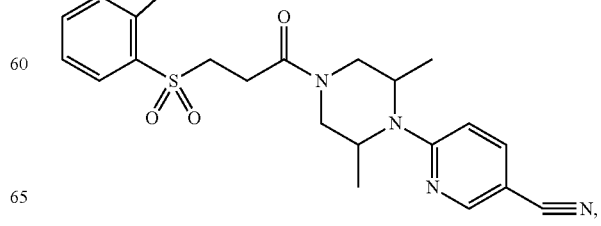

139
-continued
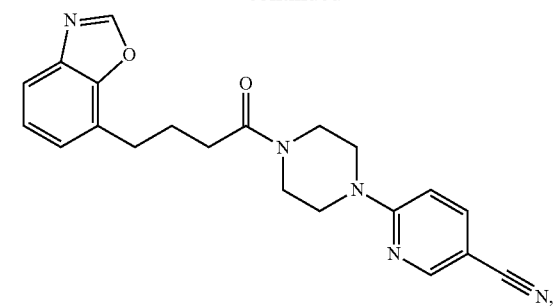
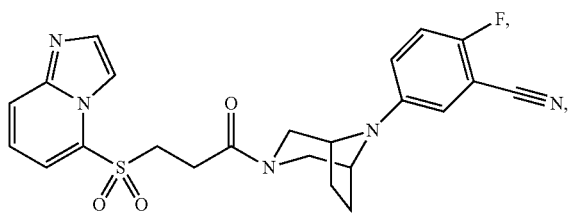
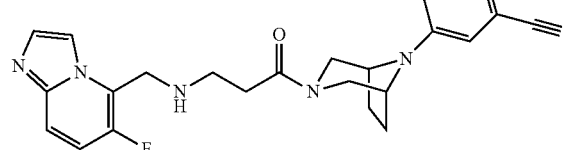
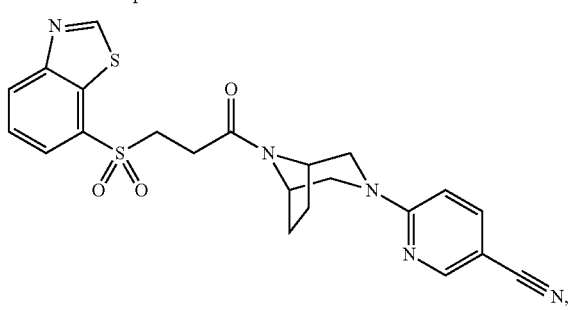
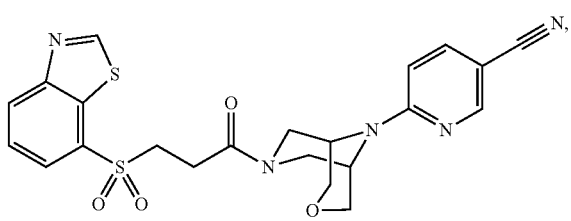
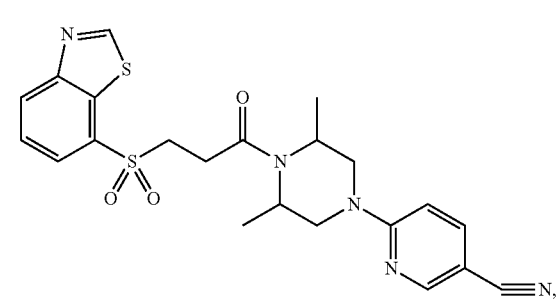
140
-continued
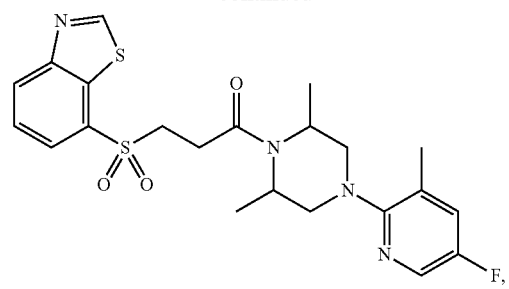
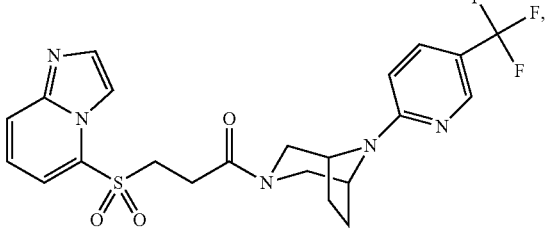
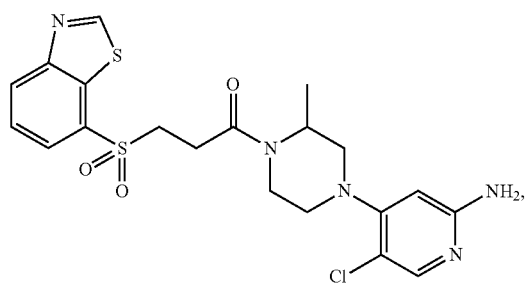
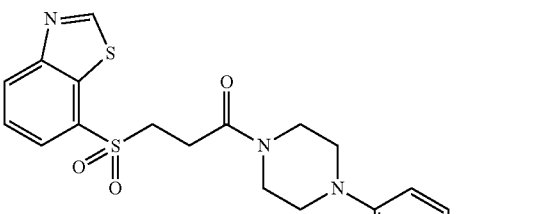
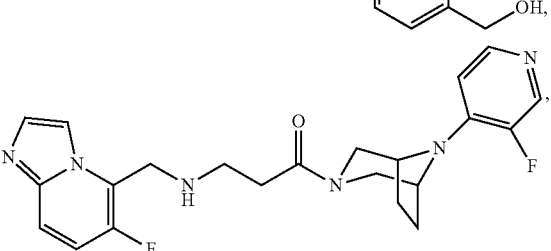
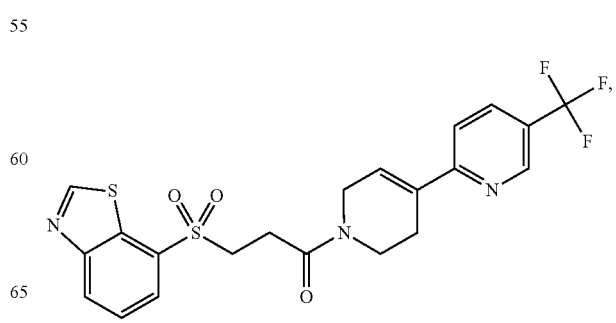

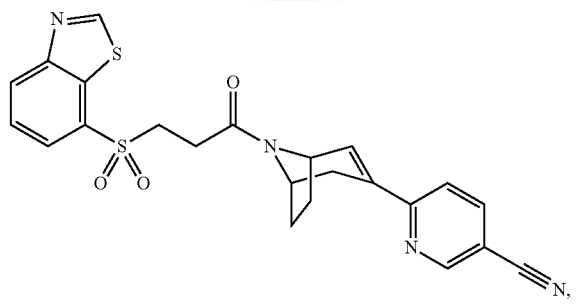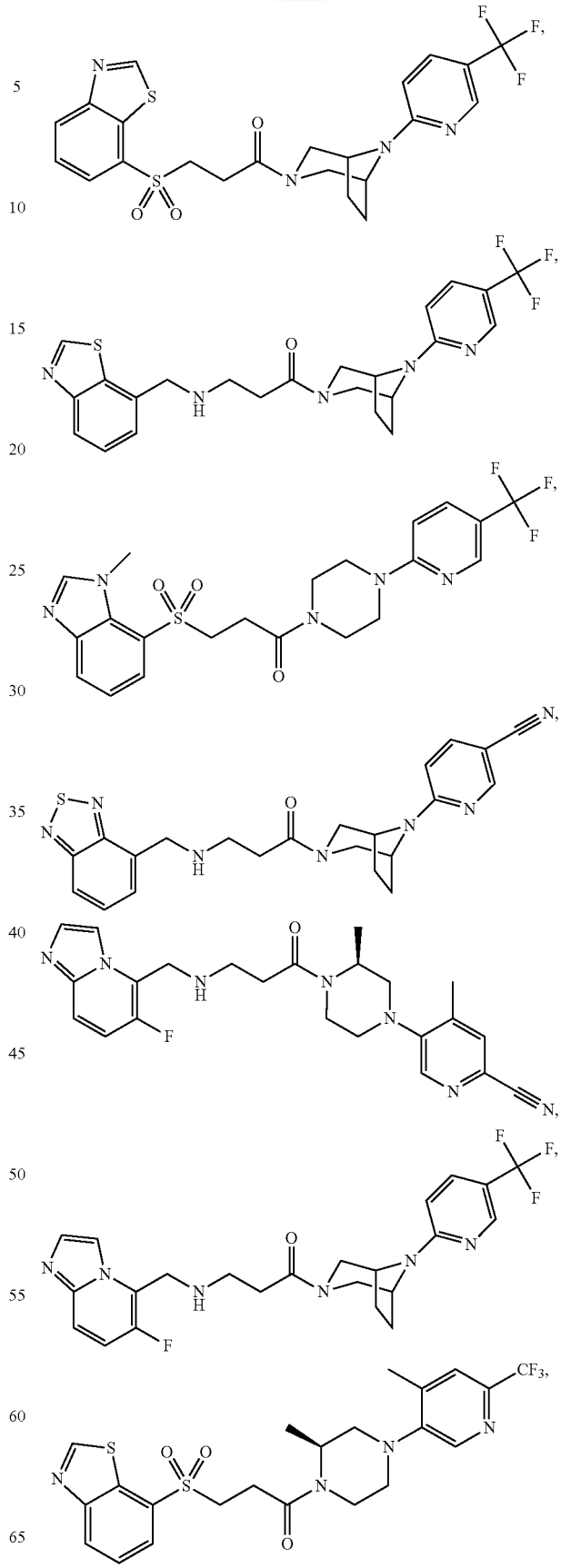

143
-continued
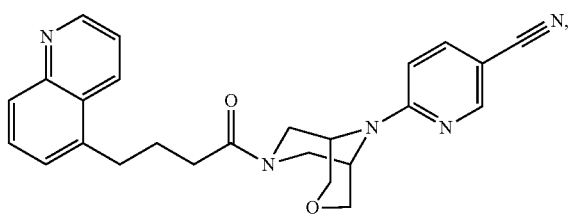
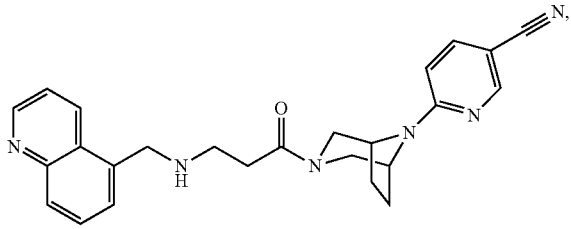
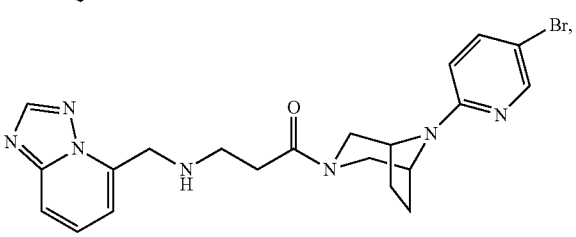
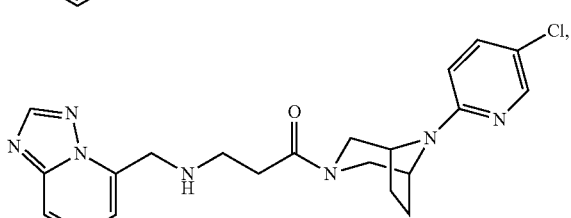
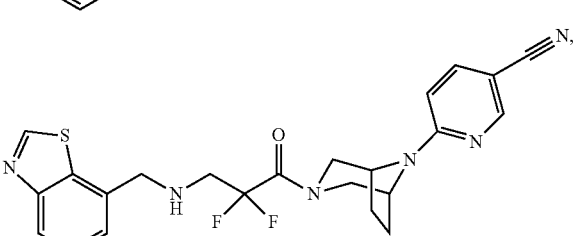
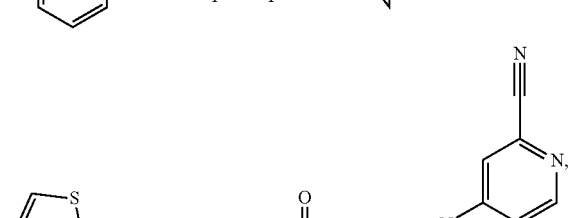
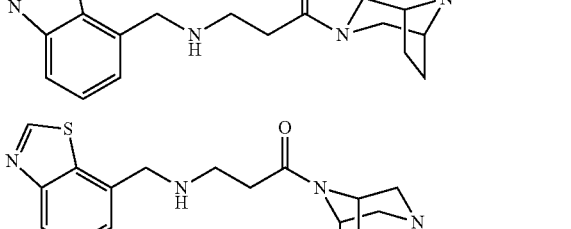
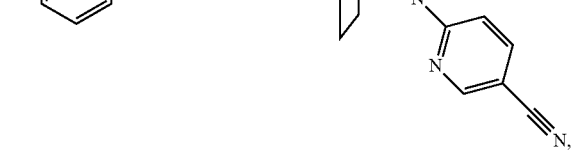
144
-continued
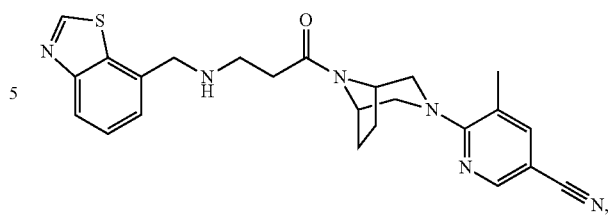
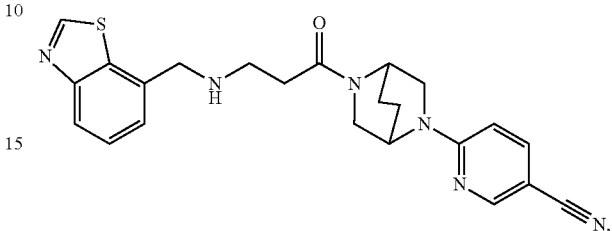
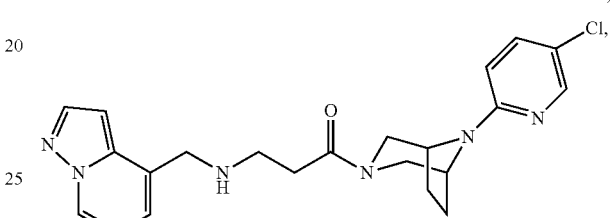
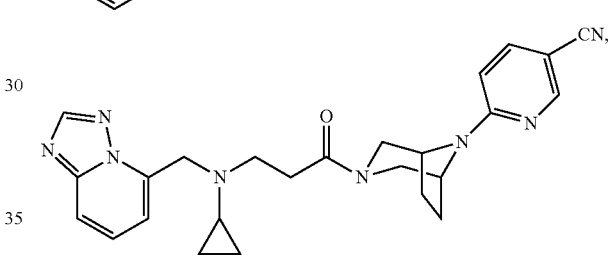
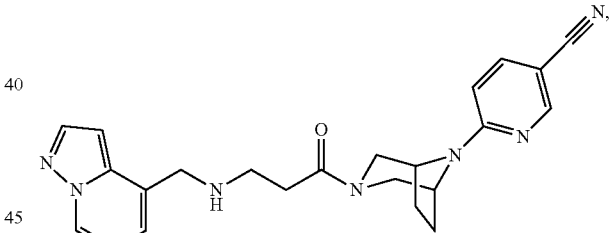
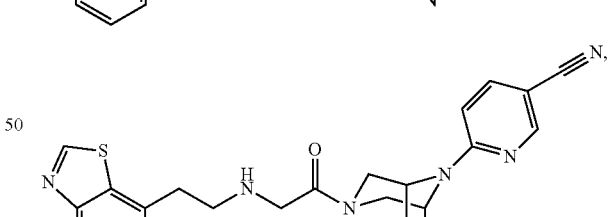
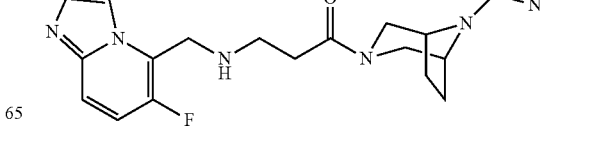

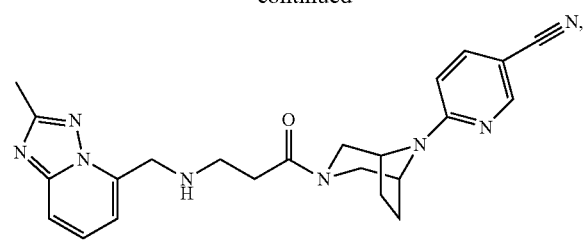
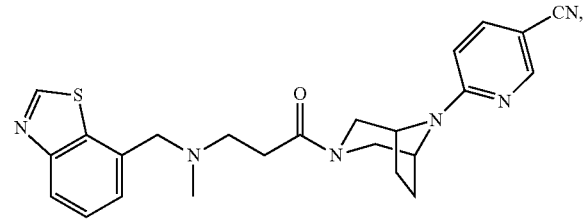
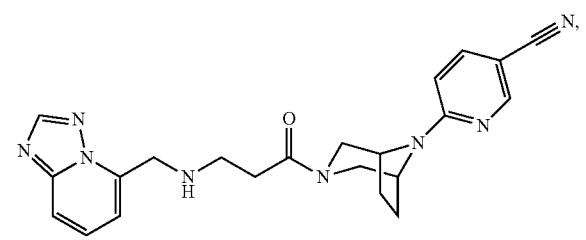
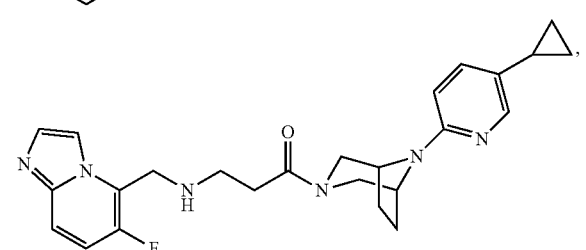
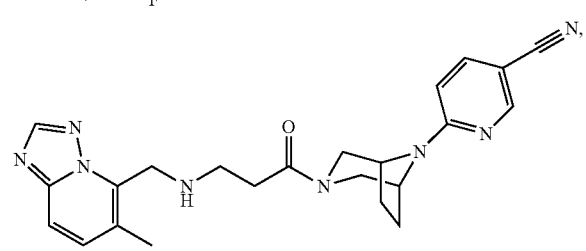
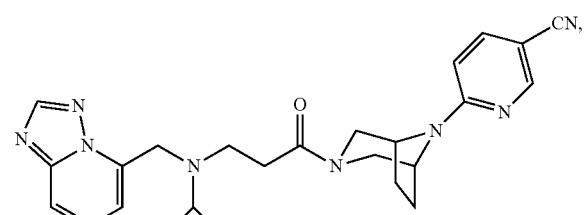
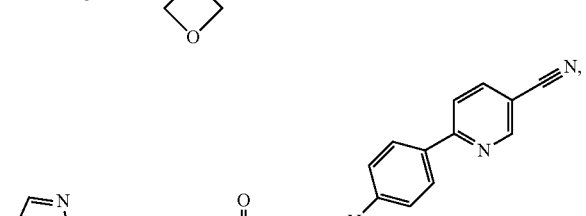
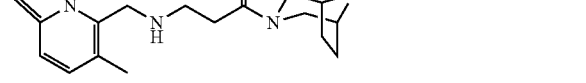
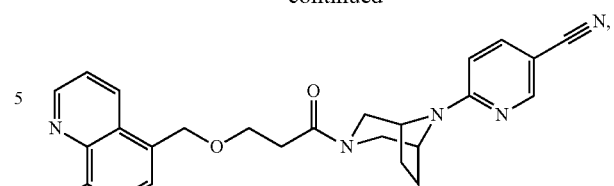
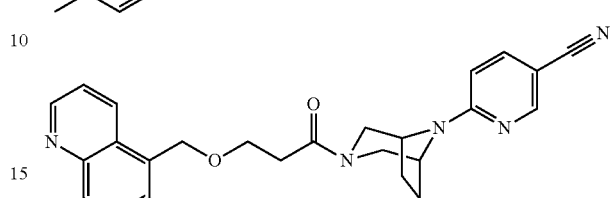
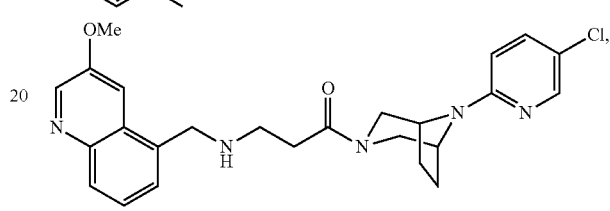
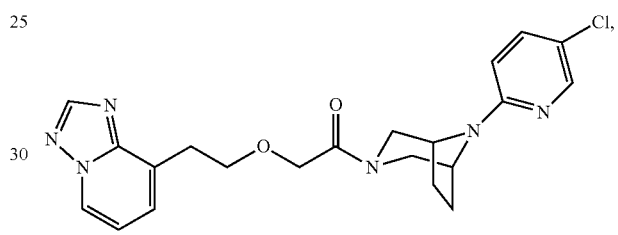
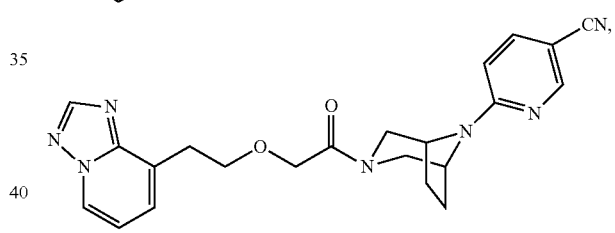
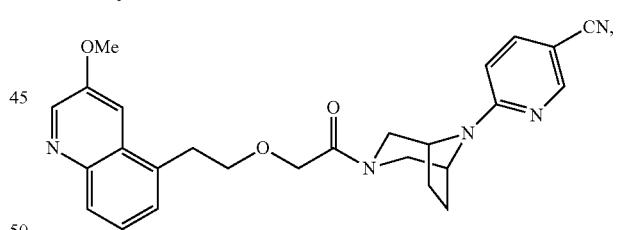
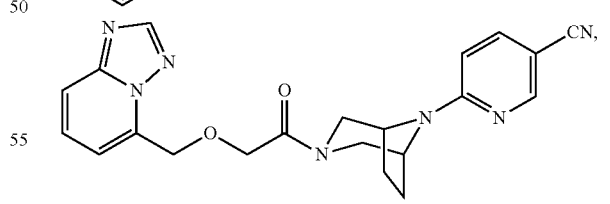
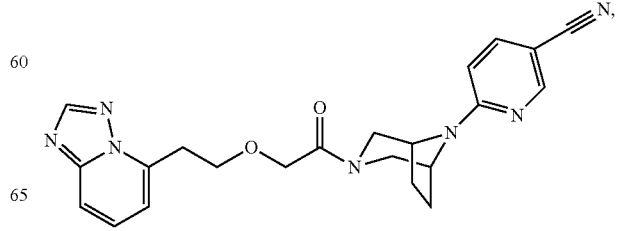

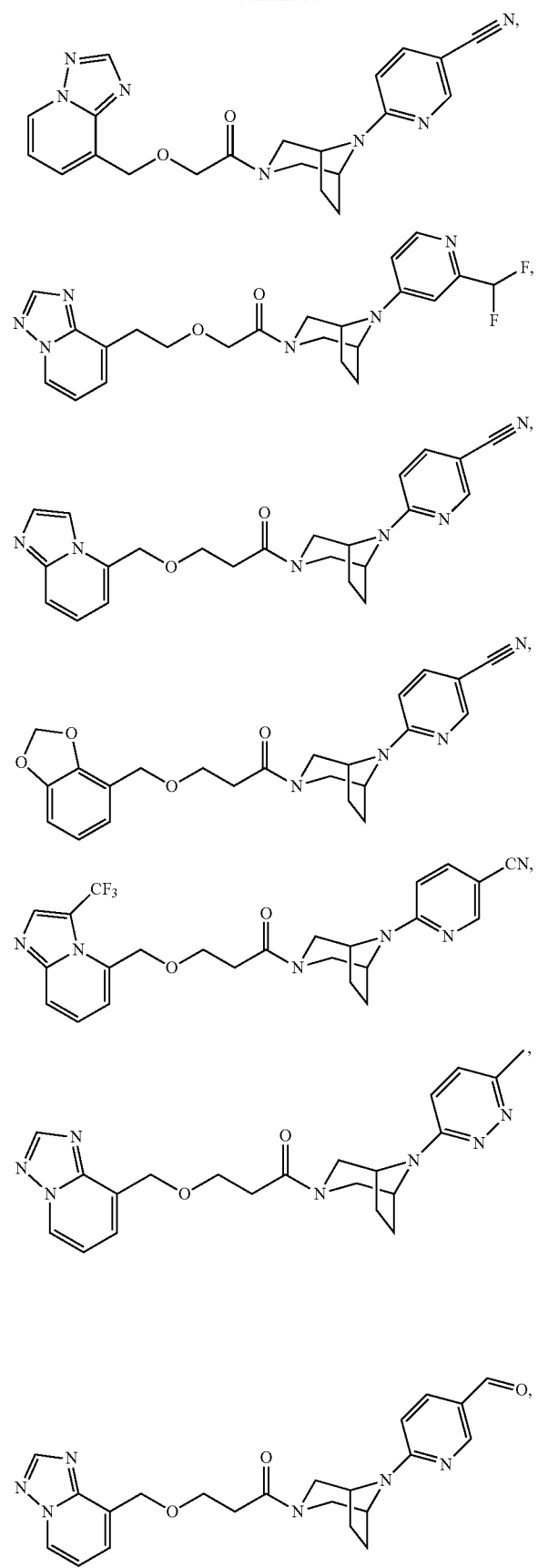
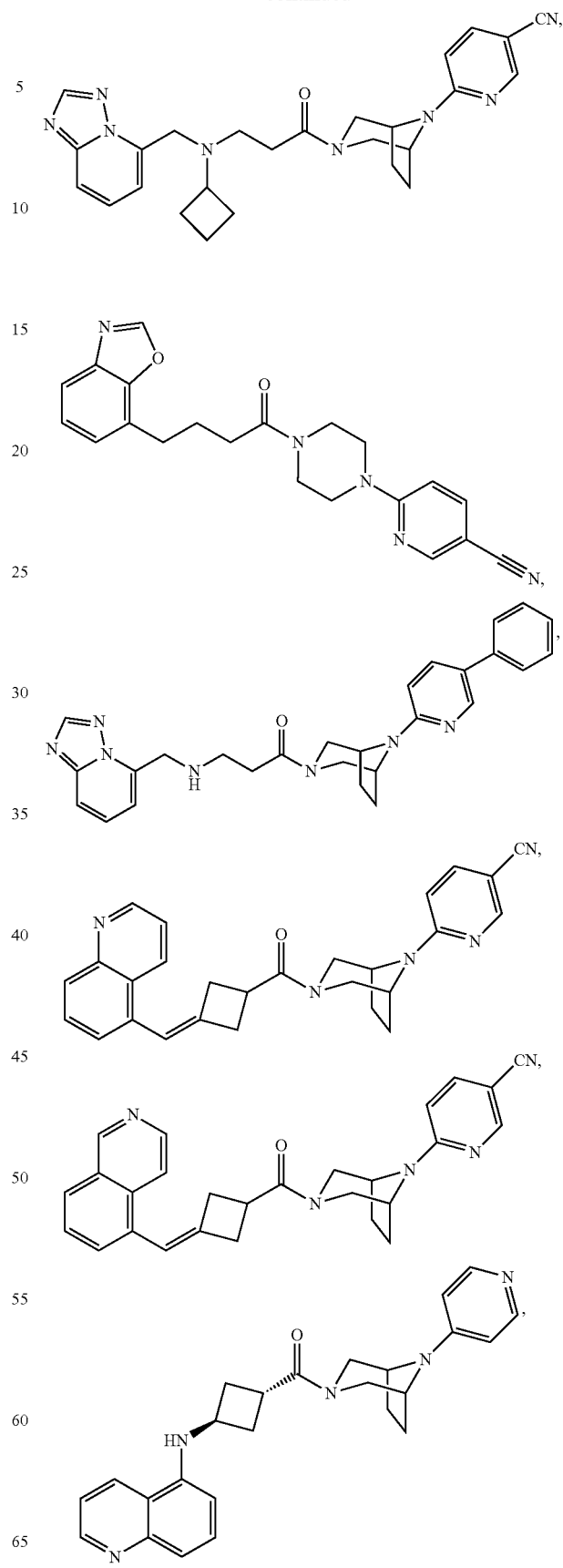

-continued

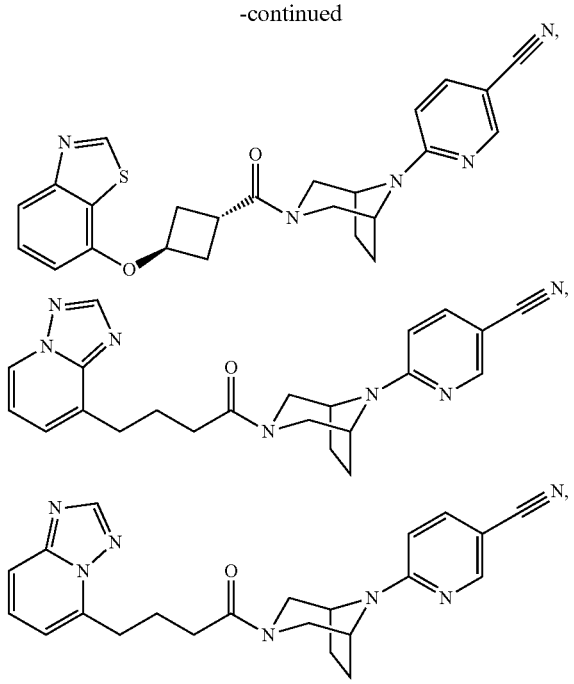

and

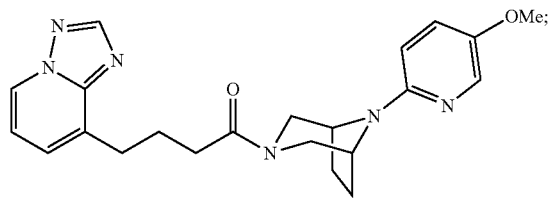 [SMILES: COc1ccc(N2C3CCC2CN(C(=O)CCCc2cccn4ncnc24)C3)nc1]

or a pharmaceutically acceptable salt or solvate thereof.

Preparation of the Compounds

The compounds used in the reactions described herein are made according to known organic synthesis techniques, starting from commercially available chemicals and/or from compounds described in the chemical literature. "Commercially available chemicals" are obtained from standard commercial sources including Acros Organics (Geel, Belgium), Aldrich Chemical (Milwaukee, Wis., including Sigma Chemical and Fluka), Apin Chemicals Ltd. (Milton Park, UK), Ark Pharm, Inc. (Libertyville, Ill.), Avocado Research (Lancashire, U.K.), BDH Inc. (Toronto, Canada), Bionet (Cornwall, U.K.), Chemservice Inc. (West Chester, Pa.), Combi-blocks (San Diego, Calif.), Crescent Chemical Co. (Hauppauge, N.Y.), eMolecules (San Diego, Calif.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Matrix Scientific, (Columbia, S.C.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Ryan Scientific, Inc. (Mount Pleasant, S.C.), Spectrum Chemicals (Gardena, Calif.), Sundia Meditech (Shanghai, China), TCI America (Portland, Oreg.), Trans World Chemicals, Inc. (Rockville, Md.), and WuXi (Shanghai, China).

Suitable reference books and treatises that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatises that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are also identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

Further Forms of the Compounds

Isomers

The compounds described herein include all possible tautomers within the formulas described herein.

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers.

In some situations, the compounds described herein possess one or more chiral centers and each center exists in the (R)-configuration, or (S)-configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as optically pure enantiomers by chiral chromatographic resolution of the racemic mixture. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

Labeled Compounds

The compounds disclosed herein, in some embodiments, are used in different enriched isotopic forms, e.g., enriched in the content of $^2H$, $^3H$, $^{11}C$, $^{13}C$ and/or $^{14}C$. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^2H$), tritium ($^3H$), iodine-125 ($^{125}I$) or carbon-14 ($^{14}C$). Isotopic substitution with $^2H$, $^{11}C$, $^{13}C$, $^{14}C$, $^{15}C$, $^{12}N$, $^{13}N$, $^{15}N$, $^{16}N$, $^{16}O$, $^{17}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, $^{125}I$ are all contemplated. All isotopic variations of the compounds of the present invention, whether radioactive or not, are encompassed within the scope of the present invention.

In certain embodiments, the compounds disclosed herein have some or all of the $^1H$ atoms replaced with $^2H$ atoms. The methods of synthesis for deuterium-containing compounds are known in the art. In some embodiments deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Raj ender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the invention, or by separately reacting a purified compound in its free form with a suitable acid or base, and isolating the salt thus formed.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran or methanol. In addition, the compounds provided herein exist in unsolvated as well as solvated forms. In general, the solvated forms are considered equivalent to the unsolvated forms for the purposes of the compounds and methods provided herein.

Prodrugs

In some embodiments, the compounds described herein exist in prodrug form. The invention provides for methods of treating diseases by administering such prodrugs. The invention further provides for methods of treating diseases by administering such prodrugs as pharmaceutical compositions.

In some embodiments, prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the present invention. The amino acid residues include but are not limited to the 20 naturally occurring amino acids and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. In other embodiments, prodrugs include compounds wherein a nucleic acid residue, or an oligonucleotide of two or more (e.g., two, three or four) nucleic acid residues is covalently joined to a compound of the present invention.

Pharmaceutically acceptable prodrugs of the compounds described herein also include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. In some embodiments, compounds having free amino, amido, hydroxy or carboxylic groups are converted into prodrugs. For instance, free carboxyl groups are derivatized as amides or alkyl esters. In certain instances, all of these prodrug moieties incorporate groups including but not limited to ether, amine and carboxylic acid functionalities.

Hydroxy prodrugs include esters, such as though not limited to, acyloxyalkyl (e.g. acyloxymethyl, acyloxyethyl) esters, alkoxycarbonyloxyalkyl esters, alkyl esters, aryl esters, phosphate esters, sulfonate esters, sulfate esters and disulfide containing esters; ethers, amides, carbamates, hemi succinates, dimethylaminoacetates and phosphoryloxymethyloxycarbonyls, as outlined in *Advanced Drug Delivery Reviews* 1996, 19, 115.

Amine derived prodrugs include, but are not limited to the following groups and combinations of groups:

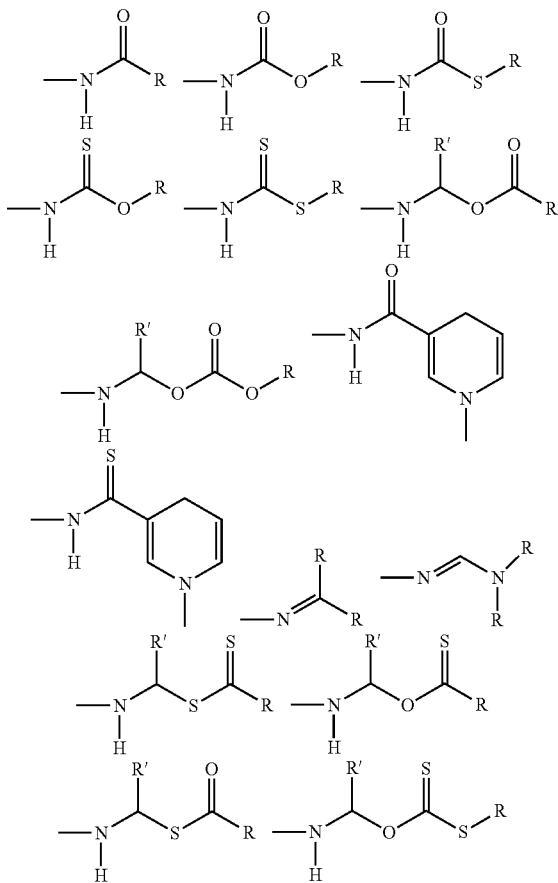

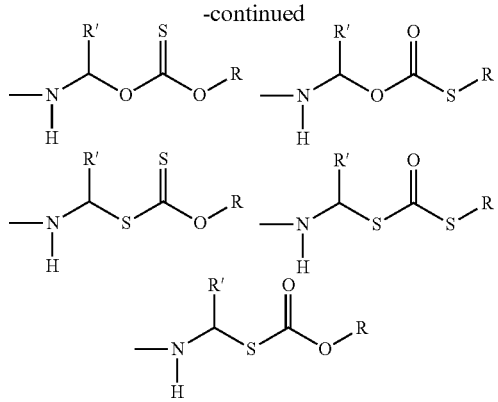

as well as sulfonamides and phosphonamides.

In certain instances, sites on any aromatic ring portions are susceptible to various metabolic reactions, therefore incorporation of appropriate substituents on the aromatic ring structures, reduce, minimize or eliminate this metabolic pathway.

Pharmaceutical Compositions

In certain embodiments, the compound of Formula (I), (I'), (Ia), (Ib), (II), (IIa), (IIb), or (III) as described herein is administered as a pure chemical. In some embodiments, the compound of Formula (I), (I'), (Ia), (Ib), (II), (IIa), (IIb), or (III) described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)).

Accordingly, provided herein is a pharmaceutical composition comprising at least one compound of Formula (I), (I'), (Ia), (Ib), (II), (IIa), (IIb), or (III) described herein, or a pharmaceutically acceptable salt or solvate thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable excipient and a compound of Formula (I), or a pharmaceutically acceptable salt thereof.

One embodiment provides a pharmaceutical composition comprising a pharmaceutically acceptable excipient and a compound of Formula (I'), or a pharmaceutically acceptable salt thereof One embodiment provides a pharmaceutical composition comprising a pharmaceutically acceptable excipient and a compound of Formula (Ia), or a pharmaceutically acceptable salt thereof.

One embodiment provides a pharmaceutical composition comprising a pharmaceutically acceptable excipient and a compound of Formula (Ib), or a pharmaceutically acceptable salt thereof.

One embodiment provides a pharmaceutical composition comprising a pharmaceutically acceptable excipient and a compound of Formula (II), or a pharmaceutically acceptable salt thereof.

One embodiment provides a pharmaceutical composition comprising a pharmaceutically acceptable excipient and a compound of Formula (IIa), or a pharmaceutically acceptable salt thereof.

One embodiment provides a pharmaceutical composition comprising a pharmaceutically acceptable excipient and a compound of Formula (IIb), or a pharmaceutically acceptable salt thereof.

One embodiment provides a pharmaceutical composition comprising a pharmaceutically acceptable excipient and a compound of Formula (III), or a pharmaceutically acceptable salt thereof.

In certain embodiments, the compound of Formula (I), (I'), (Ia), (Ib), (II), (IIa), (IIb), or (III) as described herein is substantially pure, in that it contains less than about 5%, or less than about 1%, or less than about 0.1%, of other organic small molecules, such as contaminating intermediates or by-products that are created, for example, in one or more of the steps of a synthesis method.

These pharmaceutical compositions include those suitable for oral, rectal, topical, buccal, parenteral (e.g., subcutaneous, intramuscular, intradermal, or intravenous) vaginal, ophthalmic, or aerosol administration.

Exemplary pharmaceutical compositions are used in the form of a pharmaceutical preparation, for example, in solid, semisolid or liquid form, which includes one or more of a disclosed compound, as an active ingredient, in a mixture with an organic or inorganic carrier or excipient suitable for external, enteral or parenteral applications. In some embodiments, the active ingredient is compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

In some embodiments for preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition is readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, cellulose, microcrystalline cellulose, silicified microcrystalline cellulose, lactose, sucrose, glucose, mannitol, and/or silicic acid; (2) binders, such as, for example, carboxymethylcellulose, hypromellose, alginates, gelatin, polyvinyl pyrrolidone, sucrose and/or acacia; (3) humectants, such as glycerol; (4) disintegrating agents, such as crospovidone, croscarmellose sodium, sodium starch glycolate, agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, docusate sodium, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof and (10) coloring agents. In the case of capsules, tablets and pills, in some embodiments, the compositions comprise buffering agents. In some embodiments, solid compositions of a similar type are also employed as fillers in soft and hard-filled gelatin capsules using such excipients as lactose or milk sugars, as well as high molecular weight polyethylene glycols and the like.

In some embodiments, a tablet is made by compression or molding, optionally with one or more accessory ingredients. In some embodiments, compressed tablets are prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. In some embodiments, molded tablets are made by molding in a suitable machine a mixture of the subject composition moistened with an inert liquid diluent. In some embodiments, tablets, and other solid dosage forms, such as dragees, capsules, pills and granules, are scored or prepared with coatings and shells, such as enteric coatings and other coatings.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, in some embodiments, the liquid dosage forms contain inert diluents, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

In some embodiments, suspensions, in addition to the subject composition, contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

In some embodiments, formulations for rectal or vaginal administration are presented as a suppository, which are prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. In some embodiments, the active component is mixed under sterile conditions with a pharmaceutically acceptable carrier, and with any preservatives, buffers, or propellants as required.

In some embodiments, the ointments, pastes, creams and gels contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

In some embodiments, powders and sprays contain, in addition to a subject composition, excipients such as lactose, talc, silicic acid, aluminum hydroxide, calcium silicates and polyamide powder, or mixtures of these substances. In some embodiments, sprays additionally contain customary propellants, such as chlorofluorohydrocarbons and volatile unsubstituted hydrocarbons, such as butane and propane.

In some embodiments, the compounds described herein are formulated as eye drops for ophthalmic administration.

Compositions and compounds disclosed herein alternatively are administered by aerosol. This is accomplished by preparing an aqueous aerosol, liposomal preparation or solid particles containing the compound. In some embodiments, a non-aqueous (e.g., fluorocarbon propellant) suspension is used. In some embodiments, sonic nebulizers are used because they minimize exposing the agent to shear, which results in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which are reconstituted into sterile injectable solutions or dispersions just prior to use, which, in some embodiments, contain antioxidants, buffers, bacteriostats, solutes which render the formulation isotonic with the blood of the intended recipient or suspending or thickening agents.

Examples of suitable aqueous and non-aqueous carriers which are employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity is maintained, for example, by the use of coating materials, such as lecithin, by the maintenance of the required particle size in the case of dispersions, and by the use of surfactants.

Also contemplated are enteral pharmaceutical formulations including a disclosed compound and an enteric material; and a pharmaceutically acceptable carrier or excipient thereof Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro.

The dose of the composition comprising at least one compound of Formula (I), (I'), (Ia), (Ib), (II), (IIa), (IIb), or (III) as described herein differs, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. In some embodiments, the optimal dose depends upon the body mass, weight, or blood volume of the patient.

Oral doses typically range from about 1.0 mg to about 1000 mg, one to four times, or more, per day.

Disclosed compounds are administered to subjects or patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors, with the appropriate dosage ultimately being at the discretion of the attendant physician. For treating clinical conditions and diseases noted above, a contemplated compound disclosed herein is administered orally, subcutaneously, topically, parenterally, by inhalation spray or rectally in dosage unit formulations containing conventional non-toxic pharmaceutically acceptable carriers, adjuvants and vehicles. Parenteral administration include subcutaneous injections, intravenous or intramuscular injections or infusion techniques.

Methods of Using the Compounds and Compositions

Antagonists of MAChR $M_1$

The muscarinic acetylcholine receptor $M_1$ (mAChR $M_1$) is found in both the central and peripheral nervous systems, particularly in the cerebral cortex and sympathetic ganglia. Notably, M1 is expressed on oligodendrocyte precursor cells (OPCs) in the central nervous system. Over time, OPCs will differentiate into myelin-producing oligodendrocytes. Myelin is indispensible for action potential conduction along the axon and its loss has been attributed to neurodegenerative disorders, specifically multiple sclerosis. In some embodiments, non-selective mAChR antagonists accelerate OPC differentiation into oligodendrocytes. In some embodiments, selective mAChR $M_1$ antagonists are useful in the treatment of demyelinating disorders, such as multiple sclerosis. In some embodiments, M1 antagonists are useful in treating epileptic disorders and certain movement disorders, including Parkinson's disease, dystonia, and fragile X syndrome. In one aspect, the compounds disclosed herein are antagonists of the muscarinic acetylcholine $M_1$ receptor (mAChR In some embodiments, the compounds disclosed herein are antagonists of the muscarinic acetylcholine $M_2$ receptor (mAChR $M_2$). In some embodiments, the compounds disclosed herein are antagonists of the muscarinic acetylcholine $M_3$ receptor (mAChR $M_3$). In some embodiments, the compounds disclosed herein are antagonists of the muscarinic acetylcholine $M_4$ receptor (mAChR $M_4$). In some embodiments, the compounds disclosed herein are antagonists of the muscarinic acetylcholine $M_5$ receptor (mAChR $M_5$). In some embodiments, the compounds disclosed herein are antagonists of one or more of mAChR $M_1$, mAChR $M_2$, mAChR $M_3$, mAChR $M_4$, or mAChR $M_5$. In some embodiments, the compounds disclosed herein are selective antagonists of the muscarinic acetylcholine $M_1$ receptor (mAChR $M_1$) over one or more of the mAChR $M_2$, $M_3$, $M_4$, or $M_5$ receptors. In some embodiments, a compound disclosed herein exhibits an $IC_{50}$ for the mAChR $M_1$ response which is about 5-fold less, about 10-fold less, about 20-fold less, about 30-fold less, about 50-fold less, about 100-fold less, or >100-fold less than that for mAChR $M_2$. In some embodiments, a compound disclosed herein exhibits an $IC_{50}$ for the mAChR $M_1$ response which is about 5-fold less, about 10-fold less, about 20-fold less, about 30-fold less, about 50-fold less, about 100-fold less, or >100-fold less than that for mAChR $M_3$. In some embodiments, a compound disclosed herein exhibits an $IC_{50}$ for the mAChR $M_1$ response which is about 5-fold less, about 10-fold less, about 20-fold less, about 30-fold less, about 50-fold less, about 100-fold less, or >100-fold less than that for mAChR $M_4$. In some embodiments, a compound disclosed herein exhibits an $IC_{50}$ for the mAChR $M_1$ response which is about 5-fold less, about 10-fold less, about 20-fold less, about 30-fold less, about 50-fold less, about 100-fold less, or >100-fold less than that for mAChR $M_5$. In some embodiments, a compound disclosed herein exhibits an $IC_{50}$ for the mAChR $M_1$ response which is about 5-fold less, about 10-fold less, about 20-fold less, about 30-fold less, about 50-fold less, about 100-fold less, or >100-fold less than that for mAChR $M_2$, $M_3$, $M_4$, or $M_5$, or combinations thereof.

Treatment Methods

The compounds disclosed herein are useful for treating, preventing, ameliorating, controlling or reducing the risk of a variety of disorders wherein the patient or subject would benefit from antagonism of the muscarinic acetylcholine $M_1$ receptor.

In one aspect, a treatment can include selective $M_1$ receptor antagonism to an extent effective to affect cholinergic activity. Thus, disorders for which the compounds disclosed herein are useful can be associated with cholinergic activity, for example cholinergic hyperfunction. In some embodiments, provided herein is a method of treating or preventing a disorder in a subject comprising the step of administering to the subject a compound disclosed herein, or a pharmaceutically acceptable salt or solvate thereof, or a pharmaceutical composition described herein in a dosage and amount effective to treat the disorder in the subject.

Provided herein is a method for the treatment of one or more disorders, for which muscarinic acetylcholine receptor inhibition is predicted to be beneficial, in a subject comprising the step of administering to the subject a compound disclosed herein, or a pharmaceutically acceptable salt or solvate thereof, or a pharmaceutical composition described herein in a dosage and amount effective to treat the disorder in the subject.

In some embodiments provided herein is a method of treating a neurodegenerative disorder in a subject in need thereof, comprising administering to subject a therapeutically effective amount of a compound of Formula (I), Formula (I'), Formula (Ia), Formula (Ib), Formula (II), Formula (IIa), Formula (IIb), or Formula (III), or a pharmaceutically acceptable salt or solvate thereof.

In some embodiments is a method of treating a demyelinating disease in a subject in need thereof, comprising administering to the subject a therapeutically effective amount of a compound of Formula (I), Formula (I'), Formula (Ia), Formula (Ib), Formula (II), Formula (IIa), Formula (IIb), or Formula (III), or a pharmaceutically acceptable salt or solvate thereof. In some embodiments is a method of treating a demyelinating disease in a subject in need thereof, comprising administering to the subject a therapeutically effective amount of a compound of Formula (I), Formula (I'), Formula (Ia), Formula (Ib), Formula (II), Formula (IIa), Formula (IIb), or Formula (III), or a pharmaceutically acceptable salt or solvate thereof, wherein the demyelinating disease is a demyelinating disease of the central nervous system. In some embodiments is a method of treating a demyelinating disease in a subject in need thereof, comprising administering to the subject a therapeutically effective amount of a compound of Formula (I), Formula (I'), Formula (Ia), Formula (Ib), Formula (II), Formula (IIa), Formula (IIb), or Formula (III), or a pharmaceutically acceptable salt or solvate thereof, wherein the demyelinating disease is multiple sclerosis. In some embodiments is a method of treating a demyelinating disease in a subject in need thereof, comprising administering to the subject a therapeutically effective amount of a compound of Formula (I), Formula (I'), Formula (Ia), Formula (Ib), Formula (II), Formula (IIa), Formula (IIb), or Formula (III), or a pharmaceutically acceptable salt or solvate thereof, wherein the demyelinating disease is a demyelinating disease of the peripheral nervous system.

In some embodiments is a method of modulating muscarinic acetylcholine receptor $M_1$ activity in a subject comprising administering to the subject a compound of Formula (I), Formula (I'), Formula (Ia), Formula (Ib), Formula (II), Formula (IIa), Formula (IIb), or Formula (III), or a pharmaceutically acceptable salt or solvate thereof.

Combination Therapy

Also contemplated herein are combination therapies, for example, co-administering a disclosed compound and an additional active agent, as part of a specific treatment regimen intended to provide the beneficial effect from the co-action of these therapeutic agents. In some embodiments, a compound described herein is administered in combination with one or more immunomodulatory agents. In some embodiments, a compound described herein is administered in combination with one or more immunomodulatory agents, wherein the immunomodulatory agents are selected from an IFN-β 1 molecule; a corticosteroid; a polymer of glutamic acid, lysine, alanine and tyrosine or glatiramer; an antibody or fragment thereof against alpha-4 integrin or natalizumab; an anthracenedione molecule or mitoxantrone; a fingolimod or FTY720 or other SIP1 functional modulator; a dimethyl fumarate; an antibody to the alpha subunit of the IL-2 receptor of T cells (CD25) or daclizumab; an antibody against CD52 or alemtuzumab; an antibody against CD20; and an inhibitor of a dihydroorotate dehydrogenase or teriflunomide. In some embodiments, the immunomodulatory agent is an IFN-β 1 molecule. In some embodiments, the immunomodulatory agent is a corticosteroid. In some embodiments, the immunomodulatory agent is a polymer of glutamic acid, lysine, alanine and tyrosine or glatiramer. In some embodiments, the immunomodulatory agent is an antibody or fragment thereof against alpha-4 integrin or natalizumab. In some embodiments, the immunomodulatory agent is an anthracenedione molecule or mitoxantrone. In some embodiments, the immunomodulatory agent is a fingolimod or FTY720 or other SIP1 functional modulator. In some embodiments, the immunomodulatory agent is a dimethyl fumarate. In some embodiments, the immunomodulatory agent is an antibody to the alpha subunit of the IL-2 receptor of T cells (CD25) or daclizumab. In some embodiments, the immunomodulatory agent is an antibody against CD52 or alemtuzumab. In some embodiments, the immunomodulatory agent is an antibody against CD20. In some embodiments, the immunomodulatory agent is an inhibitor of a dihydroorotate dehydrogenase or teriflunomide.

The beneficial effect of the combination includes, but is not limited to, pharmacokinetic or pharmacodynamic co-action resulting from the combination of therapeutic agents. Administration of these therapeutic agents in combination typically is carried out over a defined time period (usually weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration is accomplished, for example, by administering to the subject a single formulation or composition, (e.g., a tablet or capsule having a fixed ratio of each therapeutic agent or in multiple, single formulations (e.g., capsules) for each of the therapeutic agents. Sequential or substantially simultaneous administration of each therapeutic agent is effected by any appropriate route including, but not limited to, oral routes, intravenous routes, intramuscular routes, and direct absorption through mucous membrane tissues. The therapeutic agents are administered by the same route or by different routes. For example, a first therapeutic agent of the combination selected is administered by intravenous injection while the other therapeutic agents of the combination are administered orally. Alternatively, for example, all therapeutic agents are administered orally or all therapeutic agents are administered by intravenous injection.

Combination therapy also embraces the administration of the therapeutic agents as described above in further combination with other biologically active ingredients and non-drug therapies. Where the combination therapy further comprises a non-drug treatment, the non-drug treatment is conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination are administered to a patient simultaneously or sequentially. It will be appreciated that the components are present in the same pharmaceutically acceptable carrier and, therefore, are administered simultaneously. Alternatively, the active ingredients are present in separate pharmaceutical carriers, such as conventional oral dosage forms, that are administered either simultaneously or sequentially.

The following examples are provided merely as illustrative of various embodiments and shall not be construed to limit the invention in any way.

EXAMPLES

List of Abbreviations

As used above, and throughout the description of the invention, the following abbreviations, unless otherwise indicated, shall be understood to have the following meanings:

| | |
|---|---|
| ACN or MeCN | acetonitrile |
| BINAP | 2,2'-Bis(diphenylphosphino)-1,1'-binaphthyl |
| Bn | benzyl |
| BOC or Boc | tert-butyl carbamate |
| CDI | 1,1'-carbonyldiimidazole |
| Cy | cyclohexyl |
| DCE | dichloroethane ($ClCH_2CH_2Cl$) |
| DCM | dichloromethane ($CH_2Cl_2$) |
| DIPEA or DIEA | diisopropylethylamine |
| DMAP | 4-(N,N-dimethylamino)pyridine |
| DMF | dimethylformamide |
| DMA | N,N-dimethylacetamide |
| DMSO | dimethylsulfoxide |
| EDCI | 1-Ethyl-3-(3-dimethylaminopropyl)carbodiimide |
| eq | equivalent(s) |
| Et | ethyl |
| EtOH | ethanol |
| EtOAc | ethyl acetate |
| HATU | 1-[bis(dimethylamino)methylene]-1H-1,2,3-triazolo[4,5-b]pyridinium 3-oxid hexafluorophosphate |
| HFIP | 1,1,1,3,3,3-hexafluoropropan-2-ol |
| HOBT | Hydroxybenzotriazole |
| HPLC | high performance liquid chromatography |
| LAH | lithium aluminum hydride |
| LCMS | liquid chromatography-mass spectrometry |
| Me | methyl |
| MeOH | methanol |
| MS | mass spectroscopy |
| NMM | N-methylmorpholine |
| NMR | nuclear magnetic resonance |
| $Pd_2(dba)_3$ | Tris(dibenzylideneacetone)dipalladium |
| PMB | para-methoxybenzyl |
| rt | room temperature |
| SPhos | 2-Dicyclohexylphosphino-2',6'-dimethoxybiphenyl |
| TBAI | Tetrabutylammonium iodide |
| TEA | triethylamine |
| TFA | trifluoroacetic acid |
| THF | tetrahydrofuran |
| TLC | thin layer chromatography |

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted.

Example 1: Synthesis of 1-((1R,5S)-8-(5-fluoropyridin-2-yl)-3,8-diazabicyclo[3.2.1]octan-3-yl)-2-(quinolin-5-ylmethoxy)ethan-1-one

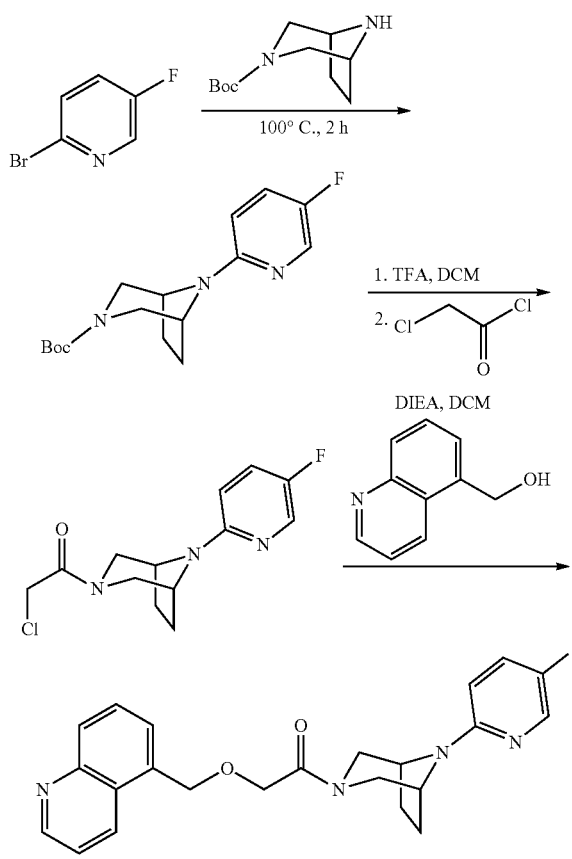

Step 1. Preparation of tert-butyl 8-(5-fluoropyridin-2-yl)-3,8-diaza-bicyclo[3.2.1]octane-3-carboxylate. Into a 250-mL round-bottom flask purged and maintained with an inert atmosphere of nitrogen, was placed 2-bromo-5-fluoropyridine (5 g, 28.6 mmol, 1 eq), tert-butyl 3,8-diaza-bicyclo[3.2.1]octane-3-carboxylate (6 g, 28.6 mmol, 1 eq), $Pd_2(dba)_3 \cdot CHCl_3$ (5.92 g, 5.72 mmol, 0.2 eq), BINAP (3.6 g, 5.72 mmol, 0.2 eq), tBuOK (9.6 g, 85.8 mmol, 3 eq), toluene (80 mL). The resulting solution was stirred for 2 h at 100° C. in an oil bath. The resulting mixture was concentrated under vacuum. The residue was applied onto a silica gel column eluting with DCM/MeOH (30:1). Approximately 5.6 g (65%) of a light brown oil was obtained.

Step 2. Preparation of 8-(5-fluoropyridin-2-yl)-3,8-diaza-bicyclo[3.2.1]octane. In a 100-mL round-bottom flask was placed tert-butyl 8-(5-fluoropyridin-2-yl)-3,8-diaza-bicyclo[3.2.1]octane-3-carboxylate (5.6 g, 18.2 mmol, 1 eq), trifluoroacetic acid (10 mL), dichloromethane (30 mL). The resulting solution was stirred for 2 h at room temperature. The solvent was removed under vacuum. The crude product was purified by a silica gel column eluting with DCM/MeOH (20:1). Approximately 3.5 g (95%) of an off-white solid was obtained.

Step 3. Preparation of 2-chloro-1-(8-(5-fluoropyridin-2-yl)-3,8-diaza-bicyclo[3.2.1]octan-3-yl)ethenone. 2-Chloroacetyl chloride (645 mg, 5.8 mmol, 1.2 eq) was added to a solution of 8-(5-fluoropyridin-2-yl)-3,8-diaza-bicyclo [3.2.1]octane (1 g, 4.8 mmol, 1 eq), DIEA (1.9 g, 14.4 mmol, 3 eq) in DCM (10 mL) at 0° C. The resulting solution was stirred for 1.5 h at room temperature. The resulting mixture was diluted with DCM and washed with saturated $NaHCO_3$. The combined organic layer was concentrated under vacuum. The crude product was purified by a silica gel column with ethyl acetate/petroleum ether (1:2). Approximately 1.15 g (85%) of a brown oil was obtained.

Step 4. Preparation of 1-(8-(5-fluoropyridin-2-yl)-3,8-diaza-bicyclo[3.2.1]octan-3-yl)-2-(quinolin-5-ylmethoxy) ethenone. 2-Chloro-1-(8-(5-fluoropyridin-2-yl)-3,8-diaza-bicyclo[3.2.1]octan-3-yl)ethanone (108 mg, 0.38 mmol, 1 eq) was added to a solution of quinolin-5-ylmethanol (60 mg, 0.38 mmol, 1 eq), NaOH (46 mg, 1.14 mmol, 3 eq), 18-crown-6 (5 mg) in DMF (5 mL). The resulting solution was stirred at room temperature overnight. The crude product was purified by HPLC to give 1-(8-(5-fluoropyridin-2-yl)-3,8-diaza-bicyclo[3.2.1]octan-3-yl)-2-(quinolin-5-ylmethoxy)ethanone as a brown solid, 35.2 mg (23%), LCMS: m/z=407.1 [M+H$^+$].

Example 2: Synthesis of 1-((1R,5S)-8-(5-fluoropyridin-2-yl)-3,8-diazabicyclo[3.2.1]octan-3-yl)-2-(1-(quinolin-5-yl)azetidin-3-yl)ethan-1-one

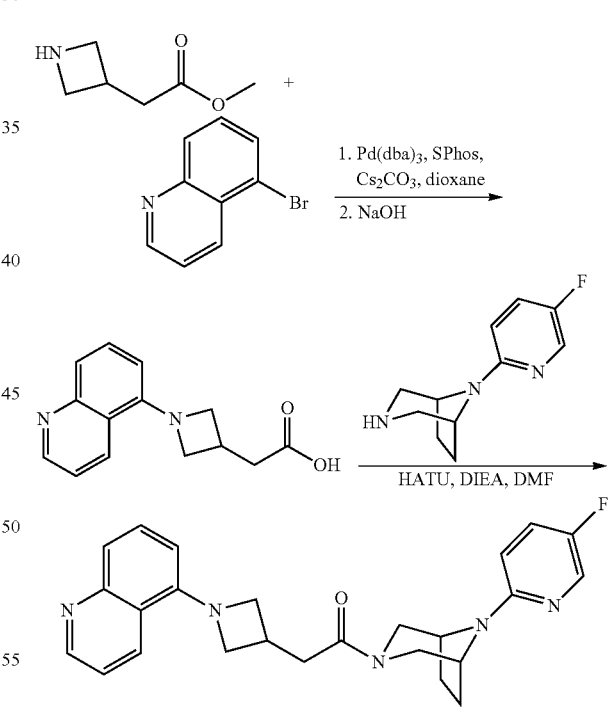

Step 1: Into a 100-mL round-bottom flask purged and maintained with an inert atmosphere of nitrogen, was placed methyl 2-(azetidin-3-yl)acetate (500 mg, 3.87 mmol, 1 eq), 5-bromoquinoline (1.6 g, 7.74 mmol, 2 eq), $Pd_2(dba)_3 \cdot CHCl_3$ (801.4 mg, 0.77 mmol, 0.2 eq), SPhos (635.7 mg, 1.55 mmol, 0.4 eq), $Cs_2CO_3$ (3784.0 mg, 11.61 mmol, 3 eq), dioxane (30.0 mL). The resulting solution was stirred for 2 h at 100° C. in an oil bath. The solids were filtered off. The resulting mixture was concentrated. The residue was applied onto a silica gel column with ethyl acetate/petroleum ether (1:4). This resulted in 700 mg (70%) of methyl 2-[1-(quinolin-5-yl)azetidin-3-yl]acetate as a yellow solid.

Step 2: In a 8-mL vial was placed methyl 2-[1-(quinolin-5-yl)azetidin-3-yl]acetate (400 mg, 1.56 mmol, 1 eq), MeOH (5 mL, 123.49 mmol, 79.1 eq), H$_2$O (1.0 mL), NaOH (124.8 mg, 3.12 mmol, 2 eq). The resulting solution was stirred for 2 h at room temperature. The resulting mixture was concentrated. The pH value of the solution was adjusted to 4 with hydrochloric acid. The solids were collected by filtration. The solid was dried in an oven under reduced pressure. This resulted in 200 mg (52%) of 2-[1-(quinolin-5-yl)azetidin-3-yl]acetic acid as a solid.

Step 3: In a 8-mL vial was placed 2-[1-(quinolin-5-yl) azetidin-3-yl]acetic acid (50 mg, 0.21 mmol, 1 eq), 8-(5-fluoropyridin-2-yl)-3,8-diazabicyclo[3.2.1]octane (51.3 mg, 0.25 mmol, 1.2 eq), DMF (4 mL), DIEA (80.0 mg, 0.62 mmol, 3 eq), HATU (117.7 mg, 0.31 mmol, 1.5 eq). The resulting solution was stirred for 2 h at room temperature. The crude product was purified by HPLC to give 1-[8-(5-fluoropyridin-2-yl)-3,8-diazabicyclo[3.2.1]octan-3-yl]-2-[1-(quinolin-5-yl)azetidin-3-yl]ethan-1-one (23.5 mg, 26%) as a yellow solid. LCMS m/z=432.2 [M+H]$^+$.

Example 3: Synthesis of ((1R,5S)-8-(5-fluoropyridin-2-yl)-3,8-diazabicyclo[3.2.1]octan-3-yl)(3-(isoquinolin-5-yloxy)azetidin-1-yl)methanone

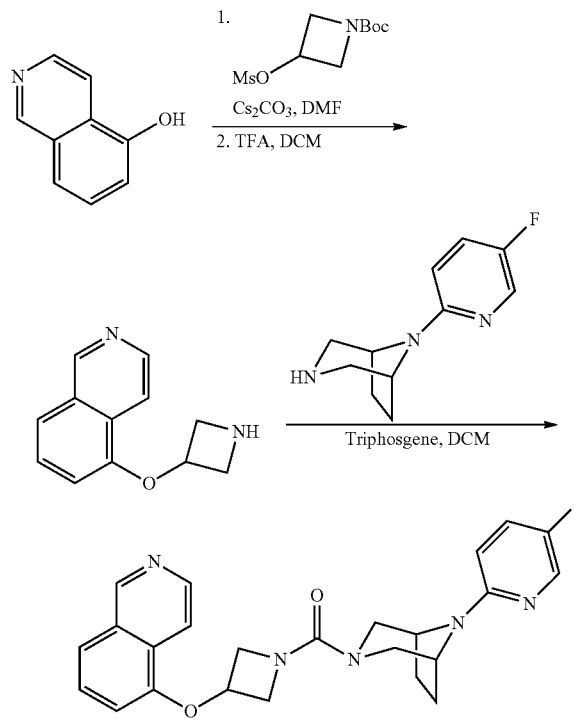

Step 1: To a solution of isoquinolin-5-ol (1.2 g, 8.27 mmol, 1 eq) in DMF (15 mL) was added tert-butyl 3-(methanesulfonyloxy) azetidine-1-carboxylate (2.1 g, 8.27 mmol, 1 eq), Cs$_2$CO$_3$ (8.1 g, 24.80 mmol, 3 eq) and 18-crown-6 (218.5 mg, 0.83 mmol, 0.1 eq). The resulting solution was stirred for 2 h at 80° C. in an oil bath. The resulting solution was extracted with 100 ml of ethyl acetate and the organic layers combined. The resulting mixture was washed with H$_2$O. The resulting mixture was concentrated. The residue was purified on a silica gel column eluting with ethyl acetate/petroleum ether (1:1) to afford tert-butyl 3-(isoquinolin-5-yloxy)azetidine-1-carboxylate (1.2 g) as a light yellow solid.

Step 2: To a solution of tert-butyl 3-(isoquinolin-5-yloxy) azetidine-1-carboxylate (1.2 g, 4.33 mmol, 1 eq) in DCM (10 mL) was added TFA (10 mL). The resulting solution was stirred for 1 h at room temperature. The resulting mixture was concentrated. The residue was dissolved in 20 mL of CH$_3$CN. The pH value of the solution was adjusted to 8 with NaHCO$_3$. The solids were filtered out. The residue was purified on a silica gel column eluted with dichloromethane/methanol (91:9) to afford 5-(azetidin-3-yloxy)isoquinoline (650 mg, 81%) as a light yellow solid.

Step 3: Under nitrogen, to a solution of 5-(azetidin-3-yloxy)isoquinoline (100 mg, 0.50 mmol, 1 eq) in DCM (4 mL) was added TEA (151.6 mg, 1.50 mmol, 3 eq). Then triphosgene (74.1 mg, 0.25 mmol, 0.5 eq) was added dropwise at 0° C. and the solution was stirred for 1 h at room temperature. Then 1, 8-(5-fluoropyridin-2-yl)-3,8-diazabicyclo[3.2.1]octane (103.5 mg, 0.50 mmol, 1 eq) was added dropwise at 0° C. and the solution was stirred at room temperature overnight. The resulting solution was extracted with ethyl acetate and the organic layers combined and concentrated. The residue was purified on a silica gel column eluted with MeOH/DCM (5%) to afford 5-[(1-[[8-(5-fluoropyridin-2-yl)-3,8-diazabicyclo[3.2.1]octan-3-yl] carbonyl]azetidin-3-yl)oxy]isoquinoline (25.8 mg, 12%) as a light yellow solid, LCMS, m/z=434.3 [M+H]$^+$.

Example 4: Synthesis of 1-(4-(pyridin-4-yl)piperazin-1-yl)-4-(quinolin-5-yl)butan-1-one

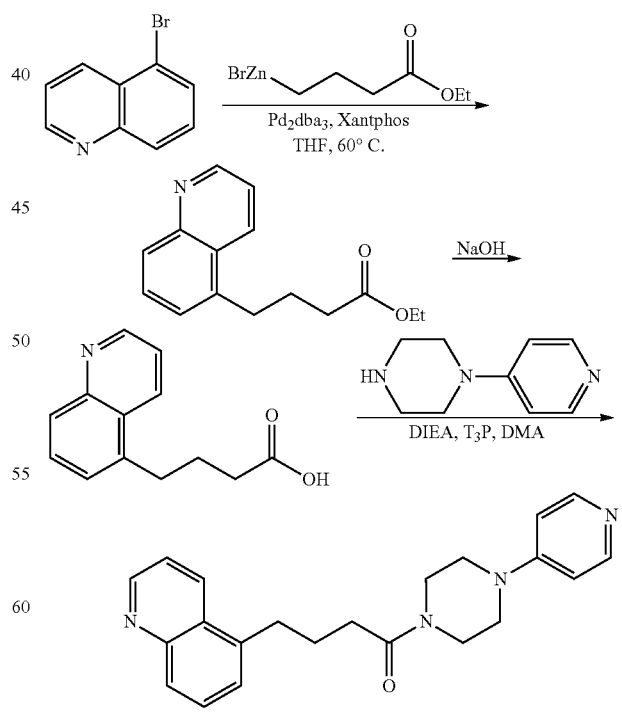

Step 1: To a solution of 5-bromoquinoline (3.50 g, 16.8 mmol, 1 eq) in THF (50.0 mL) was added (4-ethoxy-4- oxobutyl)zinc(II) bromide (0.50 M, 101 mL, 3.00 eq) under $N_2$ protection at 25° C. $Pd_2(dba)_3$ (350 mg, 0.02 eq) and Xantphos (350 mg, 0.04 eq) was added to above mixture. The mixture was stirred at 60° C. under $N_2$ protection for 12 hrs. The mixture was quenched by adding aqueous $NaHCO_3$ (50.0 mL), filtered to remove the Zn salt, the filtrate was concentrated, washed with $H_2O$ (50.0 mL), extracted with DCM. The organic layer was concentrated and purified by prep-MPLC ($SiO_2$, petroleum ether/ethyl acetate) to give ethyl 4-(quinolin-5-yl)butanoate (2.70 g, 10.9 mmol, 64% yield) as a yellow oil.

Step 2: Ethyl 4-(quinolin-5-yl)butanoate (2.00 g, 8.22 mmol, 1.00 eq) was dissolved in MeOH (20.0 mL), NaOH (2 M, 20.6 mL, 5.00 eq) was added to above mixture. The resulting mixture was stirred at 25° C. for 4 hrs. The mixture was concentrated to remove MeOH and adjusted to pH7 by adding aqueous HCl (2M). Precipitate was formed. The solid was collected to give 4-(quinolin-5-yl)butanoic acid (1.40 g, 6.31 mmol, 76%) as a white solid.

Step 3: A mixture of 4-(quinolin-5-yl)butanoic acid (0.3 mmol, 1 eq), 1-(pyridin-4-yl)piperazine (1.2 eq), propylphosphonic anhydride ($T_3P$) (2 eq) and DIEA (2 eq) in DMA (2 mL) was stirred for 16 h at 25° C. The reaction was purified by prep-HPLC to give 1-(4-(pyridin-4-yl)piperazin-1-yl)-4-(quinolin-5-yl)butan-1-one as a solid. LCMS, m/z=361.1 $[M+H]^+$.

Example 5: Synthesis of ((1R,3R)-3-(benzo[d]thiazol-7-yloxy)cyclobutyl)(4-(5-fluoropyridin-2-yl)-2-methylpiperazin-1-yl)methanone

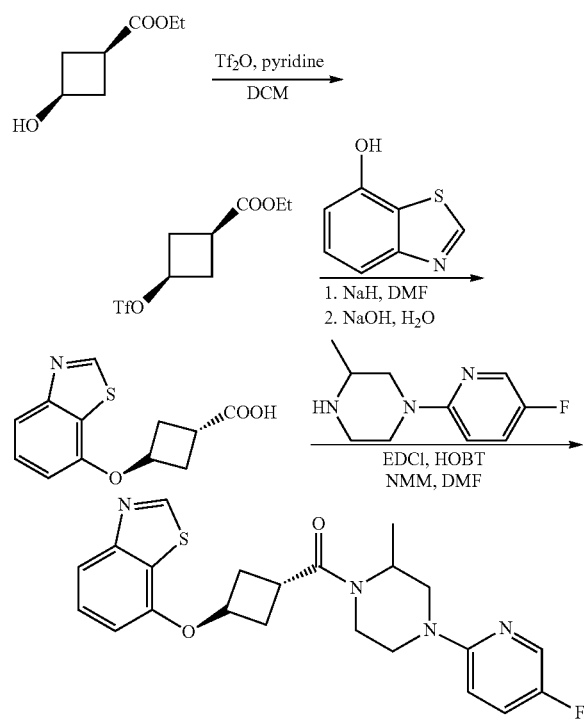

Step 1: To a solution of ethyl (1S,3S)-3-hydroxycyclobutane-1-carboxylate (2.0 g, 13.9 mmol, 1 eq) in DCM (15 mL) was added pyridine (2.19 g, 27.7 mmol, 2.24 mL, 2 eq) portion-wise and $Tf_2O$ (4.70 g, 16.6 mmol, 2.75 mL, 1.2 eq) drop-wise at 0° C. under $N_2$. The mixture was stirred at 25° C. for 2 hrs. The reaction mixture was concentrated under reduced pressure to give ethyl (1s,3s)-3-(((trifluoromethyl)sulfonyl)oxy)cyclobutane-1-carboxylate (3.5 g, crude) and it was used in the next step without further purification.

Step 2: To a solution of benzo[d]thiazol-7-ol (1.50 g, 9.92 mmol, 1 eq) in DMF (15 mL) was added NaH (794 mg, 19.8 mmol, 60%, 2 eq) at 0° C. under $N_2$. After stirred at 0° C. for 0.5 h, ethyl (1S,3S)-3-(((trifluoromethyl)sulfonyl)oxy)cyclobutane-1-carboxylate (3.0 g, 10.9 mmol, 1.09 eq) was added to the reaction mixture portion-wise at 0° C. under $N_2$. The mixture was stirred at 25° C. for 3 hrs. The reaction mixture was quenched by addition water at 0° C. After stirred at 25° C. for 0.5 h, the reaction mixture was diluted with water (15 mL) and extracted with ethyl acetate. Then the water phase was adjusted to pH 4 with HCl (1 M). After stirred at 25° C. for 0.5 h, the mixture was filtered and the filtrate was concentrated under reduced pressure to give (1R,3R)-3-(benzo[d]thiazol-7-yloxy)cyclobutane-1-carboxylic acid (1.0 g, 3.64 mmol, 36.7% yield, 91% purity) as a black brown solid, LCMS: m/z=249.9 $[M+H]^+$.

Step 3: To a solution of (1R,3R)-3-(benzo[d]thiazol-7-yloxy)cyclobutane-1-carboxylic acid (0.05 g, 0.201 mmol, 1 eq) in DMF (2 mL) was added EDCI (46.1 mg, 0.241 mmol, 1.2 eq), HOBT (32.5 mg, 0.241 mmol, 1.2 eq), NMM (40.6 mg, 0.401 mmol, 2 eq) and 1-(5-fluoropyridin-2-yl)-3-methylpiperazine (0.164 mmol, 0.8 eq). The mixture was stirred for 16 h at 25° C. The reaction was filtered to remove deposit. The residue was purified by prep-HPLC to give ((1R,3R)-3-(benzo[d]thiazol-7-yloxy)cyclobutyl)(4-(5-fluoropyridin-2-yl)-2-methylpiperazin-1-yl)methanone (30.2 mg, 37.9%) as a white solid, LCMS, m/z=427.0 $[M+H]^+$.

Example 6: Synthesis of 1-[(2S)-4-(5-fluoro-3-methylpyridin-2-yl)-2-methylpiperazin-1-yl]-4-(quinolin-5-yl)butan-1-one

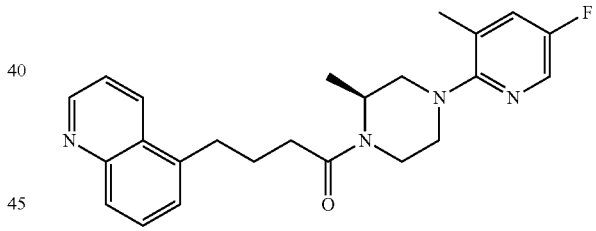

Step 1: In a 10-mL sealed tube purged and maintained with an inert atmosphere of nitrogen, was placed tert-butyl (2R)-2-methylpiperazine-1-carboxylate (200 mg, 1.00 mmol, 1 eq), dioxane (4 mL), 2-bromo-5-fluoro-3-methylpyridine (227.7 mg, 1.20 mmol, 1.20 eq), $Pd_2(dba)_3$ (365.8 mg, 0.40 mmol, 0.4 eq), Xantphos (462.2 mg, 0.80 mmol, 0.8 eq), $Cs_2CO_3$ (976.1 mg, 3.00 mmol, 3 eq). The resulting solution was stirred for 2 h at 110° C. in an oil bath. The resulting mixture was concentrated. The residue was applied onto a silica gel column with ethyl acetate/petroleum ether (1:5). This resulted in 80 mg (26%) of tert-butyl (2R)-4-(5-fluoro-3-methylpyridin-2-yl)-2-methylpiperazine-1-carboxylate as a yellow oil, LCMS: m/z=310.2 $[M+H]^+$.

Step 2: In a 25-mL round-bottom flask was placed tert-butyl (2S)-4-(5-fluoro-3-methylpyridin-2-yl)-2-methylpiperazine-1-carboxylate (60 mg, 0.19 mmol, 1 eq), DCM (4 mL), TFA (2 mL). The resulting solution was stirred at rt for 1 h. The resulting mixture was concentrated. The residue was applied onto a silica gel column with ethyl acetate/petroleum ether (1:4). This resulted in 25 mg (61.6%) of (3S)-1-(5-fluoro-3-methylpyridin-2-yl)-3-methylpiperazine as a yellow oil, LCMS: m/z=210.1 [M+H]+.

Step 3: In a 25-mL round-bottom flask was placed (3S)-1-(5-fluoro-3-methylpyridin-2-yl)-3-methylpiperazine (25 mg, 0.12 mmol, 1 eq), DMF (2 mL), 4-(quinolin-5-yl) butanoic acid (28.3 mg, 0.13 mmol, 1.1 eq), HATU (68.1 mg, 0.18 mmol, 1.5 eq), DIEA (46.3 mg, 0.36 mmol, 3 eq). The resulting solution was stirred at rt for 1 h. The crude product was purified by Prep-HPLC to give 1-[(2S)-4-(5-fluoro-3-methylpyridin-2-yl)-2-methylpiperazin-1-yl]-4-(quinolin-5-yl)butan-1-one as a white solid (16.0 mg, 33%), LCMS: m/z=407.2 [M+H]+; $^1$H NMR (300 MHz, methanol-$d_4$) δ 8.86 (m, J=4.3, 1.6 Hz, 2H), 8.74 (d, J=8.5 Hz, 2H), 8.00 (d, J=3.0 Hz, 2H), 7.93 (d, J=8.5 Hz, 2H), 7.72 (m, J=8.5, 7.0 Hz, 2H), 7.60 (m, J=8.6, 4.3 Hz, 2H), 7.53 (d, J=7.1 Hz, 2H), 7.41 (m, J=9.0, 3.0 Hz, 2H), 4.82 (s, 1H), 4.48 (d, J=13.3 Hz, 1H), 4.23 (s, 1H), 3.82 (d, J=13.3 Hz, 1H), 3.56 (m, J=12.7 Hz, 1H), 3.21 (m, J=7.9 Hz, 8H), 2.91-2.71 (m, 2H), 2.67-2.47 (m, 1H), 2.38 (s, 6H), 2.07 (s, 4H), 1.61 (s, 1H), 1.48-1.27 (m, 9H), 0.91 (m, J=6.2 Hz, 6H).

Example 7: Synthesis of 1-(benzo[d]thiazol-7-ylmethyl)azetidin-3-yl)((1R,5S)-8-(3-fluoropyridin-4-yl)-3,8-diazabicyclo [3.2.1]octan-3-yl)methanone

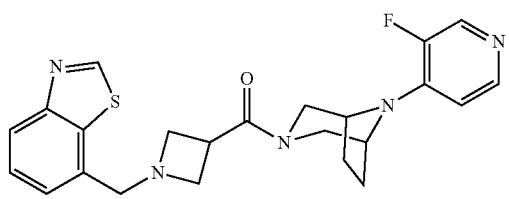 [SMILES: O=C(C1CN(Cc2cccc3ncsc23)C1)N1CC2CCC(C1)N2c1ccncc1F]

Step 1: To a solution of 1-(tert-butoxycarbonyl)azetidine-3-carboxylic acid (192 mg, 0.96 mmol, 1.00 eq) in DMF (2 ml) was added HATU (547 mg, 1.44 mmol, 1.5 eq), DIEA (371 mg, 2.88 mmol, 3.00 eq) and (1R,5S)-8-(3-fluoropyridin-4-yl)-3,8-diazabicyclo[3.2.1]octane (239 mg, 1.15 mmol, 1.20 eq). The resulting solution was stirred at r.t for 1 h. The mixture was extracted with ethyl acetate and solvent was evaporated. The residue was applied onto a silica gel column. This resulted in 270 mg (72%) of tert-butyl3-((1R,5S)-8-(3-fluoropyridin-4-yl)-3,8-diazabicyclo[3.2.1]octane-3-carbonyl)azetidine-1-carboxylate as a yellow oil; LCMS: m/z=391.2 [M+H]+.

Step 2: To a solution of 3-((1R,5S)-8-(3-fluoropyridin-4-yl)-3,8-diazabicyclo[3.2.1]octane-3-carbonyl) azetidine-1-carboxylate (260 mg, 0.67 mmol, 1.00 eq) in DCM (4 ml) was added TFA (2 ml). The resulting solution was stirred at r.t for 1 h. The mixture was evaporated. The residue was applied onto a silica gel column with MeOH/DCM (10%). This resulted in 180 mg (93%) of azetidin-3-yl((1R,5S)-8-(3-fluoropyridin-4-yl)-3,8-diazabicyclo[3.2.1]octan-3-yl) methanone as a brown oil; LCMS: m/z=291.1 [M+H]+.

Step 3: To a solution of azetidin-3-yl((1R,5S)-8-(3-fluoropyridin-4-yl)-3,8-diazabicyclo[3.2.1]octan-3-yl)methanone (46 mg, 0.16 mmol, 1.00 eq) in DMF (1 ml) was added benzo[d]thiazol-7-ylmethyl methanesulfonate (47 mg, 0.19 mmol, 1.2 eq) and DIEA (62 mg, 0.48 mmol, 3.00 eq). The resulting solution was stirred at r.t for 1 h. The crude product was purified by HPLC to give 1-(benzo[d]thiazol-7-ylmethyl)azetidin-3-yl)((1R,5S)-8-(3-fluoropyridin-4-yl)-3,8-diazabicyclo [3.2.1]octan-3-yl)methanone as a white solid (5.8 mg, 8%); LCMS: m/z=438.1 [M+H]+.

Example 8: Synthesis of 3-((benzo[d]thiazol-7-ylmethyl)amino)-1-((1R,5S)-8-(3-fluoropyridin-4-yl)-3,8-diazabicyclo[3.2.1]octan-3-yl)propan-1-one

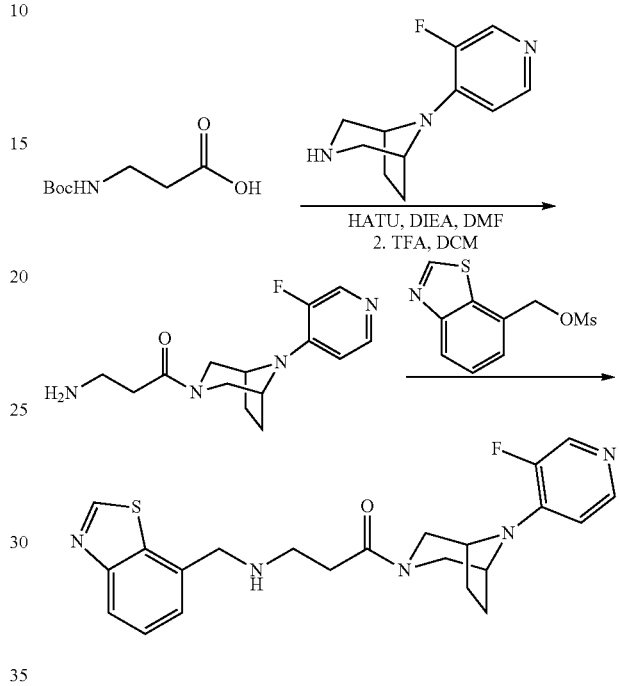

Step 1: To a solution of 3-((tert-butoxycarbonyl)amino) propanoic acid (150 mg, 0.79 mmol) in DMF (2 ml) was added HATU (452 mg, 1.19 mmol, 1.5 eq), DIEA (306 mg, 2.37 mmol, 3.00 eq) and (1R,5S)-8-(3-fluoropyridin-4-yl)-3,8-diazabicyclo[3.2.1]octane (239 mg, 1.15 mmol, 1.20 eq). The resulting solution was stirred at r.t for 1 h. The mixture was extracted with ethyl acetate and solvent was evaporated. The residue was purified by silica gel chromatography to give tert-butyl (3-((1R,5S)-8-(3-fluoropyridin-4-yl)-3,8-diazabicyclo[3.2.1]octan-3-yl)-3-oxopropyl)carbamate (170 mg, 57%) as a yellow oil, LCMS: m/z=379.2 [M+H]+.

Step 2: To a solution of tert-butyl (3-((1R,5S)-8-(3-fluoropyridin-4-yl)-3,8-diazabicyclo[3.2.1]octan-3-yl)-3-oxopropyl)carbamate (160 mg, 0.42 mmol) in DCM (4 ml) was added TFA (2 ml). The resulting solution was stirred at r.t for 1 h. The mixture was evaporated. The residue was purified by silica gel chromatography to give 3-amino-1-((1R,5S)-8-(3-fluoropyridin-4-yl)-3,8-diazabicyclo[3.2.1]octan-3-yl) propan-1-one as a yellow oil (110 mg, 94%); LCMS: m/z=279.1 [M+H]+.

Step 3: To a solution of 3-amino-1-((1R,5S)-8-(3-fluoropyridin-4-yl)-3,8-diazabicyclo[3.2.1]octan-3-yl)propan-1-one (46 mg, 0.16 mmol) in DMF (1 ml) was added benzo[d]thiazol-7-yl-methyl methanesulfonate (47 mg, 0.19 mmol, 1.2 eq) and DIEA (62 mg, 0.48 mmol, 3.00 eq). The resulting solution was stirred at r.t for 1 h. The crude product was purified by HPLC to give 3-((benzo[d]thiazol-7-ylmethyl)amino)-1-((1R,5S)-8-(3-fluoropyridin-4-yl)-3,8-diazabicyclo[3.2.1]octan-3-yl)propan-1-one as a white solid (7.9 mg, 12%); LCMS: m/z=426.2 [M+H]+.

Example 9: Synthesis of (2-((benzo[d]thiazol-7-yloxy)methyl)-cyclopropyl)((1R,5S)-8-(3-fluoropyridin-4-yl)-3,8-diazabicyclo[3.2.1]octan-3-yl)methanone

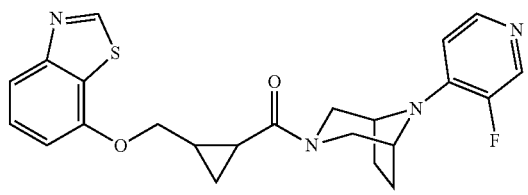 [SMILES: O=C(C1CC1COc1cccc2ncsc12)N1CC2CCC(C1)N2c1ccncc1F]

Step 1: To a solution of ethyl 2-formylcyclopropane-1-carboxylate (1.00 g, 7.03 mmol, 1 eq) in EtOH (20 mL) was added NaBH$_4$ (279 mg, 7.39 mmol, 1.05 eq) in portions at 0° C. The mixture was stirred for 2 h at room temperature. The reaction was quenched with saturated NH$_4$Cl solution (100 mL), the aqueous layer was extracted with ethyl acetate. The combined organic layer was washed with brine, dried over MgSO$_4$ and concentrated in vacuo to give ethyl 2-(hydroxymethyl)cyclopropane-1-carboxylate (0.9 g, crude) as a yellow oil.

Step 2: To a solution of ethyl 2-(hydroxymethyl)cyclopropane-1-carboxylate (0.8 g, 5.55 mmol) in DCM (15 mL) was added drop-wise TEA (674 mg, 6.66 mmol, 1.2 eq) and MsCl (763 mg, 6.66 mmol, 1.2 eq) at −15° C.~0° C. The mixture was stirred for 1 h at room temperature. The reaction was quenched with water (10 mL), the aqueous layer was extracted with ethyl acetate. The combined organic layer was washed with brine, dried over MgSO$_4$ and concentrated in vacuo to give ethyl 2-(((methylsulfonyl)oxy)methyl)cyclopropane-1-carboxylate (0.8 g, 3.60 mmol, 65%) as a white solid.

Step 3: To a solution of benzo[d]thiazol-7-ol (544 mg, 3.60 mmol) in DMF (10 mL) was added K$_2$CO$_3$ (995 mg, 7.20 mmol, 2 eq) and ethyl 2-(((methylsulfonyl)oxy)methyl)cyclopropane-1-carboxylate (0.800 g, 3.60 mmol, 1 eq). The mixture was stirred for 5 h at 50° C. The reaction was quenched with water (100 mL), the aqueous layer was extracted with ethyl acetate. The combined organic layer was washed with brine, dried over MgSO$_4$ and concentrated in vacuo. The residue was purified by MPLC (SiO$_2$, petroleum ether/ethyl acetate=50/1 to 1/1, R$_f$=0.50) to give ethyl 2-((benzo[d]thiazol-7-yloxy)methyl)cyclopropane-1-carboxylate (0.15 g, 15%) as a yellow oil, LCMS: m/z 278.2 [M+H]$^+$.

Step 4: To a solution of ethyl 2-((benzo[d]thiazol-7-yloxy)methyl)cyclopropane-1-carboxylate (0.0500 g, 0.180 mmol) in THF (2 mL) was added TMSOK (25.4 mg, 0.198 mmol, 1.1 eq). The mixture was stirred for 16 h at 25° C. The reaction was evaporated to dryness to give 2-((benzo[d]thiazol-7-yloxy)methyl)cyclopropane-1-carboxylic acid (44.0 mg, crude) as a white solid.

Step 5: To a solution of 2-((benzo[d]thiazol-7-yloxy)methyl)cyclopropane-1-carboxylic acid (0.0440 g, 0.177 mmol) in DMF (2 mL) was added EDCI (40.6 mg, 0.212 mmol, 1.2 eq), HOBT (28.6 mg, 0.212 mmol, 1.2 eq), NMM (53.6 mg, 0.530 mmol, 3 eq) and (1R,5S)-8-(3-fluoropyridin-4-yl)-3,8-diazabicyclo[3.2.1]octane (54.4 mg, 0.194 mmol, 1.1 eq, 2HCl salt). The mixture was stirred for 16 h at 25° C. The residue was purified by prep-HPLC to give (2-((benzo[d]thiazol-7-yloxy)methyl)-cyclopropyl)((1R,5S)-8-(3-fluoropyridin-4-yl)-3,8-diazabicyclo[3.2.1]octan-3-yl)methanone (36.9 mg, 45%) as a white solid. LCMS: m/z=439.1, $^1$H NMR (DMSO-d$_6$) δ=9.40-9.34 (m, 1H), 8.27-8.19 (m, 1H), 8.10-8.01 (m, 1H), 7.68 (t, J=8.4 Hz, 1H), 7.51-7.43 (m, 1H), 7.10-6.96 (m, 2H), 4.57-4.39 (m, 3H), 4.36-4.13 (m, 1H), 4.05-3.78 (m, 3H), 2.91-2.81 (m, 1H), 2.15-2.00 (m, 1H), 1.99-1.87 (m, 2H), 1.84-1.67 (m, 1H), 1.66-1.56 (m, 2H), 1.25-1.13 (m, 1H), 0.91-0.82 (m, 1H).

Example 10: Synthesis of 1-((1R,5S)-8-(3-fluoropyridin-4-yl)-3,8-diazabicyclo[3.2.1]octan-3-yl)-3-((quinolin-5-ylmethyl)amino)propan-1-one

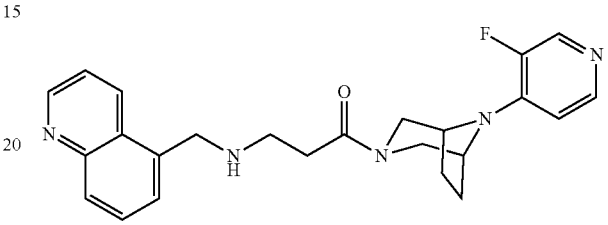

Step 1: To a solution of 3-amino-1-((1R,5S)-8-(3-fluoropyridin-4-yl)-3,8-diazabicyclo[3.2.1]octan-3-yl)propan-1-one (190 mg, 0.68 mmol, 1.00 eq) in MeOH (4 ml) was added quinoline-5-carbaldehyde (160 mg, 1.02 mmol, 1.5 eq). The resulting solution was stirred at r.t for 1 h. The mixture was extracted with ethyl acetate and solvent was evaporated. The residue was applied onto a silica gel column eluting with ethyl acetate/petroleum ether (30%). This resulted in 150 mg (53%) of 1-((1R,5S)-8-(3-fluoropyridin-4-yl)-3,8-diazabicyclo [3.2.1]octan-3-yl)-3-(((E)-quinolin-5-ylmethylene)amino)propan-1-one as a yellow oil; LCMS: m/z=418.2 [M+H]$^+$.

Step 2: To a solution of 1-((1R,5S)-8-(3-fluoropyridin-4-yl)-3,8-diazabicyclo[3.2.1]octan-3-yl)-3-(((E)-quinolin-5-ylmethylene)amino) propan-1-one (140 mg, 0.3 mmol, 1.00 eq) in MeOH (1 ml) was added NaBH$_3$(CN) (25 mg, 0.40 mmol, 1.2 eq). The resulting solution was stirred at r.t for 0.5 h. The crude product was purified by HPLC to give 1-((1R,5S)-8-(3-fluoropyridin-4-yl)-3,8-diazabicyclo[3.2.1]octan-3-yl)-3-((quinolin-5-ylmethyl)amino)propan-1-one as a white solid (26.8 mg, 22%); LCMS: m/z=420.2 [M+H]$^+$.

Example 11: Synthesis of 1-((1R,5S)-8-(3-fluoropyridin-4-yl)-3,8-diazabicyclo-[3.2.1]octan-3-yl)-2-(2-(quinolin-5-yl)ethoxy)ethan-1-one

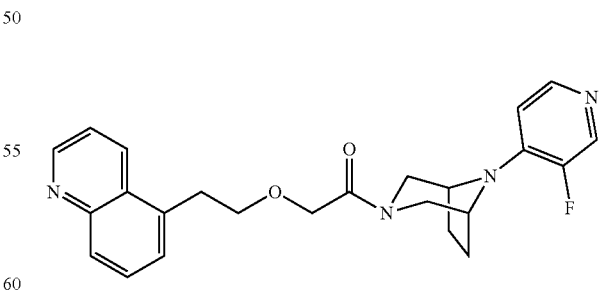

To a solution of 2-(quinolin-5-yl)ethan-1-ol (91.5 mg, 0.528 mmol, 1.5 eq) in DMF (2 mL) was added NaH (21.1 mg, 0.528 mmol, 1.5 eq) at 0° C., then the reaction mixture was stirring at 25° C. for 1 h. 2-chloro-1-((1R,5S)-8-(3-fluoropyridin-4-yl)-3,8-diazabicyclo[3.2.1]octan-3-yl)ethan-1-one (100 mg, 0.352 mmol, 1 eq) was added to the mixture at 0° C., then the reaction was stirred at 25° C. for 1 hour. The reaction mixture was quenched by adding (CF₃CO₂H/DCM=1/1, 0.5 mL) at 0° C. and then concentrated. The residue was purified by HPLC to give 1-((1R,5S)-8-(3-fluoropyridin-4-yl)-3,8-diazabicyclo-[3.2.1]octan-3-yl)-2-(2-(quinolin-5-yl)ethoxy)ethan-1-one (19.2 mg, 10%) as a yellow solid. LCMS, m/z=421.2 [M+H]⁺; ¹H NMR (DMSO, 400 MHz): δ=8.89 (br d, J=3.3 Hz, 1H), 8.55 (br d, J=8.6 Hz, 1H), 8.26 (br d, J=6.0 Hz, 1H), 8.14 (s, 1H), 8.08 (br d, J=5.6 Hz, 1H), 7.88 (br d, J=8.4 Hz, 1H), 7.66 (t, J=7.8 Hz, 1H), 7.58-7.49 (m, 2H), 7.04-6.96 (m, 1H), 4.46 (br s, 1H), 4.32 (br s, 1H), 4.24-4.16 (m, 1H), 4.11-4.04 (m, 1H), 3.98 (br d, J=12.5 Hz, 1H), 3.83-3.69 (m, 2H), 3.49-3.35 (m, 3H), 3.12 (br d, J=12.7 Hz, 1H), 2.78 (br d, J=12.7 Hz, 1H), 1.89-1.67 (m, 3H), 1.54 (br d, J=8.9 Hz, 1H).

Example 12: Synthesis of 1-((1R,5S)-8-(3-fluoropyridin-4-yl)-3,8-diazabicyclo[3.2.1]octan-3-yl)-3-(imidazo[1,2-a]pyridin-5-ylmethoxy)propan-1-one

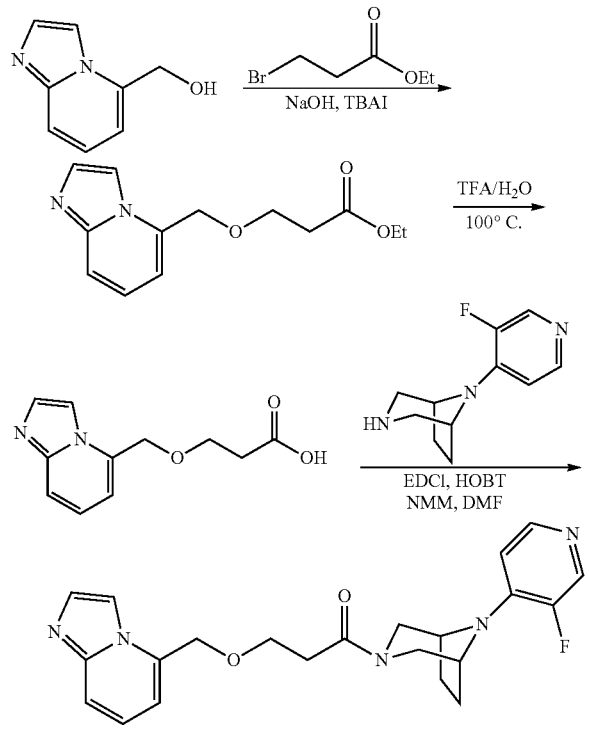

Step 1: To a solution of imidazo[1,2-a]pyridin-5-ylmethanol (0.150 g, 1.01 mmol, 1 eq) in DMF (2 mL) was added ethyl 3-bromopropanoate (367 mg, 2.02 mmol, 2 eq), NaOH (121 mg, 3.04 mmol, 3 eq) and TBAI (3.74 mg, 0.010 mmol, 0.01 eq). The mixture was stirred for 16 h at 50° C. The reaction was quenched with water (10 mL), the aqueous layer was extracted with ethyl acetate. The combined organic layer was washed with brine, dried over MgSO₄ and concentrated in vacuo. The residue was purified by prep-TLC (SiO₂, DCM/MeOH=10/1, R_f=0.42) to give ethyl 3-(imidazo[1,2-a]pyridin-5-ylmethoxy)propanoate (0.04 g, 13% yield, 80% purity) as a yellow oil, LCMS: m/z=249.3 [M+H]⁺.

Step 2: A solution of ethyl 3-(imidazo[1,2-a]pyridin-5-ylmethoxy)propanoate (0.04 g, 0.161 mmol) in H₂O (1 mL) and TFA (1 mL) was stirred for 2 h at 100° C. The reaction was evaporated to dryness to give 3-(imidazo[1,2-a]pyridin-5-ylmethoxy)propanoic acid (0.035 g, crude) as a yellow solid, LCMS: m/z=221.3 [M+H]⁺.

Step 3: To a solution of 3-(imidazo[1,2-a]pyridin-5-ylmethoxy)propanoic acid (0.035 g, 0.159 mmol) in DMF (2 mL) was added EDCI (36.6 mg, 0.191 mmol, 1.2 eq), HOBT (25.8 mg, 0.191 mmol, 1.2 eq), NMM (64.3 mg, 0.636 mmol, 4 eq) and (1R,5S)-8-(3-fluoropyridin-4-yl)-3,8-diazabicyclo[3.2.1]octane (49.0 mg, 0.175 mmol, 1.1 eq, 2HCl salt). The mixture was stirred for 16 h at 25° C. The residue was purified by prep-HPLC to give 1-((1R,5S)-8-(3-fluoropyridin-4-yl)-3,8-diazabicyclo[3.2.1]octan-3-yl)-3-(imidazo[1,2-a]pyridin-5-ylmethoxy)propan-1-one (0.02 g, 28%) as a yellow solid, LCMS: m/z=410.2 [M+H]⁺; ¹H NMR (DMSO-d₆): δ=8.25-8.16 (m, 1H), 8.08-7.98 (m, 1H), 7.83 (s, 1H), 7.61-7.49 (m, 2H), 7.22 (dd, J=6.9, 8.9 Hz, 1H), 7.04-6.90 (m, 2H), 4.77 (s, 2H), 4.53-4.35 (m, 2H), 4.05 (br d, J=12.3 Hz, 1H), 3.80-3.69 (m, 2H), 3.61 (br d, J=12.8 Hz, 1H), 2.83-2.57 (m, 3H), 1.98-1.63 (m, 4H), 1.58-1.46 (m, 1H).

Example 13: Synthesis of 1-[(2S)-4-(5-fluoro-3-methylpyridin-2-yl)-2-methylpiperazin-1-yl]-2-[[(quinolin-5-yl) methyl]amino]ethanone

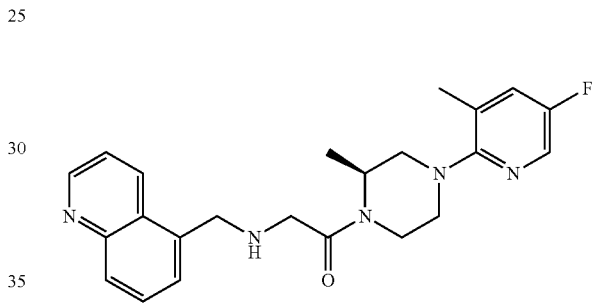

Step 1: In a 25-mL round-bottom flask was placed (3S)-1-(5-fluoro-3-methylpyridin-2-yl)-3-methylpiperazine (150 mg, 0.72 mmol, 1 eq), DMF (3 mL), 2-[[(tert-butoxy)carbonyl]amino]acetic acid (188.4 mg, 1.08 mmol, 1.5 eq), HATU (408.8 mg, 1.08 mmol, 1.5 eq), DIEA (277.9 mg, 2.15 mmol, 3 eq). The resulting solution was stirred at rt for 1 h. The resulting solution was extracted with 100 mL of dichloromethane. This resulted in 160 mg (61%) of tert-butyl N-[2-[(2S)-4-(5-fluoro-3-methylpyridin-2-yl)-2-methylpiperazin-1-yl]-2-oxoethyl]carbamate as a yellow oil, LCMS: m/z=367.2 [M+H]⁺.

Step 2: In a 25 mL round-bottom flask was placed tert-butyl N-[2-[(2S)-4-(5-fluoro-3-methylpyridin-2-yl)-2-methylpiperazin-1-yl]-2-oxoethyl] carbamate (150 mg, 0.41 mmol, 1 eq), DCM (4 mL), TFA (2 mL). The resulting solution was stirred at rt for 1 h. The resulting mixture was concentrated. The crude product was purified by Prep-HPLC. This resulted in 90 mg (83%) of 2-amino-1-[(2S)-4-(5-fluoro-3-methylpyridin-2-yl)-2-methylpiperazin-1-yl] ethan-1-one as a yellow oil. LCMS: m/z=267.1 [M+H]⁺.

Step 3: In a 25-mL round-bottom flask was placed 2-amino-1-[(2S)-4-(5-fluoro-3-methylpyridin-2-yl)-2-methylpiperazin-1-yl]ethan-1-one (40 mg, 0.15 mmol, 1 eq), MeOH (2 mL), quinoline-5-carbaldehyde (35.4 mg, 0.23 mmol, 1.50 eq). The mixture was stirred for 1 h, then NaBH₃CN (18.9 mg, 0.30 mmol, 2.00 eq) was added. The resulting solution was stirred for 3 h at r.t. The solids were filtered off. The resulting mixture was concentrated. The crude product was purified by Prep-HPLC to give 1-[(2S)-4-(5-fluoro-3-methylpyridin-2-yl)-2-methylpiperazin-1-yl]-

2-[[(quinolin-5-yl) methyl]amino]ethanone as a white solid (31.8 mg, 50%). LCMS: m/z=407.9 [M+H]+; 1H NMR (300 MHz, methanol-d4) δ 8.91-8.82 (m, 1H), 8.03-7.94 (m, 1H), 7.81-7.55 (m, 2H), 7.45-7.35 (m, 1H), 4.76 (s, 0H), 4.27 (s, 1H), 3.71 (m, J=15.0 Hz, 1H), 3.54 (d, J=12.2 Hz, 1H), 3.22 (d, J=13.4 Hz, 1H), 2.81 (m, J=26.1, 13.4 Hz, 1H), 2.36 (s, 2H), 1.41 (m, J=17.5, 6.8 Hz, 2H).

Example 14: Synthesis of 1-[8-(3-fluoropyridin-4-yl)-3,8-diazabicyclo[3.2.1]octan-3-yl]-3-[([imidazo[1,2-a]pyridin-5-yl]methyl)amino]propan-1-one

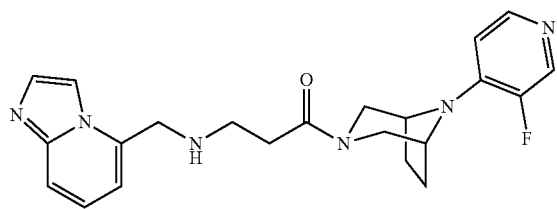 [SMILES: O=C(CCNCc1cccc2nccn12)N1CC2CCC(C1)N2c1ccncc1F]

In a 25-mL round-bottom flask was placed 3-amino-1-[8-(3-fluoropyridin-4-yl)-3,8-diazabicyclo [3.2.1]octan-3-yl] propan-1-one (30 mg, 0.11 mmol, 1 eq), MeOH (1 mL), imidazo[1,2-a]pyridine-5-carbaldehyde (18.9 mg, 0.13 mmol, 1.2 eq), NaBH3CN (13.5 mg, 0.22 mmol, 2 eq). The resulting solution was stirred for 1 h at 15° C. The solids were filtered out. The resulting mixture was concentrated. The crude product was purified by Prep-HPLC. This resulted in 12.6 mg (28.6%) of 1-[8-(3-fluoropyridin-4-yl)-3,8-diazabicyclo[3.2.1]octan-3-yl]-3-[([imidazo[1,2-a]pyridin-5-yl]methyl)amino]propan-1-one as a white solid. LCMS: m/z=409.2 [M+H]+; 1H NMR (300 MHz, methanol-d4) δ 8.15 (d, J=6.4 Hz, 1H), 8.04 (d, J=5.8 Hz, 1H), 7.95 (d, J=1.3 Hz, 1H), 7.62 (d, J=1.4 Hz, 1H), 7.52 (d, J=9.1 Hz, 1H), 7.33 (m, J=9.1, 6.9 Hz, 1H), 7.07-6.95 (m, 2H), 4.56 (s, 2H), 4.23 (d, J=13.1 Hz, 1H), 4.14 (s, 2H), 3.75-3.65 (m, 1H), 3.41 (d, J=24.9 Hz, 2H), 3.03-2.92 (m, 3H), 2.77-2.62 (m, 1H), 2.62-2.49 (m, 1H), 2.04 (d, J=6.6 Hz, 2H), 1.84 (m, J=9.5 Hz, 1H), 1.74 (m, J=8.7 Hz, 1H).

Example 15: Synthesis of compound 2-[[2-(1,3-benzothiazol-7-yl)ethyl]amino]-1-[8-(3-fluoropyridin-4-yl)-3,8-diazabicyclo[3.2.1]octan-3-yl]ethan-1-one

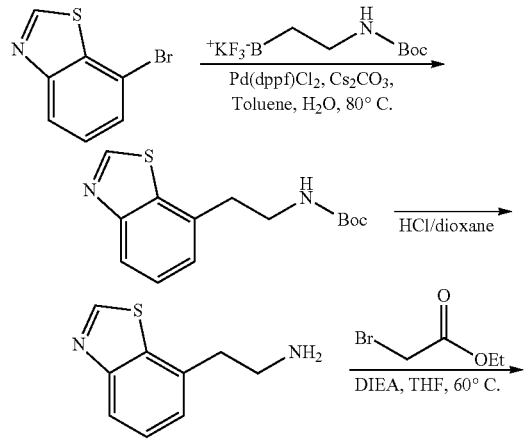

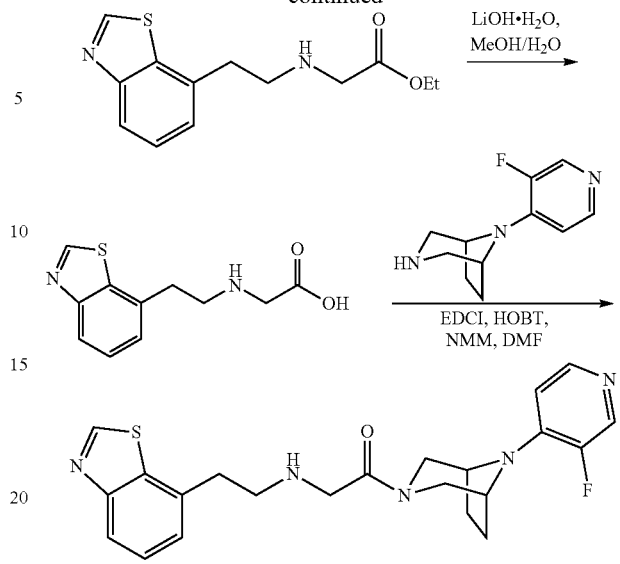

Step 1: Into a 30-mL round-bottom flask purged and maintained with an inert atmosphere of nitrogen, was placed 7-bromo-1,3-benzothiazole (340 mg, 1.59 mmol, 1 eq), potassium (2-((tert-butoxycarbonyl)amino)ethyl)trifluoroborate (400 mg, 1.59 mmol, 1.00 eq), Pd(dppf)Cl2 (117 mg, 0.16 mmol, 0.10 eq), Cs2CO3 (1 g, 3.07 mmol, 1.93 eq), toluene (5 mL), and H2O (1 mL). The resulting solution was stirred for 4 h at 80° C. in an oil bath. The resulting mixture was concentrated. The residue was applied onto a silica gel column with ethyl acetate/petroleum ether to give 200 mg of (45.2%) product.

Step 2: Into a 50-mL round-bottom flask, was placed tert-butyl N-[2-(1,3-benzothiazol-7-yl)ethyl]carbamate (200 mg, 0.72 mmol, 1 eq), dioxane (20 mL), HCl in dioxane (1 M, 20 mL). The resulting solution was stirred at rt for 1 h. The resulting mixture was concentrated. This resulted in 100 mg (55.4%) of 2-(1,3-benzothiazol-7-yl)ethan-1-amine as a yellow solid. LCMS: m/z=179[M+1]+.

Step 3: Into a 50-mL round-bottom flask, was placed 2-(1,3-benzothiazol-7-yl)ethan-1-amine (95 mg, 0.53 mmol, 1 eq), ethyl 2-bromoacetate (95 mg, 0.57 mmol, 1.07 eq), THF (20 mL), DIEA (342 mg, 2.65 mmol, 4.97 eq). The resulting solution was stirred overnight at 60° C. in an oil bath. The resulting mixture was concentrated. The residue was applied onto a silica gel column with ethyl acetate/petroleum ether. This resulted in 40 mg (28.3%) of ethyl 2-[[2-(1,3-benzothiazol-7-yl)ethyl]amino]acetate as a yellow oil.

Step 4: Into a 50-mL round-bottom flask, was placed ethyl 2-[[2-(1,3-benzothiazol-7-yl)ethyl]amino]acetate (40 mg, 0.151 mmol, 1 eq), MeOH (2 mL), H2O (2 mL), LiOH.H2O (13 mg, 0.310 mmol, 2.05 eq). The resulting solution was stirred at rt for 2 h. The resulting mixture was concentrated. The pH value of the solution was adjusted to 6-7 with HCl, then the product was concentrated. This resulted in 32 mg (89.5%) of 2-[[2-(1,3-benzothiazol-7-yl)ethyl]amino]acetic acid as a white solid; LCMS: m/z=237[M+1]+

Step 5: Into a 10-mL round-bottom flask, was placed 2-[[2-(1,3-benzothiazol-7-yl)ethyl]amino]acetic acid (32 mg, 0.14 mmol, 1 eq), HOBT (22 mg, 0.16 mmol, 1.20 eq), EDCI (31 mg, 0.16 mmol, 1.19 eq), DMF (2 mL), NMM (55 mg, 0.54 mmol, 4.02 eq), 8-(3-fluoropyridin-4-yl)-3,8-diazabicyclo[3.2.1]octane (28 mg, 0.14 mmol, 1.00 eq). The resulting solution was stirred at rt for 3 h. The crude product was purified by Prep-HPLC. This resulted in 7.4 mg (12.8%) of 2-[[2-(1,3-benzothiazol-7-yl)ethyl]amino]-1-[8-(3-fluoropyridin-4-yl)-3,8-diazabicyclo[3.2.1]octan-3-yl]ethan-1-one as a white solid. LCMS: m/z=426.1 [M+1]$^+$, $^1$H NMR (400 MHz, methanol-d4): δ 9.30 (s, 1H), 8.43-8.41 (d, J=8.1 Hz, 1H), 8.15-8.13 (d, J=6.8 Hz, 1H), 8.04-8.02 (dd, J=8.2, 1.0 Hz, 1H), 7.61-7.57 (dd, J=8.2, 7.3 Hz, 1H), 7.48-7.46 (d, J=7.3 Hz, 1H), 7.34-7.31 (m, 1H), 4.41-4.31 (m, 2H), 4.08-4.04 (d, J=16.1 Hz, 1H), 3.70-3.62 (m, 1H), 3.57 (d, J=12.8 Hz, 1H), 3.53-3.46 (m, 2H), 3.46-3.35 (m, 2H), 3.31 (m, 2H), 3.17 (d, J=13.3 Hz, 1H), 2.18 (s, 2H), 2.05 (t, J=9.5 Hz, 1H), 1.88 (t, J=8.8 Hz, 1H).

Example 16: Synthesis of 3-(benzo[d]thiazol-7-ylsulfonyl)-1-(4-(3-fluoropyridin-4-yl)piperazin-1-yl)propan-1-one

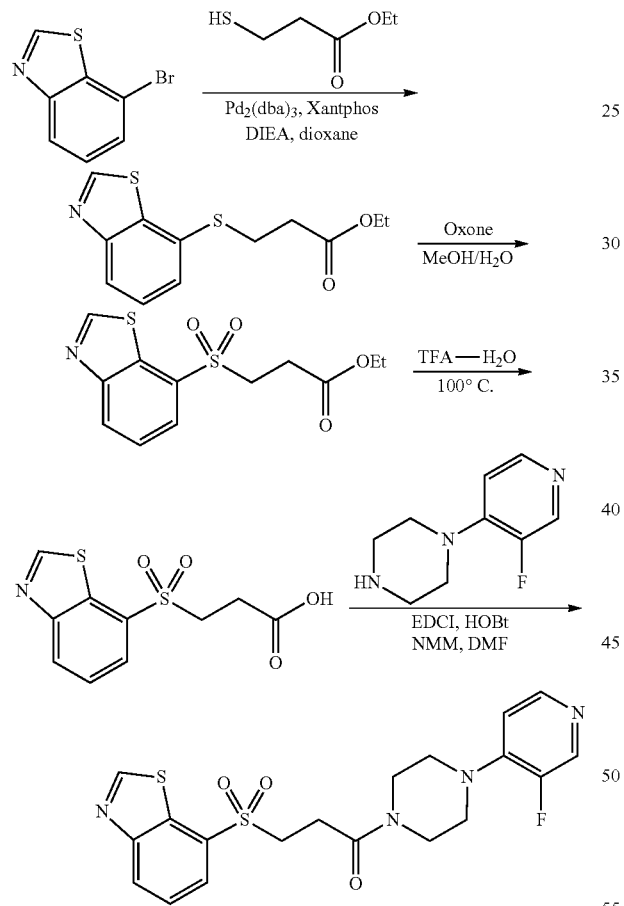

Step 1: To a solution of compound 7-bromobenzo[d]thiazole (500 mg, 2.34 mmol, 1 eq), ethyl 3-mercaptopropanoate (344 mg, 2.57 mmol, 1.1 eq), Pd$_2$(dba)$_3$ (42.7 mg, 0.02 eq), Xantphos (54.1 mg, 0.04 eq) and DIEA (603 mg, 4.67 mmol, 2 eq) in dioxane (10 mL) under N$_2$, then the reaction mixture was stirring at 110° C. for 12 hours. The reaction mixture was diluted with water (70 mL) and extracted with DCM mL (15 mL). The combined organic layers were washed with brine (20 mL), dried over MgSO$_4$, filtered and concentrated under reduced pressure to give a residue. The residue was purified by column chromatography to give ethyl 3-(benzo[d]thiazol-7-ylthio)propanoate (530 mg, 1.78 mmol, 76%) as a yellow oil. LCMS: m/z=267.9 [M+H]$^+$.

Step 2: A solution of ethyl 3-(benzo[d]thiazol-7-ylthio)propanoate (530 mg, 1.78 mmol, 1 eq) in MeOH (5 mL) was add drop-wise into the solution of Oxone (1.83 g, 1.5 eq) in H$_2$O (5 mL). The mixture was stirred at 25° C. for 1 hour. The reaction mixture was diluted with water (50 mL) and extracted with DCM (20 mL). The combined organic layers were washed with brine (20 mL), dried over MgSO$_4$, filtered and concentrated under reduced pressure to give ethyl 3-(benzo[d]thiazol-7-ylsulfonyl)propanoate (430 mg, 1.31 mmol, 66%) as a yellow oil. LCMS: m/z=299.9 [M+H]$^+$.

Step 3: A solution of ethyl 3-(benzo[d]thiazol-7-ylsulfonyl)propanoate (0.2 g, 0.668 mmol, 1 eq) in TFA (1.5 mL) and H$_2$O (1.5 mL) was stirred at 100° C. for 3 hours. The mixture was concentrated to dryness to give 3-(benzo[d]thiazol-7-ylsulfonyl)propanoic acid (180 mg, 82% yield, 83% purity) as a yellow solid, and it was used without further purification. LCMS: m/z=271.9 [M+H]$^+$.

Step 4: To a solution of 3-(benzo[d]thiazol-7-ylsulfonyl)propanoic acid (50 mg, 0.184 mmol, 1 eq) in DMF (1.5 mL) was added EDCI (42.4 mg, 0.221 mmol, 1.2 eq), HOBT (29.9 mg, 0.221 mmol, 1.2 eq), NMM (55.9 mg, 0.552 mmol, 3 eq) and 1-(3-fluoropyridin-4-yl)piperazine (40.1 mg, 0.184 mmol, 1 eq), then the reaction mixture was stirred at 25° C. for 12 hours. The residue was purified by prep-HPLC to give 3-(benzo[d]thiazol-7-ylsulfonyl)-1-(4-(3-fluoropyridin-4-yl)piperazin-1-yl)propan-1-one (37.5 mg, 44%) as a yellow solid. LCMS: m/z=435.1 [M+H]$^+$.

Example 17: Synthesis of (S)-1-(4-(5-fluoro-3-methylpyridin-2-yl)-2-methylpiperazin-1-yl)-4-((3-methoxyquinolin-5-yl)sulfonyl)butan-1-one

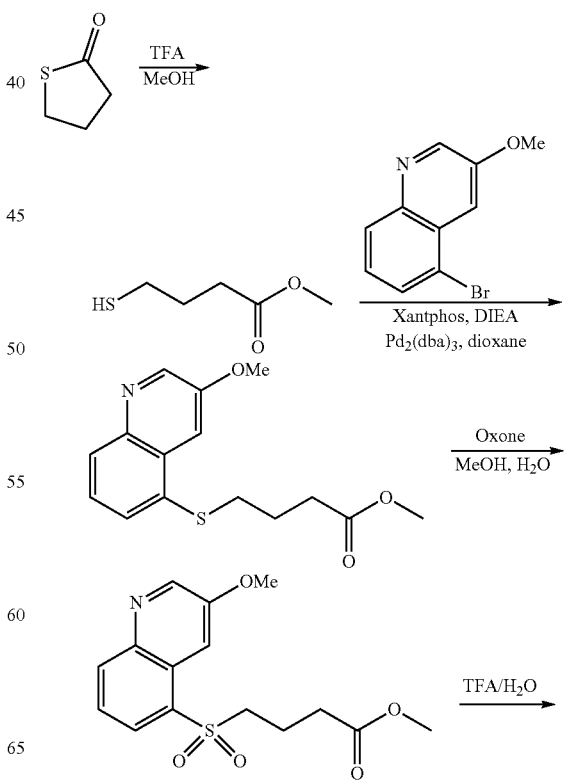

-continued

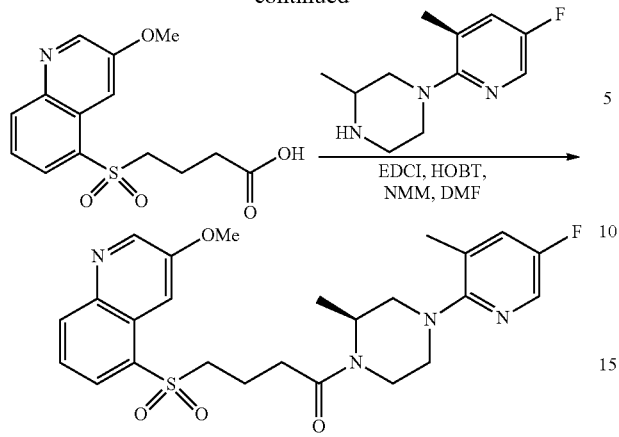

Step 1: To a solution of dihydrothiophen-2(3H)-one (0.300 g, 2.94 mmol, 1 eq) in MeOH (6 mL) was added TEA (493 mg, 4.87 mmol, 1.66 eq). The mixture was stirred for 16 h at 70° C. The reaction was evaporated to dryness to give methyl 4-mercaptobutanoate (0.39 g, crude) as a yellow oil.

Step 2: To a solution of methyl 4-mercaptobutanoate (0.195 g, 1.45 mmol, 1 eq) in dioxane (2 mL) was added 5-bromo-3-methoxyquinoline (381 mg, 1.60 mmol, 1.1 eq), DIEA (376 mg, 2.91 mmol, 2 eq), Xantphos (33.6 mg, 0.058 mmol, 0.04 eq) and Pd$_2$(dba)$_3$ (26.6 mg, 0.029 mmol, 0.02 eq). The mixture was stirred for 16 h at 110° C. under N$_2$. The reaction was quenched with water (10 mL), the aqueous layer was extracted with ethyl acetate. The combined organic layer was washed with brine, dried over MgSO$_4$ and concentrated in vacuo. The residue was purified by prep-TLC (SiO$_2$, petroleum ether/ethyl acetate=5/1, R$_f$=0.40) to give methyl 4-((3-methoxyquinolin-5-yl)thio)butanoate (0.3 g, 71%) as a yellow oil. LCMS: m/z=292.3 [M+H]$^+$.

Step 3: To a solution of Oxone (949 mg, 1.54 mmol, 1.5 eq) in H$_2$O (3 mL) was added methyl 4-((3-methoxyquinolin-5-yl)thio)butanoate (0.3 g, 1.03 mmol, 1 eq) in MeOH (2 mL) at 25° C. The mixture was stirred for 2 h at 25° C. The reaction was quenched with water, the aqueous layer was extracted with ethyl acetate. The combined organic layer was washed with brine, dried over MgSO$_4$ and concentrated in vacuo. The residue was purified by prep-TLC (SiO$_2$, petroleum ether/ethyl acetate=1/3, R$_f$=0.24) to give methyl 4-((3-methoxyquinolin-5-yl)sulfonyl)butanoate (0.16 g, 48%) as a yellow solid. LCMS: m/z=324.3 [M+H]$^+$.

Step 4: A solution of methyl 4-((3-methoxyquinolin-5-yl)sulfonyl)butanoate (0.16 g, 0.495 mmol, 1 eq) in TFA (1 mL) and H$_2$O (1 mL) was stirred for 2 h at 100° C. The reaction was evaporated to dryness to give 4-((3-methoxyquinolin-5-yl)sulfonyl)butanoic acid (0.15 g, crude) as a yellow oil. LCMS: m/z=310.2 [M+H]$^+$.

Step 5: To a solution of 4-((3-methoxyquinolin-5-yl)sulfonyl)butanoic acid (81.3 mg, 0.263 mmol, 1.1 eq) in DMF (2 mL) was added EDCI (55.0 mg, 0.287 mmol, 1.2 eq), HOBT (38.7 mg, 0.287 mmol, 1.2 eq), NMM (72.5 mg, 0.717 mmol, 3 eq) and (S)-1-(5-fluoro-3-methylpyridin-2-yl)-3-methylpiperazine (0.05 g, 0.239 mmol, 1 eq). The mixture was stirred for 16 h at 25° C. The reaction was filtered to remove deposit. The residue was purified by prep-HPLC to give (S)-1-(4-(5-fluoro-3-methylpyridin-2-yl)-2-methylpiperazin-1-yl)-4-((3-methoxyquinolin-5-yl)sulfonyl)butan-1-one (77.6 mg, 65%) as a yellow solid. LCMS: m/z=501.1 [M+H]$^+$.

Example 18: Synthesis of 3-(1,3-benzothiazole-7-sulfonyl)-1-[(2S)-4-(5-fluoro-3-methylpyridin-2-yl)-2-methylpiperazin-1-yl]propan-1-one

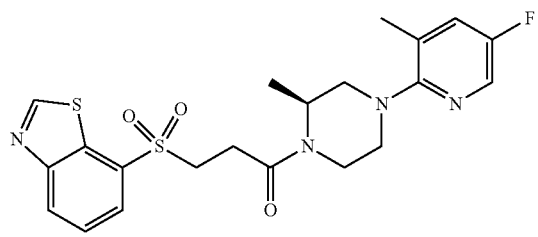 [SMILES: Cc1cc(F)cnc1N1CCN(C(=O)CCS(=O)(=O)c2cccc3ncsc23)[C@@H](C)C1]

In a 10-mL round-bottom flask was placed 3-(1,3-benzothiazole-7-sulfonyl)propanoic acid (68 mg, 0.25 mmol, 1 eq), DMF (1 mL), HOBT (40 mg, 0.30 mmol, 1.18 eq), EDCI (57 mg, 0.30 mmol, 1.19 eq), NMM (76 mg, 0.75 mmol, 3.00 eq), (3S)-1-(5-fluoro-3-methylpyridin-2-yl)-3-methylpiperazine (52 mg, 0.25 mmol, 0.99 eq). The resulting solution was stirred at rt overnight. The crude product was purified by Prep-HPLC. This resulted in 17.8 mg (15.4%) of 3-(1,3-benzothiazole-7-sulfonyl)-1-[(2S)-4-(5-fluoro-3-methylpyridin-2-yl)-2-methylpiperazin-1-yl]propan-1-one as a white solid. LCMS: m/z=463.3[M+1]$^+$, $^1$H NMR (400 MHz, DMSO-d$_6$) δ 9.59 (s, 1H), 8.48-8.46 (d, J=8.0 Hz, 1H), 8.09-8.06 (m, 2H), 7.85-7.81 (t, J=7.8 Hz, 1H), 7.55-7.52 (m, 1H), 4.40 (m, 1H), 4.09 (s, 1H), 3.70-3.63 (m, 3H), 3.22 (d, J=13.0 Hz, 1H), 3.13 (d, J=12.5 Hz, 1H), 2.90-2.49 (m, 5H), 2.28 (s, 3H), 1.31-1.29 (d, J=6.6 Hz, 1H), 1.10-1.09 (d, J=6.9 Hz, 1H).

Example 19: Synthesis of 3-(1,3-benzothiazole-7-sulfonyl)-1-[(2R)-4-(3-chloropyridin-4-yl)-2-methylpiperazin-1-yl]propan-1-one

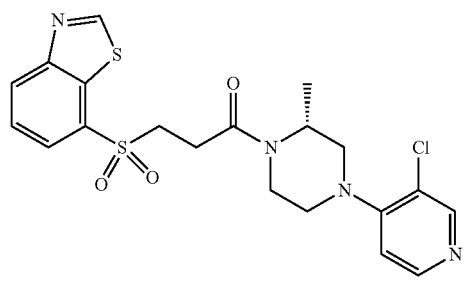 [SMILES: C[C@@H]1CN(c2ccncc2Cl)CCN1C(=O)CCS(=O)(=O)c1cccc2ncsc12]

In a 10-mL round-bottom flask was placed 3-(1,3-benzothiazole-7-sulfonyl)propanoic acid (70 mg, 0.26 mmol, 1 eq), HOBT (41 mg, 0.30 mmol, 1.18 eq), EDCI (59 mg, 0.31 mmol, 1.19 eq), NMM (125 mg, 1.24 mmol, 4.79 eq), DMF (2 mL), (3R)-1-(3-chloropyridin-4-yl)-3-methylpiperazine dihydrochloride (72 mg, 0.25 mmol, 0.98 eq). The resulting solution was stirred at rt for 2 h. The crude product was purified by Flash-Prep-HPLC. This resulted in 27.2 mg (22.6%) of 3-(1,3-benzothiazole-7-sulfonyl)-1-[(2R)-4-(3-chloropyridin-4-yl)-2-methylpiperazin-1-yl]propan-1-one as a white solid. LCMS: m/z=465.1 [M+1]+; $^1$H-NMR (400 MHz, DMSO-d$_6$) δ 9.59 (s, 1H), 8.48-8.44 (m, 2H), 8.35-8.34 (d, J=5.5 Hz, 1H), 8.08-8.06 (d, J=7.5 Hz, 1H), 7.85-7.81 (t, J=7.9 Hz, 1H), 7.06 (s, 1H), 4.41 (s, 1H), 4.10-4.08

(m, 1H), 3.70-3.69 (m, 3H), 3.50-3.35 (m, 6H), 2.94-2.61 (m, 5H), 1.30-1.29 (d, J=6.6 Hz, 1H), 1.09-1.07 (d, J=6.8 Hz, 2H).

Example 20: Synthesis of 4-(2-amino-1,3-benzothiazol-7-yl)-1-[(2S)-4-(5-fluoro-3-methylpyridin-2-yl)-2-methylpiperazin-1-yl]butan-1-one

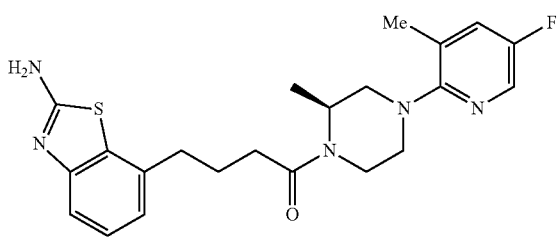 [SMILES: Cc1cc(F)cnc1N1CCN(C(=O)CCCc2cccc3nc(N)sc23)[C@@H](C)C1]

Step 1: In a 50-mL round-bottom flask was placed 7-bromo-1,3-benzothiazol-2-amine (500 mg, 2.18 mmol, 1 eq), Boc$_2$O (5715.8 mg, 26.19 mmol, 12.00 eq) and NaOH (1M, 3 mL, 0.08 mmol, 0.03 eq) in MeOH (15 mL). The resulting solution was stirred for 3 h at 80° C. The resulting mixture was concentrated, extracted with 2×100 mL of ethyl acetate and the organic layers were combined. The residue was applied onto a silica gel column with ethyl acetate/petroleum ether (1/4). This resulted in 110 mg (15.3%) of tert-butyl N-(7-bromo-1,3-benzothiazol-2-yl)carbamate as a white solid.

Step 2: In a 10-mL vial was placed tert-butyl N-(7-bromo-1,3-benzothiazol-2-yl)carbamate (90 mg, 0.27 mmol, 1 eq), (4-ethoxy-4-oxobutyl)zinc(II) bromide (106.8 mg, 0.41 mmol, 1.50 eq) and Pd(PPh$_3$)$_4$ (15.8 mg, 0.01 mmol, 0.05 eq) in THF (3 mL). The resulting solution was stirred for 4 h at 60° C. The residue was purified by silica gel column chromatography, eluted with MeOH/DCM (8%) to afford ethyl 4-(2-[[(tert-butoxy)carbonyl]amino]-1,3-benzothiazol-7-yl)butanoate (90 mg, 90.3%) as a white solid.

Step 3: In a 25-mL round-bottom flask was placed ethyl 4-(2-[[(tert-butoxy)carbonyl]amino]-1,3-benzothiazol-7-yl)butanoate (90 mg, 0.25 mmol, 1 eq) and sodium hydroxide (49.4 mg, 1.24 mmol, 5.00 eq) in MeOH (3 mL), H$_2$O (1 mL). The resulting solution was stirred at rt for 2 h. The residue was by HPLC to afford 4-(2-[[(tert-butoxy)carbonyl]amino]-1,3-benzothiazol-7-yl)butanoic acid (28 mg, 33.7%).

Step 4: In a 8-mL vial was placed 4-(2-[[(tert-butoxy)carbonyl]amino]-1,3-benzothiazol-7-yl)butanoic acid (14 mg, 0.042 mmol, 1 eq), (3S)-1-(5-fluoro-3-methylpyridin-2-yl)-3-methylpiperazine (10.45 mg, 0.050 mmol, 1.20 eq), HATU (23.74 mg, 0.062 mmol, 1.5 eq), DIEA (16.14 mg, 0.125 mmol, 3 eq), DMF (1 mL). The resulting solution was stirred for 40 min at rt. The residue was purified by Prep-HPLC to afford tert-butyl N-(7-[4-[(2S)-4-(5-fluoro-3-methylpyridin-2-yl)-2-methylpiperazin-1-yl]-4-oxobutyl]-1,3-benzothiazol-2-yl)carbamate (14.4 mg, 65.5%) as a yellow oil.

Step 5: In a 25-mL round-bottom flask was placed tert-butyl N-(7-[4-[(2S)-4-(5-fluoro-3-methylpyridin-2-yl)-2-methylpiperazin-1-yl]-4-oxobutyl]-1,3-benzothiazol-2-yl)carbamate (14 mg, 0.038 mmol, 1 eq), DCM (2 mL). This was followed by the addition of TFA (0.7 mL) at 0° C. The resulting solution was stirred at rt for 1 h. The resulting mixture was concentrated. The pH value of the solution was adjusted to 8 with NH$_3$.MeOH (7M). The resulting mixture was concentrated. The residue was purified by Prep-HPLC. This resulted in 6.2 mg (38.2%) of 4-(2-amino-1,3-benzothiazol-7-yl)-1-[(2S)-4-(5-fluoro-3-methylpyridin-2-yl)-2-methylpiperazin-1-yl]butan-1-one as a white solid. LCMS: m/z=428 [M+1]$^+$, $^1$H NMR (300 MHz, methanol-d$_4$) δ 8.0 (d, J=3.1 Hz, 1H), 7.4 (m, 1H), 7.3-7.2 (m, 2H), 6.9 (m, 1H), 4.9 (m, 1H), 4.7 (m, 0.5H), 4.1 (m, 0.5H), 3.7 (m, 1H), 3.5 (m, 1H), 3.3-3.1 (m, 2H), 2.9-2.7 (m, 4H), 2.5-2.4 (m, 1H), 2.4-2.3 (s, 3H), 2.03 (s, 2H), 1.4-1.3 (d, J=6.4 Hz, 3H).

Example 21: Synthesis of (S)-1-(4-(2-aminopyridin-4-yl)-2-methylpiperazin-1-yl)-3-(benzo[d]thiazol-7-ylsulfonyl)propan-1-one

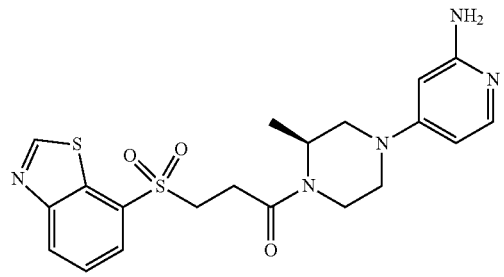 [SMILES: C[C@H]1CN(c2ccnc(N)c2)CCN1C(=O)CCS(=O)(=O)c1cccc2ncsc12]

Step 1: In a 100-mL round-bottom flask was placed tert-butyl (2S)-2-methylpiperazine-1-carboxylate (5.3 g, 3 eq), 4-fluoropyridin-2-amine (1 g, 1 eq), Cs$_2$CO$_3$ (8.7 g, 3 eq), NMP (15 mL). The resulting solution was stirred for 12 h at 140° C. The residue was purified by reverse phase HPLC to afford 500 mg (19.1%) of tert-butyl (2S)-4-(2-aminopyridin-4-yl)-2-methylpiperazine-1-carboxylate as a brown oil.

Step 2: In a 25-mL round-bottom flask was placed tert-butyl (2S)-4-(2-aminopyridin-4-yl)-2-methylpiperazine-1-carboxylate (150 mg, 0.513 mmol, 1 eq), TFA (2 mL), DCM (4 mL). The resulting solution was stirred for 45 min at rt. The resulting mixture was concentrated. The pH value of the solution was adjusted to 8 with NH$_3$.MeOH (7M). The resulting mixture was concentrated. The crude product was purified by Prep-HPLC. This resulted in 30 mg (30.4%) of 4-[(3S)-3-methylpiperazin-1-yl]pyridin-2-amine as a yellow oil.

Step 3: In a 8-mL vial was placed 3-(1,3-benzothiazole-7-sulfonyl)propanoic acid (10.8 mg, 1 eq), EDCI (6.4 mg, 1.2 eq), HOBT (9.1 mg, 1.2 eq), DMF (1 mL), NMM (12.0 mg, 3 eq), 4-[(3S)-3-methylpiperazin-1-yl]pyridin-2-amine (10 mg, 1.3 eq). The resulting solution was stirred for 45 min at rt. The residue was applied onto a reverse phase HPLC to afford (S)-1-(4-(2-aminopyridin-4-yl)-2-methylpiperazin-1-yl)-3-(benzo[d]thiazol-7-ylsulfonyl)propan-1-one (1.8 mg, 10.7%) as a colorless oil. LCMS: m/z=446.0 [M+1]$^+$; $^1$H NMR (300 MHz, methanol-d$_4$) δ 9.4 (s, 1H), 8.4 (d, J=8.1 Hz, 1H), 8.1 (m, 1H), 7.8 (t, J=7.9 Hz, 1H), 7.6 (d, J=6.5 Hz, 1H), 6.3 (d, J=6.4 Hz, 1H), 5.9 (s, 1H), 4.4-4.1 (m, 1H), 3.7-3.5 (m, 5H), 3.1 (m, 3H), 2.9-2.8 (m, 2H), 1.3-1.2 (m, 1H), 1.1 (d, J=6.7 Hz, 2H).

Example 22: Synthesis of 3-(1,3-benzothiazole-7-sulfonyl)-1-[4-[5-(trifluoromethyl)pyridin-2-yl]piperidin-1-yl]propan-1-one

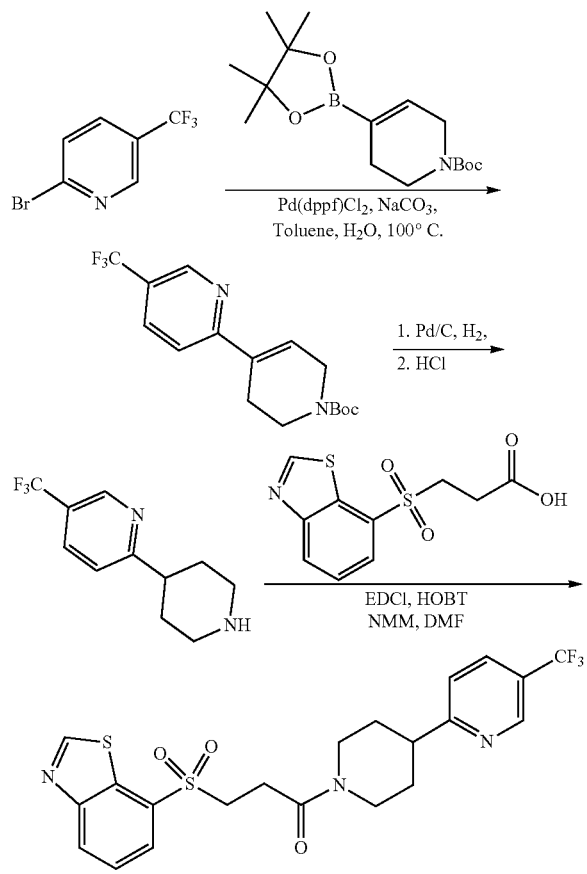

Step 1: In a 30-mL sealed tube purged and maintained with an inert atmosphere of nitrogen, was placed 2-bromo-5-(trifluoromethyl)pyridine (600 mg, 2.655 mmol, 1 eq), tert-butyl 4-(4,4,5,5-tetramethyl-1,3,2-dioxaborolan-2-yl)-1,2,3,6-tetrahydropyridine-1-carboxylate (1.5 g, 4.820 mmol, 1.82 eq), Pd(dppf)Cl₂ (196 mg, 0.268 mmol, 0.10 eq), Na₂CO₃ (565 mg, 5.331 mmol, 2.01 eq), toluene (4 mL), H₂O (0.8 mL). The resulting solution was stirred for 3 h at 85° C. in an oil bath. The resulting mixture was concentrated. The residue was applied onto a silica gel column with ethyl acetate/petroleum ether. This resulted in 800 mg (91.2%) of tert-butyl 5-(trifluoromethyl)-1,2,3,6-tetrahydro-[2,4-bipyridine]-1-carboxylate as an off-white solid.

Step 2: In a 250-mL 3-necked round-bottom flask purged and maintained with an inert atmosphere of hydrogen, was placed tert-butyl 5-(trifluoromethyl)-1,2,3,6-tetrahydro-[2,4-bipyridine]-1-carboxylate (800 mg, 2.43 mmol, 1 eq), MeOH (30 mL), Pd/C (200 mg, 1.87 mmol, 0.77 eq). The resulting solution was stirred at rt for 1 h. The solids were filtered off. The resulting mixture was concentrated. This resulted in 800 mg (99.4%) of tert-butyl 4-[5-(trifluoromethyl)pyridin-2-yl]piperidine-1-carboxylate as a colorless oil. LCMS: m/z=331[M+1]⁺

Step 3: In a 50-mL round-bottom flask was placed tert-butyl 4-[5-(trifluoromethyl)pyridin-2-yl]piperidine-1-carboxylate (35 mg, 0.106 mmol, 1 eq) and HCl/dioxane (20 mL, 4N). The resulting solution was stirred rt for 1 h. The resulting mixture was concentrated. This resulted in 20 mg (62.2%) of 2-(piperidin-4-yl)-5-(trifluoromethyl)pyridine dihydrochloride as a white solid.

Step 4: In a 10-mL round-bottom flask was placed 3-(1,3-benzothiazole-7-sulfonyl)propanoic acid (40 mg, 0.147 mmol, 1 eq), HOBT (24 mg, 0.178 mmol, 1.20 eq), EDCI (34 mg, 0.177 mmol, 1.19 eq), NMM (60 mg, 0.593 mmol, 4.00 eq), DMF (1.5 mL), 2-(piperidin-4-yl)-5-(trifluoromethyl)pyridine dihydrochloride (20 mg, 0.148 mmol, 1 eq). The resulting solution was stirred at rt for 1 h. The crude product was purified by Prep-HPLC. This resulted in 10.5 mg (15.5%) of 3-(1,3-benzothiazole-7-sulfonyl)-1-[4-[5-(trifluoromethyl)pyridin-2-yl]piperidin-1-yl]propan-1-one as a white solid. LCMS: m/z=484.1[M+1]+, ¹H-NMR (400 MHz, methanol-d₄): δ 9.43 (s, 1H), 8.81 (d, J=2.4 Hz, 1H), 8.43 (dd, J=8.2, 1.0 Hz, 1H), 8.15-8.03 (m, 2H), 7.89-7.81 (m, 1H), 7.51 (d, J=8.3 Hz, 1H), 4.43 (d, J=13.5 Hz, 1H), 3.99 (d, J=13.8 Hz, 1H), 3.71-3.66 (m, 2H), 3.24-3.16 (m, 1H), 3.08 (ddd, J=12.0, 8.2, 3.8 Hz, 1H), 2.90 (td, J=7.1, 3.9 Hz, 2H), 2.67 (td, J=13.0, 2.8 Hz, 1H), 1.97-1.86 (m, 2H), 1.76 (qd, J=12.7, 4.3 Hz, 1H), 1.60 (qd, J=12.7, 4.4 Hz, 1H).

Example 23: Synthesis of (R)-2-fluoro-5-(3-methyl-4-(4-(quinolin-5-yl)butanoyl)piperazin-1-yl)benzonitrile

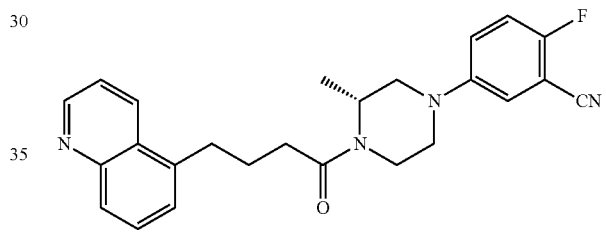

Step 1: To a solution of 5-bromo-2-fluorobenzonitrile (400 mg, 2.0 mmol, 1.00 eq) in dioxane (30 ml) was added tert-butyl (R)-2-methylpiperazine-1-carboxylate (440 mg, 2.2 mmol, 1.1 eq), Pd₂(dba)₃ (828 mg, 0.8 mmol, 0.4 eq), Xantphos (925 mg, 1.6 mmol, 0.8 eq) and Cs₂CO₃ (1.95 g, 6.0 mmol, 3.00 eq). The resulting solution was stirred at 110° C. for 2 h. The solid was filtered and the solvent was evaporated. The residue was applied onto a silica gel column with MeOH/DCM. This resulted in 240 mg (38%) of tert-butyl (R)-4-(3-cyano-4-fluorophenyl)-2-methylpiperazine-1-carboxylate as a yellow oil; LCMS: m/z=320.1 [M+H]⁺.

Step 2: To a solution of tert-butyl (R)-4-(3-cyano-4-fluorophenyl)-2-methylpiperazine-1-carboxylate (230 mg, 0.72 mmol, 1.00 eq) in DCM (6 ml) was added TFA (3 ml). The resulting solution was stirred at r.t for 1 h. The mixture was evaporated. The residue was applied onto a silica gel column with MeOH/DCM (10%). This resulted in 150 mg (95%) of (R)-2-fluoro-5-(3-methylpiperazin-1-yl) benzonitrile as a yellow oil; LCMS: m/z=220.1 [M+H]⁺.

Step 3: To a solution of (R)-2-fluoro-5-(3-methylpiperazin-1-yl) benzonitrile (30 mg, 0.14 mmol, 1.00 eq) in DMF (1 ml) was added 4-(quinolin-5-yl)butanoic acid (35 mg, 0.16 mmol, 1.2 eq), HATU (80 mg, 0.21 mmol, 1.5 eq) and DIEA (54 mg, 0.42 mmol, 3.00 eq). The resulting solution was stirred at r.t for 1 h. The crude product was purified by HPLC to give (R)-2-fluoro-5-(3-methyl-4-(4-(quinolin-5-yl)butanoyl)piperazin-1-yl)benzonitrile as a white solid 12 mg (21%); LCMS: m/z=417.2 [M+H]⁺.

Example 24: Synthesis of 6-{3-[3-(1,3-benzothiazole-7-sulfonyl)propanoyl]-3,8-diazabicyclo[3.2.1]octan-8-yl}pyridine-3-carbonitrile

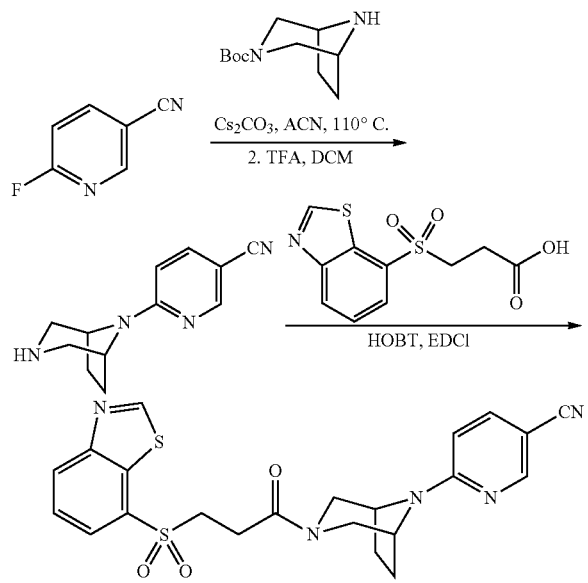

Step 1: Into a 100-mL round-bottom flask, was placed 6-fluoronicotinonitrile (2.24 g, 18.4 mmol, 1.3 eq), tert-butyl 3,8-diaza-bicyclo[3.2.1]octane-3-carboxylate (3 g, 14.1 mmol, 1 eq), Cs2CO3 (9.2 g, 28.3 mmol, 2 eq) and ACN (30 mL). The resulting solution was stirred for 3 h at 110° C. The solid was filtered out and the filtrate was concentrated. The crude was diluted with water and extracted with ethyl acetate. The organic layer was concentrated and the crude was applied onto a silica gel column eluting with MeOH/DCM. This resulted in 4.1 g (92%) of tert-butyl 8-(5-cyanopyridin-2-yl)-3,8-diaza-bicyclo[3.2.1]octane-3-carboxylate as a light yellow solid. LCMS: m/z=315.1 [M+H]+.

Step 2: Into a 25-mL round-bottom flask, was placed tert-butyl 8-(5-cyanopyridin-2-yl)-3,8-diaza-bicyclo[3.2.1]octane-3-carboxylate (4.1 g, 13 mmol, 1 eq), DCM (20 mL), TFA (5 mL). The resulting solution was stirred for 3 h at room temperature. The resulting mixture was concentrated. The pH of the solution was adjusted to 8 with NH3-MeOH (7 M). The resulting mixture was concentrated and the crude product was purified by Flash-Prep-HPLC. This resulted in 2.60 g (93%) of 6-(3,8-diaza-bicyclo[3.2.1]octan-8-yl)nicotinonitrile as a yellow semi-solid. LCMS: m/z=215.1 [M+H]+; 1H NMR (DMSO-d6) δ 8.53 (d, J=1.8 Hz, 1H), 7.91 (dd, J=9.0, 2.3 Hz, 1H), 6.92 (d, J=9.0 Hz, 1H), 4.70 (s, 2H), 3.03-2.92 (m, 4H), 2.10-1.92 (m, 4H).

Step 3: Into a 8 mL vial, was placed 6-[3,8-diazabicyclo[3.2.1]octan-8-yl]pyridine-3-carbonitrile (25 mg, 0.117 mmol, 1 eq), 3-(1,3-benzothiazole-7-sulfonyl)propanoic acid (47 mg, 0.175 mmol, 1.5 eq), HOBT (19 mg, 0.14 mmol, 1.2 eq), EDCI (27 mg, 0.14 mmol, 1.2 eq), NMM (35 mg, 0.35 mmol, 3 eq), DMF (1 mL). The resulting solution was stirred for 1 h at 25° C. The crude product was purified by Prep-HPLC. This resulted in 16 mg (30%) of 6-[3-[3-(1,3-benzothiazole-7-sulfonyl)propanoyl]-3,8-diazabicyclo[3.2.1]octan-8-yl]pyridine-3-carbonitrile as a white solid. LCMS: m/z=468.0 [M+H]+; 1H NMR (Methanol-d4): δ 9.40 (s, 1H), 8.46-8.38 (m, 2H), 8.09 (d, J=7.3 Hz, 1H), 7.85-7.74 (m, 2H), 6.84 (d, J=8.4 Hz, 1H), 4.74 (s, 1H), 4.66 (s, 1H), 4.01 (d, J=13.3 Hz, 1H), 3.75-3.60 (m, 3H), 3.00-2.90 (m, 1H), 2.80-2.70 (m, 2H), 2.05-1.95 (m, 2H), 1.87-1.60 (m, 2H), 1.31 (s, 1H).

Example 25: Synthesis of 5-[(3S)-4-[3-(1,3-benzothiazole-7-sulfonyl)propanoyl]-3-methylpiperazin-1-yl]-4-methylpyridine-2-carbonitrile

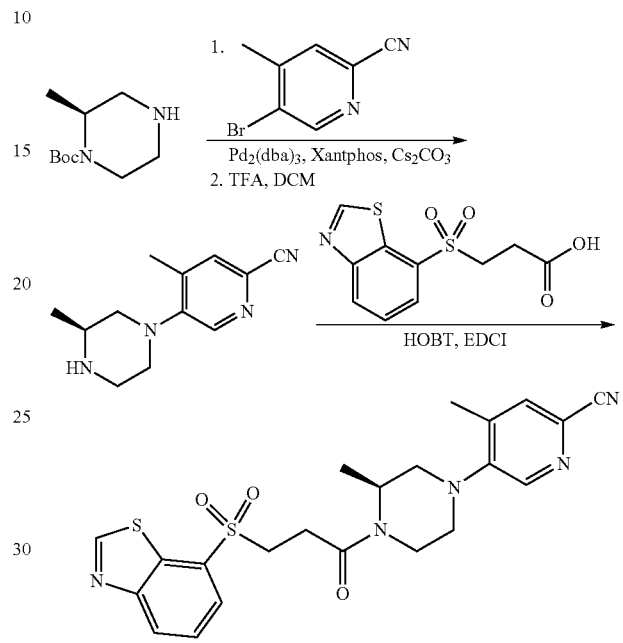

Step 1: Into a 30 mL sealed tube purged and maintained with nitrogen, was placed tert-butyl (2S)-2-methylpiperazine-1-carboxylate (975 mg, 1.2 eq), 5-bromo-4-methylpyridine-2-carbonitrile (800 mg, 1 eq), Pd2(dba)3CHCl3 (841 mg, 0.2 eq), Xantphos (939 mg, 0.4 eq), Cs2CO3 (3972 mg, 3 eq), dioxane (10 mL). The resulting solution was stirred for 2 h at 100° C. The solids were filtered out. The filtrate was applied onto a silica gel column eluting with ethyl acetate/petroleum ether. This resulted in 500 mg (39%) of tert-butyl (2S)-4-(6-cyano-4-methylpyridin-3-yl)-2-methylpiperazine-1-carboxylate as yellow oil. LCMS: m/z=317 [M+H]+.

Step 2: Into a 8 mL vial, was placed tert-butyl (2S)-4-(6-cyano-4-methylpyridin-3-yl)-2-methylpiperazine-1-carboxylate (120 mg, 0.38 mmol, 1 eq), DCM (2 mL), TFA (1 mL). The resulting solution was stirred for 1 h at 25° C. The resulting mixture was concentrated. The pH of the solution was adjusted to 8 with NH3.MeOH (7M). The resulting mixture was concentrated and purified by Flash-Prep-HPLC with ACN/Water. This resulted in 10 mg (12%) of 4-methyl-5-[(3S)-3-methylpiperazin-1-yl]pyridine-2-carbonitrile as yellow oil. LCMS: m/z=217 [M+H]+.

Step 3: The compound was made in a similar manner as Example 24 to provide 10.8 mg of 5-[(3S)-4-[3-(1,3-benzothiazole-7-sulfonyl)propanoyl]-3-methylpiperazin-1-yl]-4-methylpyridine-2-carbonitrile as a white solid. LCMS: m/z=470.3 [M+H]+; 1H NMR (Methanol-d4) δ 9.45 (s, 1H), 8.44 (d, J=8.2 Hz, 1H), 8.28 (s, 1H), 8.12 (d, J=7.5 Hz, 1H), 7.85 (t, 1H), 7.70 (s, 1H), 4.57 (s, 1H), 4.24 (d, J=12.5 Hz, 1H), 3.83-3.48 (m, 3H), 3.29-3.13 (m, 2H), 3.08-2.71 (m, 4H), 2.43 (s, 3H), 1.48-1.24 (m, 3H).

Example 26: Synthesis of 5-[(3S)-4-[3-(1,3-benzothiazole-7-sulfonyl)propanoyl]-3-methylpiperazin-1-yl]-4-chloro-1,2-dihydropyridin-2-one

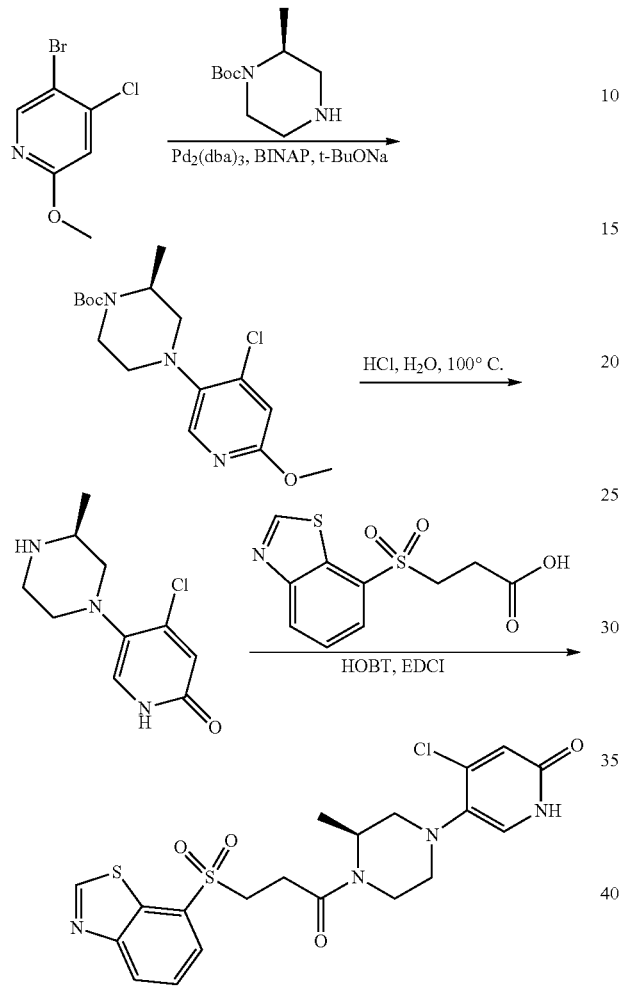

Step 1: Into a 30 mL sealed tube purged and maintained with an inert atmosphere of nitrogen, was placed 5-bromo-4-chloro-2-methoxypyridine (660 mg, 2.96 mmol, 1 eq), tert-butyl (2S)-2-methylpiperazine-1-carboxylate (1.2 g, 6 mmol, 2.02 eq), Pd$_2$(dba)$_3$.CHCl$_3$ (309 mg, 0.3 mmol, 0.10 eq), BINAP (372 mg, 0.60 mmol, 0.20 eq), t-BuONa (573 mg, 5.96 mmol, 2.01 eq) and toluene (4 mL). The resulting solution was stirred for 3 h at 95° C. in an oil bath. The crude mixture was concentrated and applied onto a silica gel column eluting with ethyl acetate/petroleum ether (1:3). This resulted in 180 mg (18%) of tert-butyl (2S)-4-(4-chloro-6-methoxypyridin-3-yl)-2-methylpiperazine-1-carboxylate as yellow oil. LCMS: m/z=342 [M+H]$^+$.

Step 2: Into a 50 mL round-bottom flask was placed tert-butyl (2S)-4-(4-chloro-6-methoxypyridin-3-yl)-2-methylpiperazine-1-carboxylate (180 mg, 0.527 mmol, 1 eq), H$_2$O (1 mL, 55.5 mmol), concentrated HCl (3 mL, 98.7 mmol). The resulting solution was stirred for 6 h at 100° C. in an oil bath. The resulting mixture was concentrated. The pH of the solution was adjusted to 8 with aqueous NaOH. The crude product was purified by Flash-Prep-HPLC. This resulted in 80 mg (66%) of 4-chloro-5-[(3S)-3-methylpiperazin-1-yl]-1,2-dihydropyridin-2-one as a light yellow solid. LCMS: m/z=228 [M+H]$^+$.

Step 3: Into a 10-mL round-bottom flask, was placed 4-chloro-5-[(3S)-3-methylpiperazin-1-yl]-1,2-dihydropyridin-2-one (34 mg, 0.15 mmol, 1 eq), 3-(1,3-benzothiazole-7-sulfonyl)propanoic acid (40 mg, 0.147 mmol, 1 eq), HOBT (24 mg, 0.178 mmol, 1.2 eq), EDCI (34 mg, 0.177 mmol, 1.2 eq), NMM (45 mg, 0.445 mmol, 2.98 eq), DMF (1.5 mL). The resulting solution was stirred for 1 h at 25° C. The crude product was purified by Flash-Prep-HPLC to provide 11 mg (15%) of 5-[(3S)-4-[3-(1,3-benzothiazole-7-sulfonyl)propanoyl]-3-methylpiperazin-1-yl]-4-chloro-1,2-dihydropyridin-2-one as a white solid. LCMS: m/z=481.2 [M+H]$^+$.

Example 27: Synthesis of 6-{2-[3-(1,3-benzothiazole-7-sulfonyl)propanoyl]-2-azabicyclo[2.2.2]oct-5-en-5-yl}pyridine-3-carbonitrile

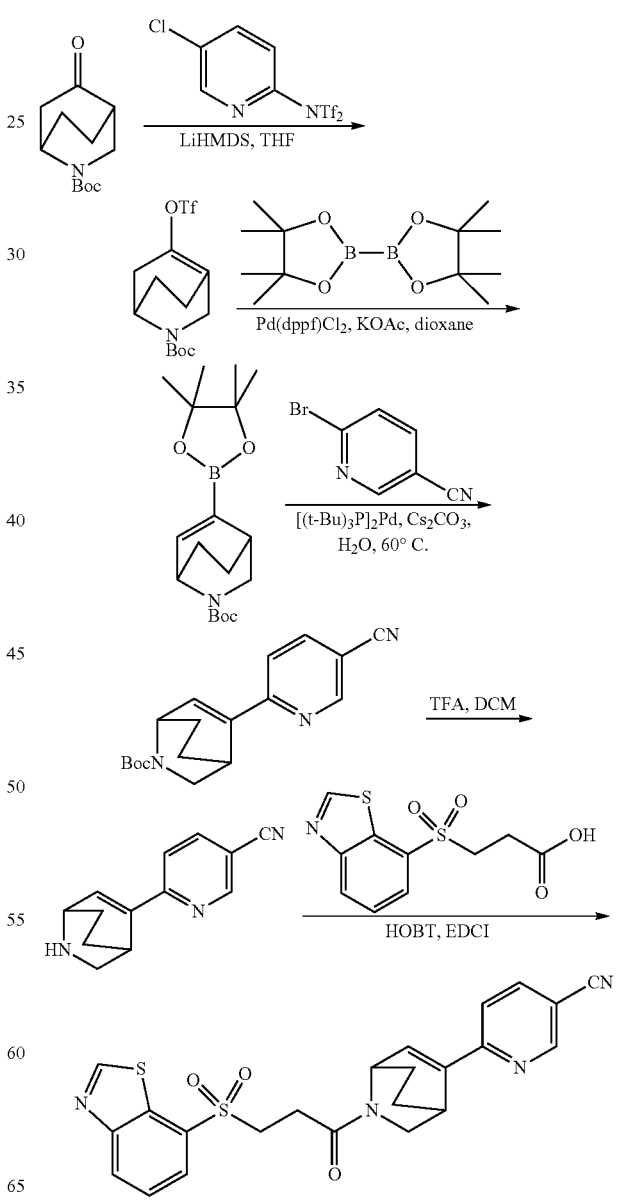

Step 1: Into a 100 mL flask purged and maintained with nitrogen, was placed tert-butyl 5-oxo-2-azabicyclo[2.2.2]octane-2-carboxylate (1 g, 4.43 mmol, 1 eq), THF (8 mL). The resulting solution was cooled in a water/ice bath. This was followed by the addition of a solution of N-(5-chloropyridin-2-yl)-1,1,1-trifluoro-N-trifluoromethanesulfonylmethanesulfonamide (2.61 g, 6.65 mmol, 1.5 eq) in THF (8 mL) dropwise with stirring at 0° C. in 10 min. The resulting solution was stirred at 0° C. To this was added a solution of LiHMDS (1.33 g, 8 mmol, 1.8 eq) in THF (8 mL) dropwise in 10 min. The resulting solution was stirred for 1 h at 0° C. The reaction was quenched with water at 0° C., extracted with 4×150 mL of ethyl acetate and the organic layers combined and dried over anhydrous sodium sulfate. The solids were filtered out. The resulting mixture was concentrated under vacuum. The residue was applied onto a silica gel column with ethyl acetate/petroleum ether. This resulted in 600 mg (37%) of tert-butyl 5-(trifluoromethanesulfonyloxy)-2-azabicyclo[2.2.2]oct-5-ene-2-carboxylate as a yellow semi-solid. LCMS: m/z=358. [M+H]⁺.

Step 2: Into a 30 mL sealed tube purged and maintained with nitrogen, was placed tert-butyl 5-(trifluoromethanesulfonyloxy)-2-azabicyclo[2.2.2]oct-5-ene-2-carboxylate (600 mg, 1.68 mmol, 1 eq), 4,4,5,5-tetramethyl-2-(4,4,5,5-tetramethyl-1,3,2-dioxaborolan-2-yl)-1,3,2-dioxaborolane (511 mg, 2.02 mmol, 1.2 eq), Pd(dppf)Cl₂ (123 mg, 0.168 mmol, 0.10 eq), dioxane (6 mL), KOAc (495 mg, 5.04 mmol, 3 eq). The resulting solution was stirred for 2 h at 60° C. in an oil bath, diluted with water and extracted with ethyl acetate and concentrated. The crude was used directly for next step. LCMS: m/z=336.1 [M+H]⁺.

Step 3: Into a 30 mL sealed tube purged and maintained with an inert atmosphere of nitrogen, was placed tert-butyl 5-(4,4,5,5-tetramethyl-1,3,2-dioxaborolan-2-yl)-2-azabicyclo[2.2.2]oct-5-ene-2-carboxylate (400 mg, 1.19 mmol, 1 eq), 6-bromopyridine-3-carbonitrile (218 mg, 1.19 mmol, 1 eq), H₂O (3.00 mL), [(t-Bu)₃P]₂Pd (50 mg, 0.1 mmol, 0.08 eq), Cs₂CO₃ (1166 mg, 3.58 mmol, 3 eq). The resulting solution was stirred for 5 h at 60° C. in an oil bath. The crude was diluted with water and extracted with ethyl acetate, and the organic layers combined and dried over anhydrous sodium sulfate. The solids were filtered out and the filtrate was concentrated under vacuum. The residue was applied onto a silica gel column eluting with ethyl acetate/petroleum ether. This resulted in 190 mg (51%) of tert-butyl 5-(5-cyanopyridin-2-yl)-2-azabicyclo[2.2.2]oct-5-ene-2-carboxylate as a yellow semi-solid. LCMS: m/z=312.1 [M+H]⁺.

Step 4: To tert-butyl 5-(5-cyanopyridin-2-yl)-2-azabicyclo[2.2.2]oct-5-ene-2-carboxylate (84 mg, 0.27 mmol, 1 eq), in DCM (5 mL) was added TFA (2 mL) dropwise. The resulting solution was stirred for 0.5 h at 25° C. The resulting mixture was concentrated. The pH of the solution was adjusted to 8-9 with NH₃-MeOH (7M). The crude was concentrated and purified by Flash-Prep-HPLC. This resulted in 50 mg (87%) of 6-[2-azabicyclo[2.2.2]oct-5-en-5-yl]pyridine-3-carbonitrile as a yellow semi-solid. LCMS: m/z=212.1 [M+H]⁺.

Step 5: Into a 8 mL vial, was placed 6-[2-azabicyclo[2.2.2]oct-5-en-5-yl]pyridine-3-carbonitrile (20 mg, 0.095 mmol, 1 eq), 3-(1,3-benzothiazole-7-sulfonyl)propanoic acid (31 mg, 0.11 mmol, 1.2 eq), HOBT (15.4 mg, 0.11 mmol, 1.2 eq), EDCI (22 mg, 0.114 mmol, 1.2 eq), NMM (28 mg, 0.28 mmol, 3 eq), DMF (1.5 mL). The resulting solution was stirred for 30 min at 25° C. and purified by Prep-HPLC. This resulted in 24 mg (52%) of 6-[2-[3-(1,3-benzothiazole-7-sulfonyl)propanoyl]-2-azabicyclo[2.2.2]oct-5-en-5-yl]pyridine-3-carbonitrile as a white solid. LCMS: m/z=487.3 [M+Na]⁺.

Example 28: Synthesis of 6-[2-[3-(1,3-benzothiazole-7-sulfonyl)propanoyl]-2-azabicyclo[2.2.2]octan-5-yl]pyridine-3-carbonitrile

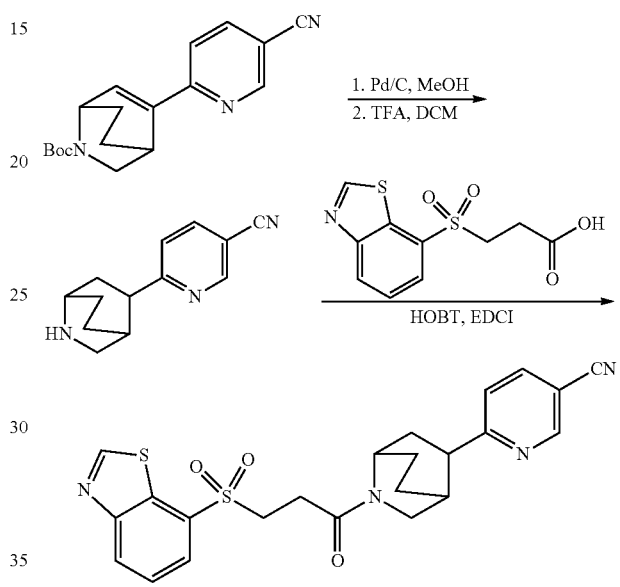

Step 1: Into a 25 mL round-bottom flask, was placed tert-butyl 5-(5-cyanopyridin-2-yl)-2-azabicyclo[2.2.2]oct-5-ene-2-carboxylate (90 mg, 0.29 mmol, 1 eq), Pd/C (50 mg, 0.047 mmol, 0.16 eq), MeOH (5 mL). The resulting solution was stirred for 2 h at 25° C. under hydrogen. The solids were filtered out. The resulting mixture was concentrated. The residue was applied onto a silica gel column eluting with ethyl acetate/petroleum ether. This resulted in 40 mg (44%) of tert-butyl 5-(5-cyanopyridin-2-yl)-2-azabicyclo[2.2.2]octane-2-carboxylate as a yellow semi-solid. LCMS: m/z=314.1 [M+1]⁺ The material was dissolved in DCM (5 mL) and TFA (1 mL) was added, the resulting solution was stirred for 0.5 h at 25° C. and concentrated. The pH of the solution was adjusted to 8-9 with NH₃-MeOH (7 M). The resulting mixture was concentrated and purified by Flash-Prep-HPLC to give 25 mg (92%) of 6-[2-azabicyclo[2.2.2]octan-5-yl]pyridine-3-carbonitrile as a yellow semi-solid. LCMS: m/z=214.1 [M+H]⁺.

Step 2: Into a 8 mL vial, was placed 6-[2-azabicyclo[2.2.2]octan-5-yl]pyridine-3-carbonitrile (25 mg, 0.12 mmol, 1 eq), 3-(1,3-benzothiazole-7-sulfonyl)propanoic acid (38 mg, 0.14 mmol, 1.2 eq), HOBT (19 mg, 0.14 mmol, 1.2 eq), EDCI (27 mg, 0.14 mmol, 1.2 eq), NMM (35 mg, 0.35 mmol, 3 eq), DMF (1 mL). The resulting solution was stirred for 1 h at 25° C. and purified by Prep-HPLC to afford 12 mg (22%) of 6-[2-[3-(1,3-benzothiazole-7-sulfonyl)-propanoyl]-2-azabicyclo[2.2.2]octan-5-yl]pyridine-3-carbonitrile as a white solid. LCMS: m/z=467.4 [M+H]⁺.

Example 29: Synthesis of 6-[3-(3-{[(1,3-benzothiazol-7-yl)methyl]amino}propanoyl)-3,8-diaza-bicyclo[3.2.1]octan-8-yl]pyridine-3-carbonitrile

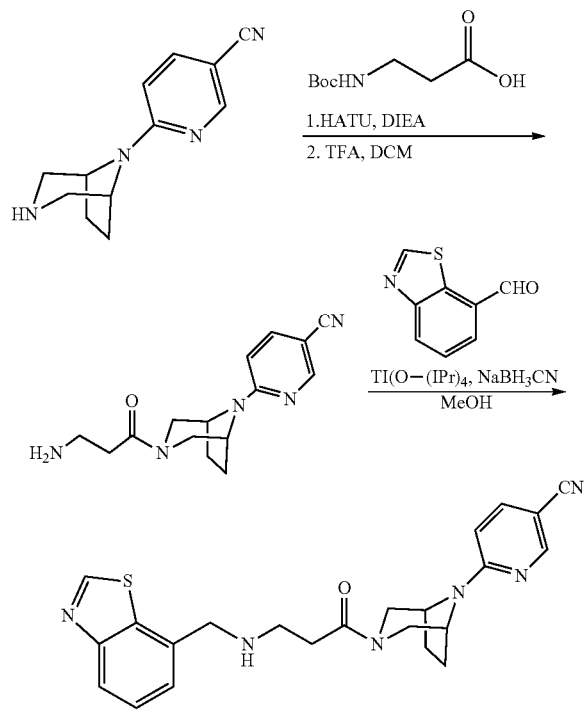

Step 1: Into a 25-mL round-bottom flask, was placed 3-(tert-butoxycarbonylamino)propanoic acid (528 mg, 2.8 mmol, 1.2 eq), DMF (8.00 mL), HATU (1.33 g, 3.50 mmol, 1.5 eq), DIEA (901 mg, 7 mmol, 3 eq), 6-(3,8-diaza-bicyclo[3.2.1]octan-8-yl)nicotinonitrile (500 mg, 2.33 mmol, 1 eq). The mixture was stirred for 1 h at room temperature. The resulting solution was diluted with water and extracted with ethyl acetate and the organic layer was concentrated in vacuum. The crude product was purified by Flash-Prep-HPLC. This resulted in 715 mg (79%) of tert-butyl 3-(8-(5-cyanopyridin-2-yl)-3,8-diaza-bicyclo[3.2.1]octan-3-yl)-3-oxopropylcarbamate as yellow oil. LCMS: m/z=386.1 [M+H]⁺. The material (715 mg, 1.85 mmol, 1 eq) was dissolved in DCM (10 mL) and TFA (5 mL) was added. The resulting solution was stirred for 1 h at room temperature. The resulting mixture was concentrated. The pH of the solution was adjusted to 8 with NH₃-MeOH (7 M). The crude product was purified by Flash-Prep-HPLC. This resulted in 436 mg (82%) of 6-(3-(3-aminopropanoyl)-3,8-diaza-bicyclo[3.2.1]octan-8-yl)nicotinonitrile as a white solid. LCMS: m/z=286.1 [M+H]⁺; ¹H NMR (300 MHz, DMSO) δ 8.52 (d, J=2.1 Hz, 1H), 7.90 (dd, J=9.0, 2.3 Hz, 1H), 6.96 (d, J=9.0 Hz, 1H), 4.75 (s, 2H), 4.13 (d, J=12.4 Hz, 1H), 3.60 (d, J=13.0 Hz, 1H), 3.27 (d, J=12.1 Hz, 1H), 3.01-2.76 (m, 4H), 2.67-2.55 (m, 1H), 2.00-1.60 (m, 4H).

Step 2: Into a 8 mL vial, was placed 6-[3-(3-aminopropanoyl)-3,8-diazabicyclo[3.2.1]octan-8-yl]pyridine-3-carbonitrile (84 mg, 0.294 mmol, 1.2 eq), 1,3-benzothiazole-7-carbaldehyde (40 mg, 0.25 mmol, 1 eq), Ti(Oi-Pr)₄ (105 mg, 0.37 mmol, 1.5 eq), MeOH (2 mL). The resulting solution was stirred for 1.5 h at 25° C. Then NaBH₃CN (46 mg, 0.74 mmol, 3 eq) was placed into the vial. The resulting solution was stirred for 0.5 h at 25° C. The reaction was then quenched by the addition of 1 mL of water. The solids were filtered out. The resulting mixture was concentrated. The crude product was purified by Prep-HPLC. This resulted in 40 mg (37%) of 6-[3-(3-[[(1,3-benzothiazol-7-yl)methyl]amino]propanoyl)-3,8-diazabicyclo[3.2.1]octan-8-yl]pyridine-3-carbonitrile as a yellow solid. LCMS: m/z=433.3 [M+H]⁺; ¹H NMR (Methanol-d₄) δ 9.22 (s, 1H), 8.44 (d, J=1.9 Hz, 1H), 7.98 (d, J=8.0 Hz, 1H), 7.77 (dd, J=9.0, 2.3 Hz, 1H), 7.55 (t, 1H), 7.48 (d, J=7.2 Hz, 1H), 6.86 (d, J=9.0 Hz, 1H), 4.73 (s, 2H), 4.25 (d, J=13.9 Hz, 1H), 4.11 (s, 2H), 3.71 (d, J=12.6 Hz, 1H), 3.36 (s, 1H), 2.94-2.84 (m, 3H), 2.73-2.52 (m, 2H), 2.06-1.98 (m, 2H), 1.88-1.72 (m, 2H).

Example 30: Synthesis of 6-[3-(3-{[(1,3-benzothiazol-7-yl)methyl]amino}cyclobutanecarbonyl)-3,8-diazabicyclo[3.2.1]octan-8-yl]pyridine-3-carbonitrile

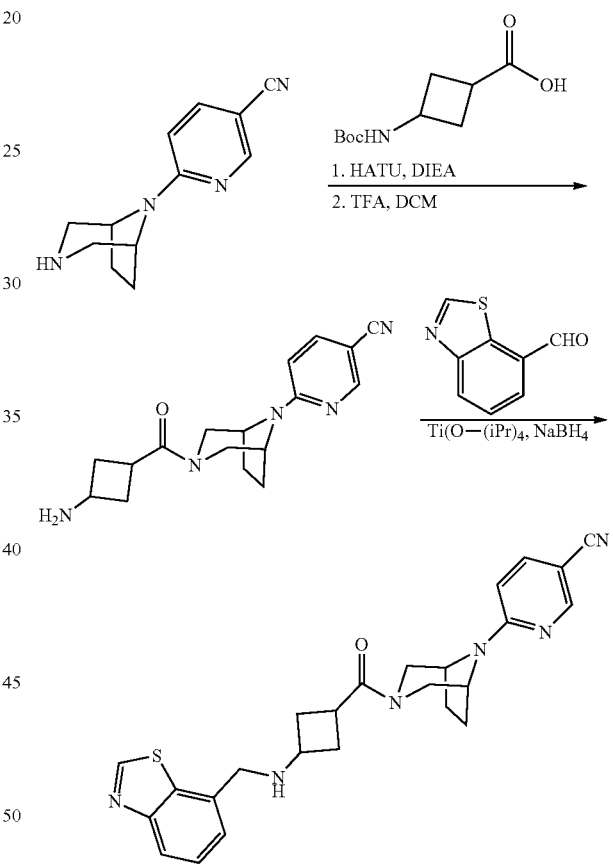

Step 1: Into a 8 mL vial, was placed 6-[3,8-diazabicyclo[3.2.1]octan-8-yl]pyridine-3-carbonitrile (120 mg, 0.56 mmol, 1 eq), 3-[[(tert-butoxy)carbonyl]amino]cyclobutane-1-carboxylic acid (181 mg, 0.84 mmol, 1.5 eq), HATU (320 mg, 0.84 mmol, 1.5 eq), DIEA (217 mg, 1.68 mmol, 3 eq), DMF (1.5 mL). The resulting solution was stirred for 1 h at 25° C. and purified by Flash-Prep-HPLC. This resulted in 179 mg (78%) of tert-butyl N-[3-[8-(5-cyanopyridin-2-yl)-3,8-diazabicyclo[3.2.1]octane-3-carbonyl]cyclobutyl]carbamate as a yellow semi-solid. LCMS: m/z=412.1 [M+H]⁺ This was dissolved in DCM (7 mL) and TFA (2 mL) was added. The resulting solution was stirred for 0.5 h at 25° C. The pH of the solution was adjusted to 8-9 with NH₃-MeOH (7M) and concentrated. The crude product was purified by Flash-Prep-HPLC. This resulted in 80 mg (59%) of 6-[3-(3-aminocyclobutanecarbonyl)-3,8-diazabicyclo[3.2.1]octan-8-yl]pyridine-3-carbonitrile as a yellow semi-solid. LCMS: m/z=312.1 [M+H]$^+$.

Step 2: Into a 8 mL vial, was placed 6-[3-(3-aminocyclobutanecarbonyl)-3,8-diazabicyclo[3.2.1]octan-8-yl]pyridine-3-carbonitrile (40 mg, 0.13 mmol, 1 eq), 1,3-benzothiazole-7-carbaldehyde (21 mg, 0.13 mmol, 1 eq), Ti(Oi-Pr)$_4$ (110 mg, 0.39 mmol, 3 eq), methanol (3 mL). The resulting solution was stirred for 1.5 h at 25° C. Then NaBH$_4$ (7.30 mg, 0.19 mmol, 1.5 eq) was placed into the vial. The resulting solution was stirred for 0.5 h at 25° C. The reaction was then quenched by the addition of water. The solids were filtered out. The resulting mixture was concentrated and purified by Prep-HPLC. This resulted in 24.8 mg (42%) of 6-[3-(3-[[(1,3-benzothiazol-7-yl)methyl]amino]cyclobutanecarbonyl)-3,8-diazabicyclo[3.2.1]octan-8-yl]pyridine-3-carbonitrile as a white solid. LCMS: m/z=459.4 [M+H]$^+$.

Example 31: Synthesis of 6-(3-{3-[(1,3-benzothiazol-7-yl)methyl]cyclobutanecarbonyl}-3,8-diazabicyclo[3.2.1]octan-8-yl)pyridine-3-carbonitrile

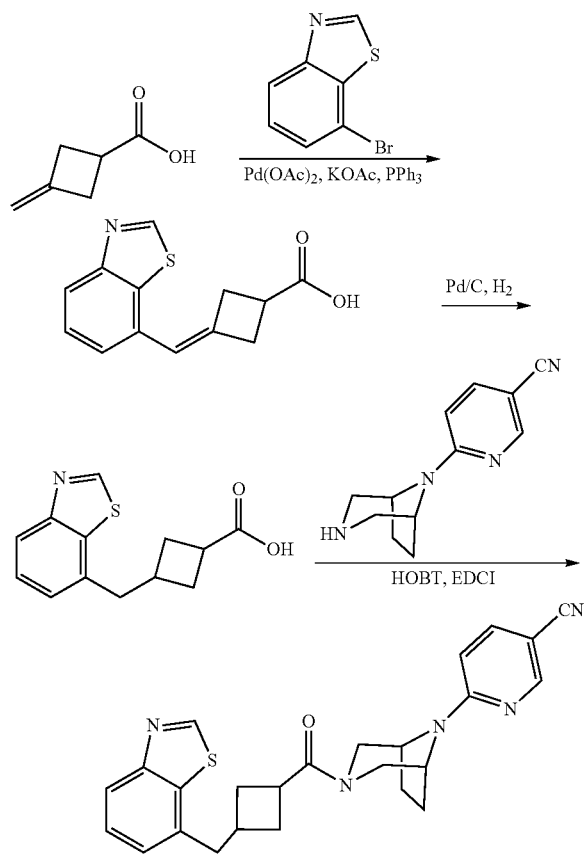

Step 1: Into a 30 mL sealed tube purged and maintained with nitrogen, was placed 3-methylidenecyclobutane-1-carboxylic acid (200 mg, 1.78 mmol, 1 eq), DMF (4 mL), 7-bromo-1,3-benzothiazole (382 mg, 1.78 mmol, 1 eq), Pd(OAc)$_2$ (40 mg, 0.18 mmol, 0.1 eq), KOAc (525 mg, 5.35 mmol, 3 eq), PPh$_3$ (94 mg, 0.36 mmol, 0.2 eq), TBAB (575 mg, 1.78 mmol, 1 eq). The resulting solution was stirred for 2 h at 90° C. in an oil bath. The solids were filtered out. The resulting mixture was concentrated and purified by Flash-Prep-HPLC. This resulted in 180 mg (41%) of 3-[(1,3-benzothiazol-7-yl)methylidene]cyclobutane-1-carboxylic acid as colorless oil.

LCMS: m/z=246.1 [M+H]$^+$.

Step 2: Into a 25-mL round-bottom flask, was placed 3-[(1,3-benzothiazol-7-yl)methylidene]cyclobutane-1-carboxylic acid (90 mg, 0.37 mmol, 1 eq), MeOH (2 mL), Pd/C (10%, 39 mg, 0.037 mmol, 0.1 eq). The resulting solution was stirred for 3 h at room temperature under H$_2$. The solids were filtered out. The resulting mixture was concentrated and purified by Flash-Prep-HPLC. This resulted in 80 mg (88%) of 3-[(1,3-benzothiazol-7-yl)methyl]cyclobutane-1-carboxylic acid as colorless oil. LCMS: m/z=248.1 [M+H]$^+$.

Step 3: The product was made in similar manner as Example 24, and 40 mg (37%) of 6-(3-[3-[(1,3-benzothiazol-7-yl)methyl]cyclobutanecarbonyl]-3,8-diazabicyclo[3.2.1]octan-8-yl)pyridine-3-carbonitrile was obtained as a white solid. LCMS: m/z=444.2 [M+H]$^+$.

Example 32: Synthesis of 3-(1,3-benzothiazole-7-sulfonyl)-1-{6-[5-(trifluoromethyl)pyridin-2-yl]-3-azabicyclo[4.1.0]heptan-3-yl}propan-1-one

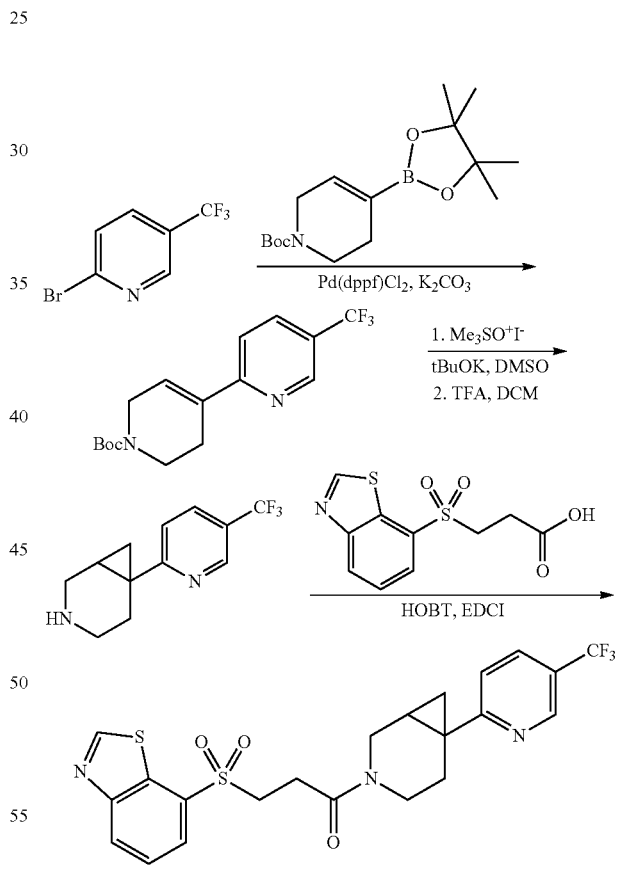

Step 1: To a stirred solution of 2-bromo-5-(trifluoromethyl)pyridine (3.6 g, 15.9 mmol, 1 eq) and tert-butyl 4-(4,4,5,5-tetramethyl-1,3,2-dioxaborolan-2-yl)-5,6-dihydropyridine-1(2H)-carboxylate (5.9 g, 19.1 mmol, 1.2 eq) in 1,4-dioxane (20 mL) and water (5 mL) was added K$_2$CO$_3$ (6.6 g, 47.8 mmol, 3 eq) and Pd(dppf)Cl$_2$ (1.16 g, 1.59 mmol, 0.1 eq). The resulting mixture was stirred for 4 h at 60° C. The residue was concentrated and applied onto a silica gel column. This resulted in 2.2 g (42%) of tert-butyl 4-(5-(trifluoromethyl)pyridin-2-yl)-5,6-dihydropyridine-1 (2H)-carboxylate as a yellow oil. LCMS: m/z=329 [M+H]+.

Step 2: A mixture of t-BuOK (1.54 g, 14 mmol, 3 eq) and trimethylsulfoxonium iodide (2.74 g, 14 mmol, 3 eq) in DMSO (10 mL) was stirred for 2 h at 50 degree under nitrogen atmosphere. Then tert-butyl 5-(trifluoromethyl)-1,2,3,6-tetrahydro-[2,4-bipyridine]-1-carboxylate (1.5 g, 4.57 mmol, 1 eq) in DMSO was added dropwise. The mixture was stirred for 2 h at 50° C. under nitrogen. The solid was filtered off and the filtrate was concentrated. The residue was purified by silica gel column chromatography to afford tert-butyl 6-[5-(trifluoromethyl)pyridin-2-yl]-3-azabicyclo[4.1.0]heptane-3-carboxylate (530 mg, 34%) as a white solid. LCMS: m/z=343 [M+H]+ Into a 25 mL round-bottom flask, was placed tert-butyl 6-[5-(trifluoromethyl) pyridin-2-yl]-3-azabicyclo[4.1.0]heptane-3-carboxylate (200 mg, 0.58 mmol, 1 eq), DCM (4 mL), TFA (2 mL). The resulting solution was stirred for 30 min at room temperature. The resulting mixture was concentrated and the pH was adjusted to 8 with NH$_3$.MeOH (7 M). The resulting mixture was concentrated and purified by Flash-Prep-HPLC. This resulted in 120 mg (85%) of 6-[5-(trifluoromethyl)pyridin-2-yl]-3-azabicyclo[4.1.0]heptane as a yellow oil.

Step 3: The product was made in similar manner as Example 24, and 39 mg (63%) of 3-(1,3-benzothiazole-7-sulfonyl)-1-[6-[5-(trifluoromethyl) pyridin-2-yl]-3-azabicyclo[4.1.0]heptan-3-yl]propan-1-one as a yellow solid. LCMS: m/z=496 [M+H]+.

Example 33: Synthesis of 6-(3-{3-[({[1,2,4]triazolo[1,5-a]pyridin-5-yl}methyl)amino]propanoyl}-3,8-diazabicyclo[3.2.1]octan-8-yl)pyridine-3-carbonitrile

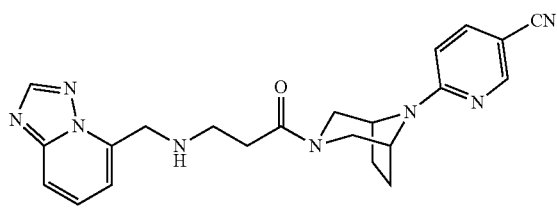 [SMILES: N#Cc1ccc(N2C3CCC2CN(C(=O)CCNCc2cccc4ncnn24)C3)nc1]

The compound was made in a similar manner as Example 29 starting with [1,2,4]triazolo[1,5-a]pyridine-5-carbaldehyde (100 mg, 0.68 mmol, 1 eq) to provide 170 mg (60%) of 6-(3-[3-[({[1,2,4]triazolo[1,5-a]pyridin-5-yl]methyl)amino]propanoyl]-3,8-diazabicyclo[3.2.1]octan-8-yl)pyridine-3-carbonitrile as a white solid. LCMS: m/z=417.4 [M+H]+; 1H NMR (Methanol-d$_4$) δ 8.46 (s, 1H), 8.44 (d, J=2.2 Hz, 1H), 7.82-7.66 (m, 3H), 7.28 (dd, J=6.3, 1.9 Hz, 1H), 6.86 (d, J=9.0 Hz, 1H), 4.74 (d, J=8.0 Hz, 2H), 4.33 (s, 2H), 4.25 (d, J=12.5 Hz, 1H), 3.74 (d, J=12.2 Hz, 1H), 3.41-3.35 (m, 1H), 2.91 (t, 3H), 2.77-2.48 (m, 2H), 2.08-1.97 (m, 2H), 1.92-1.72 (m, 2H).

Example 34: Synthesis of 6-(3-{3-[({6-fluoroimidazo[1,2-a]pyridin-5-yl}methyl)amino]propanoyl}-3,8-diazabicyclo[3.2.1]octan-8-yl)pyridine-3-carbonitrile

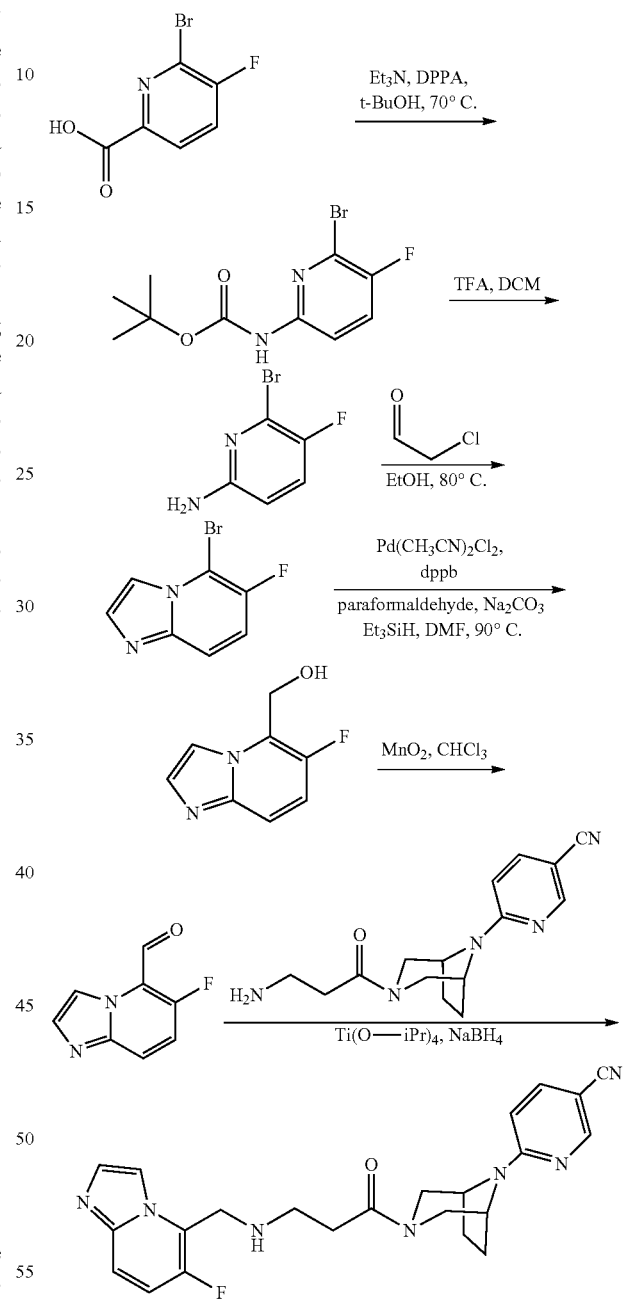

Step 1: Into a 250 mL round-bottom flask, was placed 6-bromo-5-fluoropyridine-2-carboxylic acid (6.3 g, 28.6 mmol, 1 eq), t-BuOH (50 mL), TEA (4 mL, 28.8 mmol, 1 eq), DPPA (6.2 mL, 23 mmol, 0.79 eq). The resulting solution was stirred for 20 min at 25° C. then refluxed for 2 h at 70° C. in an oil bath. The resulting solution was diluted with water, extracted with 3×350 mL of ethyl acetate, and concentrated. The residue was applied onto a silica gel column eluting with ethyl acetate/petroleum ether. This resulted in 8.67 g (99%) of tert-butyl N-(6-bromo-5-fluoro-pyridin-2-yl)carbamate as yellow oil. LCMS: m/z=291.1 [M+H]⁺.

Step 2: Into a 100 mL round-bottom flask, was placed tert-butyl N-(6-bromo-5-fluoropyridin-2-yl)carbamate (8.67 g, 29.8 mmol, 1 eq), DCM (30 mL) and TFA (25 mL). The resulting solution was stirred for 1 h at 25° C. The pH of the solution was adjusted to 8-9 with NH₃-MeOH (7 M). The resulting mixture was concentrated and purified by Flash-Prep-HPLC. This resulted in 3.08 g (54%) of 6-bromo-5-fluoropyridin-2-amine as a yellow solid. LCMS: m/z=191.1 [M+H]⁺.

Step 3: Into a 250 mL round-bottom flask, was placed 6-bromo-5-fluoropyridin-2-amine (6 g, 31.4 mmol, 1 eq), 2-chloroacetaldehyde (14.8 g, 188.5 mmol, 6 eq), ethanol (50 mL). The resulting solution was stirred for 3 h at 80° C. in an oil bath. The resulting mixture was concentrated. The resulting solution was extracted with 4×350 mL of dichloromethane and the organic layers combined and dried over anhydrous sodium sulfate. The crude product was purified by Flash-Prep-HPLC. This resulted in 2.9 g (43%) of 5-bromo-6-fluoroimidazo[1,2-a]pyridine as a brown solid. LCMS: m/z=215.1 [M+H]⁺.

Step 4: Into a 30 mL sealed tube purged and maintained with nitrogen, was placed 5-bromo-6-fluoroimidazo[1,2-a]pyridine (1 g, 4.65 mmol, 1 eq), Pd(CH₃CN)₂Cl₂ (241.30 mg, 0.93 mmol, 0.2 eq), dppb (793 mg, 1.86 mmol, 0.4 eq), paraformaldehyde (503 mg, 5.6 mmol, 1.2 eq), Et₃SiH (433 mg, 3.72 mmol, 0.8 eq), DMF (10.00 mL), Na₂CO₃ (1479 mg, 14 mmol, 3 eq). The mixture was stirred for 3 h at 90° C. in an oil bath. The resulting solution was diluted with water and extracted with ethyl acetate, and the organic layers combined and dried over anhydrous sodium sulfate. The residue was applied onto a silica gel column with ethyl acetate/petroleum ether. This resulted in 480 mg (62%) of [6-fluoroimidazo[1,2-a]pyridin-5-yl]methanol as a yellow semi-solid. LCMS: m/z=167.1 [M+H]⁺.

Step 5: Into a 100 mL round-bottom flask, was placed [6-fluoroimidazo[1,2-a]pyridin-5-yl]methanol (480 mg, 2.89 mmol, 1 eq), MnO₂ (2009 mg, 23.1 mmol, 8 eq), CHCl₃ (20 mL). The resulting solution was stirred for 48 h at 65° C. in an oil bath. Solids were filtered out and mixture was concentrated. The crude product was purified by Flash-Prep-HPLC. This resulted in 340 mg (72%) of 6-fluoroimidazo[1,2-a]pyridine-5-carbaldehyde as a yellow solid. LCMS: m/z=165.10 [M+H]⁺.

Step 6: The compound was made in a similar manner as Example 29 starting with 6-fluoroimidazo[1,2-a]pyridine-5-carbaldehyde (48 mg, 0.29 mmol, 1.2 eq) to provide 31 mg (29%) of 6-(3-[3-[([6-fluoroimidazo[1,2-a]pyridin-5-yl]methyl)amino]propanoyl]-3,8-diazabicyclo[3.2.1]octan-8-yl)pyridine-3-carbonitrile as a colorless semi-solid.

LCMS: m/z=434.3 [M+H]⁺; ¹H NMR (Methanol-d₄) δ 8.67 (s, 1H), 8.44 (s, 1H), 8.28 (s, 1H), 8.18 (dd, J=9.5, 4.1 Hz, 1H), 8.07 (t, 1H), 7.78 (d, J=10.0 Hz, 1H), 6.89 (d, J=9.0 Hz, 1H), 5.02 (s, 2H), 4.77 (s, 2H), 4.28 (d, J=12.9 Hz, 1H), 3.67 (d, J=12.3 Hz, 1H), 3.57 (s, 2H), 3.43 (d, J=12.3 Hz, 1H), 3.10-2.78 (m, 3H), 2.06 (s, 2H), 1.95-1.75 (m, 2H).

Example 35: Synthesis of 6-[3-(3-{[(1,3-benzothiazol-7-yl)methyl](cyclopropyl)amino}propanoyl)-3,8-diazabicyclo[3.2.1]octan-8-yl]pyridine-3-carbonitrile

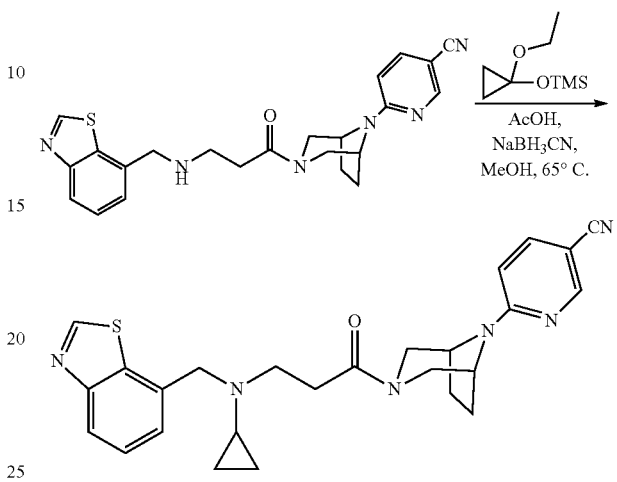

Into a 25 mL round-bottom flask, was placed 6-[3-(3-[[(1,3-benzothiazol-7-yl)methyl]amino]propanoyl)-3,8-diazabicyclo[3.2.1]octan-8-yl]pyridine-3-carbonitrile (70 mg, 0.16 mmol, 1 eq), (1-ethoxycyclopropoxy)trimethylsilane (159 mg, 0.97 mmol, 6 eq), MeOH (2.00 mL), AcOH (0.05 mL), NaBH₃CN (61 mg, 0.97 mmol, 6 eq). The resulting solution was stirred for 10 min at room temperature then heated in microwave for 1 h at 60° C. The resulting mixture was concentrated under vacuum and purified by Prep-HPLC. The fractions were extracted with DCM and concentrated in vacuo to give a semi-solid which was treated with HCl (4M in dioxane), the solid was collected and dried in the oven to give product as a white solid 44 mg (53%). LCMS: m/z=473.3 [M+H]⁺; ¹H NMR (DMSO-d₆): δ 10.9 (br, s, 1H), 9.49 (s, 1H), 8.39 (d, J=1.5 Hz, 1H), 8.53-8.52 (m, 1H), 8.19-8.18 (m, 1H), 7.92-7.89 (m, 1H), 6.98 (d, J=10 Hz, 1H), 4.83-4.69 (m, 4H), 4.10-4.07 (m, 1H), 3.69-3.66 (m, 1H), 3.57-3.39 (m, 2H), 3.31-3.28 (m, 1H), 3.23-3.16 (m, 1H), 3.00-2.92 (m, 1H), 2.80-2.75 (m, 2H), 2.00-1.90 (m, 2H), 1.86-1.80 (m, 1H), 1.62-1.58 (m, 1H), 1.17 (br, s, 1H), 0.77 (br, s, 2H), 0.55 (br, s, 1H).

Example 36: Synthesis of 6-[3-(3-[(benzo[d]thiazol-7-ylmethyl-d₂)amino]propanoyl)-3,8-diazabicyclo[3.2.1]octan-8-yl]pyridine-3-carbonitrile

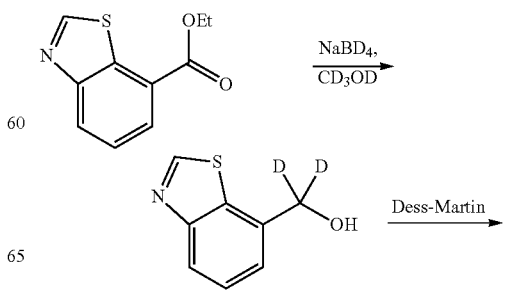

-continued

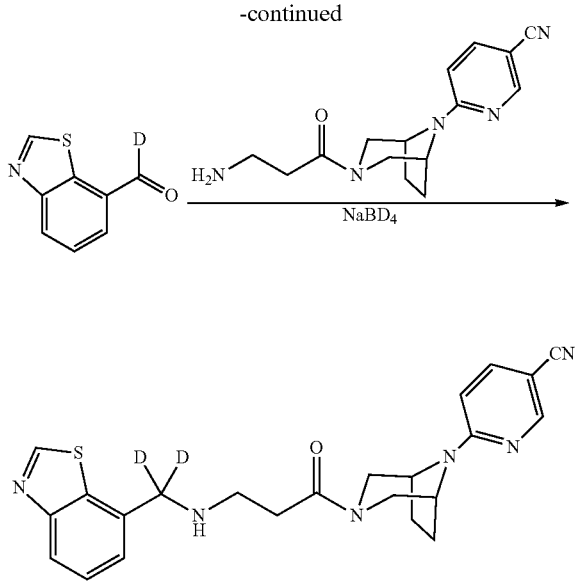

Step 1: Into a 50 mL round-bottom flask, was placed ethyl 1,3-benzothiazole-7-carboxylate (440 mg, 2.12 mmol, 1 eq), THF (10 mL), NaBD₄ (2675 mg, 63.7 mmol, 30 eq), CD₃OD (2 mL). The resulting solution was stirred for 4 h at 80° C. in an oil bath. The reaction was then quenched by the addition of 5 mL of water. The solids were filtered out. The resulting mixture was concentrated under vacuum. The crude product was purified by Flash-Prep-HPLC. This resulted in 45 mg (13%) of benzo[d]thiazol-7-ylmethan-d₂-ol as a yellow semi-solid. LCMS: m/z=168.1 [M+H]⁺.

Step 2: Into a 8 mL vial, was placed benzo[d]thiazol-7-ylmethan-d₂-ol (45 mg, 0.27 mmol, 1 eq), DCM (3.00 mL), Dess-Martin (137 mg, 0.323 mmol, 1.2 eq). The resulting solution was stirred for 1 h at 25° C. The solids were filtered out. The resulting mixture was concentrated and purified by Flash-Prep-HPLC. This resulted in 27 mg (61%) of benzo[d]thiazol-7-carbaldehyde-d as a yellow solid. LCMS: m/z=165.1 [M+H]⁺.

Step 3: Into a 8 mL vial, was placed benzo[d]thiazol-7-carbaldehyde-d (27 mg, 0.164 mmol, 1 eq), 6-[3-(3-amino-propanoyl)-3,8-diazabicyclo[3.2.1]octan-8-yl]pyridine-3-carbonitrile (51 mg, 0.18 mmol, 1.1 eq), MeOH (4.00 mL), Ti(Oi-Pr)₄ (140 mg, 0.493 mmol, 3 eq). The resulting solution was stirred for 2 h at 25° C. Then NaBD₄ (21 mg, 0.493 mmol, 3 eq) was added to the mixture. The resulting solution was stirred for 0.5 h at 25° C. The reaction was then quenched by the addition of water. The solids were filtered out. The resulting mixture was concentrated and purified by Prep-HPLC. This resulted in 8 mg (11%) of 6-[3-(3-[(benzo[d]thiazol-7-ylmethyl-d₂)amino]propanoyl)-3,8-diazabicyclo[3.2.1]octan-8-yl]pyridine-3-carbonitrile as a white solid. LCMS: m/z=435.3 [M+H]⁺; ¹H NMR (Methanol-d₄) δ 9.22 (s, 1H), 8.44 (d, J=1.9 Hz, 1H), 7.98 (dd, J=8.1, 1.0 Hz, 1H), 7.77 (dd, J=9.0, 2.3 Hz, 1H), 7.87-7.44 (m, 2H), 6.86 (d, J=8.8 Hz, 1H), 4.73 (s, 2H), 4.25 (d, J=13.1 Hz, 1H), 3.71 (d, J=12.9 Hz, 1H), 3.37 (s, 3H), 2.87 (t, 2H), 2.75-2.51 (m, 2H), 2.06-1.98 (m, 2H), 1.87-1.72 (m, 2H).

Example 37: Synthesis of 6-(3-{3-[(quinoxalin-5-yl)methoxy]propanoyl}-3,8-diazabicyclo[3.2.1]octan-8-yl)pyridine-3-carbonitrile

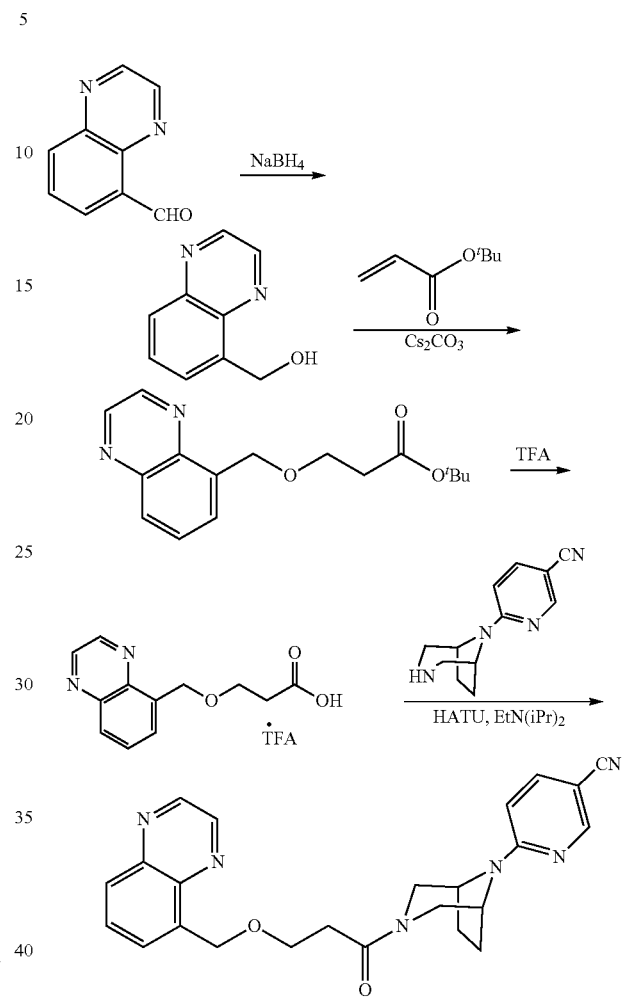

Step 1: To a suspension of quinoxaline-5-carbaldehyde (0.500 g, 3.2 mmol, 1 eq) in methanol (20 mL) and THF (5 mL) was added at 0° C. sodium borohydride (0.180 g, 4.8 mmol, 1.5 eq) portion-wise over a period of 5 min. Following an initial vigorous evolution of gas, the cooling bath was removed and the resulting suspension was stirred at room temperature for another 30 min. The unreacted borohydride was then carefully quenched with the addition of 1 N aqueous HCl and the resulting reaction mixture was then neutralized with the addition of 1 N aqueous NaOH. The volatiles were removed in vacuo and the resulting aqueous suspension was extracted with EtOAc (3×). The combined organic extracts were washed further with water and brine, dried over MgSO₄ and filtered. The filtrate thus obtained was concentrated in vacuo to afford the crude product as a brown solid. Trituration in 1:1 (v/v) diethyl ether and hexanes afforded quinoxalin-5-ylmethanol (0.28 g, 55% yield) as a tan solid, LCMS: m/z=160.7 [M+H]⁺.

Step 2: To a solution of quinoxalin-5-ylmethanol (0.105 g, 0.65 mmol, 1 eq) and cesium carbonate (0.318 g, 0.98 mmol, 1.5 eq) in tert-butanol (5 mL) was added tert-butyl acrylate (0.48 mL, 3.3 mmol, 5 eq). The resulting mixture was stirred at room temperature for 16 h. The volatiles were then removed in vacuo and the resulting residue was partitioned between water and tert-butyl methyl ether. The aqueous layer was separated and back-extracted with tert-butyl methyl ether (3×). The combined organic extracts were then washed further with 1 N aqueous NaOH, water and brine, dried over MgSO$_4$ and filtered. The filtrate thus obtained was concentrated in vacuo to afford the crude product as a yellow oil. Purification by way of column chromatography (SiO$_2$, gradient elution, 9:1 (v/v) Hex:EtOAc→3:7 (v/v) Hex:EtOAc) afforded tert-butyl 3-(quinoxalin-5-ylmethoxy)propanoate (0.106 g, 57% yield) as a colorless oil, LCMS: m/z=288.9 [M+H]$^+$.

Step 3: To a solution of tert-butyl 3-(quinoxalin-5-ylmethoxy)propanoate (22 mg, 0.076 mmol, 1 eq) in dichloromethane (1 mL) was added trifluoroacetic acid (0.35 mL, 4.6 mmol, 60 eq). The resulting mixture was stirred at room temperature for 16 h. The volatiles were then removed in vacuo and the resulting residue was further azeotroped with toluene (3×). The crude 3-(quinoxalin-5-ylmethoxy)propanoic acid trifluoroacetic acid salt thus obtained was used without further purification, LCMS: m/z=232.9 [M+H]$^+$.

Step 4: To a solution of crude 3-(quinoxalin-5-ylmethoxy)propanoic acid trifluoroacetic acid salt (0.076 mmol, 1 eq) in DMF (1 mL) was added sequentially 6-((1R,5S)-3,8-diazabicyclo[3.2.1]octan-8-yl)nicotinonitrile (17 mg, 0.076 mmol, 1 eq), HATU (35 mg, 0.091 mmol, 1.2 eq) and diisopropyl ethyl amine (0.080 mL, 0.46 mmol, 5 eq). The resulting yellow solution was stirred at room temperature for 2 h. The reaction mixture was then diluted with EtOAc and washed sequentially with water, 1 N aqueous NaOH, water and brine. The organic extract was dried over MgSO$_4$, filtered and the filtrate concentrated in vacuo. Further purification by way of column chromatography (SiO$_2$, gradient elution, EtOAc→10:1 (v/v) EtOAc:MeOH) afforded the title compound (23 mg, 71% yield over two steps) as a white solid, LCMS: m/z=429.1 [M+H]$^+$; $^1$H NMR (CDCl$_3$): δ 8.86 (d, J=2.0 Hz, 1H), 8.84 (d, J=2.0 Hz, 1H), 8.42 (d, J=2.5 Hz, 1H), 8.05 (d, J=8.5 Hz, 1H), 7.86 (d, J=6.5 Hz, 1H), 7.78-7.75 (m, 1H), 7.64 (dd, J=9.0, 2.5 Hz, 1H), 6.56 (d, J=9.0 Hz, 1H), 5.23 (s, 2H), 4.72 (br s, 1H), 4.55 (br s, 1H), 4.40 (d, J=13 Hz, 1H), 4.04-3.94 (m, 2H), 3.67 (d, J=12.5 Hz, 1H), 3.42 (d, J=12.5 Hz, 1H), 2.91 (d, J=12.5 Hz, 1H), 2.80-2.75 (m, 1H), 2.64-2.59 (m, 1H), 2.04-1.94 (m, 2H), 1.86-1.82 (m, 2H).

Example 38: Synthesis of 6-((1R, 5S)-3-(2-(quinoxalin-5-ylmethoxy)acetyl)-3,8-diazabicyclo[3.2.1]octan-8-yl)nicotinonitrile

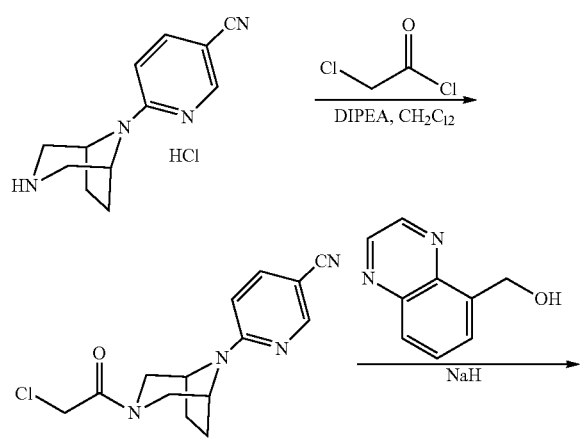

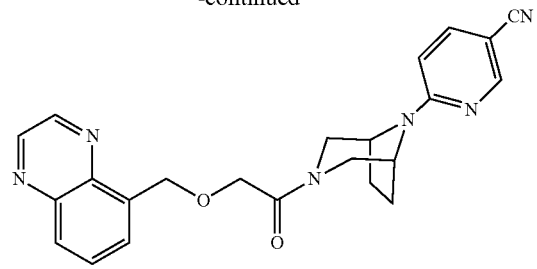

Step 1: To a solution of 6-((1R,5S)-3,8-diazabicyclo[3.2.1]octan-8-yl)nicotinonitrile hydrochloride (3.5 g, 14.0 mmol, 1.0 eq) in CH$_2$Cl$_2$ (50 mL) was added DIPEA (8.5 mL, 48.9 mmol, 3.5 eq) then 2-chloroacetyl chloride (1.2 mL, 15.4 mmol, 1.1 eq). The resulting solution was stirred at RT for 15 min. The reaction was partitioned between CH$_2$Cl$_2$ and water. The aqueous phase was separated and washed with CH$_2$Cl$_2$. The organic layers were combined, dried over MgSO$_4$, filtered and concentrated. The crude residue was purified on silica gel to afford 6-((1R,5S)-3-(2-chloroacetyl)-3,8-diazabicyclo[3.2.1]octan-8-yl)nicotinonitrile (3.2 g, 78%), LCMS: m/z=291 [M+H]$^+$.

Step 2: To a solution of quinoxalin-5-ylmethanol (38 mg, 0.24 mmol, 1.5 eq) in anhydrous THF (1 mL) was added sodium hydride (60% (w/w) dispersion in paraffin oil, 20 mg, 0.24 mmol, 1.5 eq) in one rapid portion. The resulting mixture was stirred at room temperature for 40 min before a THF (2 mL) solution of 6-((1R,5S)-3-(2-chloroacetyl)-3,8-diazabicyclo[3.2.1]octan-8-yl)nicotinonitrile (46 mg, 0.16 mmol, 1 eq) was added. The resulting mixture was stirred at room temperature for another 2 h. The reaction mixture was then diluted with EtOAc and washed sequentially with water, 1 N aqueous NaOH, water and brine. The organic extract was dried over MgSO$_4$, filtered and the filtrate concentrated in vacuo. Further purification by way of column chromatography (SiO$_2$, gradient elution, EtOAc→10:1 (v/v) EtOAc:MeOH) afforded the title compound (45 mg, 68%) as a white solid, LCMS: m/z=415.2 [M+H]$^+$; $^1$H NMR (DMSO-d$_6$): δ=8.87 (d, J=1.5 Hz, 1H), 8.82 (d, J=1.5 Hz, 1H), 8.42 (d, J=2.0 Hz, 1H), 8.08 (dd, J=8.5, 1.5 Hz, 1H), 7.90 (d, J=8.5 Hz, 1H), 7.81-7.77 (m, 1H), 7.64 (dd, J=9.5, 2.0 Hz, 1H), 6.55 (d, J=9.5 Hz, 1H), 5.28 (d, J=11.5 Hz, 1H), 5.25 (d, J=11.5 Hz, 1H), 4.67 (br s, 1H), 4.58 (br s, 1H), 4.39-4.28 (m, 3H), 3.75 (d, J=12.5 Hz, 1H), 3.41 (d, J=12.5 Hz, 1H), 2.97 (d, J=12.5 Hz, 1H), 2.10-1.97 (m, 2H), 1.91-1.86 (m, 2H).

Example 39: Synthesis of 6-{3-[3-({[1,2,4]triazolo[1,5-a]pyridin-5-yl}methoxy)propanoyl]-3,8-diazabicyclo[3.2.1]octan-8-yl}pyridine-3-carbonitrile

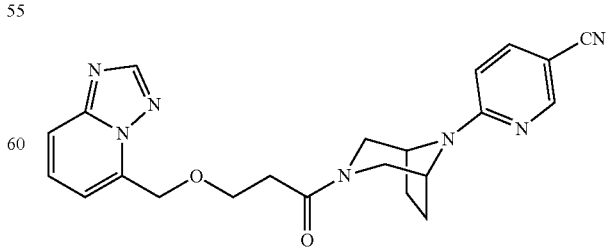

The compound was made in a similar manner as Example 37, LCMS: m/z=418.1 [M+H]$^+$; $^1$H NMR (DMSO-d$_6$): δ

8.42 (d, J=2.5 Hz, 1H), 8.36 (s, 1H), 7.74 (d, J=9.0 Hz, 1H), 7.63 (dd, J=9.0, 2.5 Hz, 1H), 7.55 (dd, J=9.0, 7.0 Hz, 1H), 7.18 (d, J=6.5 Hz, 1H), 6.56 (d, J=9.0 Hz, 1H), 5.04 (s, 2H), 4.74, (bs, 1H), 4.56 (bs, 1H), 4.39 (d, J=13.5 Hz, 1H), 4.05-4.00 (m, 2H), 3.64 (d, J=12.0 Hz, 1H), 3.44 (d, J=12.0 Hz, 1H), 2.93 (d, J=12.5 Hz, 1H), 2.78 (dt, J=15.5, 6.5 Hz, 1H), 2.62 (dt, J=14.0, 6.0 Hz, 1H), 2.04-2.01 (m, 2H), 1.88-1.77 (m, 2H).

Example 40: Synthesis of 6-((1R, 5S)-3-(3-(quinolin-5-ylmethoxy)propanoyl)-3,8-diazabicyclo[3.2.1]octan-8-yl)nicotinonitrile

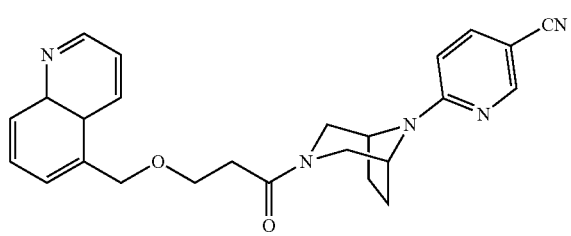 [SMILES: N#Cc1ccc(N2C3CCC2CN(C(=O)CCOCC2=CC=CC4N=CC=CC24)C3)nc1]

The compound was made in a similar manner as Example 37, LCMS: m/z=428.1 [M+H]$^+$; $^1$H NMR (DMSO-d$_6$): δ 8.89 (dd, J=4.0, 1.5 Hz, 1H), 8.48-8.49 (m, 2H), 7.96 (d, J=8.5 Hz, 1H), 7.87 (dd, J=8.5, 2.0 Hz, 1H), 7.70 (dd, J=8.5, 7.0 Hz, 1H), 7.59 (d, J=6.5 Hz, 1H), 7.51 (dd, J=8.5, 4.0 Hz, 1H), 6.89 (d, J=9 Hz, 1H), 4.92, (s, 2H), 4.64-4.68 (m, 2H), 4.13 (d, J=12.5 Hz, 1H), 3.74-3.79 (m, 2H), 3.67 (d, J=12.5 Hz, 1H), 3.17 (d, J=12 Hz, 1H), 2.69-2.76 (m, 2H), 2.52-2.55 (m, 1H), 1.82-1.84 (m, 2H), 1.72-1.75 (m, 1H), 1.54-1.58 (m, 1H).

Example 41: Synthesis of 6-(3-{3-[({6-fluoro-[1,2,4]triazolo[1,5-a]pyridin-5-yl}methyl)amino]propanoyl}-3,8-diazabicyclo[3.2.1]octan-8-yl)pyridine-3-carbonitrile

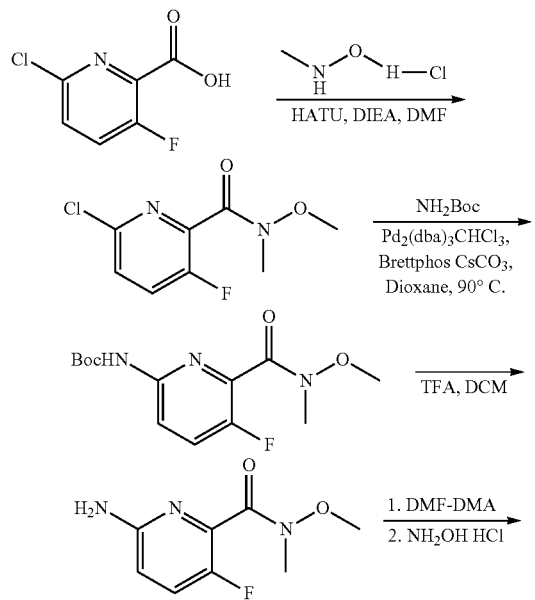

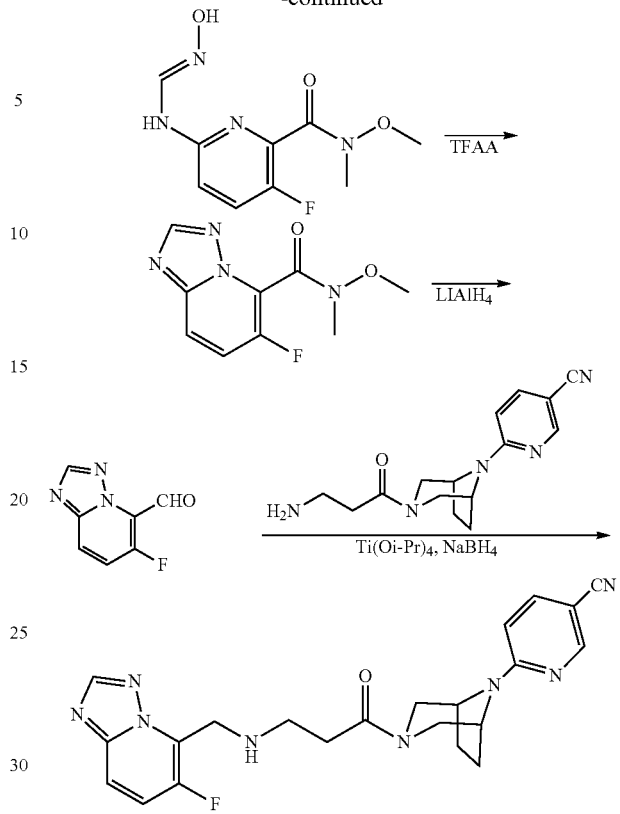

Step 1: Into a 100 mL round-bottom flask, was placed 6-chloro-3-fluoropyridine-2-carboxylic acid (3 g, 17.09 mmol, 1 eq), N,O-dimethylhydroxylamine hydrochloride (2 g, 20.5 mmol, 1.2 eq), HATU (9.8 g, 25.6 mmol, 1.5 eq), DIEA (6.63 g, 51.3 mmol, 3 eq), DMF (20 mL). The resulting solution was stirred for 1 h at 25° C. The resulting solution was diluted with 200 mL of ethyl acetate. The organic layer was washed with 3×50 mL of water. The organic phase was concentrated. The residue was applied onto a silica gel column with ethyl acetate/petroleum ether. This resulted in 3 g (80%) of 6-chloro-3-fluoro-N-methoxy-N-methylpyridine-2-carboxamide as a yellow solid. LCMS: m/z=219 [M+H]$^+$.

Step 2: Into a 250 mL round-bottom flask purged and maintained with nitrogen, was placed 6-chloro-3-fluoro-N-methoxy-N-methylpyridine-2-carboxamide (3 g, 13.7 mmol, 1 eq), Pd$_2$(dba)$_3$CHCl$_3$ (2.84 g, 2.75 mmol, 0.2 eq), NH$_2$Boc (3.15 g, 26.9 mmol, 2 eq), BrettPhos (2.95 g, 5.5 mmol, 0.4 eq), Cs$_2$CO$_3$ (13.4 g, 41.2 mmol, 3 eq), Dioxane (40 mL). The resulting solution was stirred for 2 h at 90° C. The solids were filtered out. The filtrate was concentrated and the crude was applied onto a silica gel column with ethyl acetate/petroleum ether. This resulted in 2.8 g (68%) of tert-butyl N-[5-fluoro-6-[methoxy(methyl)carbamoyl]pyridin-2-yl]carbamate as brown oil. LCMS: m/z=300 [M+H]$^+$.

Step 3: Into a 100 mL round-bottom flask, was placed tert-butyl N-[5-fluoro-6-[methoxy (methyl)carbamoyl]-pyridin-2-yl]carbamate (2.8 g, 9.36 mmol, 1 eq), TFA (5 mL), DCM (20 mL). The resulting solution was stirred for 2.5 h at 25° C. The resulting mixture was concentrated. The pH of the solution was adjusted to 8 with NH$_3$.MeOH (7M). The resulting mixture was concentrated and purified by Flash-Prep-HPLC with ACN/water. This resulted in 1.8 g (96%) of 6-amino-3-fluoro-N-methoxy-N-methylpyridine-2-carboxamide as yellow oil. LCMS: m/z=200 [M+H]⁺.

Step 4: A solution of 6-amino-3-fluoro-N-methoxy-N-methylpyridine-2-carboxamide (1.5 g, 7.53 mmol, 1 eq) and DMF-DMA (1.26 g, 10.5 mmol, 1.4 eq) in IPA (20 mL) was stirred for 3 h at 85° C. The resulting mixture was added NH₂OH.HCl (680 mg, 9.79 mmol, 1.3 eq) and stirred for 2 h at 50° C. The resulting mixture was concentrated under reduced pressure. The resulting mixture was extracted with CH₂Cl₂/MeOH (10:1) (2×200 mL). The organic layers were washed with water, dried over anhydrous Na₂SO₄, and the filtrate was concentrated under reduced pressure to afford (E)-3-fluoro-6-(N'-hydroxyformimidamido)-N-methoxy-N-methylpicolinamide (1.3 g, 71%) as light yellow solid. LCMS: m/z=243 [M+H]⁺.

Step 5: Into a 100 mL round-bottom flask, was placed (E)-3-fluoro-6-(N'-hydroxyformimidamido)-N-methoxy-N-methylpicolinamide (1.3 g, 5.36 mmol, 1 eq), THF (20 mL), TFAA (2.3 g, 10.7 mmol, 2 eq). The resulting solution was stirred for 3 h at 25° C. The pH of the solution was adjusted to 8 with aqueous NaHCO₃. The solids were filtered out. The filtrate was concentrated under reduced pressure and the crude was applied onto a silica gel column eluting with ethyl acetate/petroleum ether. This resulted in 1 g (83%) of 6-fluoro-N-methoxy-N-methyl-[1,2,4]triazolo[1,5-a]pyridine-5-carboxamide as yellow solid. LCMS: m/z=225 [M+H]⁺.

Step 6: A solution of 6-fluoro-N-methoxy-N-methyl-[1,2,4]triazolo[1,5-a]pyridine-5-carboxamide (200 mg, 0.89 mmol, 1 eq) in THF (12 mL) was allowed to cool down to −60° C.~−78° C. under nitrogen atmosphere. To the above mixture was added LiAlH₄ (1 M) (0.62 mL, 0.62 mmol, 0.7 eq) in portions over 6 min at −60° C.~−78° C. The resulting mixture was stirred for additional 25 min at −30° C.~−50° C. The reaction was quenched with aqueous NH₄Cl at −78° C. The resulting mixture was extracted with DCM. The combined organic layers were washed with water, dried over anhydrous Na₂SO₄ and concentrated under reduced pressure. The residue was purified by reverse flash chromatography with ACN/water to afford 6-fluoro-[1,2,4]triazolo[1,5-a]pyridine-5-carbaldehyde (65 mg, 44%) as yellow green oil. LCMS: m/z=166 [M+H]⁺.

Step 7: A solution of 6-fluoro-[1,2,4]triazolo[1,5-a]pyridine-5-carbaldehyde (20 mg, 0.12 mmol, 1 eq), 6-[3-(3-aminopropanoyl)-3,8-diazabicyclo[3.2.1]octan-8-yl]pyridine-3-carbonitrile (41 mg, 0.14 mmol, 1.2 eq) and Ti(OiPr)₄ (103 mg, 0.36 mmol, 3 eq) in MeOH (2 mL) was stirred for 1.5 h at room temperature. The resulting mixture was added NaBH₄ (14 mg, 0.36 mmol, 3 eq) and stirred for 30 min at room temperature. The reaction was quenched with water at room temperature. The resulting mixture was filtered. The filter cake was washed with MeOH. The filtrate was concentrated under reduced pressure. The residue was purified by reverse flash chromatography with ACN/water to afford 6-(3-[3-[([6-fluoro-[1,2,4]triazolo[1,5-a]pyridin-5-yl]methyl)amino]propanoyl]-3,8-diazabicyclo[3.2.1]octan-8-yl)pyridine-3-carbonitrile (27 mg, 51%) as white solid. LCMS: m/z=435.2 [M+H]⁺; ¹H NMR (Methanol-d₄): δ 8.50 (s, 1H), 8.43 (dd, J=2.3, 0.6 Hz, 1H), 7.83-7.72 (m, 3H), 6.85 (d, J=8.4 Hz, 1H), 4.74 (d, J=13.1 Hz, 2H), 4.41 (d, J=2.5 Hz, 2H), 4.21 (d, J=13.0 Hz, 1H), 3.71 (d, J=12.6 Hz, 1H), 3.37 (d, J=3.1 Hz, 1H), 2.91-2.84 (m, 3H), 2.74-2.65 (m, 1H), 2.55-2.45 (m, 1H), 1.99 (t, J=6.8 Hz, 2H), 1.87-1.71 (m, 2H).

Example 42: Synthesis of 6-{3-[3-({[1,2,4]triazolo[1,5-a]pyridin-8-yl}methoxy)propanoyl]-3,8-diazabicyclo[3.2.1]octan-8-yl}pyridine-3-carbonitrile

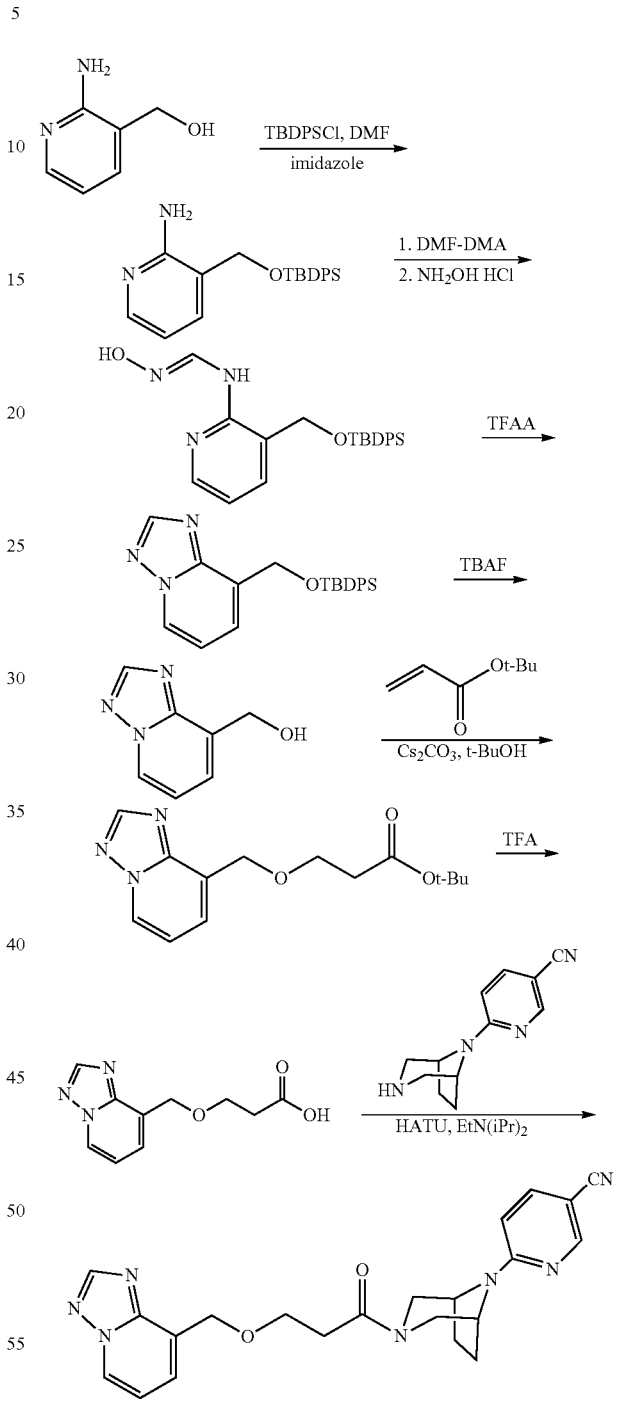

Step 1: Into a 100 mL round-bottom flask, was placed (2-aminopyridin-3-yl)methanol (1.90 g, 15.6 mmol, 1 eq), TBDPSCl (5.58 g, 20.3 mmol, 1.3 eq), imidazole (5.30 g, 78 mmol, 5 eq), DMF (15 mL). The mixture was stirred for 1.5 h at 25° C. The reaction mixture was quenched with water and this was extracted with ethyl acetate. The organic layers combined and concentrated. The residue was applied onto a silica gel column eluting with ethyl acetate/petroleum ether.

This resulted in 5.4 g (96%) of 3-[[(tert-butyldiphenylsilyl)oxy]methyl]pyridin-2-amine as off-white solid. LCMS: m/z=363 [M+H]⁺.

Step 2: A solution of 3-[[(tert-butyldiphenylsilyl)oxy]methyl]pyridin-2-amine (5.4 g, 14.8 mmol, 1 eq) and DMF-DMA (2.66 g, 22 mmol, 1.5 eq) in IPA (20.00 mL) was stirred for 1.5 h at 90° C. The resulting mixture was added NH₂OH HCl (1.35 g, 19 mmol, 1.3 eq) and stirred for 30 min at 50° C. The resulting mixture was concentrated and purified by silica gel column chromatography, eluted with petroleum ether/EtOAc to afford 5.1 g (85%) (E)-N-(3-(((tert-butyldiphenylsilyl)oxy)methyl)pyridin-2-yl)-N'-hydroxyformimidamide as off-white solid. LCMS: m/z=406.2 [M+H]⁺.

Step 3: Into a 250-mL round-bottom flask, was placed (E)-N-(3-(((tert-butyldiphenylsilyl)oxy)methyl)pyridin-2-yl)-N'-hydroxyformimidamide (5.1 g, 12.6 mmol, 1 eq), THF (30 mL). This was followed by the addition of TFAA (10.9 g, 51.8 mmol, 4 eq), in portions at 0° C. in 6 min. The mixture was stirred for 12 h at 25° C. The resulting mixture was concentrated, diluted with water and extracted with ethyl acetate. The organic layer was washed with 2×50 ml of NH₄HCO₃ (aq) and 1×100 mL of water. The residue was applied onto a silica gel column eluting with ethyl acetate/petroleum ether. This resulted in 2.92 g (59%) of 8-[[(tert-butyldiphenylsilyl)oxy]methyl]-[1,2,4]triazolo[1,5-a]pyridine as a white solid. LCMS: m/z=388.2 [M+H]⁺.

Step 4: To a stirred solution of 8-((tert-butyldiphenylsilyloxy)methyl)-[1,2,4]triazolo[1,5-a]pyridine (2.92 g, 7.55 mmol, 1 eq) in THF was added TBAF (7.55 mL, 15.1 mmol, 2 eq) in portions at 0° C. and stirred for 1 h at rt. The resulting mixture was quenched with water and extracted with CH₂Cl₂. The organic layer was washed with 2×200 mL of sodium bicarbonate solution (1M). The organic layer was concentrated and purified by reverse flash chromatography with ACN/water to afford [1,2,4]triazolo[1,5-a]pyridin-8-ylmethanol (1.1 g, 100%) as a light yellow solid. LCMS: m/z=150 [M+H]⁺.

Step 5: The product was made in a similar manner as Example 37 to afford 6-[3-(3-[[1,2,4]triazolo[1,5-a]pyridin-8-ylmethoxy]propanoyl)-3,8-diazabicyclo[3.2.1]octan-8-yl]pyridine-3-carbonitrile as a white solid. LCMS: m/z=418.2 [M+H]⁺; ¹H NMR (300 MHz, DMSO-d₆) δ 8.88 (d, J=5.9 Hz, 1H), 8.51 (d, J=1.9 Hz, 1H), 8.48 (s, 1H), 7.88 (dd, J=9.0, 2.3 Hz, 1H), 7.63 (dd, J=7.1, 1.0 Hz, 1H), 7.20 (t, J=7.0 Hz, 1H), 6.93 (d, J=8.9 Hz, 1H), 4.84 (s, 2H), 4.71 (s, 2H), 4.15 (d, J=12.9 Hz, 1H), 3.93-3.64 (m, 3H), 3.25 (d, J=11.6 Hz, 1H), 2.92-2.67 (m, 2H), 2.65-2.51 (m, 1H), 1.96-1.74 (m, 3H), 1.61 (t, J=8.9 Hz, 1H).

Example 43: Synthesis of 6-(3-{2-[2-(quinoxalin-5-yl)ethoxy]acetyl}-3,8-diazabicyclo[3.2.1]octan-8-yl)pyridine-3-carbonitrile

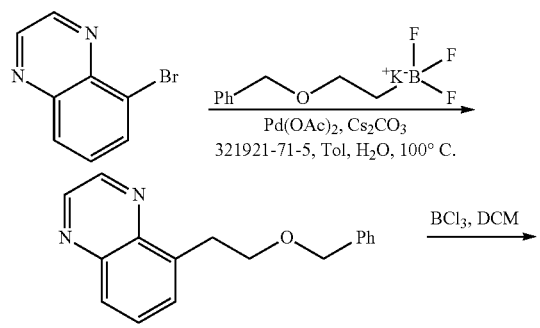

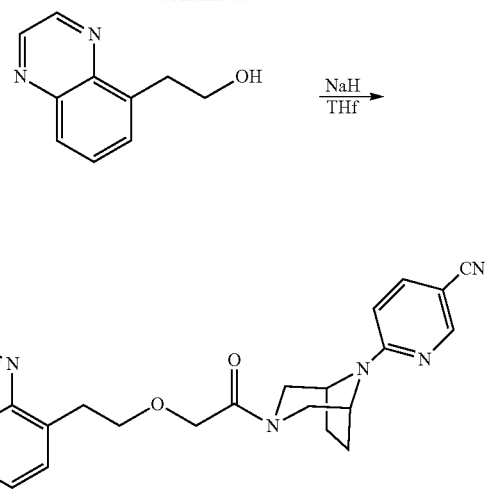

Step 1: A mixture of 5-bromoquinoxaline (300 mg, 1.43 mmol, 1 eq), potassium [2-(benzyloxy)ethyl]-trifluoroboranuide (695 mg, 2.87 mmol, 2 eq), Pd(OAc)₂ (65 mg, 0.29 mmol, 0.2 eq), Butyldi-1-adamantylphosphine (103 mg, 0.29 mmol, 0.2 eq) and Cs₂CO₃ (1169 mg, 3.59 mmol, 2.5 eq) in Toluene (4 mL) and H₂O (1 mL) was stirred overnight at 100° C. The reaction was quenched with water and extracted with EtOAc. The resulting mixture was concentrated under reduced pressure. The residue was purified by silica gel column chromatography, eluted with petroleum ether/EtOAc to afford 5-[2-(benzyloxy)ethyl]quinoxaline (321 mg, 85%) as a yellow oil. LCMS: m/z=265.1 [M+H]⁺.

Step 2: To a stirred mixture of 5-[2-(benzyloxy)ethyl]quinoxaline (200 mg, 0.76 mmol, 1 eq) in DCM (3.5 mL) was added boron trichloride (2.7 mL) dropwise at −30° C. under nitrogen atmosphere. The resulting mixture was stirred for 3 h at −30° C. under nitrogen atmosphere. Then EtOH (3 mL) was added. The resulting mixture was stirred for 2 h at 80° C. The reaction was quenched with water and extracted with DCM. The resulting mixture was concentrated under reduced pressure. The residue was purified by silica gel column chromatography to afford 2-(quinoxalin-5-yl)ethanol (121 mg, 91%) as a white solid. LCMS: m/z=175.0 [M+H]⁺.

Step 3: To a stirred solution of NaH (33 mg, 1.38 mmol, 3 eq) in THF (4.00 mL) was added 2-(quinoxalin-5-yl)ethanol (80 mg, 0.46 mmol, 1 eq) dropwise at 0° C. The resulting mixture was stirred for 1.5 h at 0° C. followed by addition of 6-[3-(2-chloroacetyl)-3,8-diazabicyclo[3.2.1]octan-8-yl]pyridine-3-carbonitrile (134 mg, 0.46 mmol, 1 eq) at 0° C. The resulting mixture was stirred for 1.5 h at room temperature. The reaction was quenched with water and extracted with CH₂Cl₂. The residue was purified by silica gel column chromatography to afford 6-(3-[2-[2-(quinoxalin-5-yl)ethoxy]acetyl]-3,8-diazabicyclo[3.2.1]octan-8-yl)pyridine-3-carbonitrile (39 mg, 20%) as a white solid. LCMS: m/z=451.4 [M+H]⁺; ¹H NMR (MeOD) δ 8.90 (d, J=1.8 Hz, 1H), 8.86 (d, J=1.8 Hz, 1H), 8.44 (dd, J=2.3, 0.6 Hz, 1H), 7.95 (dd, J=7.6, 2.3 Hz, 1H), 7.81-7.73 (m, 3H), 6.81 (d, J=8.5 Hz, 1H), 4.72-4.54 (m, 2H), 4.28-4.10 (m, 3H), 3.99-3.87 (m, 2H), 3.62-3.52 (m, 3H), 3.13 (d, J=12.1 Hz, 1H), 2.83 (d, J=13.3 Hz, 1H), 2.03-1.86 (m, 2H), 1.82-1.63 (m, 2H).

Example 44: Synthesis of 6-{3-[5-(1,3-benzothi-azol-7-yl)pentanoyl]-3,8-diazabicyclo[3.2.1]octan-8-yl}pyridine-3-carbonitrile

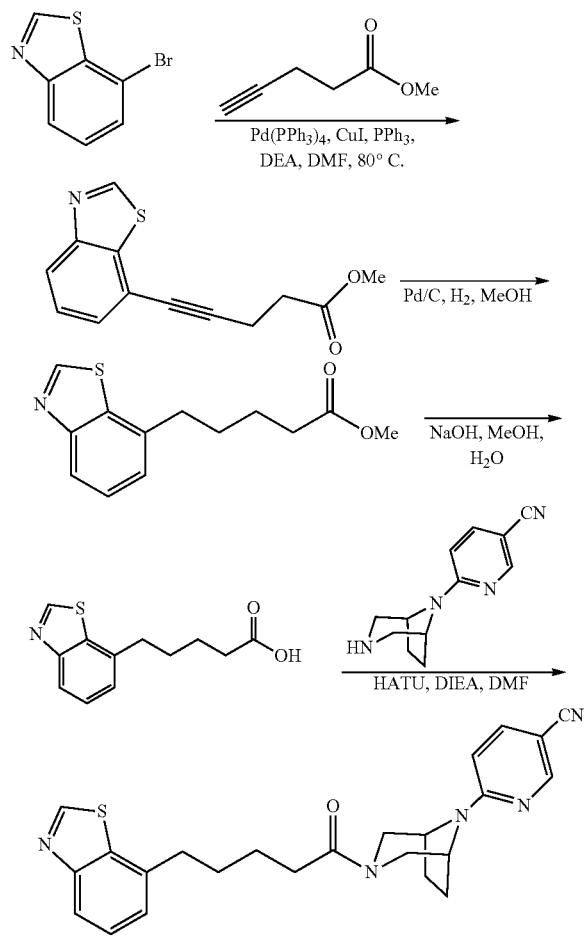

Step 1: Into a 30-mL sealed tube purged and maintained with nitrogen, was placed 7-bromo-1,3-benzothiazole (400 mg, 1.87 mmol, 1 eq), DMF (5 mL), methyl pent-4-ynoate (251.4 mg, 2.24 mmol, 1.2 eq), Pd(PPh$_3$)$_4$ (108 mg, 0.093 mmol, 0.05 eq), CuI (18 mg, 0.093 mmol, 0.05 eq), PPh$_3$ (98 mg, 0.374 mmol, 0.2 eq), DEA (1394 mg, 9.34 mmol, 5 eq). The resulting solution was stirred for 2 h at 80° C. in an oil bath. The solids were filtered out. The resulting solution was extracted with ethyl acetate. The residue was applied onto a silica gel column. This resulted in 130 mg (28%) of methyl 5-(1,3-benzothiazol-7-yl)pent-4-ynoate as yellow oil. LCMS: m/z=246.1 [M+H]$^+$.

Step 2: Into a 25-mL round-bottom flask, was placed methyl 5-(1,3-benzothiazol-7-yl)pent-4-ynoate (130 mg, 0.53 mmol, 1 eq), MeOH (5 mL), Pd/C (10%, 112 mg, 0.11 mmol, 0.2 eq). The resulting solution was stirred overnight at room temperature under H$_2$. The solids were filtered out. The resulting mixture was concentrated. The crude product was purified by Flash-Prep-HPLC. This resulted in 80 mg (60%) of methyl 5-(1,3-benzothiazol-7-yl)pentanoate as a white solid. LCMS: m/z=250.1 [M+H]$^+$.

Step 3: Into a 25-mL round-bottom flask, was placed methyl 5-(1,3-benzothiazol-7-yl)pentanoate (80 mg, 0.32 mmol, 1 eq), MeOH (4 mL), NaOH (38 mg, 0.96 mmol, 3 eq), H$_2$O (1 mL). The resulting solution was stirred for 2 h at room temperature. The resulting mixture was concentrated. The crude product was purified by Flash-Prep-HPLC. This resulted in 50 mg (66%) of 5-(1,3-benzothiazol-7-yl)pentanoic acid as a white solid. LCMS: m/z=236.1 [M+H]$^+$.

Step 4: The product was made in a similar manner as Example 37 step 4 to give 32 mg (44%) of 6-[3-[5-(1,3-benzothiazol-7-yl)pentanoyl]-3,8-diazabicyclo[3.2.1]octan-8-yl]pyridine-3-carbonitrile as a white solid. LCMS: m/z=432.1 [M+H]$^+$.

Example 45: Synthesis of 6-(3-{3-[(quinolin-5-yl)amino]cyclobutanecarbonyl}-3,8-diazabicyclo[3.2.1]octan-8-yl)pyridine-3-carbonitrile

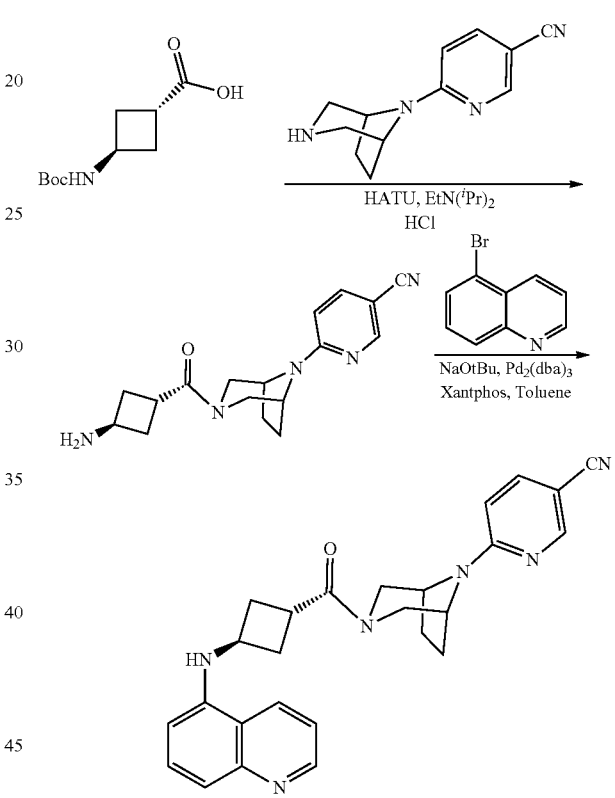

Step 1: To a solution of trans (tert-butoxycarbonyl)amino) cyclobutane-1-carboxylic acid (300 mg, 1.4 mmol, 1 eq) in DMF (3 mL) was added HATU (640 mg, 1.7 mmol, 1.2 eq), 6-(3,8-diazabicyclo[3.2.1]octan-8-yl)nicotinonitrile (300 mg, 1.4 mmol, 1 eq, 1HCl salt) and DIPEA (1.2 mL, 7 mmol, 1.2 eq). The mixture was stirred for 1 h at 25° C. The reaction mixture was then diluted with EtOAc and washed sequentially with water and brine. The organic extract was dried over MgSO$_4$, filtered and the filtrate concentrated in vacuo. The residue was purified by silica gel column to give 6-(3-((1r,3R)-3-(((11-methyl)(11-oxidanyl)boraneyl) amino)cyclobutane-1-carbonyl)-3,8-diazabicyclo[3.2.1]octan-8-yl)nicotinonitrile (436 mg, 77%). LCMS: m/z=412.4 [M+H]$^+$.

Step 2: A solution of tert-butyl ((1R,3r)-3-(8-(5-cyano-pyridin-2-yl)-3,8-diazabicyclo[3.2.1]octane-3-carbonyl)cyclobutyl)carbamate (436 mg, 1.06 mmol) in DCM (10 mL) and 4N HCl in dioxane (1.3 mL, 5.3 mmol, 5 eq) was stirred for 13 h at 25° C. The reaction was evaporated to dryness to give 6-(3-((1r,3R)-3-aminocyclobutane-1-carbonyl)-3,8-diazabicyclo[3.2.1]octan-8-yl)nicotinonitrile as a white solid, LCMS: m/z=312.4 [M+H]$^+$.

Step 3: To a solution of 5-bromoquinoline (20 mg, 0.096 mmol, 1 eq), 6-((1R,5S)-3-((1r,3R)-3-aminocyclobutane-1-carbonyl)-3,8-diazabicyclo[3.2.1]octan-8-yl)nicotinonitrile (40 mg, 0.115 mmol, 1.2 eq), sodium tert-butoxide (20 mg, 0.21 mmol, 2.2 eq) in toluene (3 mL) was sub surface purged with nitrogen. Tris (dibenzylideneacetone)-dipalladium(0) (13 mg, 0.0144 mmol, 0.15 eq) and Xantphos (14 mg, 0.288 mmol, 0.3 eq) added to the purged solution and heated in a sealed flask for 16 h at 80° C. The residue was purified by prep-HPLC to give 6-(3-((1r,3R)-3-(quinolin-5-ylamino)cyclobutane-1-carbonyl)-3,8-diazabicyclo[3.2.1]octan-8-yl) nicotinonitrile as a white solid (18 mg, 16%). LCMS: m/z=439.5 [M+H]$^+$; $^1$H NMR (DMSO-d$_6$): δ 8.79 (dd, 1H), 8.67 (d, 1H), 8.51 (d, 1H), 7.89 (dd, 1H), 7.48 (t, 1H), 7.42-7.39 (m, 1H), 7.23 (d, 1H), 6.93 (d, 1H), 6.58 (d, 1H), 6.32 (d, 1H), 4.73 (d, 1H), 4.19 (d, 1H), 3.94 (m, 3H), 3.57-3.42 (m, 4H), 3.24 (d, 2H), 2.84 (d, 2H), 2.73 (m, 1H), 2.54 (m, 1H), 2.30-2.23 (m, 2H), 1.98-1.88 (m, 2H), 1.78 (m, 1H), 1.68 (m, 1H).

Example 46: Synthesis of 6-(3-{3-[(quinolin-5-yl)methylidene]azetidine-1-carbonyl}-3,8-diazabicyclo-[3.2.1]octan-8-yl)pyridine-3-carbonitrile

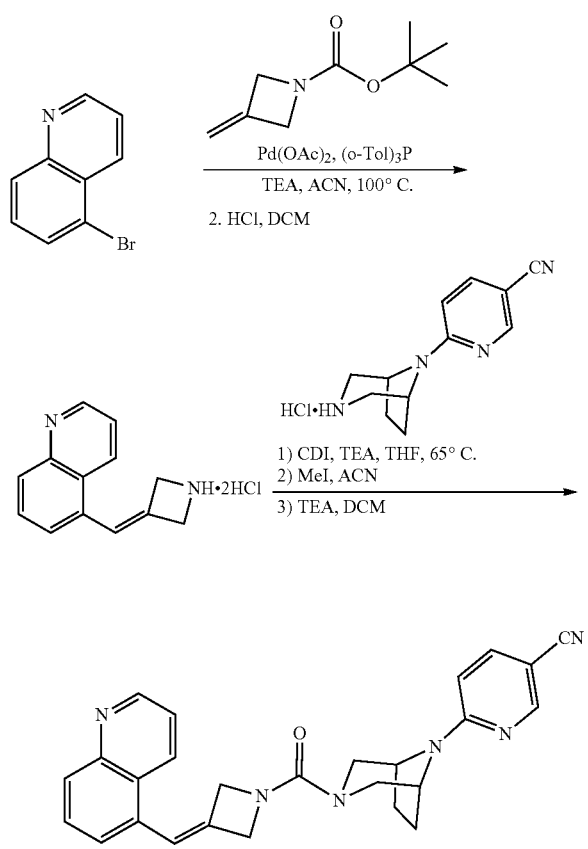

Step 1: In a thick-wall, sealable glass reaction vessel equipped with a Teflon screwcap and a magnetic stirrer was combined 5-bromoquinoline (0.30 g, 1.4 mmol, 1 eq), tert-butyl 3-methyleneazetidine-1-carboxylate (0.0.37 g, 2.2 mmol, 1.5 eq) and triethylamine (0.6 mL, 4.3 mmol, 3.0 eq) in acetonitrile (3 mL). The mixture was sparged with nitrogen. Pd(OAc)$_2$ (0.032 g, 0.14 mmol, 0.1 eq) and (o-Tol)$_3$P (0.088 g, 0.29 mmol, 0.2 eq) were added and the reaction vessel was sealed and heated to 100° C. for 19 h. The reaction mixture was cooled to RT, diluted with water and EtOAc, and filtered though celite. The organic phase was separated, washed with brine, dried over MgSO$_4$, filtered and concentrated. The crude residue was purified on silica gel to give tert-butyl 3-(quinolin-5-ylmethylene)azetidine-1-carboxylate (0.35 g, 82% yield), LCMS: m/z=297 [M+H]$^+$.

Step 2: To a solution of tert-butyl 3-(quinolin-5-ylmethylene)azetidine-1-carboxylate (0.18 g, 0.62 mmol, 1 eq) in DCM (2 mL) and MeOH (2 mL) was added 4M HCl in dioxane (2 mL, 8.0 mmol, 13 eq). The resulting mixture was stirred at RT for 4 days. The volatiles were removed in vacuo to give 5-(azetidin-3-ylidenemethyl)quinoline as a dihydrochloride salt which was used without further purification, LCMS: m/z=197 [M+H]$^+$.

Step 3: To a solution of crude 5-(azetidin-3-ylidenemethyl)quinoline dihydrochloride (0.62 mmol, 1 eq) in THF (2 mL) and DCM (2 mL) was added TEA (0.17 mL, 1.2 mmol, 2 eq) and CDI (0.11 g, 0.68 mmol, 1.1 eq). The resulting mixture was heated to 65° C. for 1.5 h. The reaction was partitioned between DCM and water. The organic phase was separated, dried over MgSO$_4$, filtered and concentrated to give (1H-imidazol-1-yl)(3-(quinolin-5-ylmethylene)azetidin-1-yl)methanone which was used without further purification, LCMS: m/z=291 [M+H]$^+$.

Step 4: To a solution of crude (1H-imidazol-1-yl)(3-(quinolin-5-ylmethylene)azetidin-1-yl)methanone (0.62 mmol, 1 eq) in acetonitrile (2 mL) was added iodomethane (0.15 mL, 2.5 mmol, 4.0 eq). The reaction was stirred at RT for 18 h, then concentrated to give 3-methyl-1-(3-(quinolin-5-ylmethylene)azetidine-1-carbonyl)-1H-imidazol-3-ium which was used without further purification, LCMS: m/z=433 [M+H]$^+$.

Step 5: To a solution of crude 3-methyl-1-(3-(quinolin-5-ylmethylene)azetidine-1-carbonyl)-1H-imidazol-3-ium (0.62 mmol, 1 eq) in DCM (2 mL) was added TEA (0.21 mL, 1.6 mmol, 2.5 eq) and 6-((1R,5S)-3,8-diazabicyclo[3.2.1]octan-8-yl)nicotinonitrile hydrochloride (0.15 g, 0.62 mmol, 1.0 eq). The reaction was stirred at RT for 4 h, then partitioned between DCM and water. The organic phase was separated, dried over MgSO$_4$, filtered and concentrated. The crude material was purified on silica gel to give the title compound (0.027 g, 10% yield over 4 steps), LCMS: m/z=437 [M+H]$^+$.

Examples 47-200

Examples 47-200 were prepared by similar procedures as described in Examples 1-46.

| Example | Structure | Name | [M + H]⁺ |
|---|---|---|---|
| 47 | 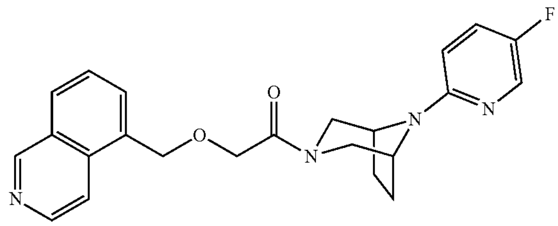 [SMILES: O=C(COCc1cccc2cnccc12)N1CC2CCC(C1)N2c1ccc(F)cn1] | 1-((1R,5S)-8-(5-fluoropyridin-2-yl)-3,8-diazabicyclo[3.2.1]octan-3-yl)-2-(isoquinolin-5-ylmethoxy)ethan-1-one | 407.1 |
| 48 | 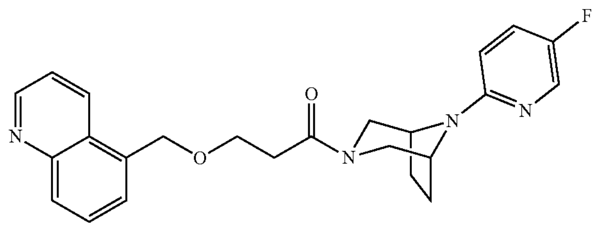 [SMILES: O=C(CCOCc1cccc2ncccc12)N1CC2CCC(C1)N2c1ccc(F)cn1] | 1-((1R,5S)-8-(5-fluoropyridin-2-yl)-3,8-diazabicyclo[3.2.1]octan-3-yl)-3-(quinolin-5-ylmethoxy)propan-1-one | 421.2 |
| 49 | 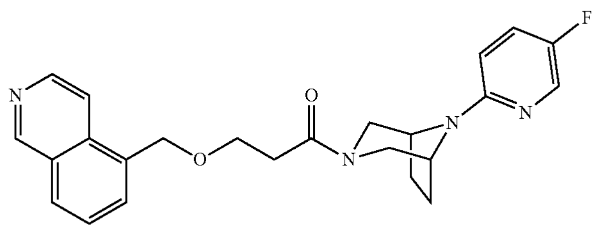 [SMILES: O=C(CCOCc1cccc2cnccc12)N1CC2CCC(C1)N2c1ccc(F)cn1] | 1-((1R,5S)-8-(5-fluoropyridin-2-yl)-3,8-diazabicyclo[3.2.1]octan-3-yl)-3-(isoquinolin-5-ylmethoxy)propan-1-one | 421.2 |
| 50 | 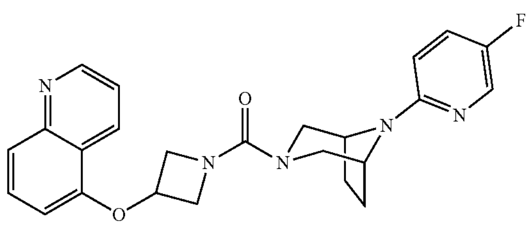 [SMILES: O=C(N1CC(Oc2cccc3ncccc23)C1)N1CC2CCC(C1)N2c1ccc(F)cn1] | ((1R,5S)-8-(5-fluoropyridin-2-yl)-3,8-diazabicyclo[3.2.1]octan-3-yl)(3-(quinolin-5-yloxy)azetidin-1-yl)methanone | 434.2 |
| 51 | 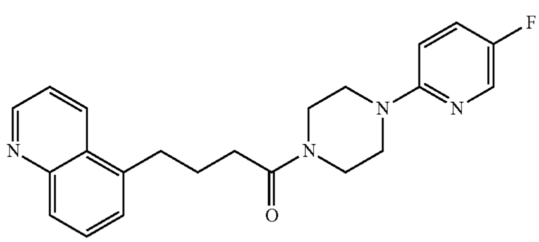 [SMILES: O=C(CCCc1cccc2ncccc12)N1CCN(c2ccc(F)cn2)CC1] | 1-(4-(5-fluoropyridin-2-yl)piperazin-1-yl)-4-(quinolin-5-yl)butan-1-one | 379.1 |
| 52 | 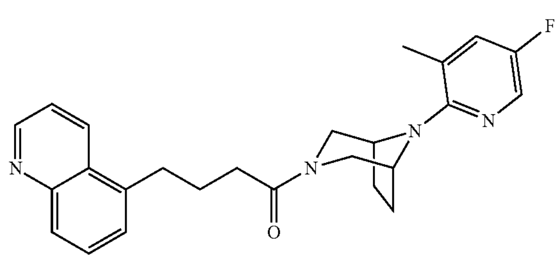 [SMILES: Cc1cc(F)cnc1N1C2CCC1CN(C(=O)CCCc1cccc3ncccc13)C2] | 1-((1R,5S)-8-(5-fluoro-3-methylpyridin-2-yl)-3,8-diazabicyclo[3.2.1]octan-3-yl)-4-(quinolin-5-yl)butan-1-one | 419.2 |

-continued

| Example | Structure | Name | [M + H]+ |
|---|---|---|---|
| 53 | 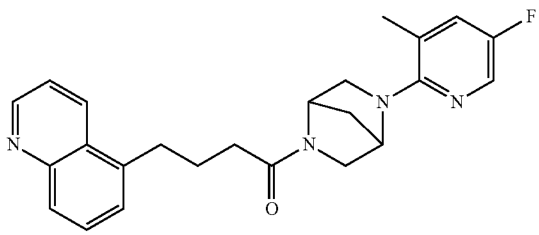 [SMILES: Cc1cc(F)cnc1N1CC2CC1CN2C(=O)CCCc1cccc2ncccc12] | rac-1-((1R,4R)-5-(5-fluoro-3-methylpyridin-2-yl)-2,5-diazabicyclo[2.2.1]heptan-2-yl)-4-(quinolin-5-yl)butan-1-one | 405.1 |
| 54 | 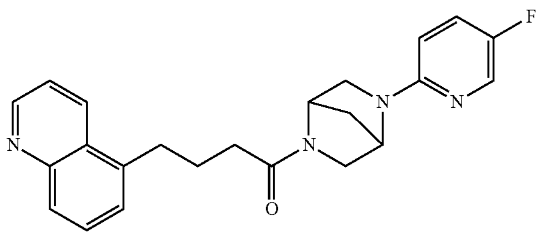 [SMILES: O=C(CCCc1cccc2ncccc12)N1CC2CC1CN2c1ccc(F)cn1] | rac-1-((1R,4R)-5-(5-fluoropyridin-2-yl)-2,5-diazabicyclo[2.2.1]heptan-2-yl)-4-(quinolin-5-yl)butan-1-one | 391.1 |
| 55 | 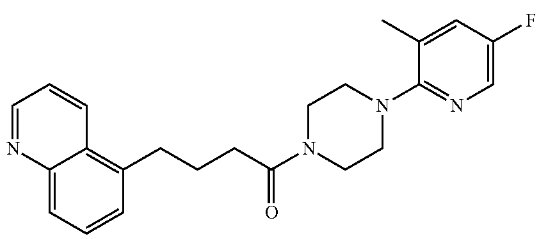 [SMILES: Cc1cc(F)cnc1N1CCN(C(=O)CCCc2cccc3ncccc23)CC1] | 1-(4-(5-fluoro-3-methylpyridin-2-yl)piperazin-1-yl)-4-(quinolin-5-yl)butan-1-one | 393.1 |
| 56 | 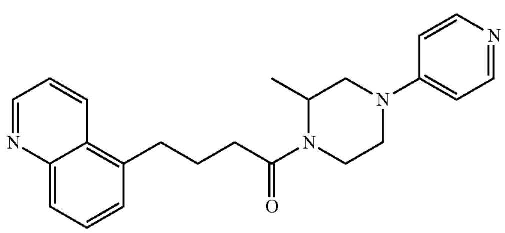 [SMILES: CC1CN(c2ccncc2)CCN1C(=O)CCCc1cccc2ncccc12] | 1-(2-methyl-4-(pyridin-4-yl)piperazin-1-yl)-4-(quinolin-5-yl)butan-1-one | 375.2 |
| 57 | 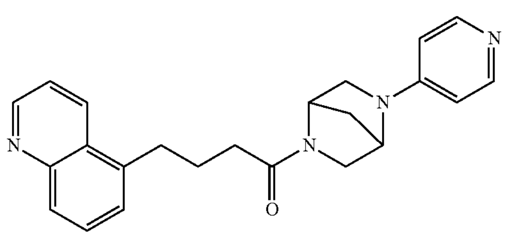 [SMILES: O=C(CCCc1cccc2ncccc12)N1CC2CC1CN2c1ccncc1] | 1-(5-(pyridin-4-yl)-2,5-diazabicyclo[2.2.1]heptan-2-yl)-4-(quinolin-5-yl)butan-1-one | 373.1 |
| 58 | 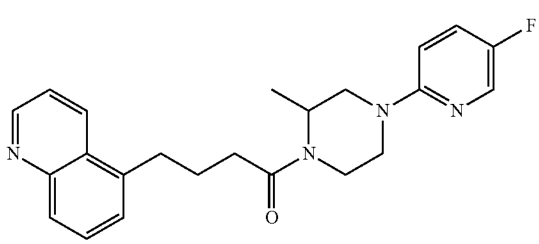 [SMILES: CC1CN(c2ccc(F)cn2)CCN1C(=O)CCCc1cccc2ncccc12] | 1-(4-(5-fluoropyridin-2-yl)-2-methylpiperazin-1-yl)-4-(quinolin-5-yl)butan-1-one | 393.1 |

-continued

| Example | Structure | Name | [M + H]+ |
|---|---|---|---|
| 59 | 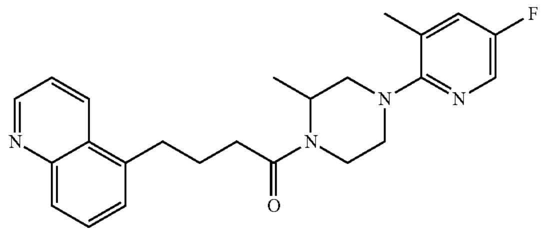 [SMILES: Cc1cc(F)cnc1N1CCN(C(=O)CCCc2cccc3ncccc23)C(C)C1] | 1-(4-(5-fluoro-3-methylpyridin-2-yl)-2-methylpiperazin-1-yl)-4-(quinolin-5-yl)butan-1-one | 407.1 |
| 60 | 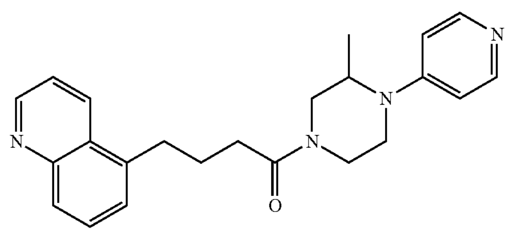 [SMILES: CC1CN(C(=O)CCCc2cccc3ncccc23)CCN1c1ccncc1] | 1-(3-methyl-4-(pyridin-4-yl)piperazin-1-yl)-4-(quinolin-5-yl)butan-1-one | 375.2 |
| 61 | 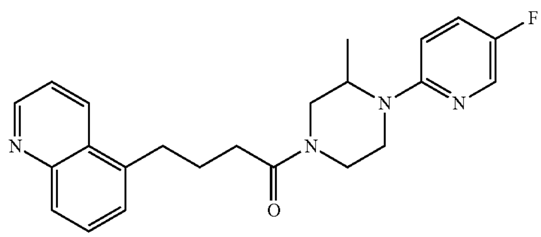 [SMILES: CC1CN(C(=O)CCCc2cccc3ncccc23)CCN1c1ccc(F)cn1] | 1-(4-(5-fluoropyridin-2-yl)-3-methylpiperazin-1-yl)-4-(quinolin-5-yl)butan-1-one | 393.1 |
| 62 | 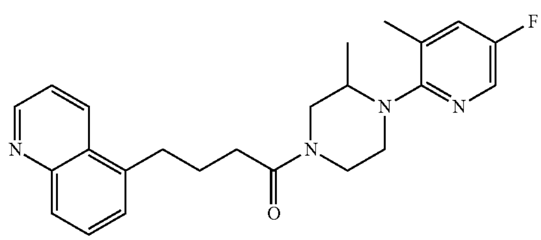 [SMILES: Cc1cc(F)cnc1N1CCN(C(=O)CCCc2cccc3ncccc23)CC1C] | 1-(4-(5-fluoro-3-methylpyridin-2-yl)-3-methylpiperazin-1-yl)-4-(quinolin-5-yl)butan-1-one | 407.2 |
| 63 | 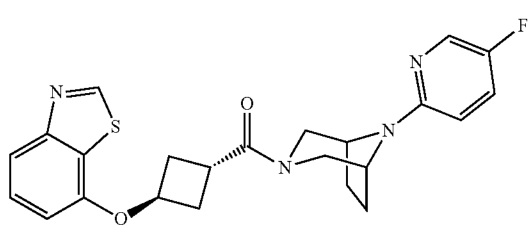 [SMILES: O=C([C@H]1C[C@H](Oc2cccc3ncsc23)C1)N1CC2CCC(C1)N2c1ccc(F)cn1] | ((1r,3R)-3-(benzo[d]thiazol-7-yloxy)cyclobutyl)((1R,5S)-8-(5-fluoropyridin-2-yl)-3,8-diazabicyclo[3.2.1]octan-3-yl)methanone | 439.0 |
| 64 | 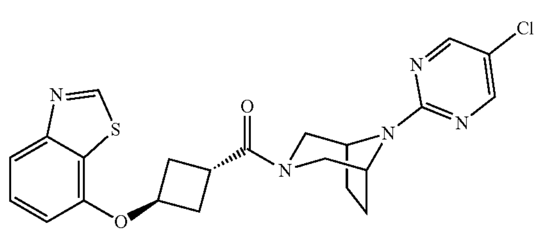 [SMILES: O=C([C@H]1C[C@H](Oc2cccc3ncsc23)C1)N1CC2CCC(C1)N2c1ncc(Cl)cn1] | ((1r,3R)-3-(benzo[d]thiazol-7-yloxy)cyclobutyl)((1R,5S)-8-(5-chloropyrimidin-2-yl)-3,8-diazabicyclo[3.2.1]octan-3-yl)methanone | 456.2 |

-continued

| Example | Structure | Name | [M + H]+ |
|---|---|---|---|
| 65 | 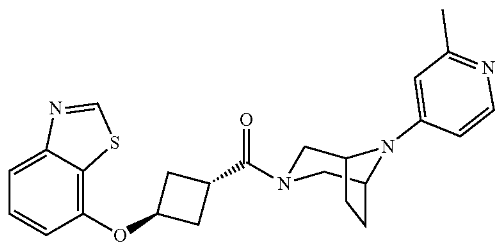 [SMILES: Cc1cc(N2C3CCC2CN(C(=O)[C@H]2C[C@H](Oc4cccc5ncsc45)C2)C3)ccn1] | ((1r,3R)-3-(benzo[d]thiazol-7-yloxy)cyclobutyl)((1R,5S)-8-(2-methylpyridin-4-yl)-3,8-diazabicyclo[3.2.1]octan-3-yl)methanone | 435.1 |
| 66 | 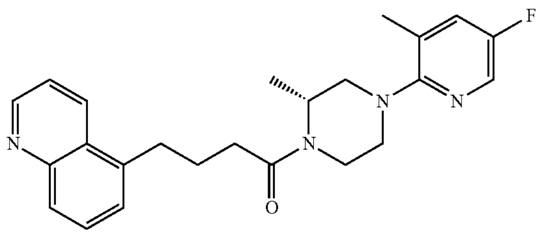 [SMILES: Cc1cc(F)cnc1N1CCN(C(=O)CCCc2cccc3ncccc23)[C@H](C)C1] | (R)-1-(4-(5-fluoro-3-methylpyridin-2-yl)-2-methylpiperazin-1-yl)-4-(quinolin-5-yl)butan-1-one | 407.2 |
| 67 | 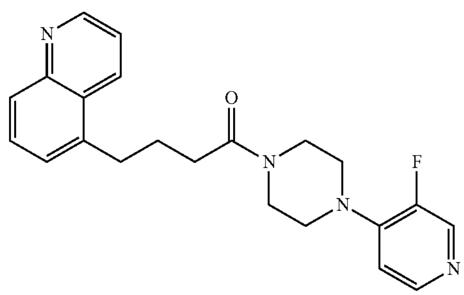 [SMILES: O=C(CCCc1cccc2ncccc12)N1CCN(c2ccncc2F)CC1] | 1-(4-(3-fluoropyridin-4-yl)piperazin-1-yl)-4-(quinolin-5-yl)butan-1-one | 379.1 |
| 68 | 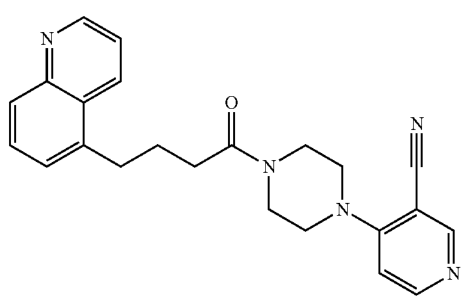 [SMILES: N#Cc1cnccc1N1CCN(C(=O)CCCc2cccc3ncccc23)CC1] | 4-(4-(4-(quinolin-5-yl)butanoyl)piperazin-1-yl)nicotinonitrile | 386.3 |
| 69 | 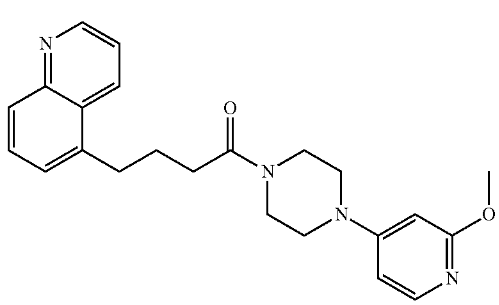 [SMILES: COc1cc(N2CCN(C(=O)CCCc3cccc4ncccc34)CC2)ccn1] | 1-(4-(2-methoxypyridin-4-yl)piperazin-1-yl)-4-(quinolin-5-yl)butan-1-one | 391.1 |

| Example | Structure | Name | [M + H]+ |
|---|---|---|---|
| 70 | 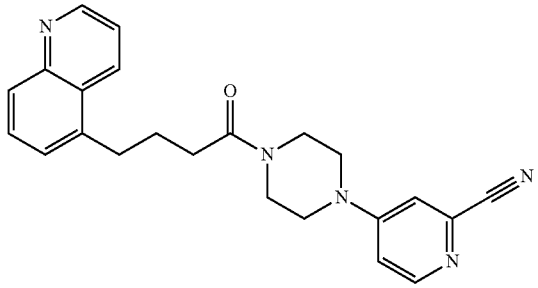 [SMILES: N#Cc1cc(N2CCN(C(=O)CCCc3cccc4ncccc34)CC2)ccn1] | 4-(4-(4-(quinolin-5-yl)butanoyl)piperazin-1-yl)picolinonitrile | 386.1 |
| 71 | 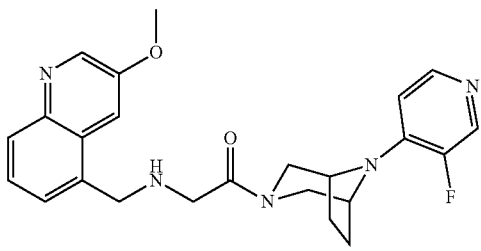 [SMILES: COc1cnc2cccc(CNCC(=O)N3CC4CCC(C3)N4c3ccncc3F)c2c1] | 1-((1R,5S)-8-(3-fluoropyridin-4-yl)-3,8-diazabicyclo[3.2.1]octan-3-yl)-2-(((3-methoxyquinolin-5-yl)methyl)amino)ethan-1-one | 436.2 |
| 72 | 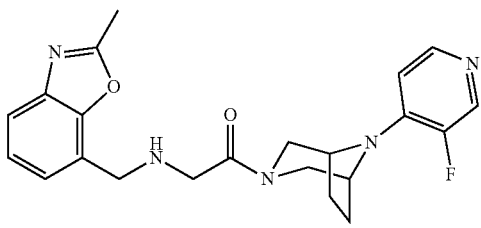 [SMILES: Cc1nc2cccc(CNCC(=O)N3CC4CCC(C3)N4c3ccncc3F)c2o1] | 1-((1R,5S)-8-(3-fluoropyridin-4-yl)-3,8-diazabicyclo[3.2.1]octan-3-yl)-2-(((2-methylbenzo[d]oxazol-7-yl)methyl)amino)ethan-1-one | 410.1 |
| 73 | 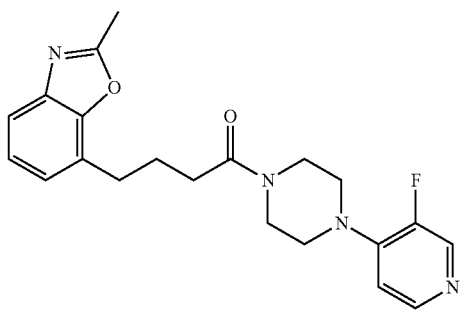 [SMILES: Cc1nc2cccc(CCCC(=O)N3CCN(c4ccncc4F)CC3)c2o1] | 1-(4-(3-fluoropyridin-4-yl)piperazin-1-yl)-4-(2-methylbenzo[d]oxazol-7-yl)butan-1-one | 383.2 |
| 74 | 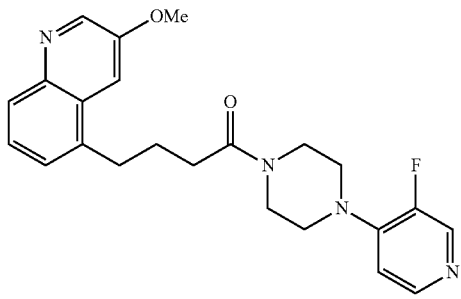 [SMILES: COc1cnc2cccc(CCCC(=O)N3CCN(c4ccncc4F)CC3)c2c1] | 1-(4-(3-fluoropyridin-4-yl)piperazin-1-yl)-4-(3-methoxyquinolin-5-yl)butan-1-one | 409.1 |

-continued

| Example | Structure | Name | [M + H]+ |
|---|---|---|---|
| 75 | 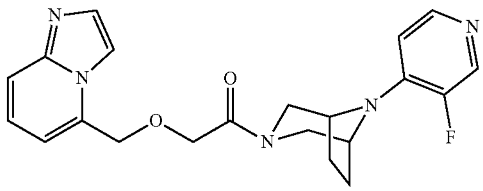 [SMILES: O=C(COCc1cccc2nccn12)N1CC2CCC(C1)N2c1ccncc1F] | 1-((1R,5S)-8-(3-fluoropyridin-4-yl)-3,8-diazabicyclo[3.2.1]octan-3-yl)-2-(imidazol[1,2-a]pyridin-5-ylmethoxy)ethan-1-one | 396.1 |
| 76 | 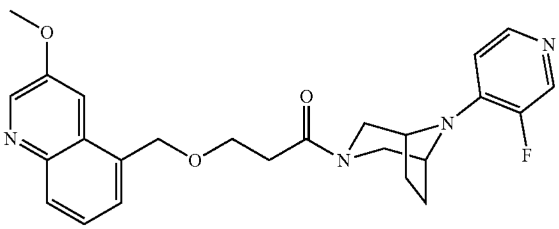 [SMILES: COc1cnc2cccc(COCCC(=O)N3CC4CCC(C3)N4c3ccncc3F)c2c1] | 1-((1R,5S)-8-(3-fluoropyridin-4-yl)-3,8-diazabicyclo[3.2.1]octan-3-yl)-3-((3-methoxyquinolin-5-yl)methoxy)propan-1-one | 451.2 |
| 77 | 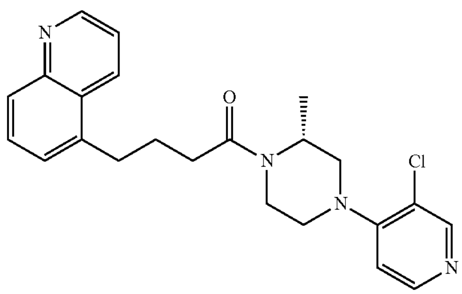 [SMILES: C[C@@H]1CN(c2ccncc2Cl)CCN1C(=O)CCCc1cccc2ncccc12] | (R)-1-(4-(3-chloropyridin-4-yl)-2-methylpiperazin-1-yl)-4-(quinolin-5-yl)butan-1-one | 409.1 |
| 78 | 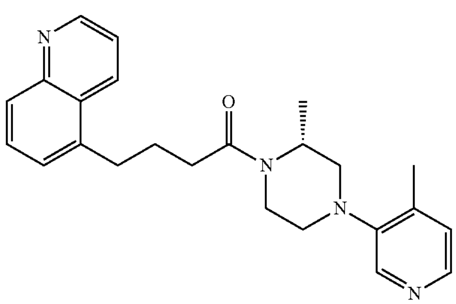 [SMILES: Cc1ccncc1N1CCN(C(=O)CCCc2cccc3ncccc23)[C@H](C)C1] | (R)-1-(2-methyl-4-(4-methylpyridin-3-yl)piperazin-1-yl)-4-(quinolin-5-yl)butan-1-one | 389.2 |
| 79 | 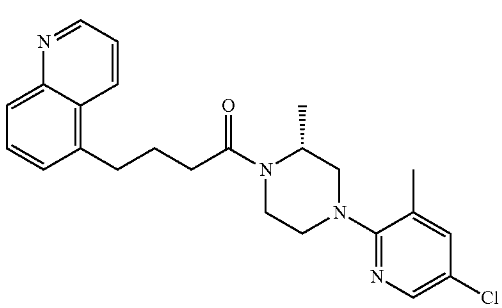 [SMILES: Cc1cc(Cl)cnc1N1CCN(C(=O)CCCc2cccc3ncccc23)[C@H](C)C1] | (R)-1-(4-(5-chloro-3-methylpyridin-2-yl)-2-methylpiperazin-1-yl)-4-(quinolin-5-yl)butan-1-one | 423 |

-continued

| Example | Structure | Name | [M + H]+ |
|---|---|---|---|
| 80 | 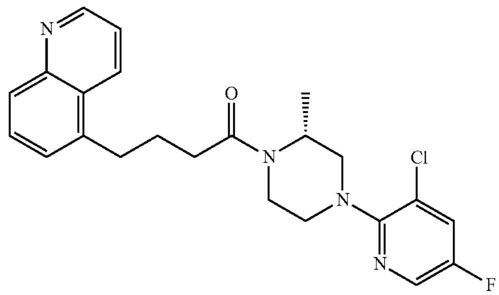 [SMILES: C[C@@H]1CN(c2ncc(F)cc2Cl)CCN1C(=O)CCCc1cccc2ncccc12] | (R)-1-(4-(3-chloro-5-fluoropyridin-2-yl)-2-methylpiperazin-1-yl)-4-(quinolin-5-yl)butan-1-one | 426.9 |
| 81 | 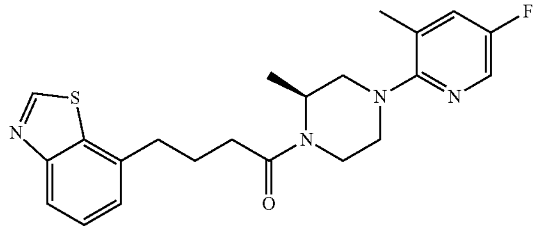 [SMILES: Cc1cc(F)cnc1N1CCN(C(=O)CCCc2cccc3ncsc23)[C@@H](C)C1] | (S)-4-(benzo[d]thiazol-7-yl)-1-(4-(5-fluoro-3-methylpyridin-2-yl)-2-methylpiperazin-1-yl)butan-1-one | 412.9 |
| 82 | 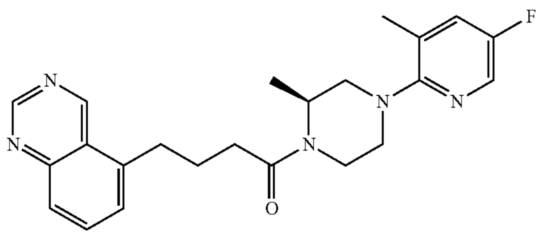 [SMILES: Cc1cc(F)cnc1N1CCN(C(=O)CCCc2cccc3ncncc23)[C@@H](C)C1] | (S)-1-(4-(5-fluoro-3-methylpyridin-2-yl)-2-methylpiperazin-1-yl)-4-(quinazolin-5-yl)butan-1-one | 408.2 |
| 83 | 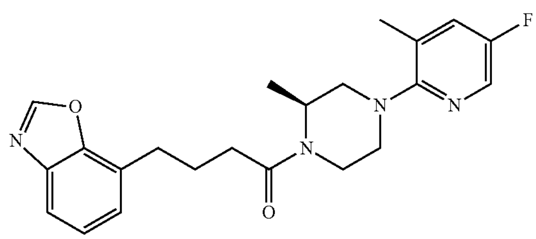 | (S)-4-(benzo[d]oxazol-7-yl)-1-(4-(5-fluoro-3-methylpyridin-2-yl)-2-methylpiperazin-1-yl)butan-1-one | 397.1 |
| 84 | 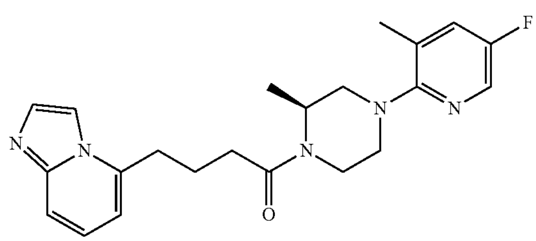 [SMILES: Cc1cc(F)cnc1N1CCN(C(=O)CCCc2cccc3nccn23)[C@@H](C)C1] | (S)-1-(4-(5-fluoro-3-methylpyridin-2-yl)-2-methylpiperazin-1-yl)-4-(imidazo[1,2-a]pyridin-5-yl)butan-1-one | 395.9 |
| 85 | 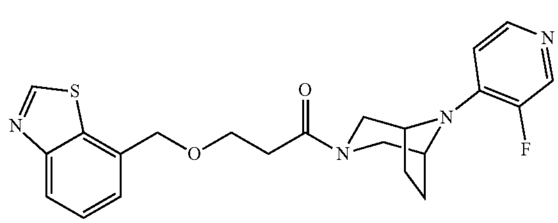 [SMILES: O=C(CCOCc1cccc2ncsc12)N1CC2CCC(C1)N2c1ccncc1F] | 3-(benzo[d]thiazol-7-ylmethoxy)-1-((1R,5S)-8-(3-fluoropyridin-4-yl)-3,8-diazabicyclo[3.2.1]octan-3-yl)propan-1-one | 427.1 |

-continued

| Example | Structure | Name | [M + H]⁺ |
|---|---|---|---|
| 86 | 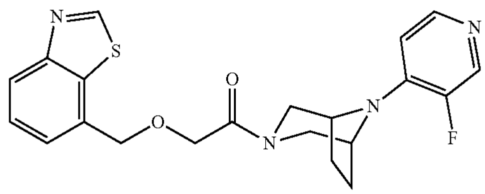 [SMILES: O=C(COCc1cccc2ncsc12)N1CC2CCC(C1)N2c1ccncc1F] | 2-(benzo[d]thiazol-7-ylmethoxy)-1-((1R,5S)-8-(3-fluoropyridin-4-yl)-3,8-diazabicyclo[3.2.1]octan-3-yl)ethan-1-one | 413.1 |
| 87 | 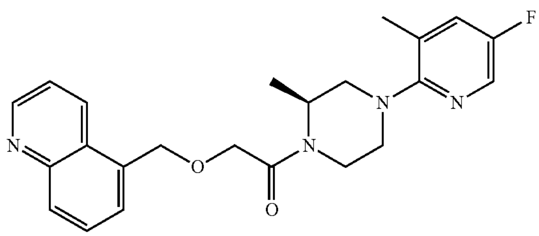 [SMILES: Cc1cc(F)cnc1N1CCN(C(=O)COCc2cccc3ncccc23)[C@@H](C)C1] | (S)-1-(4-(5-fluoro-3-methylpyridin-2-yl)-2-methylpiperazin-1-yl)-2-(quinolin-5-ylmethoxy)ethan-1-one | 409.2 |
| 88 | 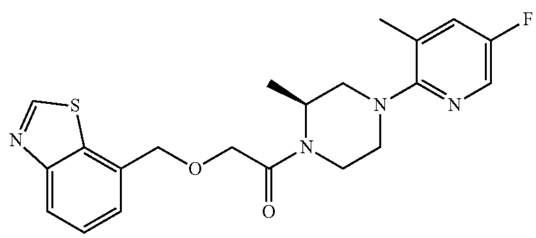 | (S)-2-(benzo[d]thiazol-7-ylmethoxy)-1-(4-(5-fluoro-3-methylpyridin-2-yl)-2-methylpiperazin-1-yl)ethan-1-one | 415.1 |
| 89 | 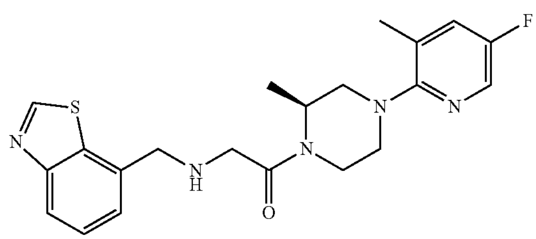 [SMILES: Cc1cc(F)cnc1N1CCN(C(=O)CNCc2cccc3ncsc23)[C@@H](C)C1] | (S)-2-((benzo[d]thiazol-7-ylmethyl)amino)-1-(4-(5-fluoro-3-methylpyridin-2-yl)-2-methylpiperazin-1-yl)ethan-1-one | 413.8 |
| 90 | 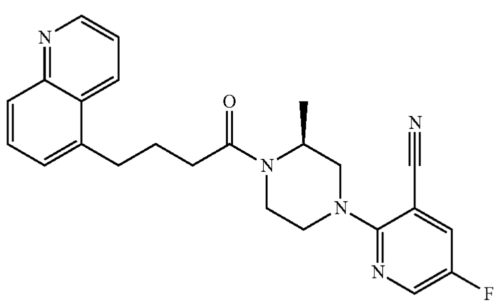 [SMILES: C[C@H]1CN(c2ncc(F)cc2C#N)CCN1C(=O)CCCc1cccc2ncccc12] | (S)-5-fluoro-2-(3-methyl-4-(4-(quinolin-5-yl)butanoyl)piperazin-1-yl)nicotinonitrile | 418.2 |
| 91 | 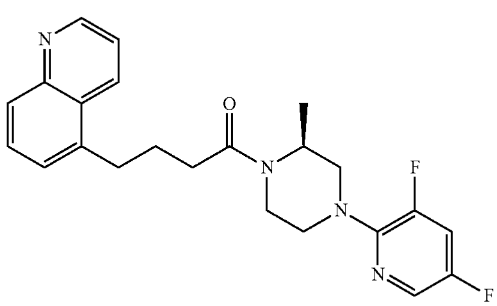 [SMILES: C[C@H]1CN(c2ncc(F)cc2F)CCN1C(=O)CCCc1cccc2ncccc12] | (S)-1-(4-(3,5-difluoropyridin-2-yl)-2-methylpiperazin-1-yl)-4-(quinolin-5-yl)butan-1-one | 410.9 |

-continued

| Example | Structure | Name | [M + H]+ |
|---|---|---|---|
| 92 | 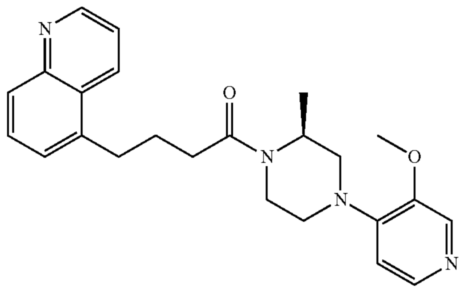 [SMILES: COc1cnccc1N1CCN(C(=O)CCCc2cccc3ncccc23)[C@@H](C)C1] | (S)-1-(4-(3-methoxypyridin-4-yl)-2-methylpiperazin-1-yl)-4-(quinolin-5-yl)butan-1-one | 404.9 |
| 93 | 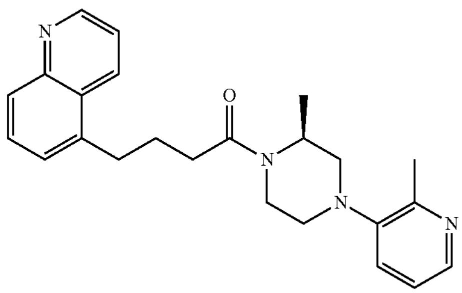 [SMILES: Cc1ncccc1N1CCN(C(=O)CCCc2cccc3ncccc23)[C@@H](C)C1] | (S)-1-(2-methyl-4-(2-methylpyridin-3-yl)piperazin-1-yl)-4-(quinolin-5-yl)butan-1-one | 388.9 |
| 94 | 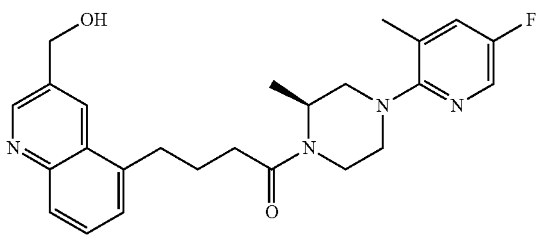 [SMILES: Cc1cc(F)cnc1N1CCN(C(=O)CCCc2cccc3ncc(CO)cc23)[C@@H](C)C1] | (S)-1-(4-(5-fluoro-3-methylpyridin-2-yl)-2-methylpiperazin-1-yl)-4-(3-(hydroxymethyl)quinolin-5-yl)butan-1-one | 436.2 |
| 95 | 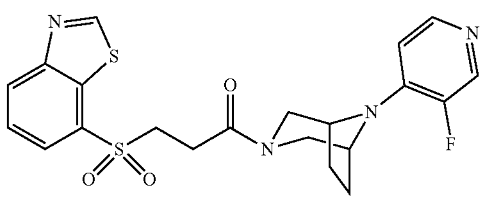 [SMILES: O=C(CCS(=O)(=O)c1cccc2ncsc12)N1CC2CCC(C1)N2c1ccncc1F] | 3-(benzo[d]thiazol-7-ylsulfonyl)-1-((1R,5S)-8-(3-fluoropyridin-4-yl)-3,8-diazabicyclo[3.2.1]octan-3-yl)propan-1-one | 461.1 |
| 96 | 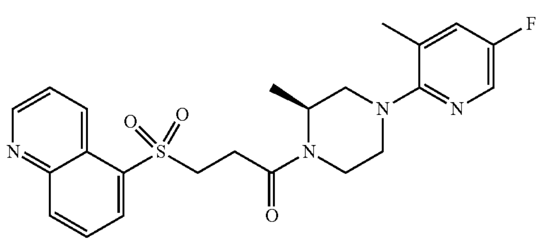 [SMILES: Cc1cc(F)cnc1N1CCN(C(=O)CCS(=O)(=O)c2cccc3ncccc23)[C@@H](C)C1] | (S)-1-(4-(5-fluoro-3-methylpyridin-2-yl)-2-methylpiperazin-1-yl)-3-(quinolin-5-ylsulfonyl)propan-1-one | 457.1 |
| 97 | 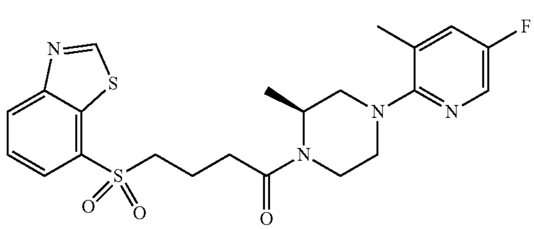 [SMILES: Cc1cc(F)cnc1N1CCN(C(=O)CCCS(=O)(=O)c2cccc3ncsc23)[C@@H](C)C1] | (S)-4-(benzo[d]thiazol-7-ylsulfonyl)-1-(4-(5-fluoro-3-methylpyridin-2-yl)-2-methylpiperazin-1-yl)butan-1-one | 477.1 |

-continued

| Example | Structure | Name | [M + H]⁺ |
|---|---|---|---|
| 98 | 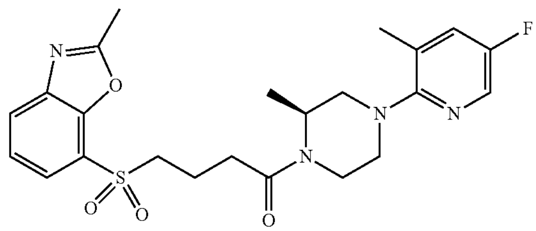 [SMILES: Cc1nc2cccc(S(=O)(=O)CCCC(=O)N3CCN(c4ncc(F)cc4C)C[C@@H]3C)c2o1] | (S)-1-(4-(5-fluoro-3-methylpyridin-2-yl)-2-methylpiperazin-1-yl)-4-((2-methylbenzo[d]oxazol-7-yl)sulfonyl)butan-1-one | 475.1 |
| 99 | 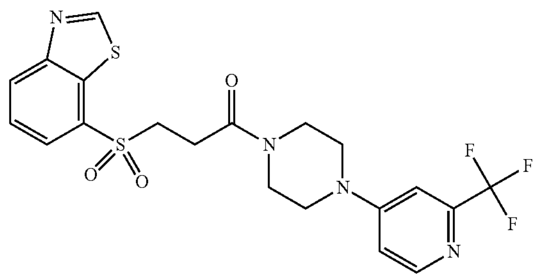 [SMILES: O=C(CCS(=O)(=O)c1cccc2ncsc12)N1CCN(c2ccnc(C(F)(F)F)c2)CC1] | 3-(benzo[d]thiazol-7-ylsulfonyl)-1-(4-(2-(trifluoromethyl)pyridin-4-yl)piperazin-1-yl)propan-1-one | 485.1 |
| 100 | 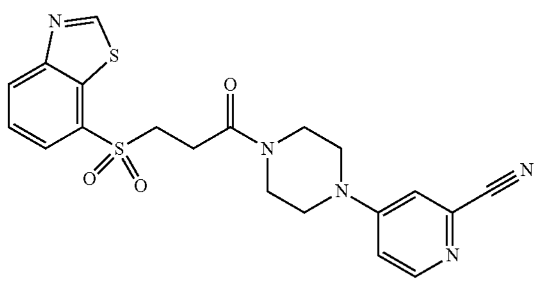 [SMILES: N#Cc1cc(N2CCN(C(=O)CCS(=O)(=O)c3cccc4ncsc34)CC2)ccn1] | 4-(4-(3-(benzo[d]thiazol-7-ylsulfonyl)propanoyl)piperazin-1-yl)picolinonitrile | 442.0 |
| 101 | 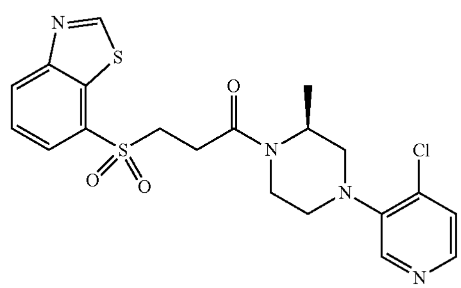 [SMILES: C[C@H]1CN(c2cnccc2Cl)CCN1C(=O)CCS(=O)(=O)c1cccc2ncsc12] | (S)-3-(benzo[d]thiazol-7-ylsulfonyl)-1-(4-(4-chloropyridin-3-yl)-2-methylpiperazin-1-yl)propan-1-one | 465.1 |
| 102 | 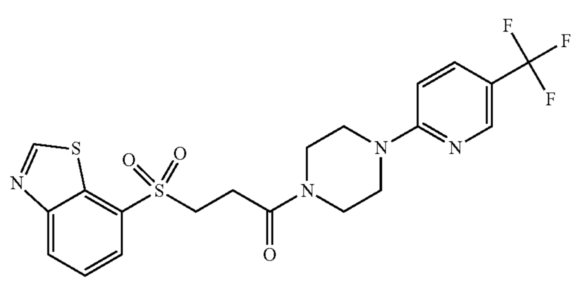 [SMILES: O=C(CCS(=O)(=O)c1cccc2ncsc12)N1CCN(c2ccc(C(F)(F)F)cn2)CC1] | 3-(benzo[d]thiazol-7-ylsulfonyl)-1-(4-(5-(trifluoromethyl)pyridin-2-yl)piperazin-1-yl)propan-1-one | 485.1 |

-continued

| Example | Structure | Name | [M + H]+ |
|---|---|---|---|
| 103 | 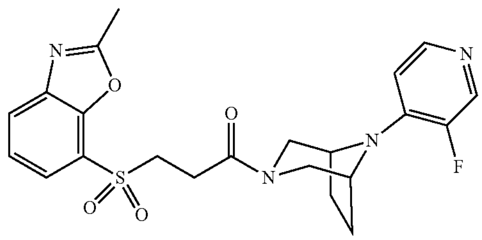 [SMILES: Cc1nc2cccc(S(=O)(=O)CCC(=O)N3CC4CCC(C3)N4c3ccncc3F)c2o1] | 1-((1R,5S)-8-(3-fluoropyridin-4-yl)-3,8-diazabicyclo[3.2.1]octan-3-yl)-3-((2-methylbenzo[d]oxazol-7-yl)sulfonyl)propan-1-one | 459.1 |
| 104 | 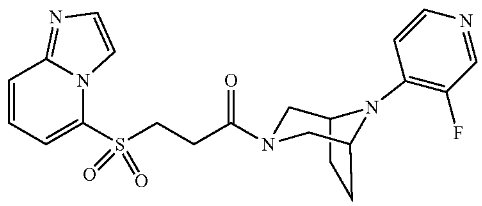 [SMILES: O=C(CCS(=O)(=O)c1cccc2nccn12)N1CC2CCC(C1)N2c1ccncc1F] | 1-((1R,5S)-8-(3-fluoropyridin-4-yl)-3,8-diazabicyclo[3.2.1]octan-3-yl)-3-(imidazo[1,2-a]pyridin-5-ylsulfonyl)propan-1-one | 444.1 |
| 105 | 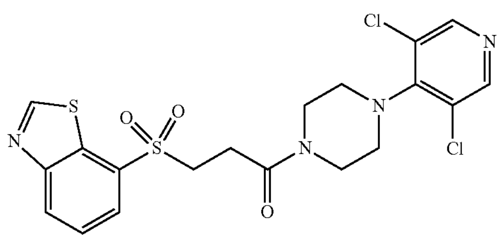 [SMILES: O=C(CCS(=O)(=O)c1cccc2ncsc12)N1CCN(c2c(Cl)cncc2Cl)CC1] | 3-(benzo[d]thiazol-7-ylsulfonyl)-1-(4-(3,5-dichloropyridin-4-yl)piperazin-1-yl)propan-1-one | 485.0 |
| 106 | 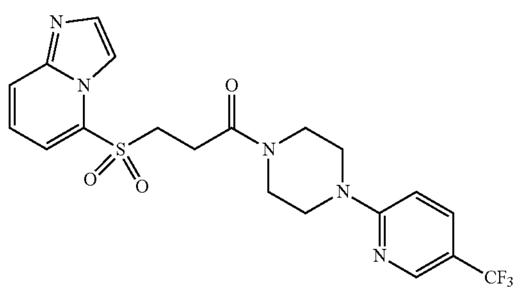 [SMILES: O=C(CCS(=O)(=O)c1cccc2nccn12)N1CCN(c2ccc(C(F)(F)F)cn2)CC1] | 3-(imidazo[1,2-a]pyridin-5-ylsulfonyl)-1-(4-(5-(trifluoromethyl)pyridin-2-yl)piperazin-1-yl)propan-1-one | 468.1 |
| 107 | 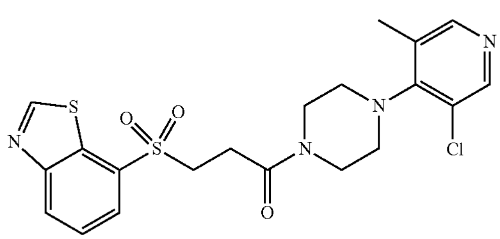 [SMILES: Cc1cncc(Cl)c1N1CCN(C(=O)CCS(=O)(=O)c2cccc3ncsc23)CC1] | 3-(benzo[d]thiazol-7-ylsulfonyl)-1-(4-(3-chloro-5-methylpyridin-4-yl)piperazin-1-yl)propan-1-one | 464.7 |
| 108 | 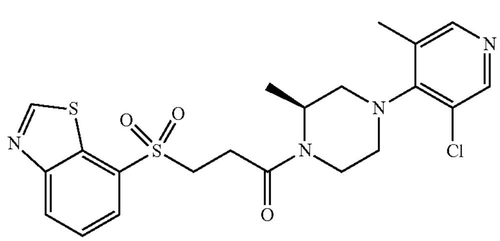 [SMILES: Cc1cncc(Cl)c1N1CCN(C(=O)CCS(=O)(=O)c2cccc3ncsc23)[C@@H](C)C1] | (S)-3-(benzo[d]thiazol-7-ylsulfonyl)-1-(4-(3-chloro-5-methylpyridin-4-yl)-2-methylpiperazin-1-yl)propan-1-one | 478.9 |

-continued

| Example | Structure | Name | [M + H]+ |
|---|---|---|---|
| 109 | 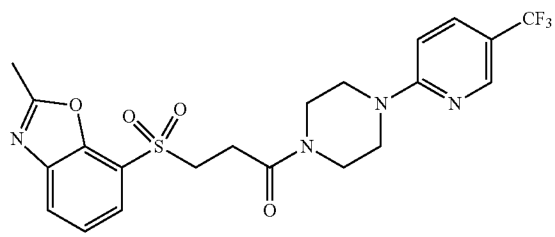 [SMILES: Cc1nc2cccc(S(=O)(=O)CCC(=O)N3CCN(c4ccc(C(F)(F)F)cn4)CC3)c2o1] | 3-((2-methylbenzo[d]oxazol-7-yl)sulfonyl)-1-(4-(5-(trifluoromethyl)pyridin-2-yl)piperazin-1-yl)propan-1-one | 483.2 |
| 110 | 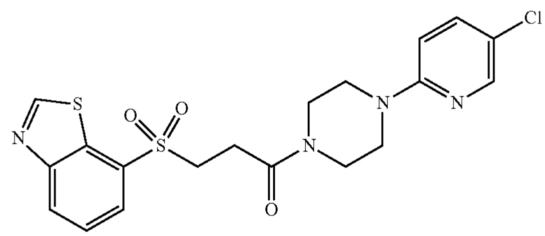 [SMILES: O=C(CCS(=O)(=O)c1cccc2ncsc12)N1CCN(c2ccc(Cl)cn2)CC1] | 3-(benzo[d]thiazol-7-ylsulfonyl)-1-(4-(5-chloropyridin-2-yl)piperazin-1-yl)propan-1-one | 450.9 |
| 111 | 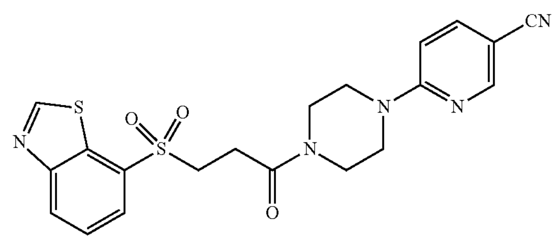 [SMILES: N#Cc1ccc(N2CCN(C(=O)CCS(=O)(=O)c3cccc4ncsc34)CC2)nc1] | 6-(4-(3-(benzo[d]thiazol-7-ylsulfonyl)propanoyl)piperazin-1-yl)nicotinonitrile | 441.9 |
| 112 | 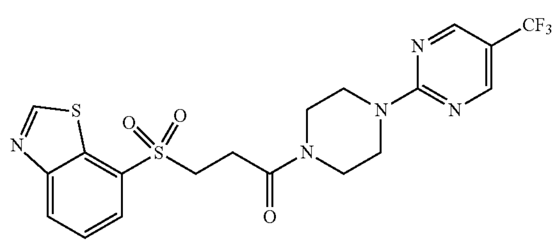 [SMILES: O=C(CCS(=O)(=O)c1cccc2ncsc12)N1CCN(c2ncc(C(F)(F)F)cn2)CC1] | 3-(benzo[d]thiazol-7-ylsulfonyl)-1-(4-(5-(trifluoromethyl)pyrimidin-2-yl)piperazin-1-yl)propan-1-one | 485.9 |
| 113 | 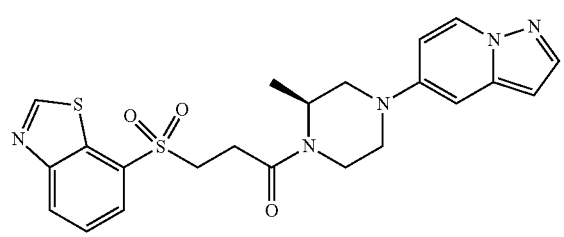 [SMILES: C[C@H]1CN(c2ccn3nccc3c2)CCN1C(=O)CCS(=O)(=O)c1cccc2ncsc12] | (S)-3-(benzo[d]thiazol-7-ylsulfonyl)-1-(2-methyl-4-(pyrazolo[1,5-a]pyridin-5-yl)piperazin-1-yl)propan-1-one | 470.0 |
| 114 | 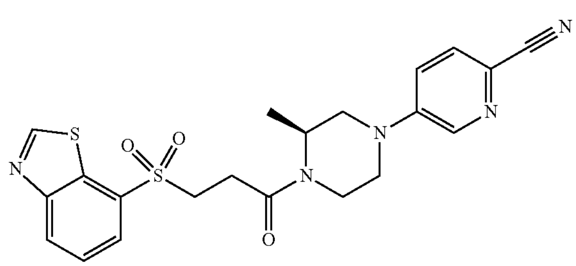 [SMILES: C[C@H]1CN(c2ccc(C#N)nc2)CCN1C(=O)CCS(=O)(=O)c1cccc2ncsc12] | (S)-5-(4-(3-(benzo[d]thiazol-7-ylsulfonyl)propanoyl)-3-methylpiperazin-1-yl)picolinonitrile | 456.1 |

-continued

| Example | Structure | Name | [M + H]+ |
|---|---|---|---|
| 115 | 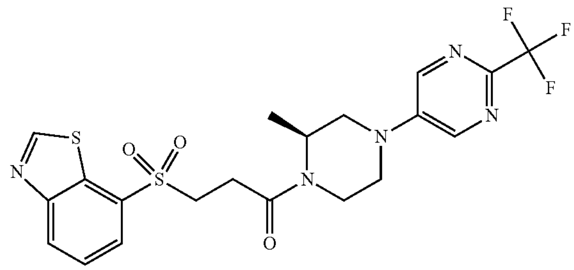 [SMILES: C[C@H]1CN(c2cnc(C(F)(F)F)nc2)CCN1C(=O)CCS(=O)(=O)c1cccc2ncsc12] | (S)-3-(benzo[d]thiazol-7-ylsulfonyl)-1-(2-methyl-4-(2-(trifluoromethyl)pyrimidin-5-yl)piperazin-1-yl)propan-1-one | 500.1 |
| 116 | 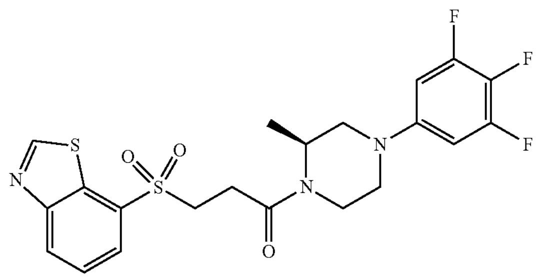 [SMILES: C[C@H]1CN(c2cc(F)c(F)c(F)c2)CCN1C(=O)CCS(=O)(=O)c1cccc2ncsc12] | (S)-3-(benzo[d]thiazol-7-ylsulfonyl)-1-(2-methyl-4-(3,4,5-trifluorophenyl)piperazin-1-yl)propan-1-one | 483.9 |
| 117 | 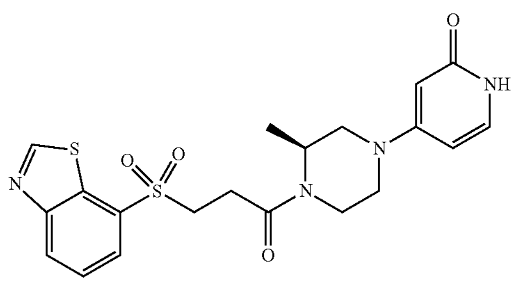 [SMILES: C[C@H]1CN(c2cc[nH]c(=O)c2)CCN1C(=O)CCS(=O)(=O)c1cccc2ncsc12] | (S)-4-(4-(3-(benzo[d]thiazol-7-ylsulfonyl)propanoyl)-3-methylpiperazin-1-yl)pyridin-2(1H)-one | 447.0 |
| 118 | 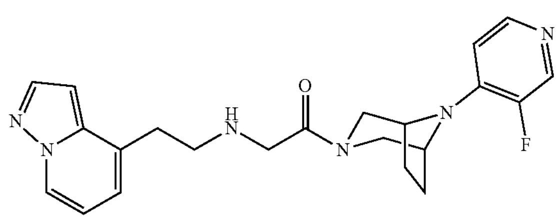 [SMILES: O=C(CNCCc1cccn2nccc12)N1CC2CCC(C1)N2c1ccncc1F] | 1-((1R,5S)-8-(3-fluoropyridin-4-yl)-3,8-diazabicyclo[3.2.1]octan-3-yl)-2-((2-(pyrazolo[1,5-a]pyridin-4-yl)ethyl)amino)ethan-1-one | 409.05 |
| 119 | 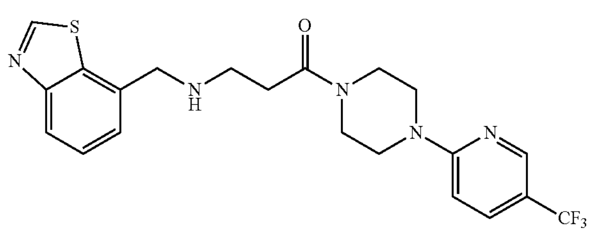 [SMILES: O=C(CCNCc1cccc2ncsc12)N1CCN(c2ccc(C(F)(F)F)cn2)CC1] | 3-{[(1,3-benzothiazol-7-yl)methyl]amino}-1-{4-[5-(trifluoromethyl)pyridin-2-yl]piperazin-1-yl}propan-1-one | 450.1 |
| 120 | 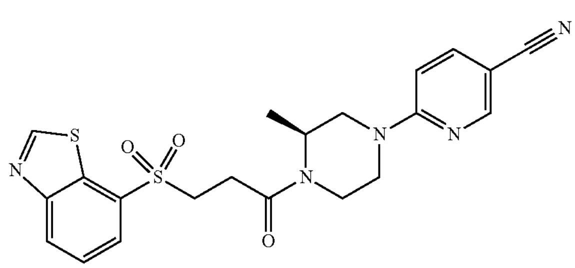 [SMILES: C[C@H]1CN(c2ccc(C#N)cn2)CCN1C(=O)CCS(=O)(=O)c1cccc2ncsc12] | 6-[(3S)-4-[3-(1,3-benzothiazole-7-sulfonyl)propanoyl]-3-methylpiperazin-1-yl]pyridine-3-carbonitrile | 456.1 |

-continued

| Example | Structure | Name | [M + H]+ |
|---|---|---|---|
| 121 | 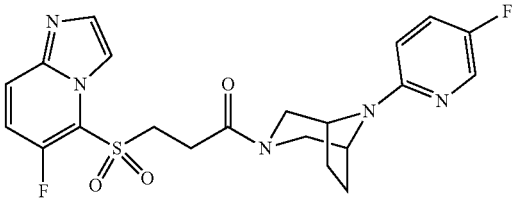 [SMILES: O=C(CCS(=O)(=O)c1c(F)ccc2nccn12)N1CC2CCC(C1)N2c1ccc(F)cn1] | 3-({6-fluoroimidazo[1,2-a]pyridin-5-yl}sulfonyl)-1-[8-(5-fluoropyridin-2-yl)-3,8-diazabicyclo[3.2.1]octan-3-yl]propan-1-one | 462.1 |
| 122 | 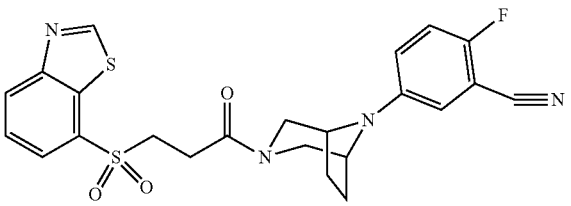 [SMILES: N#Cc1cc(N2C3CCC2CN(C(=O)CCS(=O)(=O)c2cccc4ncsc24)C3)ccc1F] | 5-{3-[3-(1,3-benzothiazole-7-sulfonyl)propanoyl]-3,8-diazabicyclo[3.2.1]octan-8-yl}-2-fluorobenzonitrile | 485.1 |
| 123 | 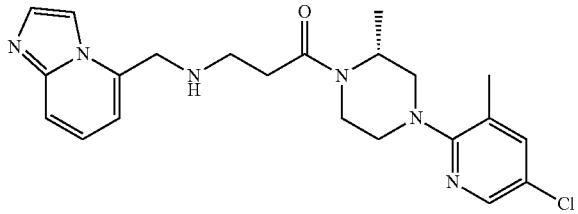 [SMILES: Cc1cc(Cl)cnc1N1CCN(C(=O)CCNCc2cccc3nccn23)[C@H](C)C1] | 1-[(2R)-4-(5-chloro-3-methylpyridin-2-yl)-2-methylpiperazin-1-yl]-3-[({imidazo[1,2-a]pyridin-5-yl}methyl)amino]propan-1-one | 427.2 |
| 124 | 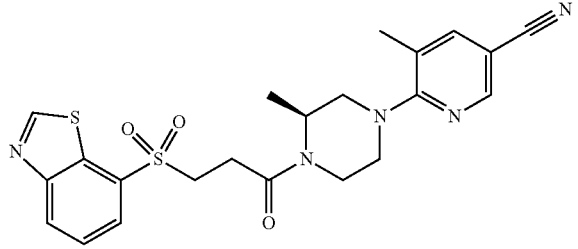 [SMILES: Cc1cc(C#N)cnc1N1CCN(C(=O)CCS(=O)(=O)c2cccc3ncsc23)[C@@H](C)C1] | 6-[(3S)-4-[3-(1,3-benzothiazole-7-sulfonyl)propanoyl]-3-methylpiperazin-1-yl]-5-methylpyridine-3-carbonitrile | 470.1 |
| 125 | 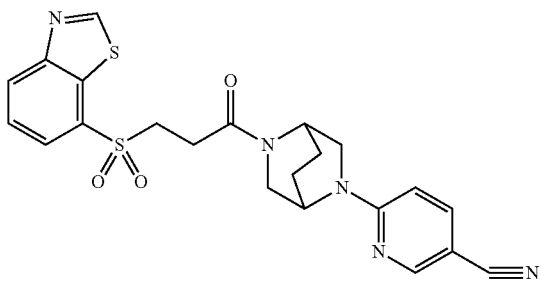 [SMILES: N#Cc1ccc(N2CC3CCC2CN3C(=O)CCS(=O)(=O)c2cccc3ncsc23)nc1] | 6-{5-[3-(1,3-benzothiazole-7-sulfonyl)propanoyl]-2,5-diazabicyclo[2.2.2]octan-2-yl}pyridine-3-carbonitrile | 468.2 |
| 126 | 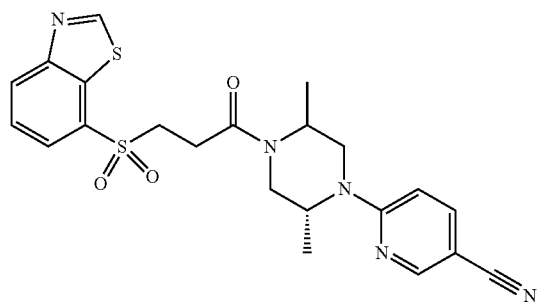 [SMILES: CC1CN(c2ccc(C#N)cn2)[C@H](C)CN1C(=O)CCS(=O)(=O)c1cccc2ncsc12] | 6-[(2R)-4-[3-(1,3-benzothiazole-7-sulfonyl)propanoyl]-2,5-dimethylpiperazin-1-yl]pyridine-3-carbonitrile | 470.1 |

| Example | Structure | Name | [M + H]+ |
|---|---|---|---|
| 127 | 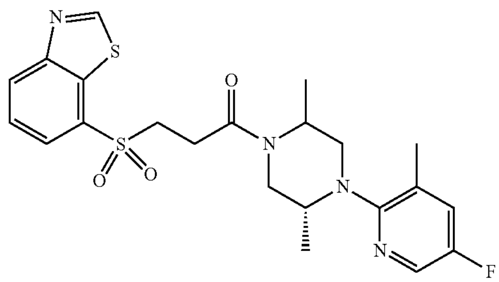 [SMILES: Cc1cc(F)cnc1N1CC(C)N(C(=O)CCS(=O)(=O)c2cccc3ncsc23)C[C@H]1C] | 3-(1,3-benzothiazole-7-sulfonyl)-1-[(5R)-4-(5-fluoro-3-methylpyridin-2-yl)-2,5-dimethylpiperazin-1-yl]propan-1-one | 477.3 |
| 128 | 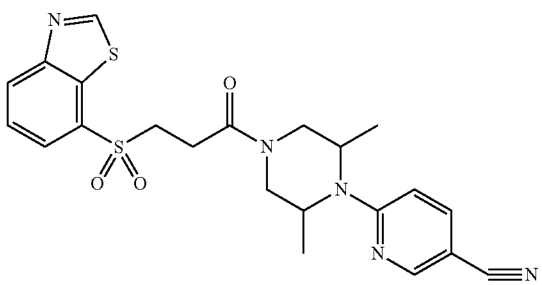 [SMILES: CC1CN(C(=O)CCS(=O)(=O)c2cccc3ncsc23)CC(C)N1c1ccc(C#N)cn1] | 6-{4-[3-(1,3-benzothiazole-7-sulfonyl)propanoyl]-2,6-dimethylpiperazin-1-yl}pyridine-3-carbonitrile | 470.4 |
| 129 | 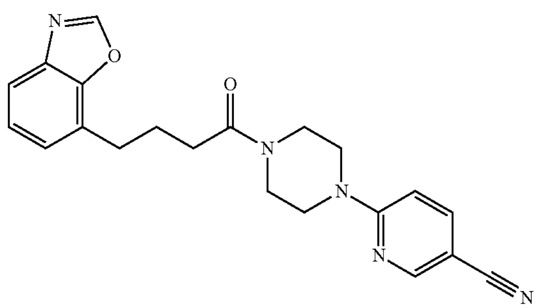 [SMILES: N#Cc1ccc(N2CCN(C(=O)CCCc3cccc4ncoc34)CC2)nc1] | 6-{4-[4-(1,3-benzoxazol-7-yl)butanoyl)piperazin-1-yl}pyridine-3-carbonitrile | 376 |
| 130 | 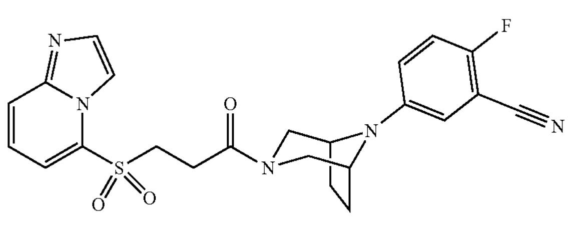 [SMILES: N#Cc1cc(N2C3CCC2CN(C(=O)CCS(=O)(=O)c2cccc4nccn24)C3)ccc1F] | 2-fluoro-5-[3-(3-{imidazo[1,2-a]pyridine-5-sulfonyl}propanoyl)-3,8-diazabicyclo[3.2.1]octan-8-yl]benzonitrile | 468 |
| 131 | 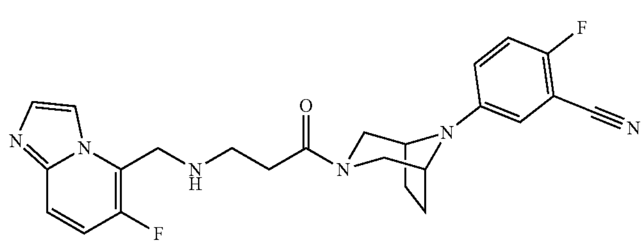 [SMILES: N#Cc1cc(N2C3CCC2CN(C(=O)CCNCc2c(F)ccc4nccn24)C3)ccc1F] | 2-fluoro-5-(3-{3-[({6-fluoroimidazo[1,2-a]pyridin-5-yl}methyl)amino]propanoyl}-3,8-diazabicyclo[3.2.1]octan-8-yl)benzonitrile | 451.1 |

| Example | Structure | Name | [M + H]+ |
|---|---|---|---|
| 132 | 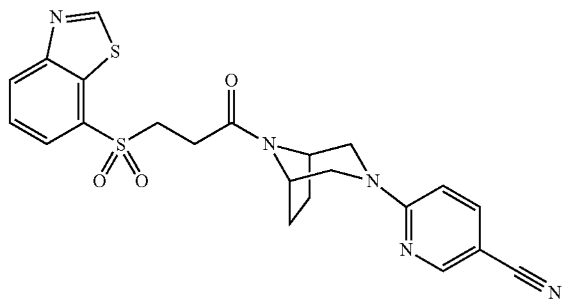 [SMILES: N#Cc1ccc(N2CC3CCC(C2)N3C(=O)CCS(=O)(=O)c2cccc3ncsc23)nc1] | 6-{8-{3-(1,3-benzothiazole-7-sulfonyl)propanoyl]-3,8-diazabicyclo[3.2.1]octan-3-yl}pyridine-3-carbonitrile | 468 |
| 133 | 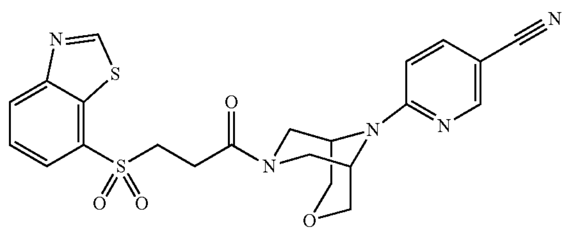 [SMILES: N#Cc1ccc(N2C3COCC2CN(C(=O)CCS(=O)(=O)c2cccc4ncsc24)C3)nc1] | 6-{7-[3-(1,3-benzothiazole-7-sulfonyl)propanoyl]-3-oxa-7,9-diazabicyclo[3.3.1]nonan-9-yl}pyridine-3-carbonitrile | 484.1 |
| 134 | 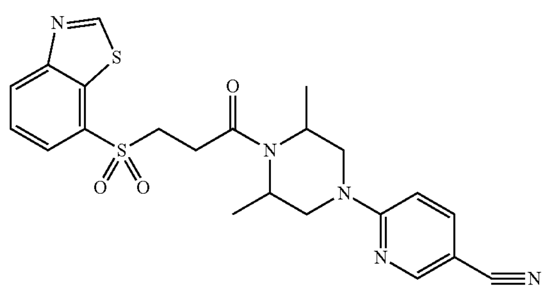 [SMILES: CC1CN(c2ccc(C#N)cn2)CC(C)N1C(=O)CCS(=O)(=O)c1cccc2ncsc12] | 6-{4-[3-(1,3-benzothiazole-7-sulfonyl)propanoyl]-3,5-dimethylpiperazin-1-yl}pyridine-3-carbonitrile | 470.3 |
| 135 | 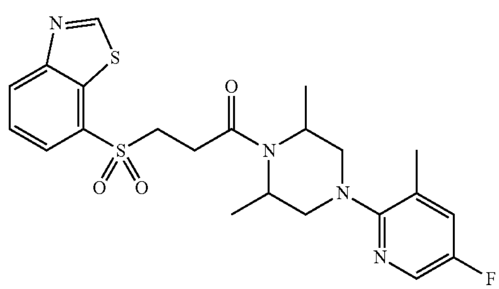 [SMILES: Cc1cc(F)cnc1N1CC(C)N(C(=O)CCS(=O)(=O)c2cccc3ncsc23)C(C)C1] | 3-(1,3-benzothiazole-7-sulfonyl)-1-[4-(5-fluoro-3-methylpyridin-2-yl)-2,6-dimethylpiperazin-1-yl]propan-1-one | 477.3 |
| 136 | 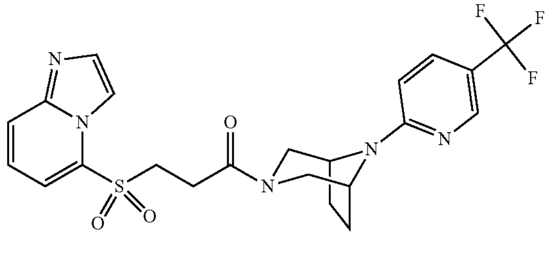 [SMILES: O=C(CCS(=O)(=O)c1cccc2nccn12)N1CC2CCC(C1)N2c1ccc(C(F)(F)F)cn1] | 3-{imidazo[1,2-a]pyridine-5-sulfonyl}-1-{8-[5-(trifluoromethyl)pyridin-2-yl]-3,8-diazabicyclo[3.2.1]octan-3-yl}propan-1-one | 493.9 |

-continued

| Example | Structure | Name | [M + H]+ |
|---|---|---|---|
| 137 | 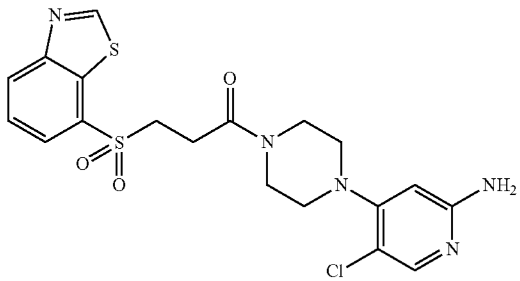 [SMILES: Nc1cc(N2CCN(C(=O)CCS(=O)(=O)c3cccc4ncsc34)CC2)c(Cl)cn1] | 1-[4-(2-amino-5-chloropyridin-4-yl)piperazin-1-yl]-3-(1,3-benzothiazole-7-sulfonyl)propan-1-one | 466.3 |
| 138 | 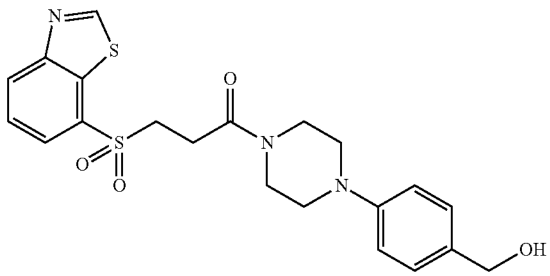 [SMILES: O=C(CCS(=O)(=O)c1cccc2ncsc12)N1CCN(c2ccc(CO)cc2)CC1] | 3-(1,3-benzothiazole-7-sulfonyl)-1-{4-[4-(hydroxymethyl)phenyl]piperazin-1-yl}propan-1-one | 446.3 |
| 139 | 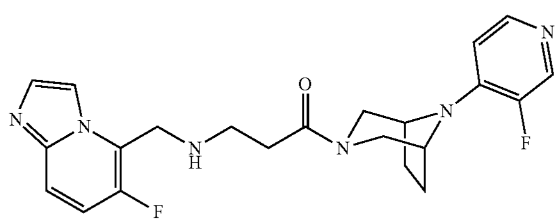 [SMILES: O=C(CCNCc1c(F)ccc2nccn12)N1CC2CCC(C1)N2c1ccncc1F] | 3-[({6-fluoroimidazo[1,2-a]pyridin-5-yl}methyl)amino]-1-[8-(3-fluoropyridin-4-yl)-3,8-diazabicyclo[3.2.1]octan-3-yl]propan-1-one | 427.2 |
| 140 | 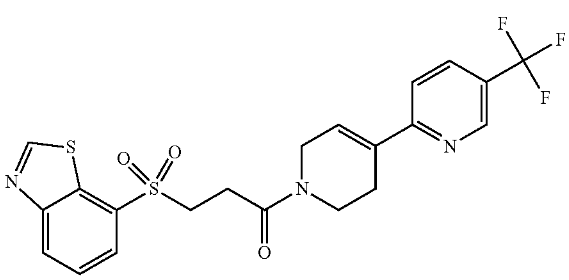 [SMILES: O=C(CCS(=O)(=O)c1cccc2ncsc12)N1CC=C(c2ccc(C(F)(F)F)cn2)CC1] | 3-(1,3-benzothiazole-7-sulfonyl)-1-[5-(trifluoromethyl)-1',2',3',6'-tetrahydro-[2,4'-bipyridin]-1'-yl]propan-1-one | 482.2 |
| 141 | 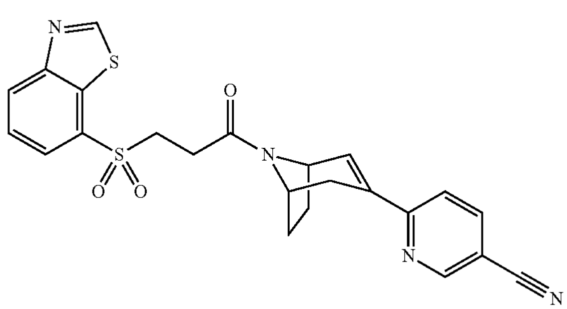 [SMILES: N#Cc1ccc(C2=CC3CCC(C2)N3C(=O)CCS(=O)(=O)c2cccc3ncsc23)nc1] | 6-{8-[3-(1,3-benzothiazole-7-sulfonyl)propanoyl]-8-azabicyclo[3.2.1]oct-2-en-3-yl}pyridine-3-carbonitrile | 487.3 |

-continued

| Example | Structure | Name | [M + H]+ |
|---|---|---|---|
| 142 | 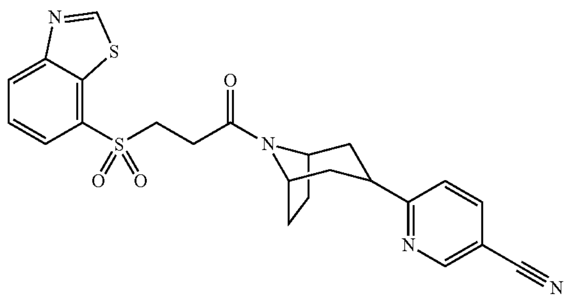 [SMILES: N#Cc1ccc(C2CC3CCC(C2)N3C(=O)CCS(=O)(=O)c2cccc3ncsc23)nc1] | 6-{8-[3-(1,3-benzothiazole-7-sulfonyl)propanoyl]-8-azabicyclo[3.2.1]octan-3-yl}pyridine-3-carbonitrile | 467.3 |
| 143 | 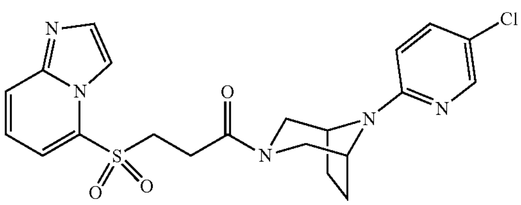 [SMILES: O=C(CCS(=O)(=O)c1cccc2nccn12)N1CC2CCC(C1)N2c1ccc(Cl)cn1] | 1-[8-(5-chloropyridin-2-yl)-3,8-diazabicyclo[3.2.1]octan-3-yl]-3-{imidazo[1,2-a]pyridine-5-sulfonyl}propan-1-one | 459.9 |
| 144 | 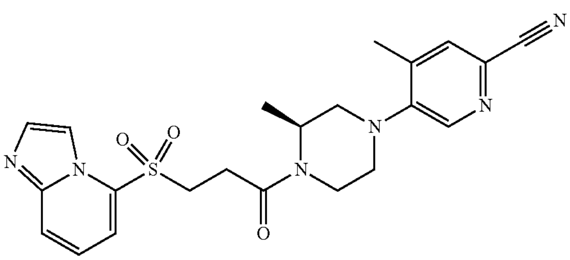 [SMILES: Cc1cc(C#N)ncc1N1CCN(C(=O)CCS(=O)(=O)c2cccc3nccn23)[C@@H](C)C1] | 5-[(3S)-4-(3-{imidazo[1,2-a]pyridine-5-sulfonyl}propanoyl)-3-methylpiperazin-1-yl]-4-methylpyridine-2-carbonitrile | 453.5 |
| 145 | 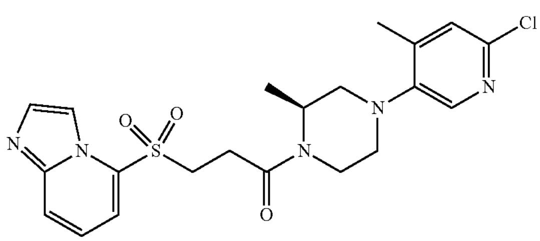 [SMILES: Cc1cc(Cl)ncc1N1CCN(C(=O)CCS(=O)(=O)c2cccc3nccn23)[C@@H](C)C1] | 1-[(2S)-4-(5-chloro-3-methylpyridin-2-yl)-2-methylpiperazin-1-yl]-3-{imidazo[1,2-a]pyridine-5-sulfonyl}propan-1-one | 462.3 |
| 146 | 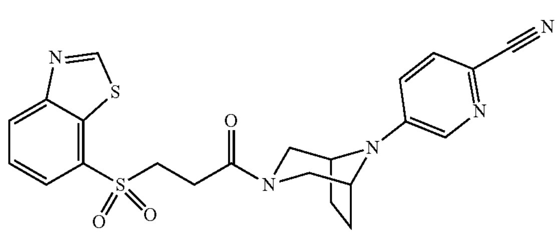 [SMILES: N#Cc1ccc(N2C3CCC2CN(C(=O)CCS(=O)(=O)c2cccc4ncsc24)C3)cn1] | 5-{3-[3-(1,3-benzothiazole-7-sulfonyl)propanoyl]-3,8-diazabicyclo[3.2.1]octan-8-yl}pyridine-2-carbonitrile | 468.1 |
| 147 | 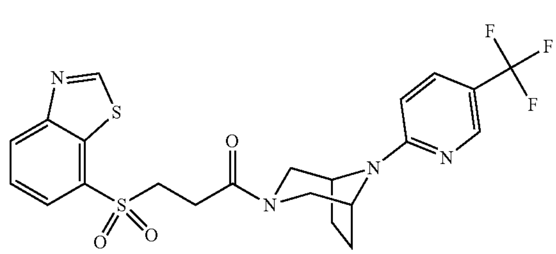 [SMILES: O=C(CCS(=O)(=O)c1cccc2ncsc12)N1CC2CCC(C1)N2c1ccc(C(F)(F)F)cn1] | 3-(1,3-benzothiazole-7-sulfonyl)-1-{8-[5-(trifluoromethyl)pyridin-2-yl]-3,8-diazabicyclo[3.2.1]octan-3-yl}propan-1-one | 511.1 |

-continued

| Example | Structure | Name | [M + H]⁺ |
|---|---|---|---|
| 148 | 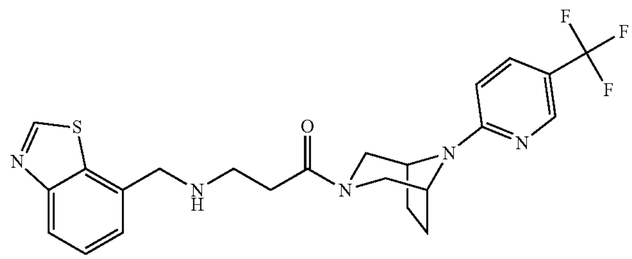 [SMILES: O=C(CCNCc1cccc2ncsc12)N1CC2CCC(C1)N2c1ccc(C(F)(F)F)cn1] | 3-{[(1,3-benzothiazol-7-yl)methyl]amino}-1-{8-[5-(trifluoromethyl)pyridin-2-yl]-3,8-diazabicyclo[3.2.1]octan-3-yl}propan-1-one | 476.4 |
| 149 | 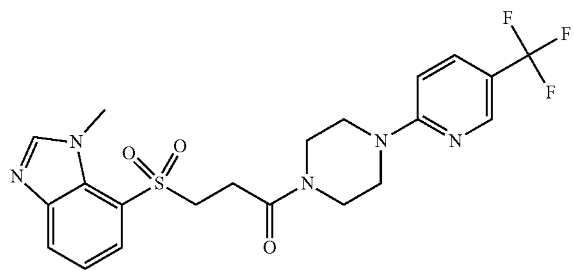 [SMILES: Cn1cnc2cccc(S(=O)(=O)CCC(=O)N3CCN(c4ccc(C(F)(F)F)cn4)CC3)c21] | 3-[(1-methyl-1H-1,3-benzodiazol-7-yl)sulfonyl]-1-{4-[5-(trifluoromethyl)pyridin-2-yl]piperazin-1-yl}propan-1-one | 482.3 |
| 150 | 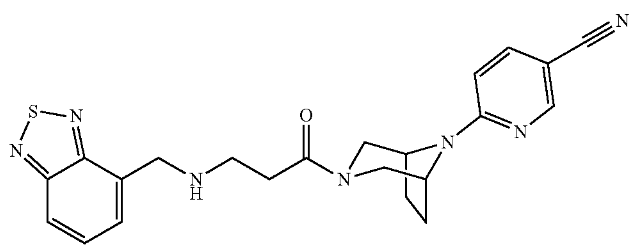 [SMILES: N#Cc1ccc(N2C3CCC2CN(C(=O)CCNCc2cccc4nsnc24)C3)nc1] | 6-[3-(3-{[(2,1,3-benzothiadiazol-4-yl)methyl]amino}propanoyl)-3,8-diazabicyclo[3.2.1]octan-8-yl]pyridine-3-carbonitrile | 434.1 |
| 151 | 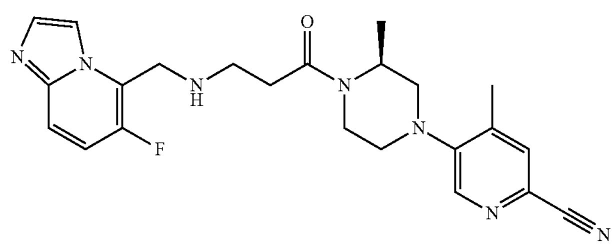 [SMILES: Cc1cc(C#N)ncc1N1CCN(C(=O)CCNCc2c(F)ccc3nccn23)[C@@H](C)C1] | 5-[(3S)-4-{3-[({6-fluoroimidazo[1,2-a]pyridin-5-yl}methyl)amino]propanoyl}-3-methylpiperazin-1-yl]-4-methylpyridine-2-carbonitrile | 436.6 |
| 152 | 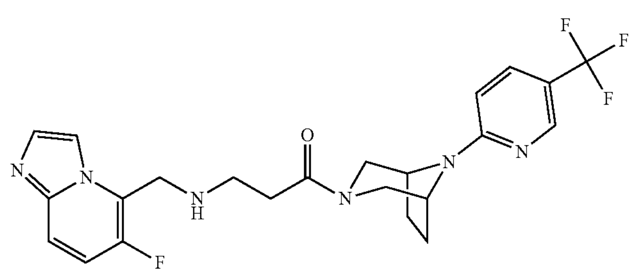 [SMILES: O=C(CCNCc1c(F)ccc2nccn12)N1CC2CCC(C1)N2c1ccc(C(F)(F)F)cn1] | 3-[({6-fluoroimidazo[1,2-a]pyridin-5-yl}methyl)amino]-1-{8-[5-(trifluoromethyl)pyridin-2-yl]-3,8-diazabicyclo[3.2.1]octan-3-yl}propan-1-one | 477.4 |
| 153 | 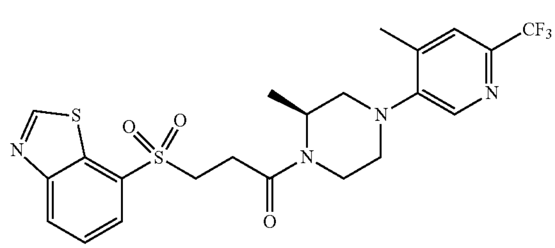 [SMILES: Cc1cc(C(F)(F)F)ncc1N1CCN(C(=O)CCS(=O)(=O)c2cccc3ncsc23)[C@@H](C)C1] | 3-(1,3-benzothiazole-7-sulfonyl)-1-[(2S)-2-methyl-4-[4-methyl-6-(trifluoromethyl)pyridin-3-yl]piperazin-1-yl]propan-1-one | 535.1 |

-continued

| Example | Structure | Name | [M + H]+ |
|---|---|---|---|
| 154 | 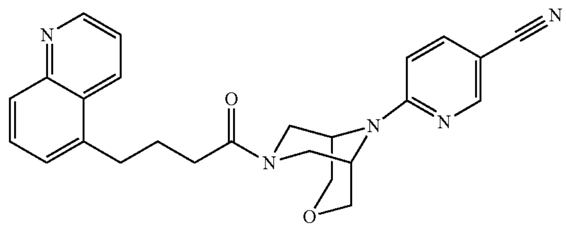 [SMILES: N#Cc1ccc(N2C3COCC2CN(C(=O)CCCc2cccc4ncccc24)C3)nc1] | 6-{7-[4-(quinolin-5-yl)butanoyl]-3-oxa-7,9-diazabicyclo[3.3.1]nonan-9-yl}pyridine-3-carbonitrile | 428.2 |
| 155 | 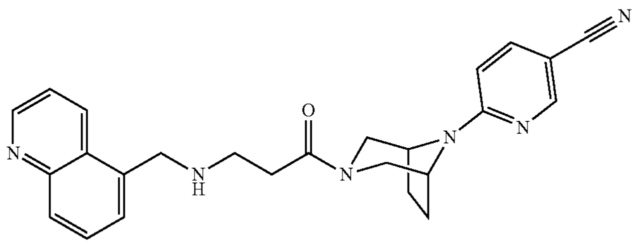 [SMILES: N#Cc1ccc(N2C3CCC2CN(C(=O)CCNCc2cccc4ncccc24)C3)nc1] | 6-[3-(3-{[(quinolin-5-yl)methyl]amino}propanoyl)-3,8-diazabicyclo[3.2.1]octan-8-yl]pyridine-3-carbonitrile | 427.2 |
| 156 | 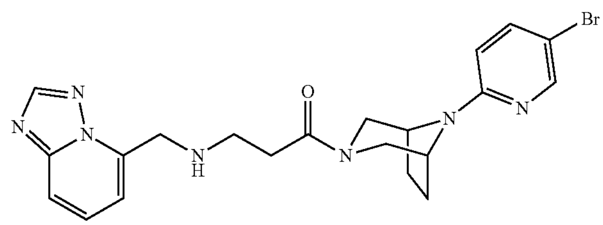 [SMILES: O=C(CCNCc1cccc2ncnn12)N1CC2CCC(C1)N2c1ccc(Br)cn1] | 1-[8-(5-bromopyridin-2-yl)-3,8-diazabicyclo[3.2.1]octan-3-yl]-3-[({[1,2,4]triazolo[1,5-a]pyridin-5-yl}methyl)amino]propan-1-one | 470.2 |
| 157 | 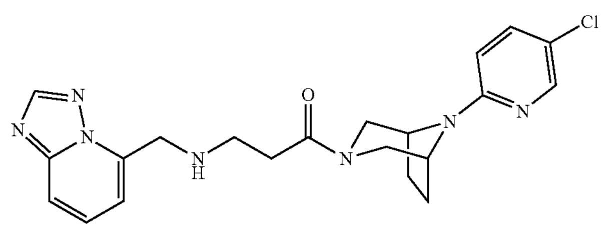 [SMILES: O=C(CCNCc1cccc2ncnn12)N1CC2CCC(C1)N2c1ccc(Cl)cn1] | 1-[8-(5-chloropyridin-2-yl)-3,8-diazabicyclo[3.2.1]octan-3-yl]-3-[({[1,2,4]triazolo[1,5-a]pyridin-5-yl}methyl)amino]propan-1-one | 448.1 |
| 158 | 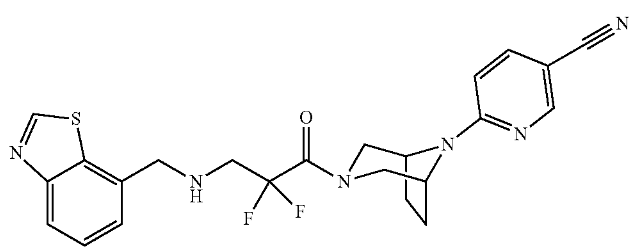 [SMILES: N#Cc1ccc(N2C3CCC2CN(C(=O)C(F)(F)CNCc2cccc4ncsc24)C3)nc1] | 6-[3-(3-{[(1,3-benzothiazol-7-yl)methyl]amino}-2,2-difluoropropanoyl)-3,8-diazabicyclo[3.2.1]octan-8-yl]pyridine-3-carbonitrile | 491.1 |
| 159 | 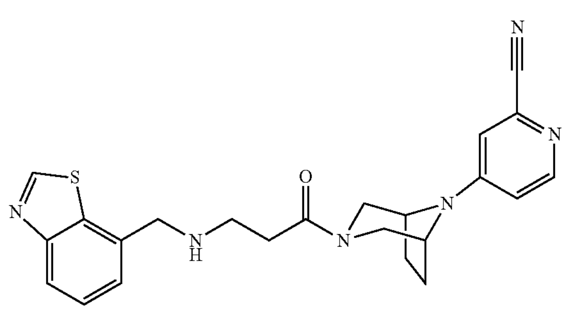 [SMILES: N#Cc1cc(N2C3CCC2CN(C(=O)CCNCc2cccc4ncsc24)C3)ccn1] | 4-[3-(3-{[(1,3-benzothiazol-7-yl)methyl]amino}propanoyl)-3,8-diazabicyclo[3.2.1]octan-8-yl]pyridine-2-carbonitrile | 433.1 |

-continued

| Example | Name | [M + H]+ |
|---|---|---|
| 160 | 6-[8-(3-{[(1,3-benzothiazol-7-yl)methyl]amino}propanoyl)-3,8-diazabicyclo[3.2.1]octan-3-yl]pyridine-3-carbonitrile | 433.3 |
| 161 | 6-[8-(3-{[(1,3-benzothiazol-7-yl)methyl]amino}propanoyl)-3,8-diazabicyclo[3.2.1]octan-3-yl]-5-methylpyridine-3-carbonitrile | 447.4 |
| 162 | 6-[5-(3-{[(1,3-benzothiazol-7-yl)methyl]amino}propanoyl)-2,5-diazabicyclo[2.2.2]octan-2-yl]pyridine-3-carbonitrile | 433.2 |
| 163 | 1-[8-(5-chloropyridin-2-yl)-3,8-diazabicyclo[3.2.1]octan-3-yl]-3-[({pyrazolo[1,5-a]pyridin-4-yl}methyl)amino]propan-1-one | 425.1 |
| 164 | 6-(3-{3-[cyclopropyl({[1,2,4]triazolo[1,5-a]pyridin-5-yl}methyl)amino]propanoyl}-3,8-diazabicyclo[3.2.1]octan-8-yl)pyridine-3-carbonitrile | 457.1 |
| 165 | 6-(3-{3-[({pyrazolo[1,5-a]pyridin-4-yl}methyl)amino]propanoyl}-3,8-diazabicyclo[3.2.1]octan-8-yl)pyridine-3-carbonitrile | 416.5 |

-continued

| Example | Structure | Name | [M + H]⁺ |
|---|---|---|---|
| 166 | 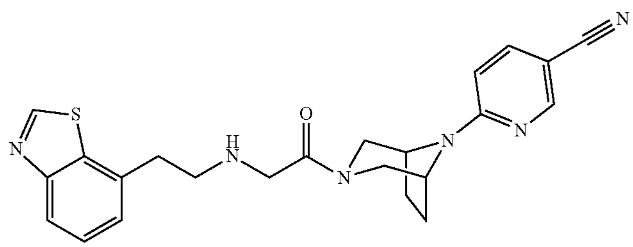 [SMILES: N#Cc1ccc(N2C3CCC2CN(C(=O)CNCCc2cccc4ncsc24)C3)nc1] | 6-[3-(2-{[2-(1,3-benzothiazol-7-yl)ethyl]amino}acetyl)-3,8-diazabicyclo[3.2.1]octan-8-yl]pyridine-3-carbonitrile | 433.3 |
| 167 | 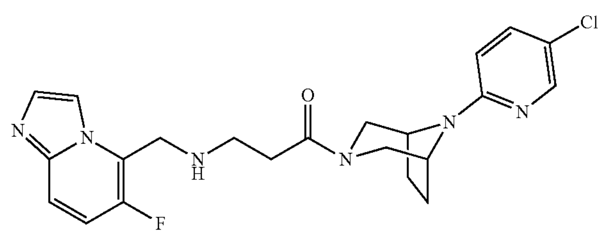 [SMILES: O=C(CCNCc1c(F)ccc2nccn12)N1CC2CCC(C1)N2c1ccc(Cl)cn1] | 1-[8-(5-chloropyridin-2-yl)-3,8-diazabicyclo[3.2.1]octan-3-yl]-3-[({6-fluoroimidazo[1,2-a]pyridin-5-yl}methyl)amino]propan-1-one | 443.4 |
| 168 | 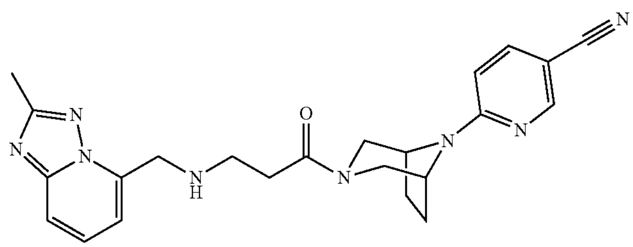 [SMILES: Cc1nc2cccc(CNCCC(=O)N3CC4CCC(C3)N4c3ccc(C#N)cn3)n2n1] | 6-(3-{3-[({2-methyl-[1,2,4]triazolo[1,5-a]pyridin-5-yl}methyl)amino]propanoyl}-3,8-diazabicyclo[3.2.1]octan-8-yl)pyridine-3-carbonitrile | 431.5 |
| 169 | 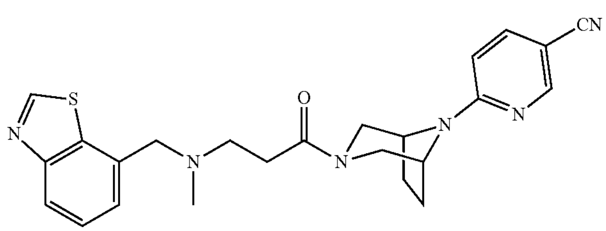 [SMILES: CN(CCC(=O)N1CC2CCC(C1)N2c1ccc(C#N)cn1)Cc1cccc2ncsc12] | 6-[3-(3-{[(1,3-benzothiazol-7-yl)methyl](methyl)amino}propanoyl)-3,8-diazabicyclo[3.2.1]octan-8-yl]pyridine-3-carbonitrile | 447.1 |
| 170 | 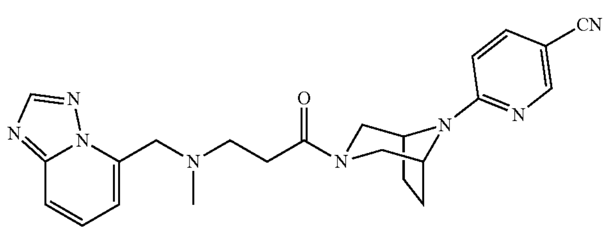 [SMILES: CN(CCC(=O)N1CC2CCC(C1)N2c1ccc(C#N)cn1)Cc1cccc2ncnn12] | 6-(3-{3-[methyl({[1,2,4]triazolo[1,5-a]pyridin-5-yl}methyl)amino]propanoyl}-3,8-diazabicyclo[3.2.1]octan-8-yl)pyridine-3-carbonitrile | 431.1 |
| 171 | 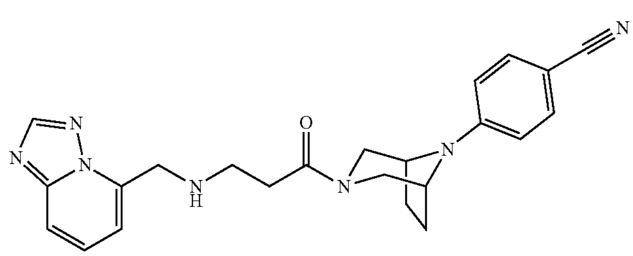 [SMILES: N#Cc1ccc(N2C3CCC2CN(C(=O)CCNCc2cccc4ncnn24)C3)cc1] | 4-(3-{3-[({[1,2,4]triazolo[1,5-a]pyridin-5-yl}methyl)amino]propanoyl}-3,8-diazabicyclo[3.2.1]octan-8-yl)benzonitrile | 416.5 |

-continued

| Example | Structure | Name | [M + H]+ |
|---|---|---|---|
| 172 | 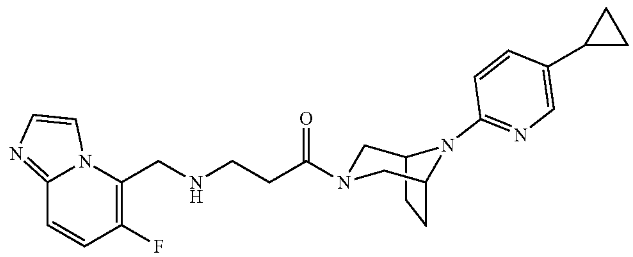 [SMILES: O=C(CCNCc1c(F)ccc2nccn12)N1CC2CCC(C1)N2c1ccc(C2CC2)cn1] | 1-[8-(5-cyclopropylpyridin-2-yl)-3,8-diazabicyclo[3.2.1]octan-3-yl]-3-[({6-fluoroimidazo[1,2-a]pyridin-5-yl}methyl)amino]propan-1-one | 449.5 |
| 173 | 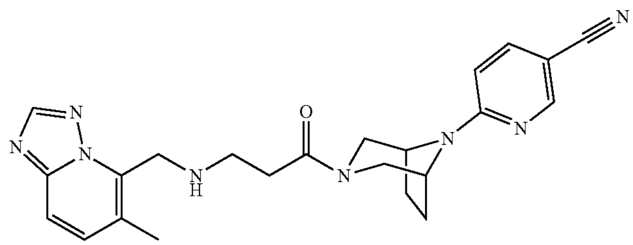 [SMILES: Cc1ccc2ncnn2c1CNCCC(=O)N1CC2CCC(C1)N2c1ccc(C#N)cn1] | 6-(3-{3-[({6-methyl-[1,2,4]triazolo[1,5-a]pyridin-5-yl}methyl)amino]propanoyl}-3,8-diazabicyclo[3.2.1]octan-8-yl)pyridine-3-carbonitrile | 431.4 |
| 174 | 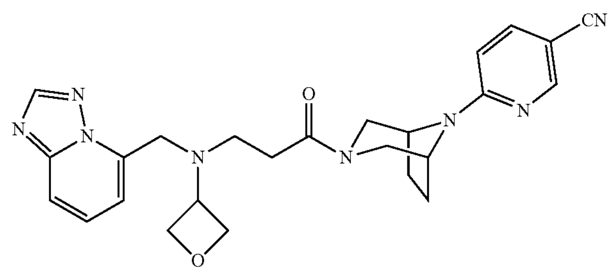 [SMILES: N#Cc1ccc(N2C3CCC2CN(C(=O)CCN(Cc2cccc4ncnn24)C2COC2)C3)nc1] | 6-(3-{3-[(oxetan-3-yl)({[1,2,4]triazolo[1,5-a]pyridin-5-yl}methyl)amino]propanoyl}-3,8-diazabicyclo[3.2.1]octan-8-yl)pyridine-3-carbonitrile | 473 |
| 175 | 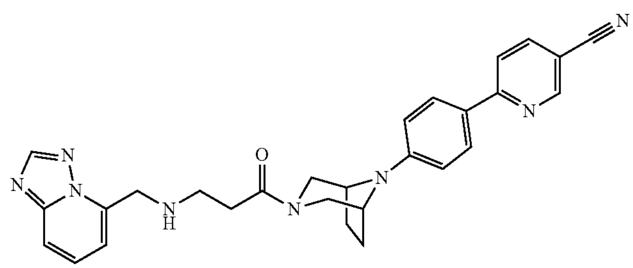 [SMILES: N#Cc1ccc(-c2ccc(N3C4CCC3CN(C(=O)CCNCc3cccc5ncnn35)C4)cc2)nc1] | 6-[4-(3-{3-[({[1,2,4]triazolo[1,5-a]pyridin-5-yl}methyl)amino]propanoyl}-3,8-diazabicyclo[3.2.1]octan-8-yl)phenyl]pyridine-3-carbonitrile | 493.4 |
| 176 | 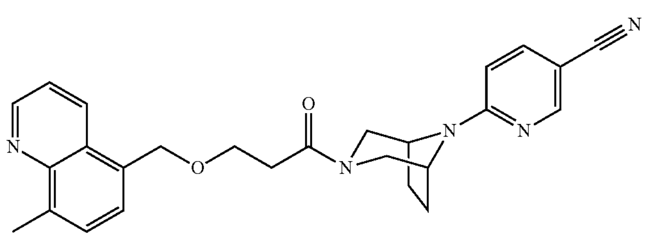 [SMILES: Cc1ccc(COCCC(=O)N2CC3CCC(C2)N3c2ccc(C#N)cn2)c2cccnc12] | 6-(3-{3-[(8-methylquinolin-5-yl)methoxy]propanoyl}-3,8-diazabicyclo[3.2.1]octan-8-yl)pyridine-3-carbonitrile | 442.1 |
| 177 | 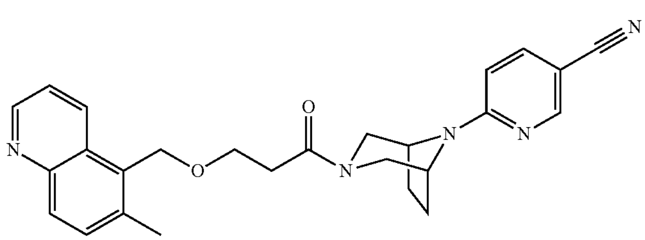 [SMILES: Cc1ccc2ncccc2c1COCCC(=O)N1CC2CCC(C1)N2c1ccc(C#N)cn1] | 6-(3-{3-[(6-methylquinolin-5-yl)methoxy]propanoyl}-3,8-diazabicyclo[3.2.1]octan-8-yl)pyridine-3-carbonitrile | 442.2 |

-continued

| Example | Structure | Name | [M + H]+ |
|---|---|---|---|
| 178 | 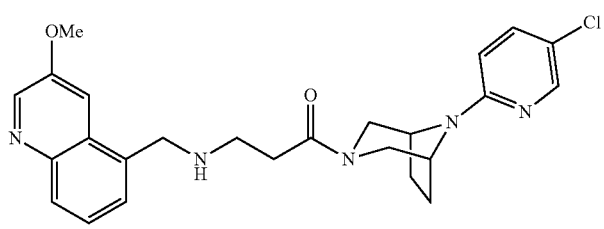 [SMILES: COc1cnc2cccc(CNCCC(=O)N3CC4CCC(C3)N4c3ccc(Cl)cn3)c2c1] | 1-[8-(5-chloropyridin-2-yl)-3,8-diazabicyclo[3.2.1]octan-3-yl]-3-{[(3-methoxyquinolin-5-yl)methyl]amino}propan-1-one | 466.5 |
| 179 | 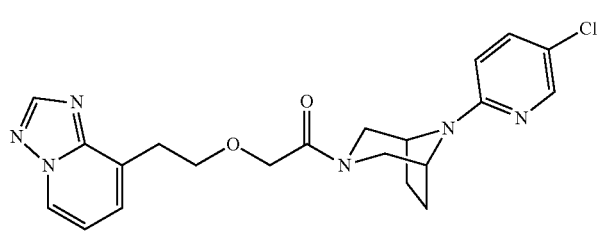 [SMILES: O=C(COCCc1cccn2ncnc12)N1CC2CCC(C1)N2c1ccc(Cl)cn1] | 1-[8-(5-chloropyridin-2-yl)-3,8-diazabicyclo[3.2.1]octan-3-yl]-2-(2-{[1,2,4]triazolo[1,5-a]pyridin-8-yl}ethoxy)ethan-1-one | 449.2 |
| 180 | 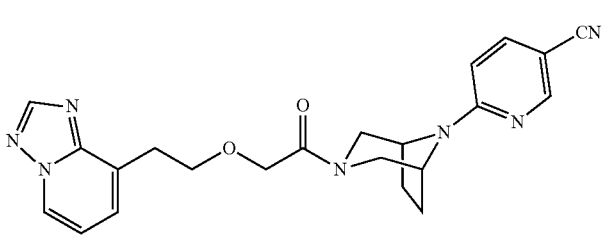 [SMILES: N#Cc1ccc(N2C3CCC2CN(C(=O)COCCc2cccn4ncnc24)C3)nc1] | 6-{3-[2-(2-{[1,2,4]triazolo[1,5-a]pyridin-8-yl}ethoxy)acetyl]-3,8-diazabicyclo[3.2.1]octan-8-yl}pyridine-3-carbonitrile | 440.2 |
| 181 | 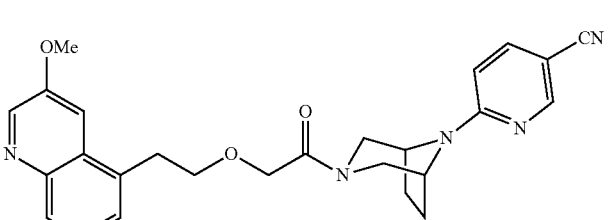 | 6-(3-{2-[2-(3-methoxyquinolin-5-yl)ethoxy]acetyl}-3,8-diazabicyclo[3.2.1]octan-8-yl)pyridine-3-carbonitrile | 458.3 |
| 182 | 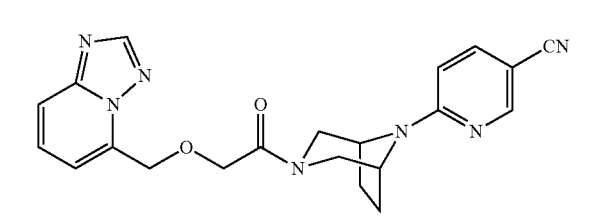 [SMILES: N#Cc1ccc(N2C3CCC2CN(C(=O)COCc2cccc4ncnn24)C3)nc1] | 6-{3-[2-({[1,2,4]triazolo[1,5-a]pyridin-5-yl}methoxy)acetyl]-3,8-diazabicyclo[3.2.1]octan-8-yl}pyridine-3-carbonitrile | 404.1 |
| 183 | 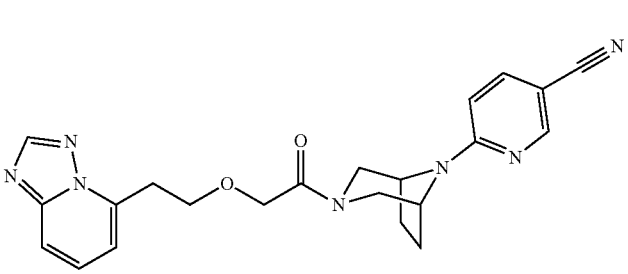 [SMILES: N#Cc1ccc(N2C3CCC2CN(C(=O)COCCc2cccc4ncnn24)C3)nc1] | 6-{3-[2-(2-{[1,2,4]triazolo[1,5-a]pyridin-5-yl}ethoxy)acetyl]-3,8-diazabicyclo[3.2.1]octan-8-yl}pyridine-3-carbonitrile | 418.1 |

| Example | Structure | Name | [M + H]+ |
|---|---|---|---|
| 184 | 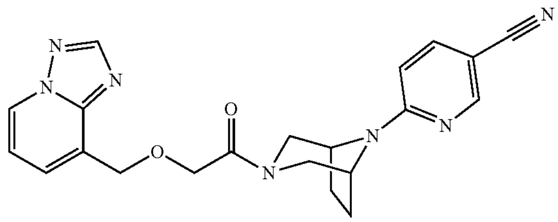 [SMILES: N#Cc1ccc(N2C3CCC2CN(C(=O)COCc2cccn4ncnc24)C3)nc1] | 6-{3-[2-({[1,2,4]triazolo[1,5-a]pyridin-8-yl}methoxy)acetyl]-3,8-diazabicyclo[3.2.1]octan-8-yl}pyridine-3-carbonitrile | 404.1 |
| 185 | 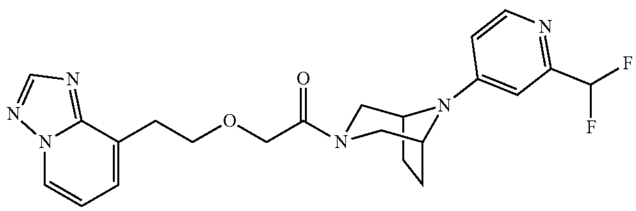 [SMILES: O=C(COCCc1cccn2ncnc12)N1CC2CCC(C1)N2c1ccnc(C(F)F)c1] | 1-{8-[2-(difluoromethyl)pyridin-4-yl]-3,8-diazabicyclo[3.2.1]octan-3-yl}-3-({[1,2,4]triazolo[1,5-a]pyridin-8-yl}methoxy)propan-1-one | 443.4 |
| 186 | 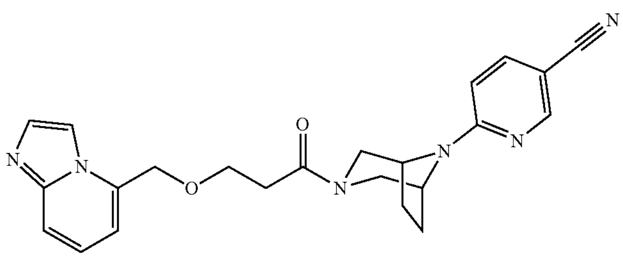 [SMILES: N#Cc1ccc(N2C3CCC2CN(C(=O)CCOCc2cccc4nccn24)C3)nc1] | 6-{3-[3-({imidazo[1,2-a]pyridin-5-yl}methoxy)propanoyl]-3,8-diazabicyclo[3.2.1]octan-8-yl}pyridine-3-carbonitrile | 417.3 |
| 187 | 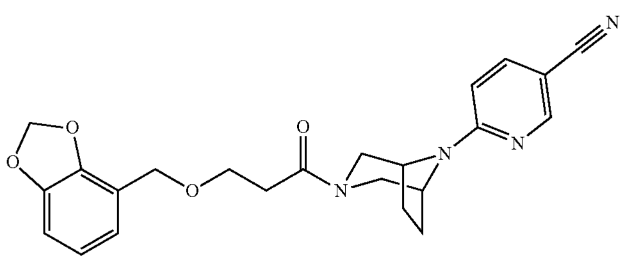 [SMILES: N#Cc1ccc(N2C3CCC2CN(C(=O)CCOCc2cccc4c2OCO4)C3)nc1] | 6-(3-{3-[(2H-1,3-benzodioxol-4-yl)methoxy]propanoyl}-3,8-diazabicyclo[3.2.1]octan-8-yl)pyridine-3-carbonitrile | 443.3 |
| 188 | 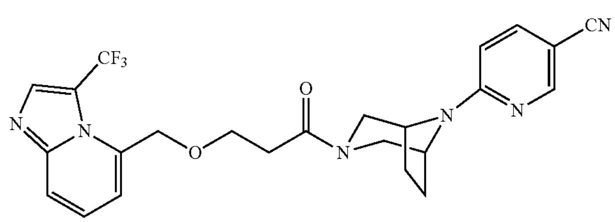 [SMILES: N#Cc1ccc(N2C3CCC2CN(C(=O)CCOCc2cccc4ncc(C(F)(F)F)n24)C3)nc1] | 6-[3-(3-{[3-(trifluoromethyl)imidazo[1,2-a]pyridin-5-yl]methoxy}propanoyl)-3,8-diazabicyclo[3.2.1]octan-8-yl]pyridine-3-carbonitrile | 485 |
| 189 | 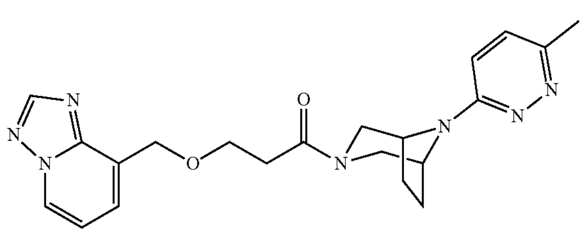 [SMILES: Cc1ccc(N2C3CCC2CN(C(=O)CCOCc2cccn4ncnc24)C3)nn1] | 1-[8-(6-methylpyridazin-3-yl)-3,8-diazabicyclo[3.2.1]octan-3-yl]-3-({[1,2,4]triazolo[1,5-a]pyridin-8-yl}methoxy)propan-1-one | 408.1 |

-continued

| Example | Structure | Name | [M + H]+ |
|---|---|---|---|
| 190 | 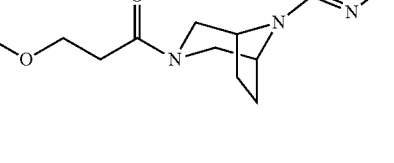 | 6-{3-[3-({[1,2,4]triazolo[1,5-a]pyridin-8-yl}methoxy)propanoyl]-3,8-diazabicyclo[3.2.1]octan-8-yl}pyridine-3-carbaldehyde | 421.2 |
| 191 | 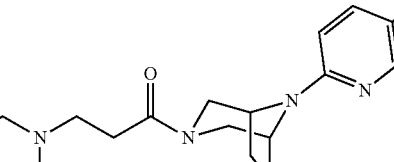 | 6-(3-{3-[cyclobutyl({[1,2,4]triazolo[1,5-a]pyridin-5-yl}methyl)amino]propanoyl}-3,8-diazabicyclo[3.2.1]octan-8-yl)pyridine-3-carbonitrile | 471.1 |
| 192 | 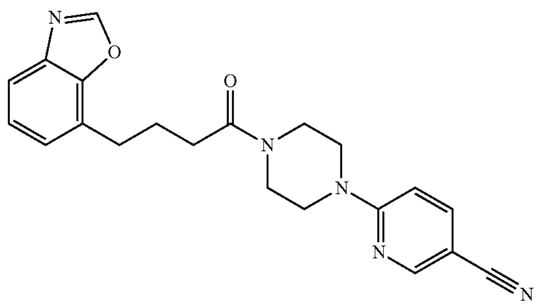 [SMILES: N#Cc1ccc(N2CCN(C(=O)CCCc3cccc4ncoc34)CC2)nc1] | 6-{4-[4-(1,3-benzoxazol-7-yl)butanoyl]piperazin-1-yl}pyridine-3-carbonitrile | 376 |
| 193 | 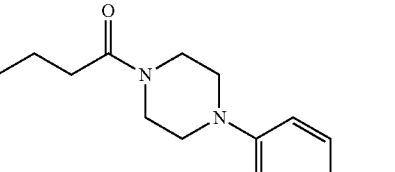 | 1-[8-(5-phenylpyridin-2-yl)-3,8-diazabicyclo[3.2.1]octan-3-yl]-3-[({[1,2,4]triazolo[1,5-a]pyridin-5-yl}methyl)amino]propan-1-one | 468.1 |
| 194 | 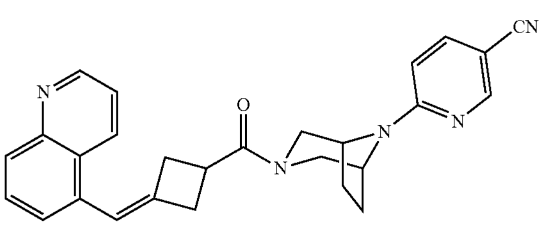 [SMILES: N#Cc1ccc(N2C3CCC2CN(C(=O)C2CC(=Cc4cccc5ncccc45)C2)C3)nc1] | 6-(3-{3-[(quinolin-5-yl)methylidene]cyclobutanecarbonyl}-3,8-diazabicyclo[3.2.1]octan-8-yl)pyridine-3-carbonitrile | 436.1 |
| 195 | 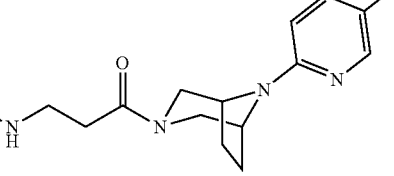 | 6-(3-{3-[(isoquinolin-5-yl)methylidene]cyclobutanecarbonyl}-3,8-diazabicyclo[3.2.1]octan-8-yl)pyridine-3-carbonitrile | 436.1 |

| Example | Structure | Name | [M + H]⁺ |
|---|---|---|---|
| 196 | 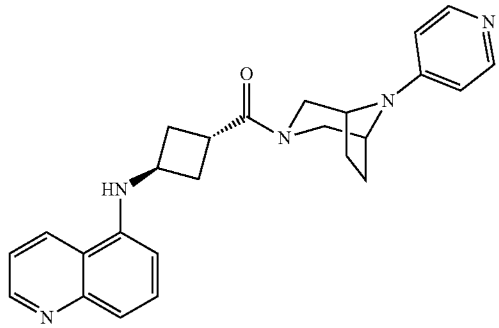 [SMILES: O=C([C@H]1C[C@H](Nc2cccc3ncccc23)C1)N1CC2CCC(C1)N2c1ccncc1] | N-[(1r,3r)-3-[8-(pyridin-4-yl)-3,8-diazabicyclo[3.2.1]octane-3-carbonyl]cyclobutyl]quinolin-5-amine | 414.2 |
| 197 | 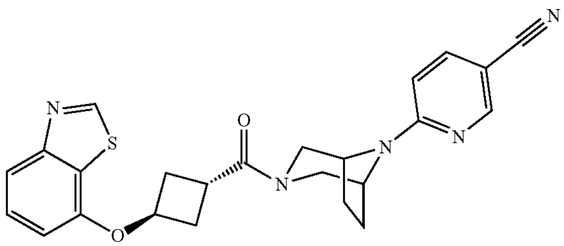 [SMILES: N#Cc1ccc(N2C3CCC2CN(C(=O)[C@H]2C[C@H](Oc4cccc5ncsc45)C2)C3)nc1] | 6-{3-[(1r,3r)-3-(1,3-benzothiazol-7-yloxy)cyclobutanecarbonyl]-3,8-diazabicyclo[3.2.1]octan-8-yl}pyridine-3-carbonitrile | 446.3 |
| 198 | 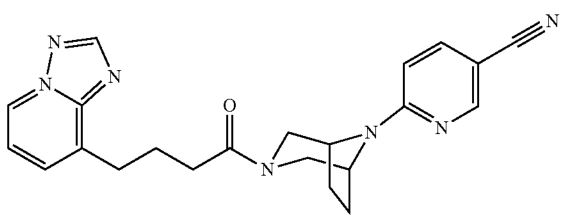 | 6-[3-(4-{[1,2,4]triazolo[1,5-a]pyridin-8-yl}butanoyl)-3,8-diazabicyclo[3.2.1]octan-8-yl]pyridine-3-carbonitrile | 402.2 |
| 199 | 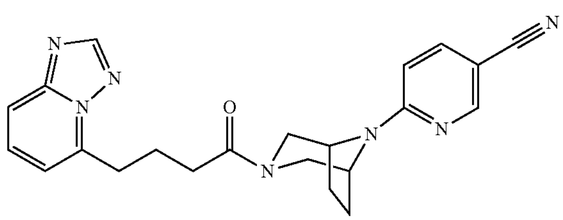 | 6-[3-(4-{[1,2,4]triazolo[1,5-a]pyridin-5-yl}butanoyl)-3,8-diazabicyclo[3.2.1]octan-8-yl]pyridine-3-carbonitrile | 402.2 |
| 200 | 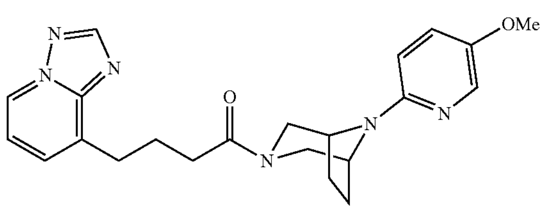 | 1-[8-(5-methoxypyridin-2-yl)-3,8-diazabicyclo[3.2.1]octan-3-yl]-4-{[1,2,4]triazolo[1,5-a]pyridin-8-yl}butan-1-one | 407.2 |

II. Biological Evaluation

Example 201: In Vitro Functional Assay of Muscarinic Acetylcholine Receptor Activity CHO-K1 cells stably expressing human M1 receptor with Aequorin (Perkin Elmer) were grown in F12 media, 10% FBS with 0.4 mg/mL geneticin and 0.25 mg/mL. Cells were grown to confluence and frozen down to be assayed at a later date. On the day of the experiment cells were thawed in a 37° C. water bath, resuspended in DMEM/HAM's F12 with HEPES (Invitrogen)+0.1% protease-free BSA (assay buffer), and spun down to remove freezing media. After centrifugation, supernatant was removed and 12 mL of assay buffer was added. Coelenterazine h (Promega) was added to the cells at a final concentration of 5 uM and incubated for 4 hours at room temperature in the dark. Compound master plate-96 deep well (Corning) were formatted in a 8-point DRC in assay buffer with 0.2% DMSO at a starting concentration of 60 uM (2×). After 4 hours of incubation, cells were plated at a concentration of 5×10⁵ cells/well in 96 well white-walled, tissue culture-treated, clear-bottom plates (VWR). Compounds were added to the daughter plate, and cells plus compound were incubated at room temperature for 30 minutes in the dark.

Calcium flux was measured using the FlexStation 3 (Molecular Devices). To measure the antagonist dose-response, the EC80 of Acetylcholine was injected to the daughter plate using the automated compound transfer function of the Flex Station, and the increase in luminescence was measured over time. Antagonist activity was analyzed as a concentration dependent decrease in the EC80 acetylcholine response. Dose response curves were generated using Prism (GraphPad Software). The $IC_{50}$ of the compounds was calculated from the dose response curve. Results are shown in Table 1.

TABLE 1

| Example | M1 $IC_{50}$ | M2 $IC_{50}$ | M3 $IC_{50}$ |
|---|---|---|---|
| 1 | A | C | D |
| 2 | C | C | D |
| 3 | D | B | C |
| 4 | A | C | C |
| 5 | D | D | D |
| 6 | A | C | C |
| 7 | C | D | D |
| 8 | A | C | C |
| 9 | D | C | C |
| 10 | C | D | D |
| 11 | B | C | D |
| 12 | B | C | D |
| 13 | B | C | C |
| 14 | B | D | D |
| 15 | B | C | D |
| 16 | B | C | D |
| 17 | B | B | C |
| 18 | A | C | C |
| 19 | A | B | D |
| 20 | B | C | C |
| 21 | A | B | C |
| 22 | B | C | C |
| 23 | A | C | C |
| 24 | A | B | B |
| 25 | A | B | D |
| 26 | B | D | D |
| 27 | A | B | C |
| 28 | A | B | C |
| 29 | A | C | C |
| 30 | B | C | D |
| 31 | A | C | C |
| 32 | B | C | C |
| 33 | A | C | D |
| 34 | A | C | C |
| 35 | A | B | B |
| 36 | A | C | C |
| 37 | A | C | D |
| 38 | A | B | C |
| 39 | A | C | C |
| 40 | A | B | D |
| 41 | A | C | D |
| 42 | A | C | C |
| 43 | B | C | D |
| 44 | A | B | C |
| 45 | B | C | D |
| 46 | B | C | C |
| 47 | C | C | D |
| 48 | B | C | D |
| 49 | B | C | D |
| 50 | C | C | D |
| 51 | B | C | D |
| 52 | B | B | C |
| 53 | C | C | D |
| 54 | B | C | D |
| 55 | A | B | C |
| 56 | B | B | C |
| 57 | B | C | C |
| 58 | C | C | C |
| 59 | A | A | B |

TABLE 1-continued

| Example | M1 $IC_{50}$ | M2 $IC_{50}$ | M3 $IC_{50}$ |
|---|---|---|---|
| 60 | A | B | C |
| 61 | C | C | C |
| 62 | A | B | C |
| 63 | C | B | D |
| 64 | D | C | C |
| 65 | C | C | D |
| 66 | A | B | B |
| 67 | B | D | C |
| 68 | C | D | C |
| 69 | B | D | C |
| 70 | A | B | C |
| 71 | B | B | C |
| 72 | B | C | D |
| 73 | B | C | D |
| 74 | C | D | D |
| 75 | C | C | D |
| 76 | A | C | C |
| 77 | A | C | C |
| 78 | A | C | C |
| 79 | A | A | B |
| 80 | B | C | C |
| 81 | A | B | C |
| 82 | A | C | C |
| 83 | B | C | C |
| 84 | C | D | D |
| 85 | A | C | C |
| 86 | C | C | D |
| 87 | C | C | C |
| 88 | C | C | D |
| 89 | C | D | D |
| 90 | D | C | D |
| 91 | B | C | C |
| 92 | A | B | C |
| 93 | D | D | D |
| 94 | B | B | C |
| 95 | A | A | B |
| 96 | B | C | D |
| 97 | C | C | C |
| 98 | C | C | D |
| 99 | C | C | D |
| 100 | B | D | C |
| 101 | B | C | D |
| 102 | A | C | C |
| 103 | A | B | C |
| 104 | A | C | C |
| 105 | C | C | C |
| 106 | C | C | D |
| 107 | C | D | C |
| 108 | B | D | C |
| 109 | C | D | D |
| 110 | B | D | C |
| 111 | A | C | C |
| 112 | C | D | C |
| 113 | C | C | D |
| 114 | B | C | C |
| 115 | D | D | C |
| 116 | C | C | C |
| 117 | C | D | D |
| 118 | C | D | D |
| 100 | B | D | C |
| 101 | B | C | D |
| 102 | A | C | C |
| 103 | A | B | C |
| 104 | A | C | C |
| 105 | C | C | C |
| 106 | C | C | D |
| 107 | C | D | C |
| 108 | B | D | C |
| 109 | C | D | D |
| 110 | B | D | C |
| 111 | A | C | C |
| 112 | C | D | C |
| 113 | C | C | D |
| 114 | B | C | C |
| 115 | D | D | C |
| 116 | C | C | C |
| 117 | C | D | D |
| 118 | C | D | D |

TABLE 1-continued

| Example | M1 IC$_{50}$ | M2 IC$_{50}$ | M3 IC$_{50}$ |
|---|---|---|---|
| 119 | C | NT | D |
| 120 | B | C | C |
| 121 | A | B | A |
| 122 | A | D | A |
| 123 | C | D | C |
| 124 | A | B | B |
| 125 | A | B | B |
| 126 | B | D | D |
| 127 | A | B | C |
| 128 | A | C | C |
| 129 | B | C | D |
| 130 | A | C | D |
| 131 | B | D | D |
| 132 | A | B | C |
| 133 | A | B | D |
| 134 | B | D | D |
| 135 | A | B | C |
| 136 | A | C | C |
| 137 | C | D | D |
| 138 | B | D | D |
| 139 | B | D | D |
| 140 | A | C | C |
| 141 | B | C | D |
| 142 | C | C | C |
| 143 | A | C | C |
| 144 | A | D | D |
| 145 | A | C | C |
| 146 | A | B | B |
| 147 | A | A | A |
| 148 | B | C | C |
| 149 | A | B | C |
| 150 | B | C | D |
| 151 | C | C | D |
| 152 | A | C | D |
| 153 | A | B | B |
| 154 | A | C | B |
| 155 | C | D | D |
| 156 | B | C | C |
| 157 | A | D | D |
| 158 | B | B | C |
| 159 | A | C | D |
| 160 | B | C | D |
| 161 | B | C | D |
| 162 | B | C | C |
| 163 | B | C | D |
| 164 | A | C | C |
| 165 | B | C | C |
| 166 | B | C | C |
| 167 | A | C | D |
| 168 | B | C | D |
| 169 | B | B | C |
| 170 | B | C | C |
| 171 | B | D | D |
| 172 | C | C | D |
| 173 | B | D | D |
| 174 | B | D | D |
| 175 | B | C | D |
| 176 | B | C | D |
| 177 | A | C | C |
| 178 | B | D | D |
| 179 | A | D | D |
| 180 | A | C | D |
| 181 | A | C | C |
| 182 | C | D | D |
| 183 | A | D | C |
| 184 | A | D | D |
| 185 | B | D | D |
| 186 | A | D | C |
| 187 | B | D | D |
| 188 | C | C | D |
| 189 | B | NT | NT |
| 190 | A | NT | NT |
| 191 | C | NT | NT |
| 192 | B | C | D |
| 193 | C | D | C |
| 194 | A | B | C |
| 195 | C | C | C |
| 196 | C | NT | NT |
| 197 | B | D | D |
| 198 | A | NT | NT |
| 199 | A | NT | NT |
| 200 | NT | NT | NT |

A = IC$_{50}$ of less than 100 nM; B = IC$_{50}$ less than 1 uM (1000 nM) but greater than or equal to 100 nM; C = IC$_{50}$ less than 10 uM (10000 nM) but greater than or equal to 1 uM (1000 nM); D = IC$_{50}$ greater than 10 uM (10000 nM); NT = not tested.

We claim:

1. A compound of Formula (I'):

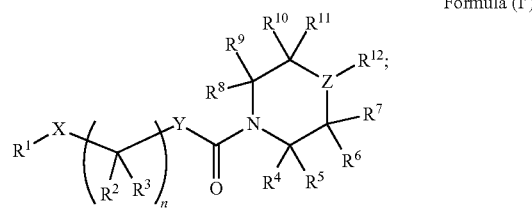

Formula (I')

wherein:
X is —CH$_2$CH$_2$—, —CH$_2$O—, —CH$_2$CH$_2$O—, —O—, —N(R$^{14}$)—, S(O)$_2$, —CH$_2$N(R$^{14}$)—, or —CH$_2$CH$_2$N(R$^{14}$)—;
Y is a bond, —C(R$^{16}$)(R$^{17}$)—, or —N(R$^{15}$)—;
Z is —N— or —C(H)—;
R$^1$ is

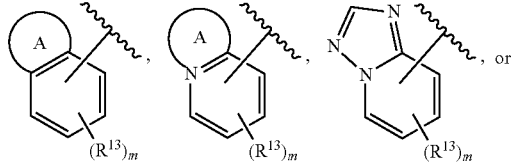

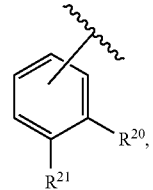

wherein ring A is a heteroaryl ring optionally substituted with halogen, —CN, —N(R$^{22}$)$_2$, C$_{1-6}$alkyl, C$_{1-6}$alkyl-OH, C$_{1-6}$alkoxy, C$_{1-6}$ haloalkyl, or C$_{1-6}$ haloalkoxy, wherein the heteroaryl ring contains 1 or 2 heteroatoms selected from the group consisting of O, N, or S;
  each R$^2$ is independently selected from H, halogen, and C$_{1-6}$alkyl;
  each R$^3$ is independently selected from H, halogen, and C$_{1-6}$alkyl;
  R$^4$, R$^6$, R$^8$, and R$^{10}$ are each independently selected from H and C$_{1-6}$alkyl;
  R$^5$, R$^7$, R$^9$, and R$^{11}$ are each independently selected from H and C$_{1-6}$alkyl; and wherein: (i) R$^7$ and R$^{11}$ combine to form a bridged C$_{3-15}$cycloalkyl or bridged 3 to 18 membered heterocycloalkyl; or (ii) R$^5$ and R$^9$ combine to form a bridged C$_{3-15}$cycloalkyl or bridged 3 to 18 membered heterocycloalkyl; or (iii) R$^7$ and R$^9$ combine to form a bridged C$_{4-15}$cycloalkyl or bridged 4 to 18 membered heterocycloalkyl;

271

$R^{12}$ is

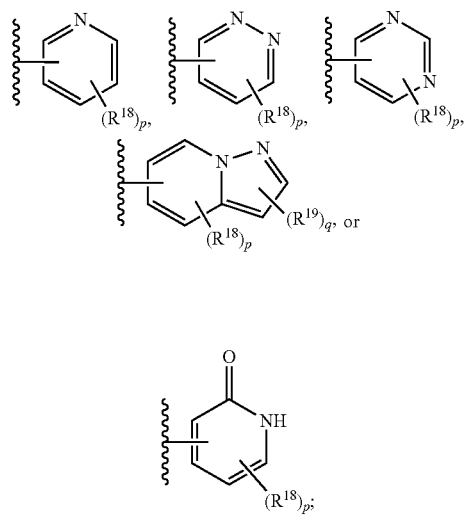

each $R^{13}$ is independently selected from halogen, —CN, $C_{1-6}$ alkyl, $C_{1-6}$alkoxy, $C_{1-6}$haloalkyl, and $C_{1-6}$ haloalkoxy;

$R^{14}$ is H, $C_{1-6}$ alkyl, $C_{3-6}$ cycloalkyl, or $C_{2-9}$ heterocycloalkyl; or $R^{14}$ and one $R^3$ combine to form a 4-, 5-, or 6-membered heterocycloalkyl ring;

$R^{15}$ is H or $C_{1-6}$ alkyl; or $R^{15}$ and one $R^3$ combine to form a 4-, 5-, or 6-membered heterocycloalkyl ring;

$R^{16}$ is H or $C_{1-6}$ alkyl;

$R^{17}$ is H or $C_{1-6}$ alkyl; or $R^{17}$ and one $R^3$ combine to form a 3-, 4-, 5-, or 6-membered cycloalkyl ring;

each $R^{18}$ and each $R^{19}$ is independently selected from halogen, —CN, —N($R^{22}$)$_2$, $C_{1-6}$ alkyl, $C_{3-6}$ cycloalkyl, hydroxy, $C_{1-6}$ alkoxy, $C_{1-6}$ haloalkyl, $C_{1-6}$ haloalkoxy, and phenyl;

$R^{20}$ and $R^{21}$ combine to form a 5- or 6-membered cycloalkyl ring or a 5-membered heterocycloalkyl ring;

each $R^{22}$ is independently selected from H and $C_{1-6}$alkyl;

m is 0, 1, 2, or 3;

n is 1, 2, 3, 4, or 5;

p is 0, 1, 2, or 3; and q is 0, 1, or 2;

or a pharmaceutically acceptable salt or solvate thereof.

2. A compound of Formula (I):

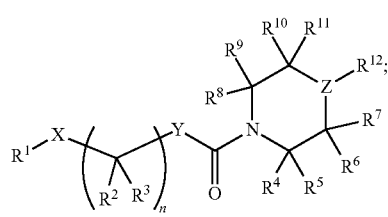

Formula (I)

wherein:

X is —CH$_2$CH$_2$—, —CH$_2$O—, —CH$_2$CH$_2$O—, —O—, —N($R^{14}$)—, S(O)$_2$, —CH$_2$N($R^{14}$)—, or —CH$_2$CH$_2$N($R^{14}$)—;

Y is a bond, —C($R^{16}$)($R^{17}$)—, or —N($R^{15}$)—;

Z is —N— or —C(H)—;

272

$R^1$ is

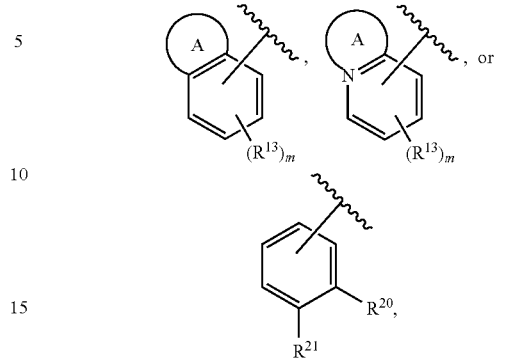

wherein ring A is a heteroaryl ring optionally substituted with halogen, —CN, —N($R^{22}$)$_2$, $C_{1-6}$alkyl, $C_{1-6}$alkyl-OH, $C_{1-6}$alkoxy, $C_{1-6}$haloalkyl, or $C_{1-6}$ haloalkoxy, wherein the heteroaryl ring contains 1 or 2 heteroatoms selected from the group consisting of O, N, or S;

each $R^2$ is independently selected from H and $C_{1-6}$alkyl;

each $R^3$ is independently selected from H and $C_{1-6}$alkyl;

$R^4$, $R^6$, $R^8$, and $R^{10}$ are each independently selected from H and $C_{1-6}$alkyl;

$R^5$, $R^7$, $R^9$, and $R^{11}$ are each independently selected from H and $C_{1-6}$alkyl; and wherein: (i) $R^7$ and $R^{11}$ combine to form a bridged $C_{3-15}$cycloalkyl or bridged 3 to 18 membered heterocycloalkyl; or (ii) $R^5$ and $R^9$ combine to form a bridged $C_{3-15}$cycloalkyl or bridged 3 to 18 membered heterocycloalkyl; or (iii) $R^7$ and $R^9$ combine to form a bridged $C_{4-15}$cycloalkyl or bridged 4 to 18 membered heterocycloalkyl;

$R^{12}$ is

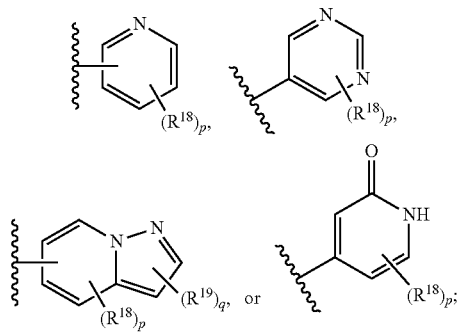

each $R^{13}$ is independently selected from halogen, —CN, $C_{1-6}$ alkyl, $C_{1-6}$alkoxy, $C_{1-6}$haloalkyl, and $C_{1-6}$ haloalkoxy;

$R^{14}$ is H or $C_{1-6}$alkyl; or $R^{14}$ and one $R^3$ combine to form a 4-, 5-, or 6-membered heterocycloalkyl ring;

$R^{15}$ is H or $C_{1-6}$alkyl; or $R^{15}$ and one $R^3$ combine to form a 4-, 5-, or 6-membered heterocycloalkyl ring;

$R^{16}$ is H or $C_{1-6}$alkyl;

$R^{17}$ is H or $C_{1-6}$alkyl; or $R^{17}$ and one $R^3$ combine to form a 3-, 4-, 5-, or 6-membered cycloalkyl ring;

each $R^{18}$ and each $R^{19}$ is independently selected from halogen, —CN, $C_{1-6}$alkyl, hydroxy, $C_{1-6}$ alkoxy, $C_{1-6}$haloalkyl, and $C_{1-6}$haloalkoxy;

$R^{20}$ and $R^{21}$ combine to form a 5- or 6-membered cycloalkyl ring or a 5-membered heterocycloalkyl ring;

each $R^{22}$ is independently selected from H and $C_{1-6}$alkyl;
m is 0, 1, 2, or 3;
n is 1, 2, 3, 4, or 5;
p is 0, 1, 2, or 3; and
q is 0, 1, or 2;
or a pharmaceutically acceptable salt or solvate thereof.

3. The compound of claim 1, or a pharmaceutically acceptable salt or solvate thereof, wherein $R^1$ is

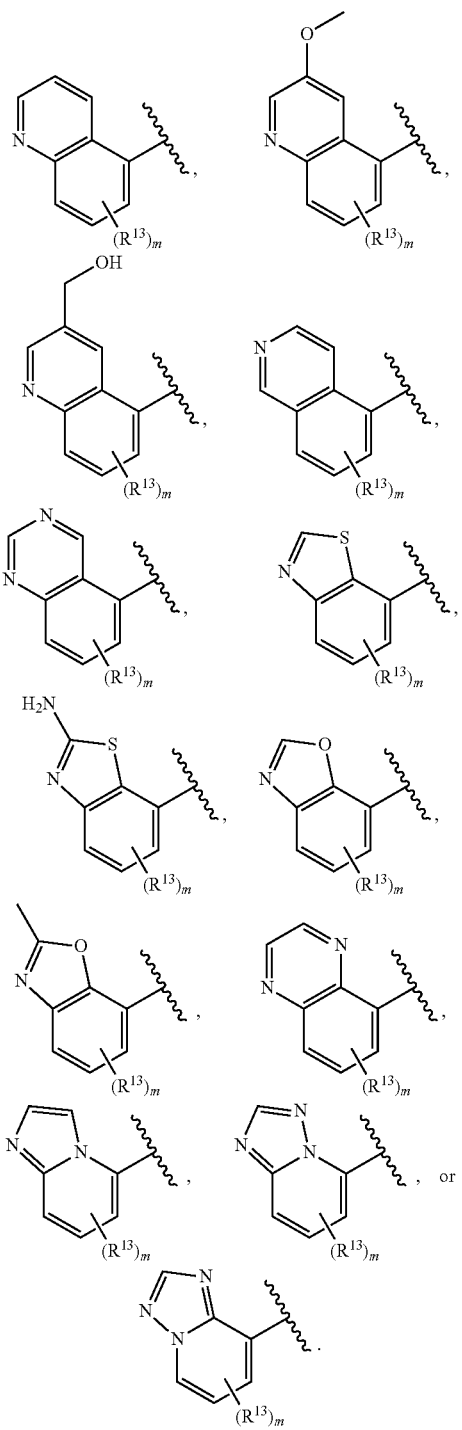

4. The compound of claim 1, or a pharmaceutically acceptable salt or solvate thereof, wherein m is 0.

5. The compound of claim 1, or a pharmaceutically acceptable salt or solvate thereof, having the structure of Formula (Ia) or Formula (Ib):

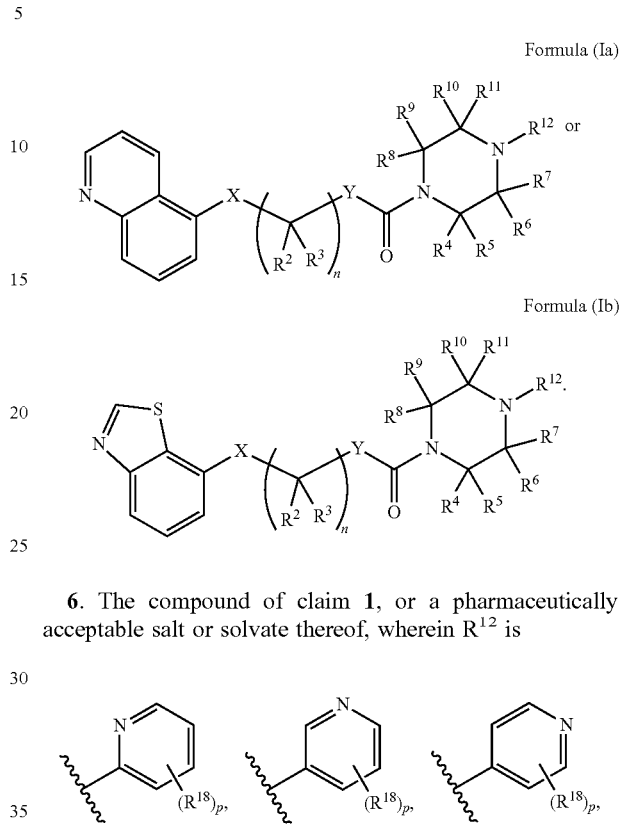

6. The compound of claim 1, or a pharmaceutically acceptable salt or solvate thereof, wherein $R^{12}$ is

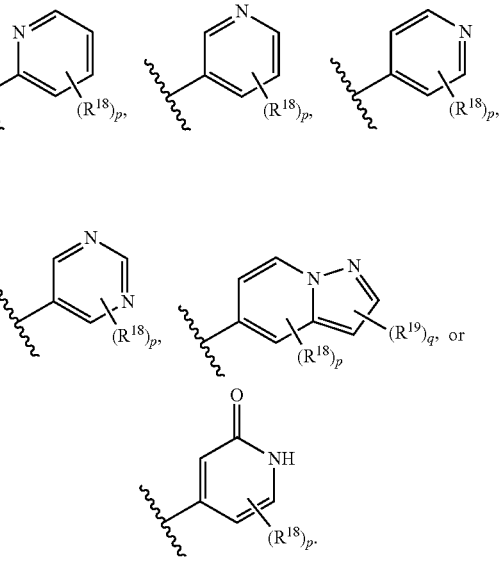

7. A compound of Formula (II):

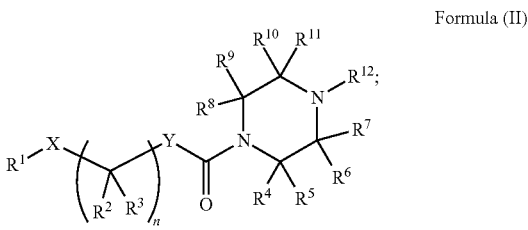

Formula (II)

wherein:
X is —CH₂CH₂—, —CH₂O—, —CH₂CH₂O—, —O—, —N(R¹⁴)—, —S(O)₂—, —CH₂N(R¹⁴)—, or —CH₂CH₂N(R¹⁴)—;
Y is a bond, —C(R¹⁶)(R¹⁷)—, or —N(R¹⁵)—;
Z is —N— or —C(H)—;
R¹ is

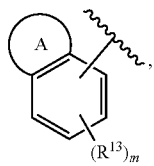

wherein ring A is a heteroaryl ring optionally substituted with halogen, —CN, —N(R²²)₂, C₁₋₆alkyl, C₁₋₆alkyl-OH, C₁₋₆ alkoxy, C₁₋₆haloalkyl, or C₁₋₆haloalkoxy, wherein the heteroaryl ring contains 1 nitrogen atom and 0 or 1 oxygen or sulfur atoms;

each R² is independently selected from H and C₁₋₆alkyl;
each R³ is independently selected from H and C₁₋₆alkyl;
R⁴, R⁶, R⁸, and R¹⁰ are each independently selected from H and C₁₋₆alkyl;
R⁵, R⁷, R⁹, and R¹¹ are each independently selected from H and C₁₋₆alkyl; and wherein: (i) R⁷ and R¹¹ combine to form a bridged C₃₋₁₅cycloalkyl or bridged 3 to 18 membered heterocycloalkyl; or (ii) R⁵ and R⁹ combine to form a bridged C₃₋₁₅cycloalkyl or bridged 3 to 18 membered heterocycloalkyl; or (iii) R⁷ and R⁹ combine to form a bridged C₄₋₁₅cycloalkyl or bridged 4 to 18 membered heterocycloalkyl;
R¹² is

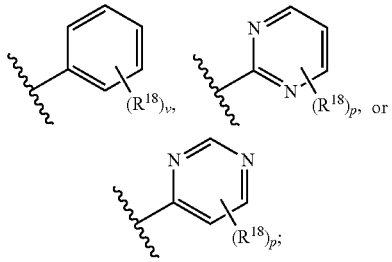

each R¹³ is independently selected from halogen, —CN, C₁₋₆ alkyl, C₁₋₆alkoxy, C₁₋₆haloalkyl, and C₁₋₆ haloalkoxy;
R¹⁴ is H or C₁₋₆alkyl; or R¹⁴ and one R³ combine to form a 4-, 5-, or 6-membered heterocycloalkyl ring;
R¹⁵ is H or C₁₋₆alkyl; or R¹⁵ and one R³ combine to form a 4-, 5-, or 6-membered heterocycloalkyl ring;
R¹⁶ is H or C₁₋₆alkyl;
R¹⁷ is H or C₁₋₆alkyl; or R¹⁷ and one R³ combine to form a 3-, 4-, 5-, or 6-membered cycloalkyl ring;
each R¹⁸ is independently selected from halogen, —CN, C₁₋₆ alkyl, C₁₋₆alkoxy, C₁₋₆haloalkyl, and C₁₋₆ haloalkoxy;
each R²² is independently selected from H and C₁₋₆alkyl;
m is 0, 1, 2, or 3;
n is 1, 2, 3, 4, or 5;
p is 0, 1, 2, or 3; and
v is 0, 1, 2, 3, 4, or 5;
or a pharmaceutically acceptable salt or solvate thereof.

8. The compound of claim 7, or a pharmaceutically acceptable salt or solvate thereof, wherein R¹ is

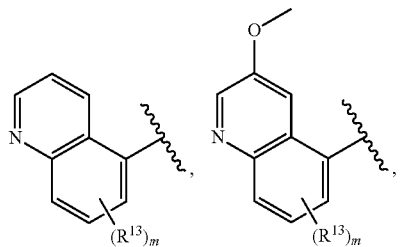

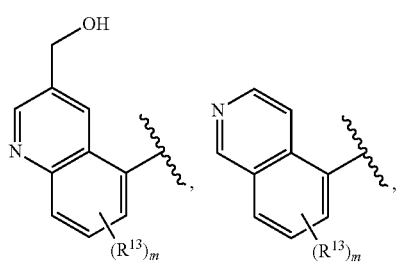

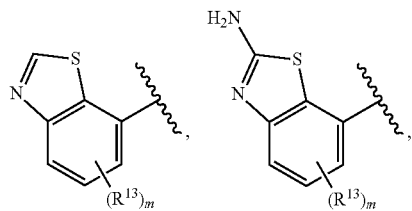

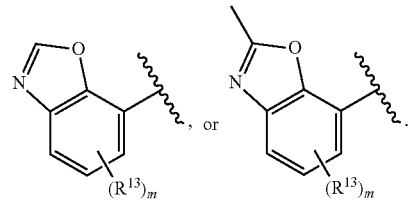

9. The compound of claim 7, or a pharmaceutically acceptable salt or solvate thereof, having the structure of Formula (IIa) or Formula (IIb):

Formula (IIa)

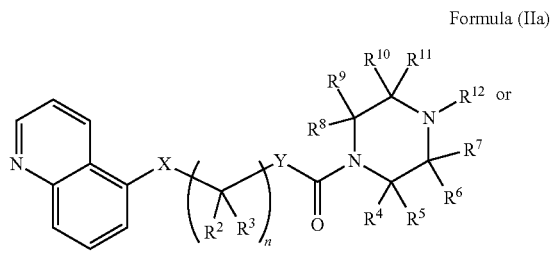

Formula (IIb)

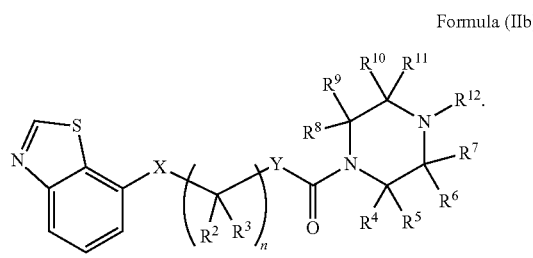

10. The compound of claim 1, or a pharmaceutically acceptable salt or solvate thereof, wherein (a) X is —CH₂CH₂—, —CH₂O—, —CH₂N(H)—, or —S(O)₂—; and (b) Y is a bond.

11. The compound of claim 1, or a pharmaceutically acceptable salt or solvate thereof, wherein each $R^2$ and each $R^3$ is H.

12. The compound of claim 1, or a pharmaceutically acceptable salt or solvate thereof, wherein
   (a) X is —O—, Y is —C($R^{16}$)($R^{17}$)—, and $R^{17}$ and one $R^3$ combine to form a 3- or 4-membered cycloalkyl ring;
   (b) X is —N($R^{14}$)—; Y is bond; and $R^{14}$ and one $R^3$ combine to form a 4-, 5-, or 6-membered heterocycloalkyl ring; or
   (c) X is —O—; Y is —N($R^{15}$)—; and $R^{15}$ and one $R^3$ combine to form a 4-, 5-, or 6-membered heterocycloalkyl ring.

13. The compound of claim 1, or a pharmaceutically acceptable salt or solvate thereof, wherein
   (a) $R^4$, $R^6$, $R^8$, and $R^{10}$ are H;
   (b) $R^5$ and $R^9$ are H, and $R^7$ and $R^{11}$ combine to form a bridged $C_{3-15}$cycloalkyl or bridged 3 to 18 membered heterocycloalkyl;
   (c) $R^5$ and $R^{11}$ are H, and $R^7$ and $R^9$ combine to form a bridged $C_{4-15}$cycloalkyl or bridged 4 to 18 membered heterocycloalkyl; or
   (d) $R^7$ and $R^{11}$ are H, and $R^5$ and $R^9$ combine to form a bridged $C_{3-15}$cycloalkyl or bridged 3 to 18 membered heterocycloalkyl.

14. A compound selected from:

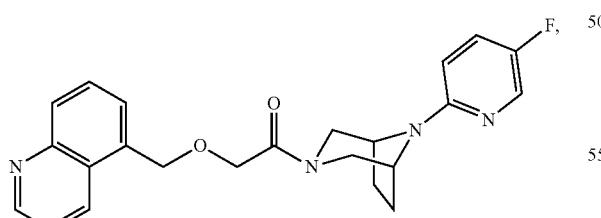

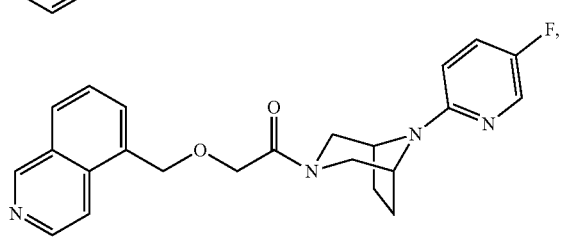

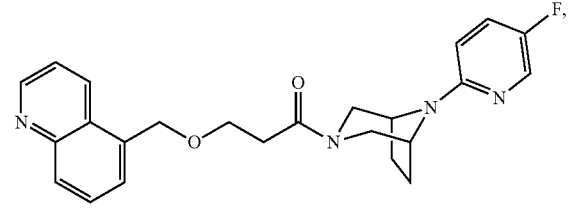

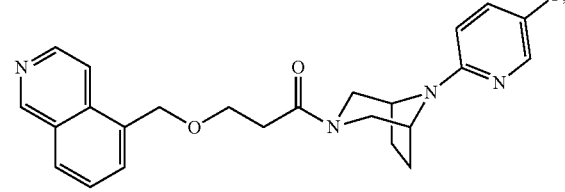

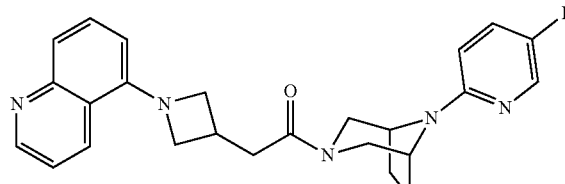

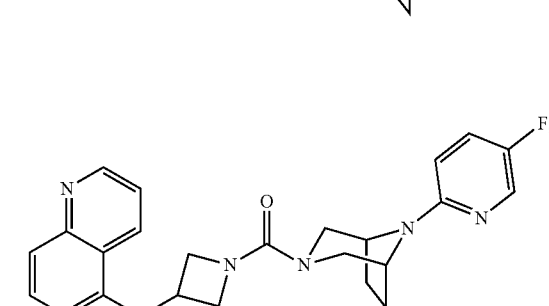

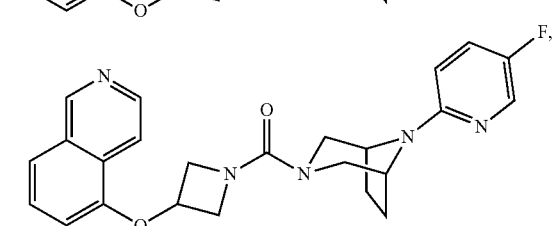

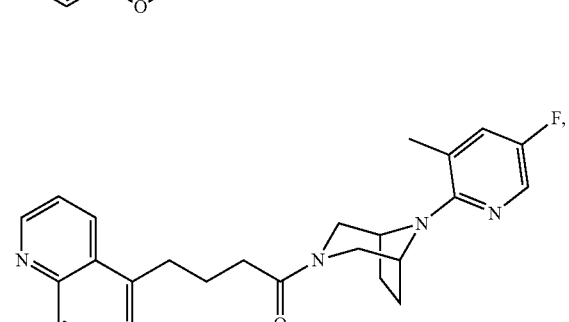

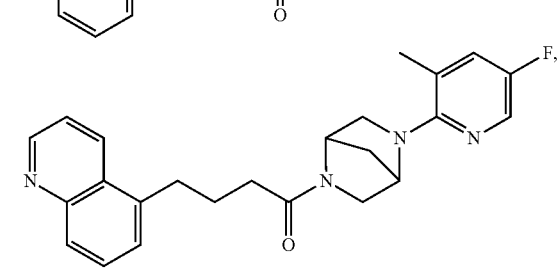

279  280
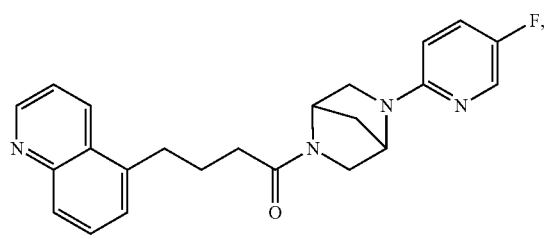 [SMILES: O=C(CCCc1cccc2ncccc12)N1CC2CC1CN2c1ccc(F)cn1]
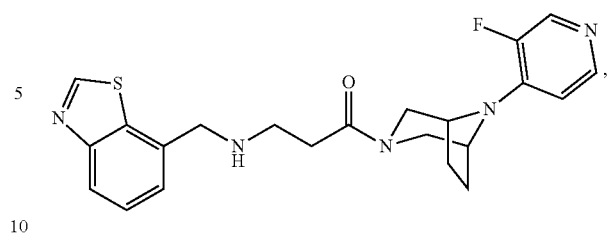
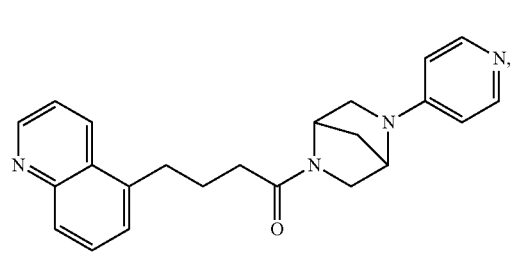 [SMILES: O=C(CCCc1cccc2ncccc12)N1CC2CC1CN2c1ccncc1]
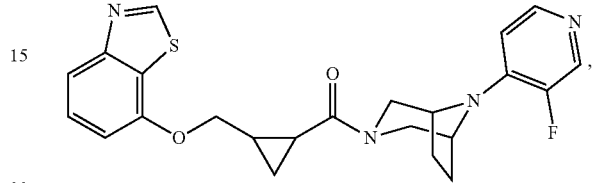
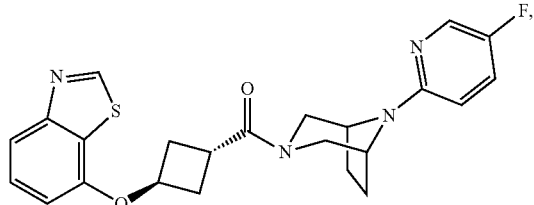
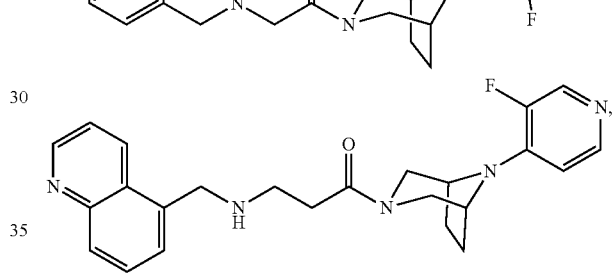
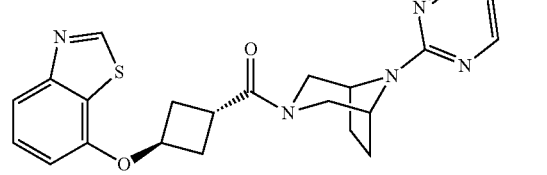
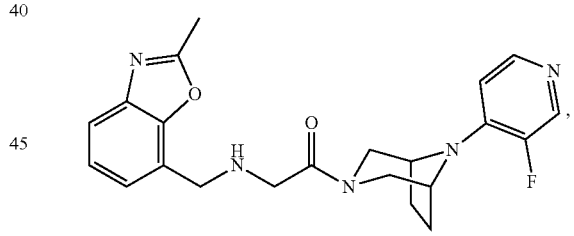
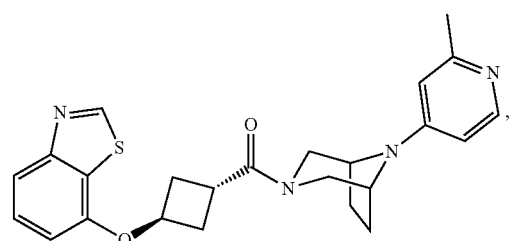
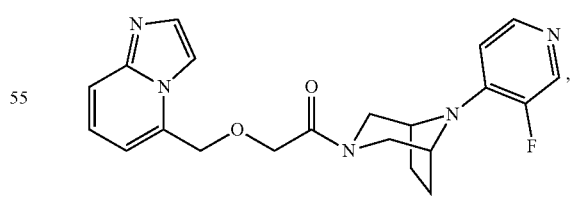
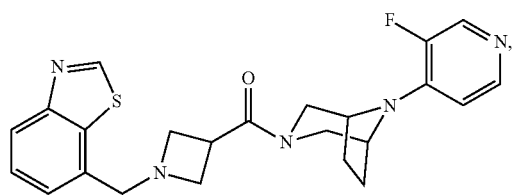 [SMILES: O=C(C1CN(Cc2cccc3ncsc23)C1)N1CC2CCC(C1)N2c1ccncc1F]
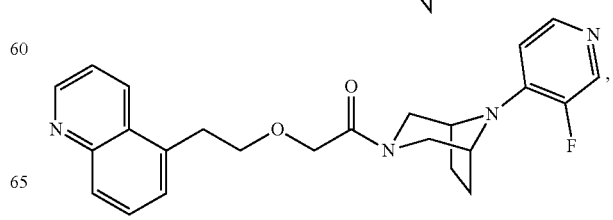

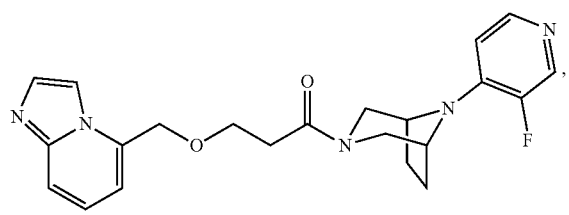
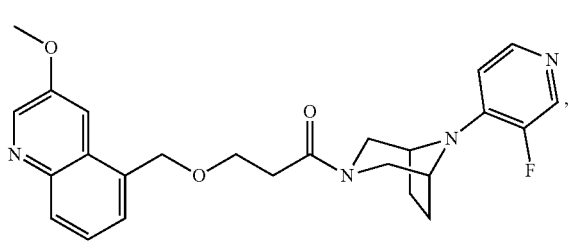 [SMILES: COc1cnc2cccc(COCCC(=O)N3CC4CCC(C3)N4c3ccncc3F)c2c1]
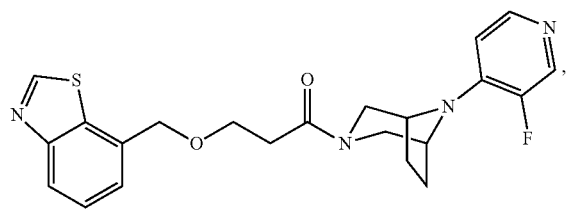 [SMILES: O=C(CNCCc1cccc2ncsc12)N1CC2CCC(C1)N2c1ccncc1F]
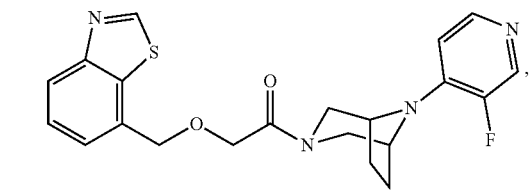
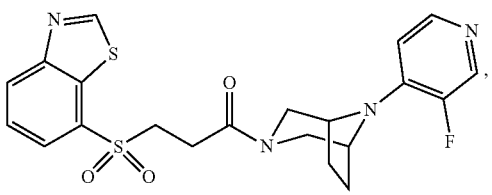 [SMILES: O=C(CCS(=O)(=O)c1cccc2ncsc12)N1CC2CCC(C1)N2c1ccncc1F]
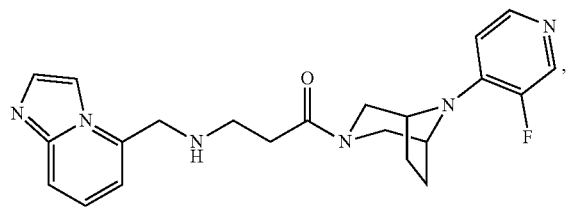
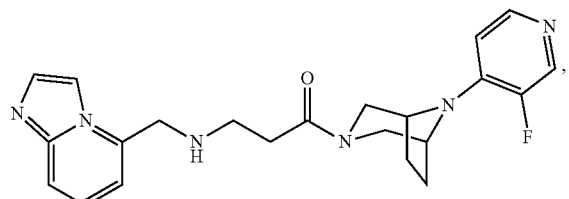
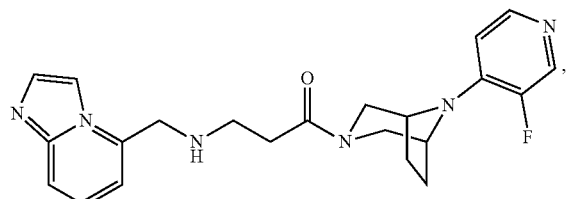
and
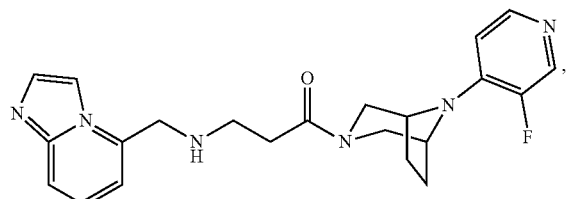
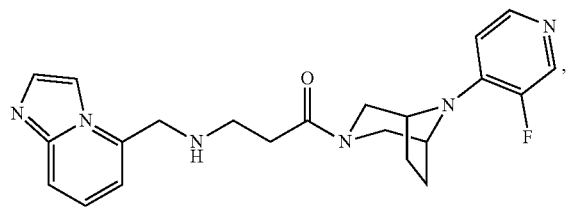
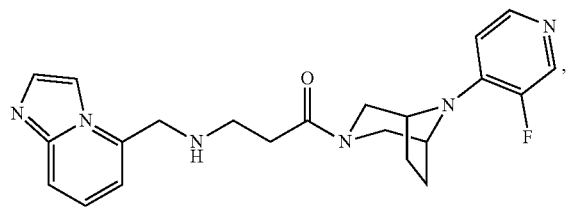
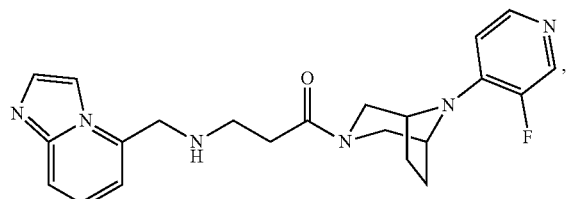
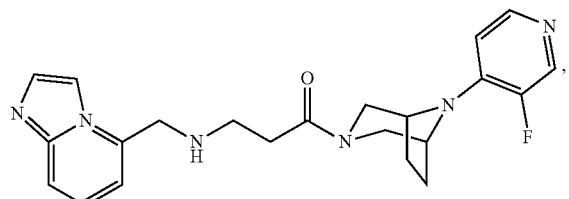
or a pharmaceutically acceptable salt or solvate thereof.
15. A compound selected from:
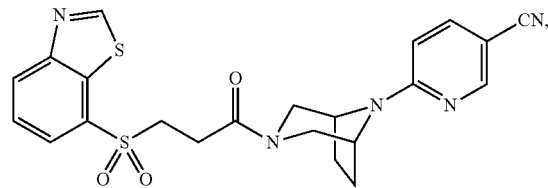 [SMILES: N#Cc1ccc(N2C3CCC2CN(C(=O)CCS(=O)(=O)c2cccc4ncsc24)C3)nc1]
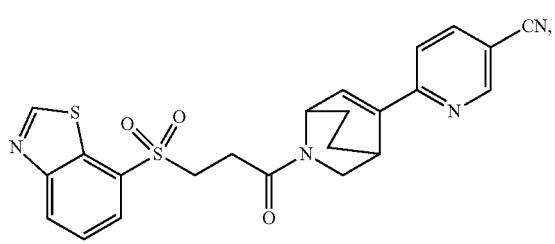

283
-continued
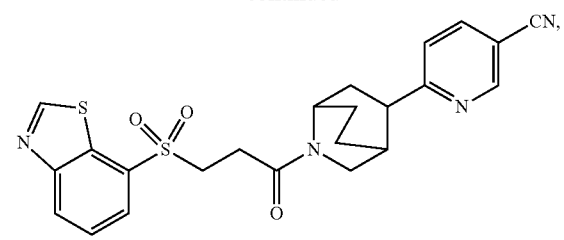
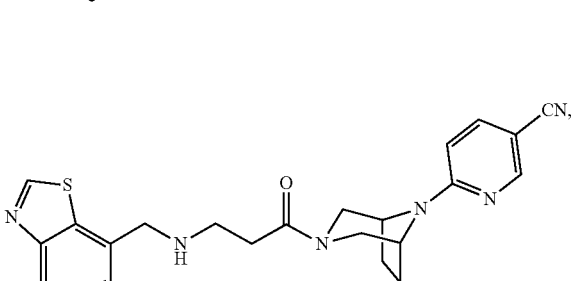
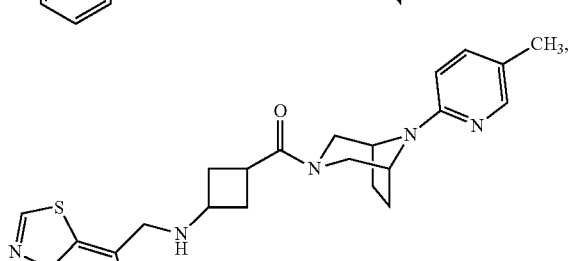
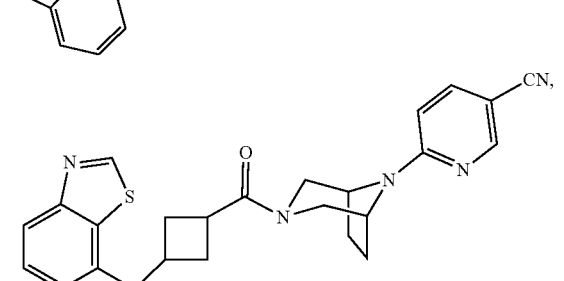
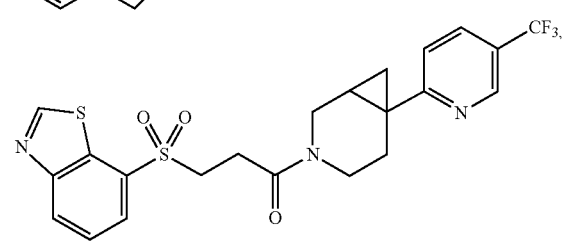
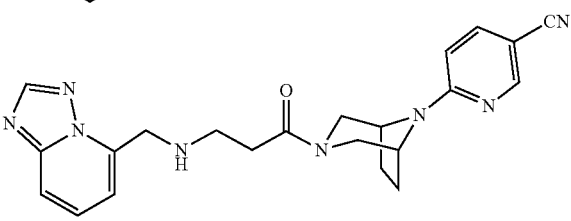
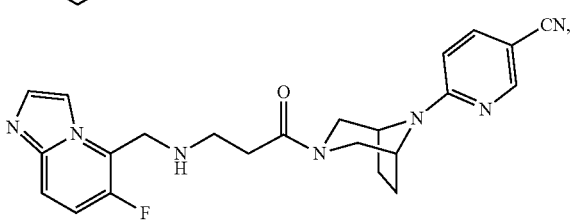
284
-continued
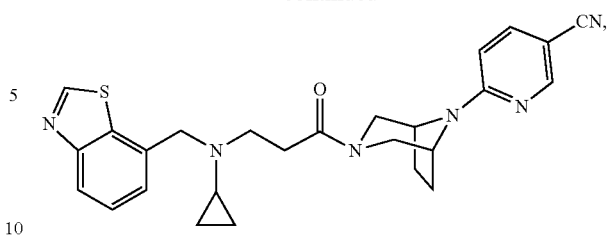
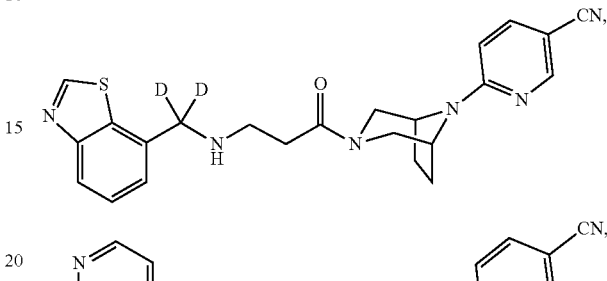
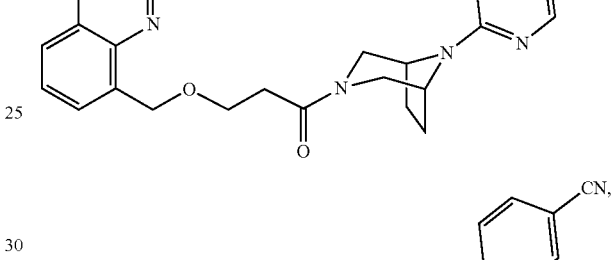
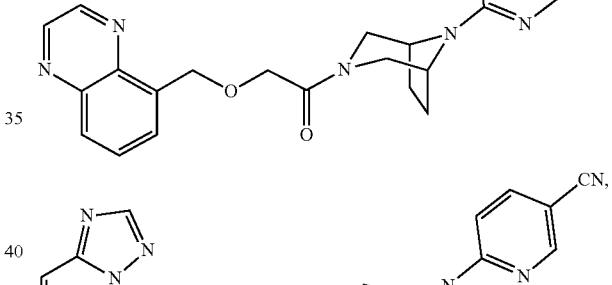
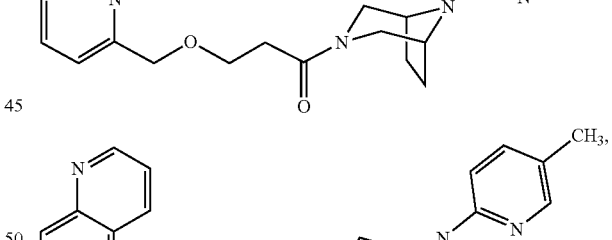
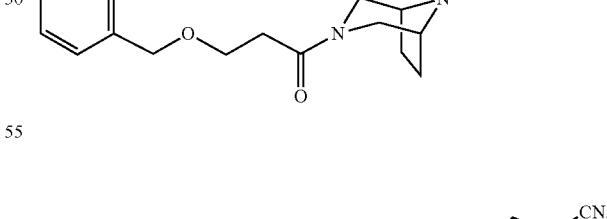
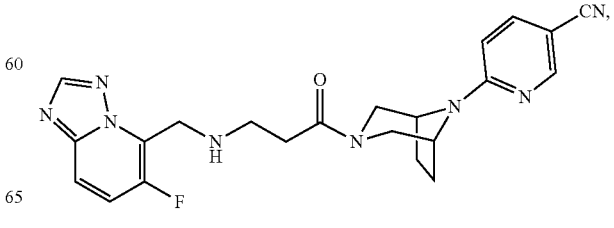

285
-continued
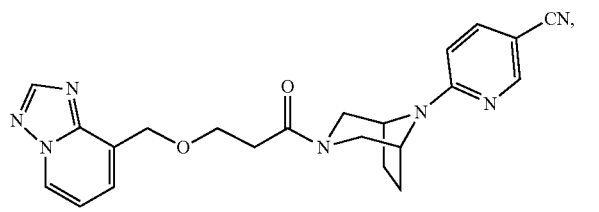
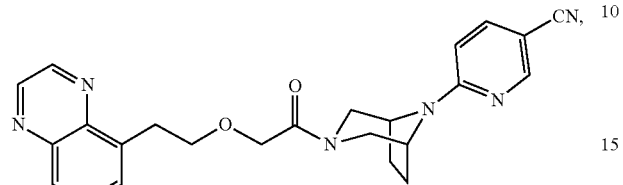
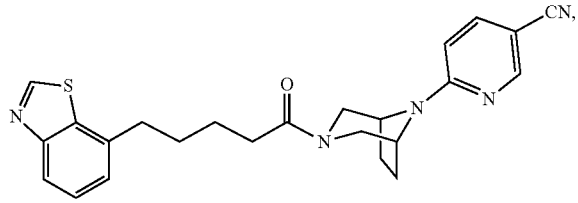
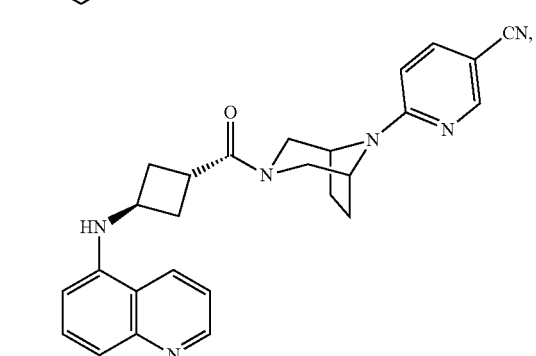
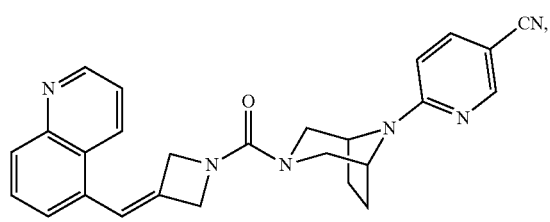 [SMILES: N#Cc1ccc(N2C3CCC2CN(C(=O)N2CC(=Cc4cccc5ncccc45)C2)C3)nc1]
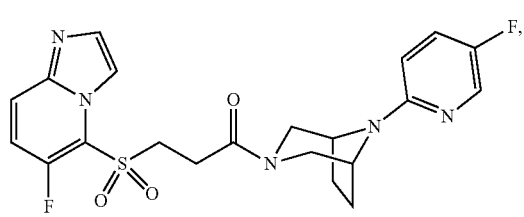
286
-continued
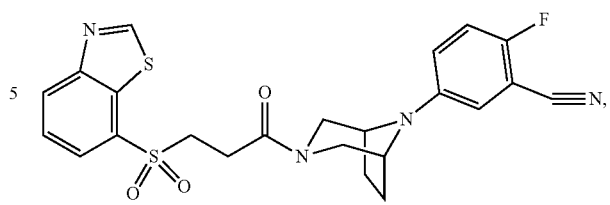
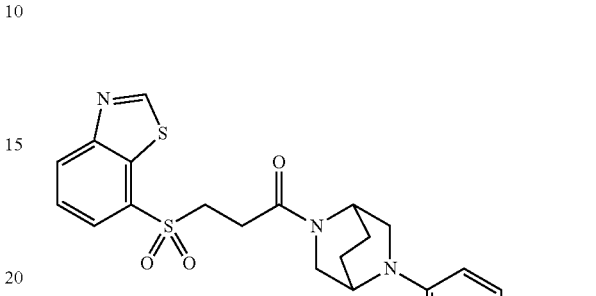
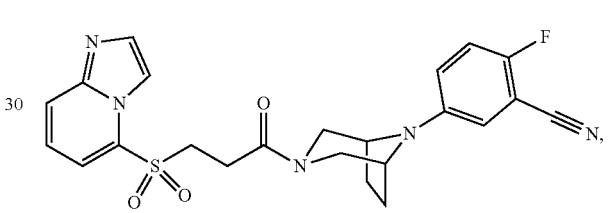
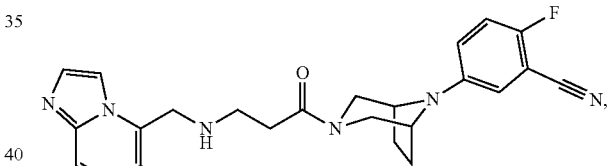
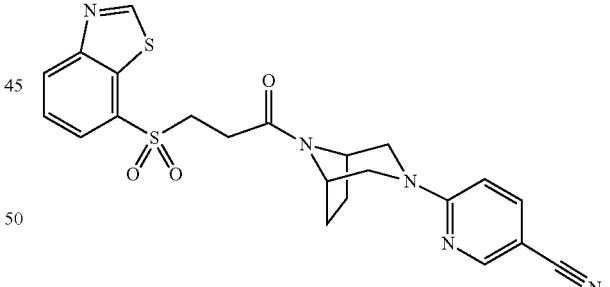
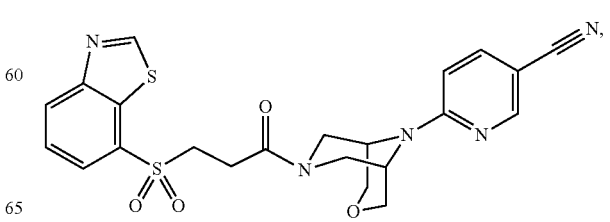

287 288
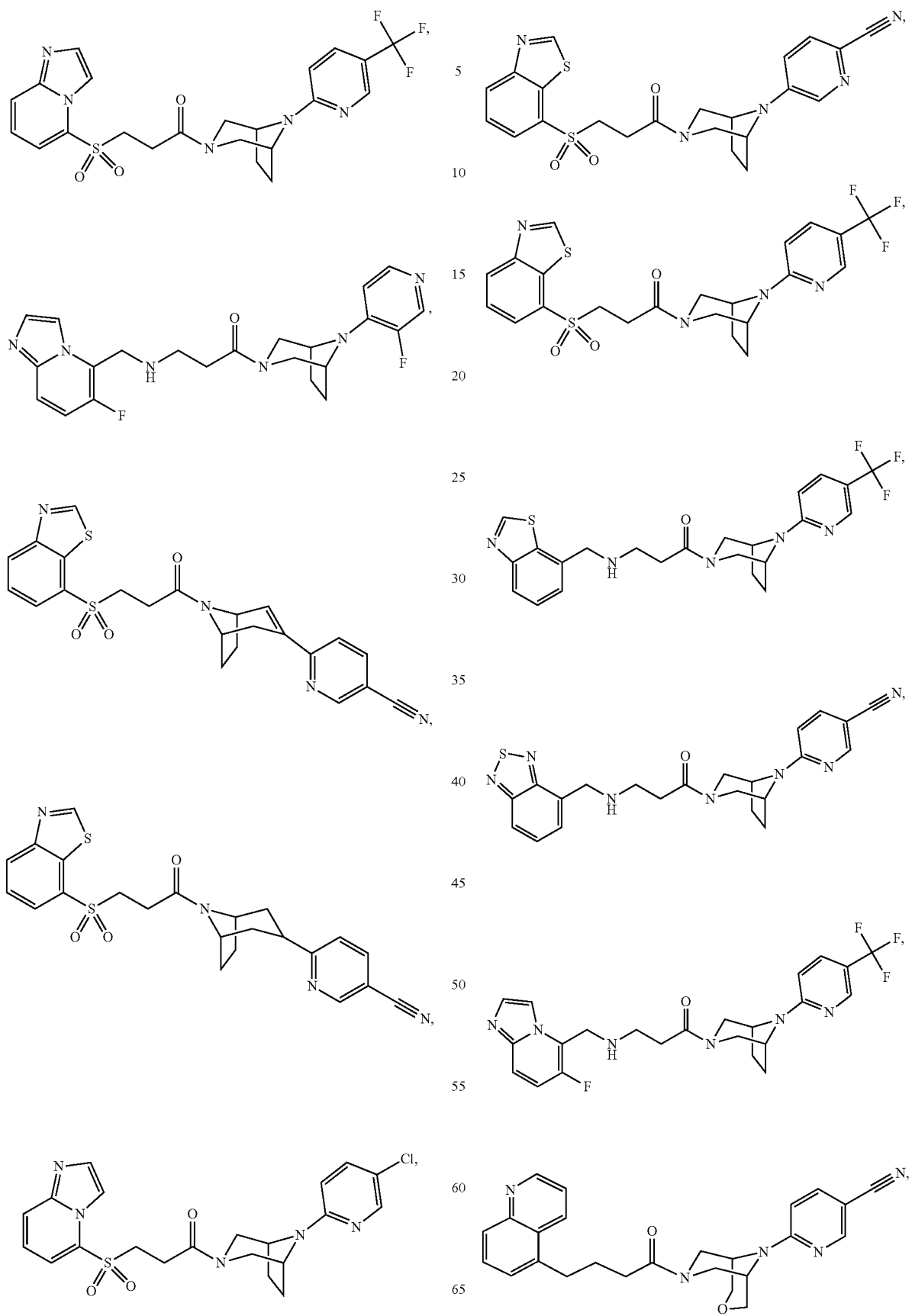

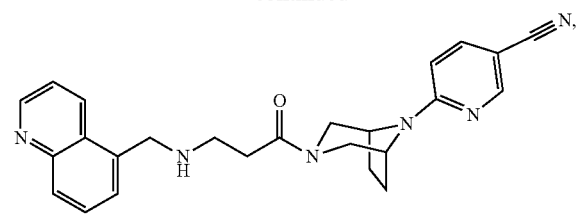
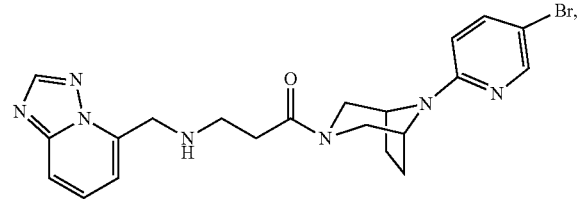
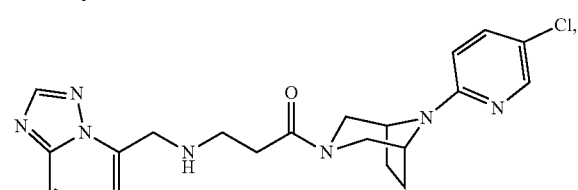
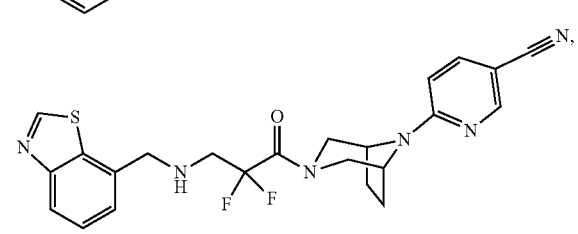
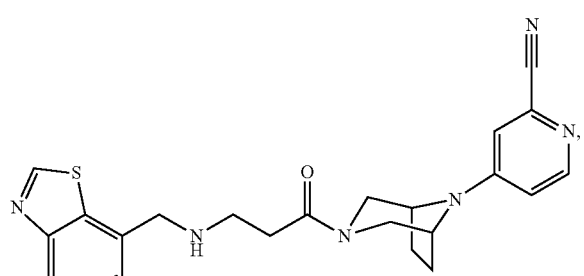
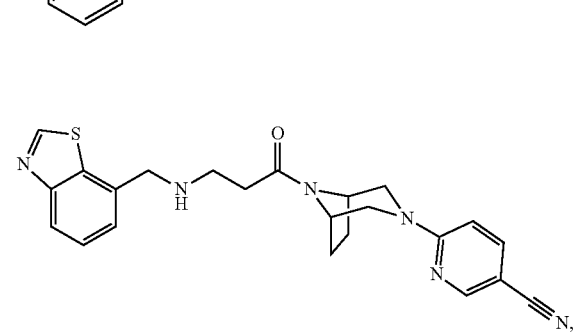
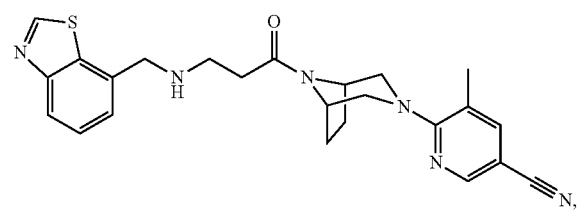
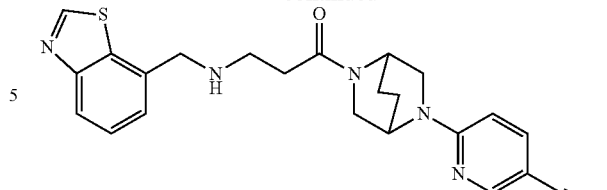
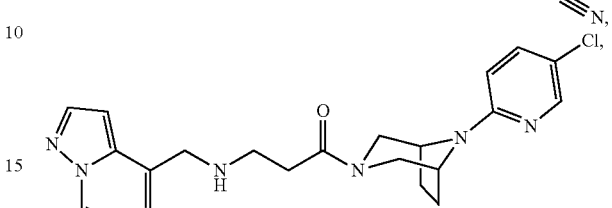
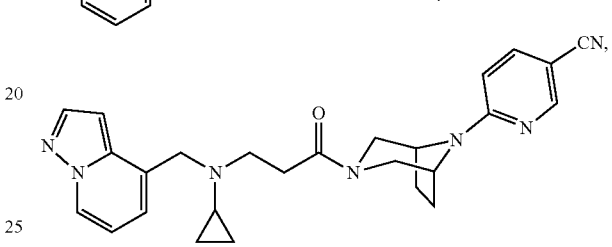
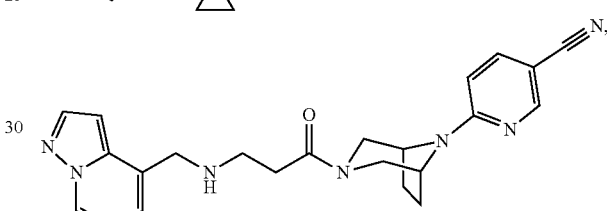
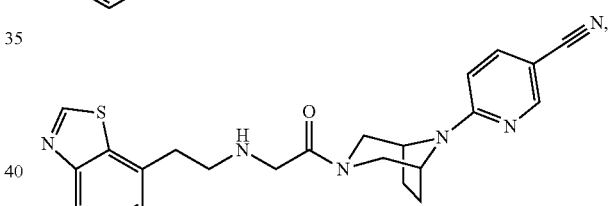
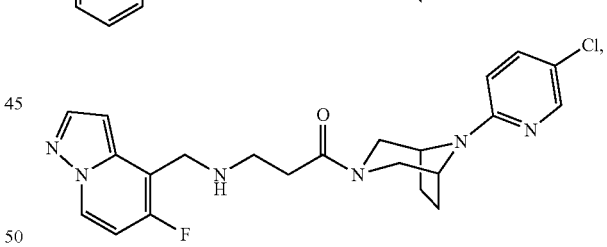
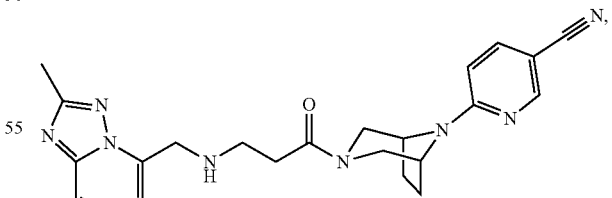
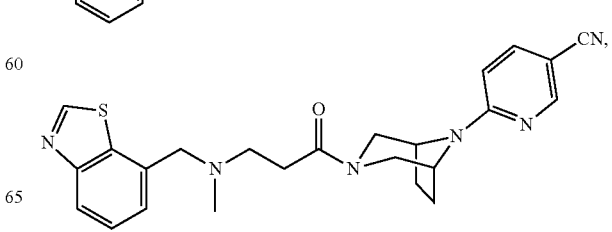

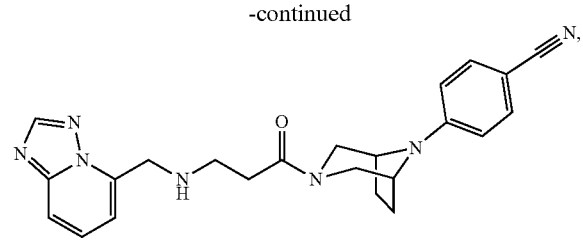
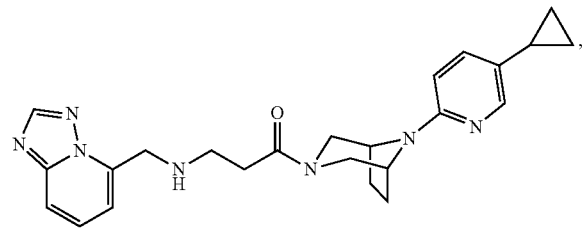
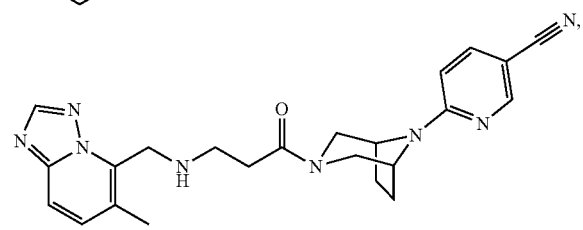
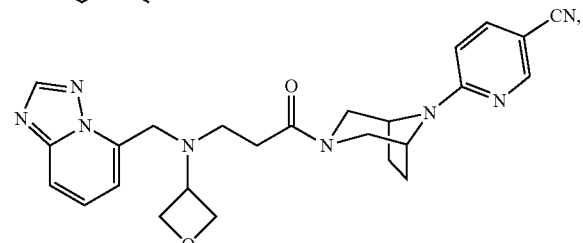
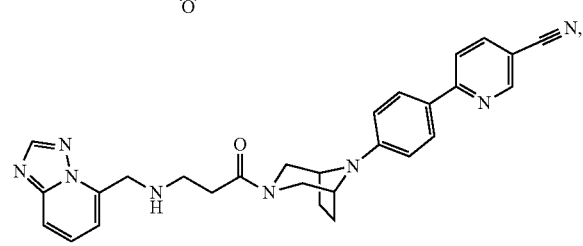
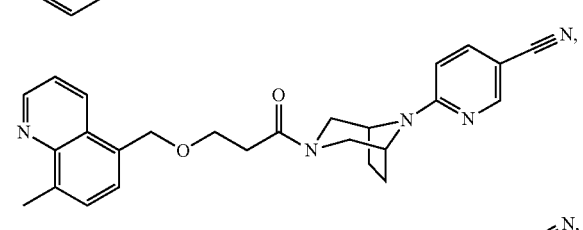
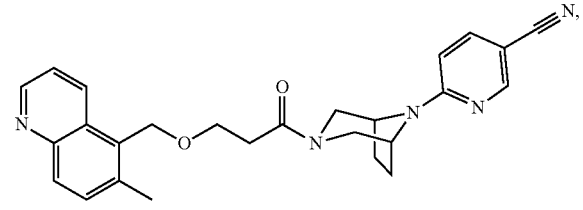
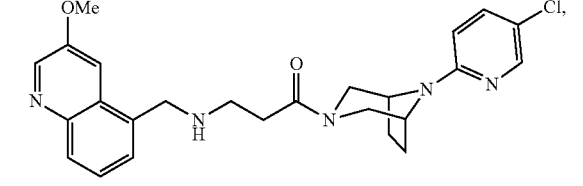
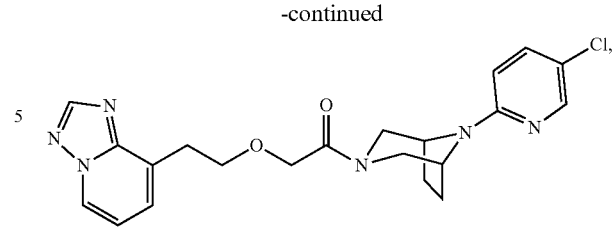
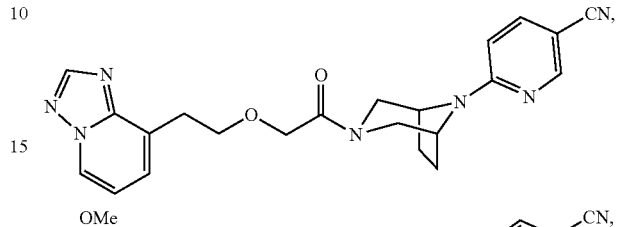
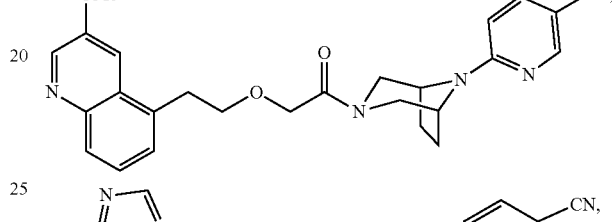
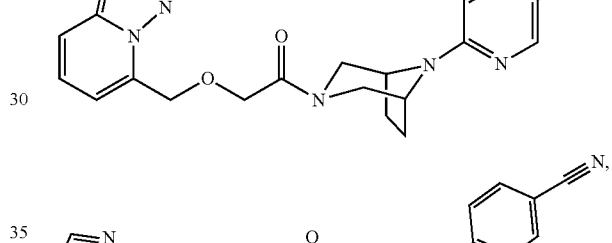
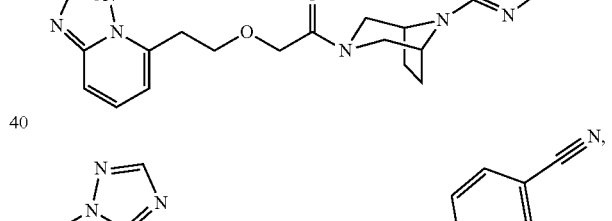
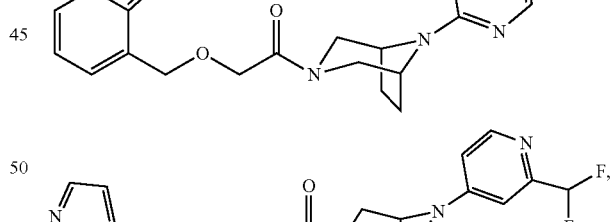
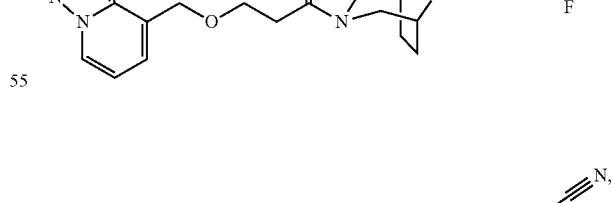
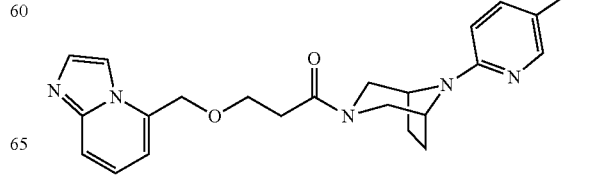

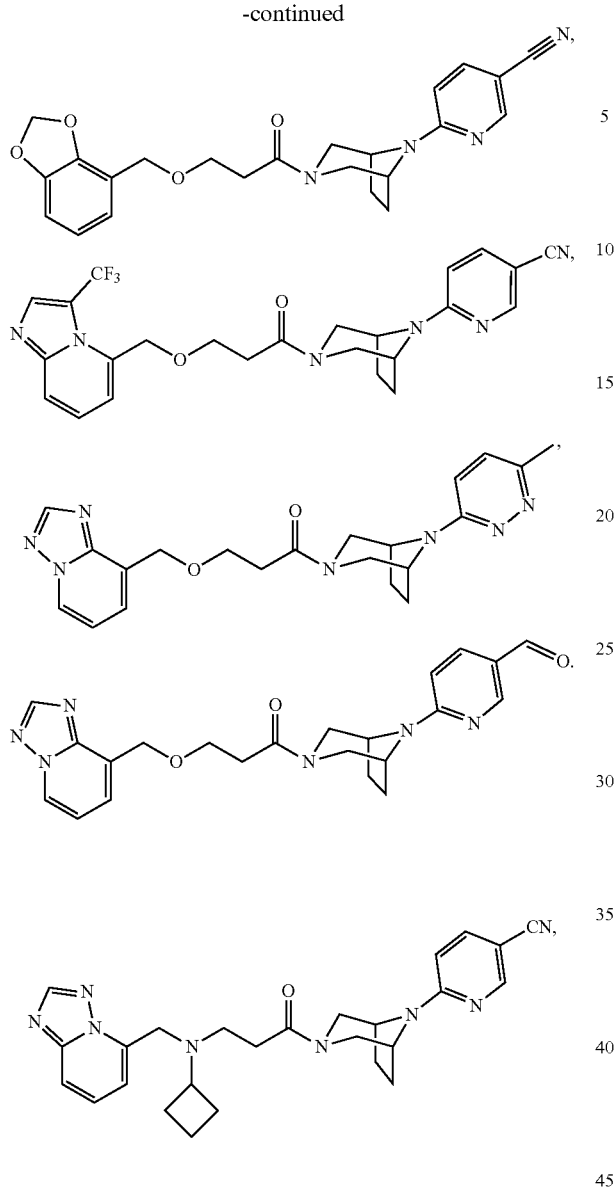

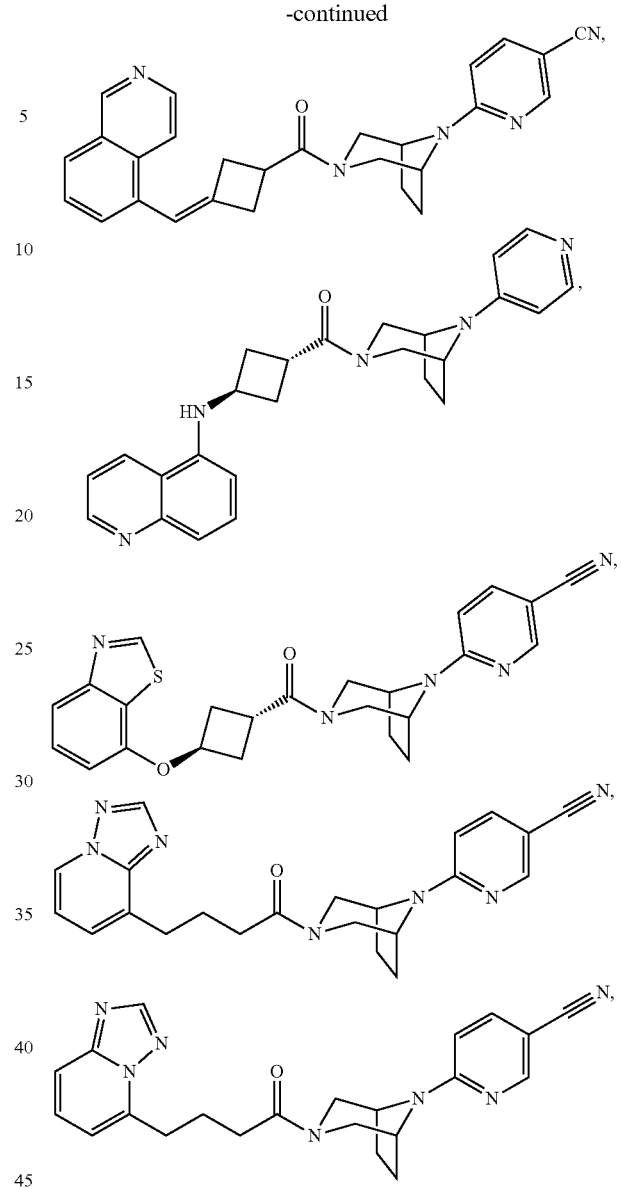

and

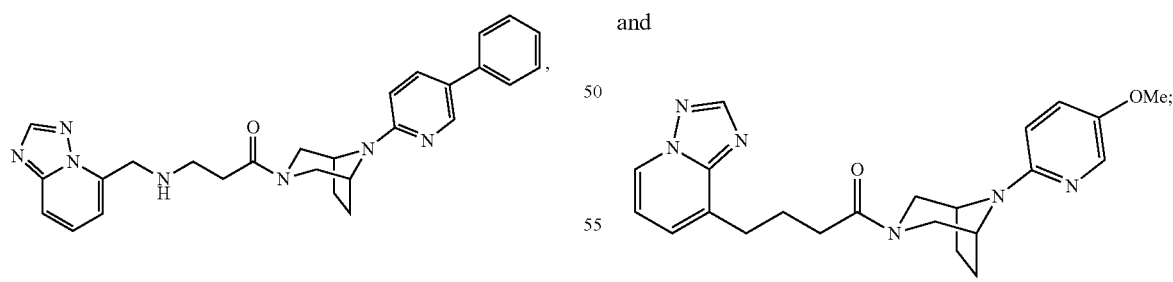

or a pharmaceutically acceptable salt or solvate thereof.

16. A pharmaceutical composition comprising a compound of claim 1, or a pharmaceutically acceptable salt or solvate thereof, and at least one pharmaceutically acceptable excipient.

17. A method of treating multiple sclerosis, Parkinson's disease, dystonia, and fragile X syndrome in a subject in need thereof, comprising administering to the subject a

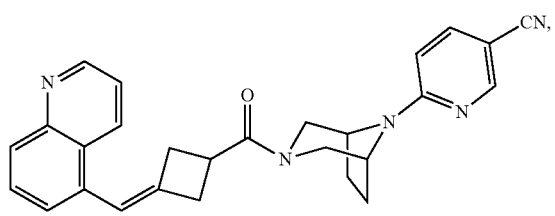

therapeutically effective amount of a compound of claim 1, or a pharmaceutically acceptable salt or solvate thereof.

18. The compound of claim 1, wherein: (i) $R^7$ and $R^{11}$ combine to form a bridged $C_{5-15}$cycloalkyl or bridged 5 to 15 membered heterocycloalkyl; or (ii) $R^5$ and $R^9$ combine to form a bridged $C_{5-15}$cycloalkyl or bridged 5 to 15 membered heterocycloalkyl; or (iii) $R^7$ and $R^9$ combine to form a bridged $C_{5-15}$cycloalkyl or bridged 5 to 15 membered heterocycloalkyl.

19. The compound of claim 1, wherein: (i) $R^7$ and $R^{11}$ combine to form a bridged $C_{5-7}$cycloalkyl or bridged 5 to 7 membered heterocycloalkyl; or (ii) $R^5$ and $R^9$ combine to form a bridged $C_{5-7}$cycloalkyl or bridged 5 to 7 membered heterocycloalkyl; or (iii) $R^7$ and $R^9$ combine to form a bridged $C_{5-7}$cycloalkyl or bridged 5 to 7 membered heterocycloalkyl.

\* \* \* \* \*